United States Patent
Chen et al.

(10) Patent No.: US 10,543,198 B2
(45) Date of Patent: Jan. 28, 2020

(54) INHIBITOR OF LYSINE SPECIFIC DEMETHYLASE-1

(71) Applicant: Celgene Quanticel Research, Inc., San Diego, CA (US)

(72) Inventors: Young K. Chen, San Marcos, CA (US); Toufike Kanouni, La Jolla, CA (US); Jeffrey Alan Stafford, San Diego, CA (US); James Marvin Veal, Apex, NC (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

(21) Appl. No.: 15/723,050

(22) Filed: Oct. 2, 2017

(65) Prior Publication Data

US 2018/0028508 A1 Feb. 1, 2018

Related U.S. Application Data

(62) Division of application No. 14/845,120, filed on Sep. 3, 2015, now Pat. No. 9,822,119.

(60) Provisional application No. 62/046,842, filed on Sep. 5, 2014.

(51) Int. Cl.
| | | |
|---|---|---|
| *A61K 31/495* | (2006.01) | |
| *A61K 31/50* | (2006.01) | |
| *A61K 31/4427* | (2006.01) | |
| *A61K 31/44* | (2006.01) | |
| *A61K 31/437* | (2006.01) | |
| *C07D 471/04* | (2006.01) | |
| *C07D 401/12* | (2006.01) | |
| *C07D 401/14* | (2006.01) | |
| *C07D 403/12* | (2006.01) | |
| *C07D 413/12* | (2006.01) | |
| *C07D 471/10* | (2006.01) | |
| *C07D 487/04* | (2006.01) | |
| *C07D 487/10* | (2006.01) | |
| *C07D 498/08* | (2006.01) | |
| *A61K 31/4155* | (2006.01) | |
| *A61K 31/454* | (2006.01) | |
| *A61K 31/4545* | (2006.01) | |
| *A61K 31/497* | (2006.01) | |
| *A61K 31/506* | (2006.01) | |
| *A61K 31/5377* | (2006.01) | |
| *A61K 31/5386* | (2006.01) | |
| *A61K 31/55* | (2006.01) | |

(52) U.S. Cl.
CPC ........ *A61K 31/437* (2013.01); *A61K 31/4155* (2013.01); *A61K 31/454* (2013.01); *A61K 31/4545* (2013.01); *A61K 31/497* (2013.01); *A61K 31/506* (2013.01); *A61K 31/5377* (2013.01); *A61K 31/5386* (2013.01); *A61K 31/55* (2013.01); *C07D 401/12* (2013.01); *C07D 401/14* (2013.01); *C07D 403/12* (2013.01); *C07D 413/12* (2013.01); *C07D 471/04* (2013.01); *C07D 471/10* (2013.01); *C07D 487/04* (2013.01); *C07D 487/10* (2013.01); *C07D 498/08* (2013.01)

(58) Field of Classification Search
CPC .. A61K 31/495; A61K 31/50; A61K 31/4427; A61K 31/44
USPC .................... 514/247, 252.03, 341, 344, 357
See application file for complete search history.

(56) References Cited

U.S. PATENT DOCUMENTS

| | | |
|---|---|---|
| 2003/0045523 A1 | 6/2003 | Schmitt et al. |
| 2010/0317698 A1 | 12/2010 | Goldstein et al. |
| 2012/0142784 A1 | 6/2012 | Schuele et al. |
| 2012/0289505 A1 | 11/2012 | Jadhav et al. |
| 2013/0035377 A1 | 2/2013 | Minucci |
| 2014/0155339 A1 | 6/2014 | McCord |

FOREIGN PATENT DOCUMENTS

| | | |
|---|---|---|
| JP | 2016-538535 | 12/2016 |
| WO | 2004048365 A1 | 6/2004 |
| WO | 2006/113704 A2 | 10/2006 |
| WO | 2015089192 A1 | 6/2015 |
| WO | WO 2015/089192 A1 | 6/2015 |
| WO | 2016/007727 A1 | 1/2016 |

OTHER PUBLICATIONS

Berge et al., "Pharmaceutical Salts," Journal of Pharmaceutical Sciences. 66(1):1-19 (Jan. 1977).
Bundgard et al., Design of Prodrugs, pp. 7-9, 21-24 (1985).
Higuchi et al., Pro-drugs as Novel Delivery Systems. A.C.S. Symposium Series, 1975, vol. 14.
Constable et al., "4-Substituted and 4,5-Distributed 3,6-Di(2-pyridyl)pyridyl)pyridazines: Ligands for Supramolecular Assemblies", Eur. J. Org. Chem. (2008). pp. 1597-1607.
Grodowska et al., "Organic Solvents in the Pharmaceutical Industry.", Acta Poloniae Pharmaceutica—Drug Research 67(1)(2010)., pp. 3-12.

(Continued)

*Primary Examiner* — Raymond J Henley, III
(74) *Attorney, Agent, or Firm* — Foley & Lardner LLP

(57) ABSTRACT

The present invention relates generally to compositions and methods for treating cancer and neoplastic disease. Provided herein are substituted heterocyclic derivative compounds and pharmaceutical compositions comprising said compounds. The subject compounds and compositions are useful for inhibition of lysine specific demethylase-1. Furthermore, the subject compounds and compositions are useful for the treatment of cancer, such as prostate cancer, breast cancer, bladder cancer, lung cancer and/or melanoma and the like.

36 Claims, No Drawings

(56) References Cited

OTHER PUBLICATIONS

International Preliminary Report on Patentability dated Mar. 16, 2017 in International Application No. PCT/US2014/048429, filed Sep. 3, 2015.
International Search Report and Written Opinion dated Jan. 19, 2016, in International Application No. PCT/US2014/048429, filed Sep. 3, 2015.
Wustrow, et al., "(Bioorg. Med. Chem. Lett.", 18(11), pp. 3376-3381 (2008).
Pubchem, Substance Record for SID 579871816, Create Date: Jun. 12, 2009 (retrieved on Oct. 7, 2015), Retrieved from the Internet, <URL:http://pubchem.ncbi.nlm.nih.gov/substance/79871816#section>, entire document.
Search Report, dated Oct. 3, 2017, issued in related Singapore Application No. 11201701683X, filed Mar. 2, 2017.
Written Opinion, dated Oct. 20, 2017, issued in related Singapore Application No. 11201701683X, filed Mar. 2, 2017.
Office Action issued in co-pending Japanese Patent Application No. 2017-512320, dated May 22, 2019.
Thinnes, et al., "Targeting Histone Lysine Demethylases—Progress, Challenges, and the Future," *Biochimica et Biophysica Acta*, vol. 1839, pp. 1416-1432 (2014).
Doebelin, et al., "Fully Regiocontrolled Polyarylation of Pyridine", The Journal of Organic Chemistry, vol. 79, No. 3, Jan. 13, 2014 (Jan. 13, 2014), pp. 908-918.
Hitchin et al., "Development and evaluation of selective, reversible LSD1 inhibitors derived from fragments", Medchemm, vol. 4, No. 11, 2013, pp. 1513-1522.
Mould et al., "Reversible inhibitors of LSD1 as therapeutic agents in acute myeloid leukemia: clinical significance and progress to date", Medicinal Research Reviews, vol. 35, No. 3, Nov. 24, 2014 (Nov. 24, 2014), pp. 586-618.
Extended European Search Report and Search Opinion, dated Jan. 26, 2018 in European Patent Application No. 15838524.5, filed Mar. 15, 2017.

INHIBITOR OF LYSINE SPECIFIC DEMETHYLASE-1

CROSS REFERENCE

This application is a division of U.S. application Ser. No. 14/845,120, filed Sep. 3, 2015, which claims the priority benefit of U.S. Provisional Application No. 62/046,862, filed Sep. 5, 2014, the contents of which are hereby incorporated by reference in their entireties for all purposes.

BACKGROUND

A need exists in the art for an effective treatment of cancer and neoplastic disease.

BRIEF SUMMARY OF THE INVENTION

Provided herein are substituted heterocyclic derivative compounds and pharmaceutical compositions comprising said compounds. The subject compounds and compositions are useful for inhibition lysine specific demethylase-1 (LSD-1). Furthermore, the subject compounds and compositions are useful for the treatment of cancer, such as prostate cancer, breast cancer, bladder cancer, lung cancer and/or melanoma and the like. The substituted heterocyclic derivative compounds described herein are based upon a central heterocyclic ring system, such as pyrazine, 4-azaindole, 4-azaindazole, pyrimidine or pyrazole, or the like. Said central heterocyclic ring system is further substituted with a 4-cyanophenyl group and a heterocyclyl group.

One embodiment provides a compound having the structure of Formula (I), or a pharmaceutically acceptable salt thereof,

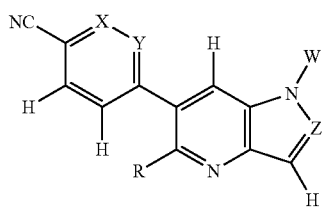

(I)

wherein,

X and Y are each independently chosen from C—H, C—F, C—CH$_3$, or N;

Z is chosen from C—H or N;

R is chosen from hydrogen, halogen, aryl, heteroaryl, heterocyclyl, carbocyclyl, alkoxy, cycloalkylalkyloxy, or aralkyloxy;

W is -L-G, heterocyclyl, or heteroaryl;

L is alkylene;

G is —N(R$^1$)$_2$, heterocyclyl, or heteroaryl; and

R$^1$ is hydrogen or alkyl.

One embodiment provides a compound having the structure of Formula (II), or a pharmaceutically acceptable salt thereof,

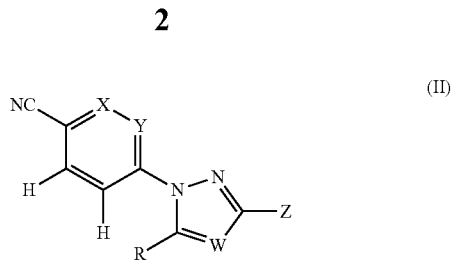

(II)

wherein,

X and Y are each independently chosen from C—H, C—F, C—CH3, or N;

W is chosen from C—H, C—F, C—Cl, C—CH3, C—CF3, C—OCH3, C—OCH2CH3, or N;

Z is chosen -G, —CH2-G, —CH2-CH2-G, —N(R1)-G, —N(R1)-CH2-G, —O-G, —O—CH2-G, or —C(O)N(R2)(R3);

G is carbocyclyl, aryl, heterocyclyl or heteroaryl;

R1 is hydrogen or alkyl;

R2 and R3 are independently selected from hydrogen, alkyl, heterocyclyl, heterocyclylalkyl, or optionally, R2 and R3 join to form an N-linked heterocyclyl ring system; and R is chosen from aryl, halogen, heteroaryl, heterocyclyl, carbocyclyl, alkoxy, cycloalkylalkyloxy, or aralkyloxy.

One embodiment provides a compound having the structure of Formula (III), or a pharmaceutically acceptable salt thereof,

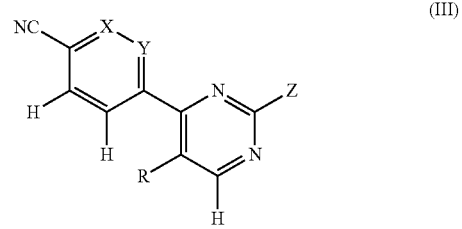

(III)

wherein,

X and Y are each independently chosen from C—H, C—F, C—CH$_3$, or N;

Z is chosen -G, —CH$_2$-G, —CH$_2$—CH$_2$-G, —N(R$^1$)-G, —N(R$^1$)—CH$_2$-G, —O-G, —O—CH$_2$-G, or —C(O)N(R$^2$)(R$^3$);

G is carbocyclyl, aryl, heterocyclyl or heteroaryl;

R$^1$ is hydrogen or alkyl;

R$^2$ and R$^3$ are independently selected from hydrogen, alkyl, heterocyclyl, heterocyclylalkyl, or optionally, R$^2$ and R$^3$ join to form an N-linked heterocyclyl ring system; and R is chosen from alkoxy, carbocyclylalkyloxy, carbocyclyl, carbocyclylalkyl, aryl, aralkyl, heteroaryl, heterocyclyl, alkynyl, or carbocyclylalkynyl.

One embodiment provides a compound having the structure of Formula (IV), or a pharmaceutically acceptable salt thereof, $$\text{(IV)}$$

wherein,

X and Y are each independently chosen from C—H, C—F, C—CH$_3$, or N;

Z is chosen -G, —CH$_2$-G, —CH$_2$—CH$_2$-G, —N(R$^1$)-G, —N(R$^1$)—CH$_2$-G, —O-G, —O—CH$_2$-G, or —C(O)N(R$^2$)(R$^3$);

X$^1$, X$^2$, and X$^3$ are each independently selected from N or C—R$^4$; provided that at least one of X$^1$, X$^2$, or X$^3$ is N;

G is carbocyclyl, aryl, heterocyclyl or heteroaryl;

R$^1$ is hydrogen or alkyl;

R$^2$ and R$^3$ are independently selected from hydrogen, alkyl, heterocyclyl, heterocyclylalkyl, or optionally, R$^2$ and R$^3$ join to form an N-linked heterocyclyl ring system;

R$^4$ is hydrogen, halogen, C$_1$-C$_3$ alkyl or C$_1$-C$_3$ alkoxy; and

R is aryl, heteroaryl, alkynyl, or cycloalkylalkynylene.

One embodiment provides a pharmaceutical composition comprising a compound of Formula (I), or a pharmaceutically acceptable salt thereof, and a pharmaceutically acceptable excipient.

One embodiment provides a pharmaceutical composition comprising a compound of Formula (II), or a pharmaceutically acceptable salt thereof, and a pharmaceutically acceptable excipient.

One embodiment provides a pharmaceutical composition comprising a compound of Formula (III), or a pharmaceutically acceptable salt thereof, and a pharmaceutically acceptable excipient.

One embodiment provides a pharmaceutical composition comprising a compound of Formula (IV), or a pharmaceutically acceptable salt thereof, and a pharmaceutically acceptable excipient.

One embodiment provides a method of regulating gene transcription in a cell comprising inhibiting lysine-specific demethylase 1 activity by exposing the lysine-specific demethylase 1 enzyme to a compound of Formula (I).

One embodiment provides a method of regulating gene transcription in a cell comprising inhibiting lysine-specific demethylase 1 activity by exposing the lysine-specific demethylase 1 enzyme to a compound of Formula (II).

One embodiment provides a method of regulating gene transcription in a cell comprising inhibiting lysine-specific demethylase 1 activity by exposing the lysine-specific demethylase 1 enzyme to a compound of Formula (III).

One embodiment provides a method of regulating gene transcription in a cell comprising inhibiting lysine-specific demethylase 1 activity by exposing the lysine-specific demethylase 1 enzyme to a compound of Formula (IV).

One embodiment provides a method of treating cancer in a patient in need thereof, comprising administering to the patient a compound of Formula (I), or a pharmaceutically acceptable salt thereof.

One embodiment provides a method of treating cancer in a patient in need thereof, comprising administering to the patient a compound of Formula (II), or a pharmaceutically acceptable salt thereof.

One embodiment provides a method of treating cancer in a patient in need thereof, comprising administering to the patient a compound of Formula (III), or a pharmaceutically acceptable salt thereof.

One embodiment provides a method of treating cancer in a patient in need thereof, comprising administering to the patient a compound of Formula (IV), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH2 radical.
"Cyano" refers to the —CN radical.
"Nitro" refers to the —NO2 radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazine" refers to the =N—NH2 radical.
"Alkyl" refers to a straight or branched hydrocarbon chain radical consisting solely of carbon and hydrogen atoms, containing no unsaturation, having from one to fifteen carbon atoms (e.g., C1-C15 alkyl). In certain embodiments, an alkyl comprises one to thirteen carbon atoms (e.g., C1-C13 alkyl). In certain embodiments, an alkyl comprises one to eight carbon atoms (e.g., C1-C8 alkyl). In other embodiments, an alkyl comprises one to five carbon atoms (e.g., C1-C5 alkyl). In other embodiments, an alkyl comprises one to four carbon atoms (e.g., C1-C4 alkyl). In other embodiments, an alkyl comprises one to three carbon atoms (e.g., C1-C3 alkyl). In other embodiments, an alkyl comprises one to two carbon atoms (e.g., C1-C2 alkyl). In other embodiments, an alkyl comprises one carbon atom (e.g., C1 alkyl). In other embodiments, an alkyl comprises five to fifteen carbon atoms (e.g., C5-C15 alkyl). In other embodiments, an alkyl comprises five to eight carbon atoms (e.g., C5-C8 alkyl). In other embodiments, an alkyl comprises two to five carbon atoms (e.g., C2-C5 alkyl). In other embodiments, an alkyl comprises three to five carbon atoms (e.g., C3-C5 alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, rimethylsilanyl, —ORa, —SRa, —OC(O)—Ra, —N(Ra)2, —C(O)Ra, —C(O)ORa, —C(O)N(Ra)2, —N(Ra)C(O)ORa, —OC(O)—N(Ra)2, —N(R)C(O)R, —N(R)S(O)tR (where t is 1 or 2), —S(O)tORa (where t is 1 or 2), —S(O)tRa (where t is 1 or 2) and —S(O)tN(Ra)2 (where t is 1 or 2) where each Ra is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)O R^a$, —OC(O)— $N(R^a)_2$, —$N(R^a)C(O)R^a$, —$N(R^a)S(O)tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)tR^a$ (where t is 1 or 2), —S(O)tORa (where t is 1 or 2), —$S(O)tR^a$ (where t is 1 or 2) and —$S(O)tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)O R$^a$, —OC(O)— N(R$^a$)$_2$, —N(R$^a$)C(O)R$^a$, —N(R$^a$)S(O)tR$^a$ (where t is 1 or 2), —S(O)$_t$ORa (where t is 1 or 2), —S(O)$_t$Ra (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)O R$^a$, —OC(O)—N(R$^a$)$_2$, —N(R$^a$)C(O)R$^a$, —N(R$^a$)S(O)tR$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)tR$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(Ra)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$_d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O) $R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each Rb is independently a direct bond or a straight or branched alkylene or alkenylene chain, and Rc is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

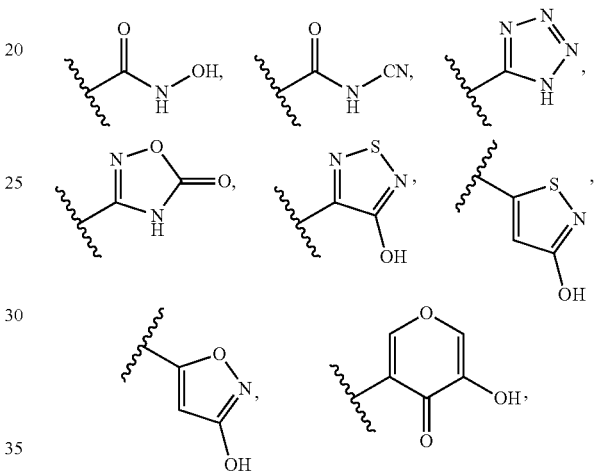

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)2, —$R^b$—N($R^a$)2, —$R^b$—C(O) $R^a$, —$R^b$—C(O)$OR^a$, —$R^b$—C(O)N($R^a$)2, —$R^b$—O—$R^c$—C(O)N($R^a$)2, —Rb—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)t$OR^a$ (where t is 1 or 2) and —$R^b$—S(O)$_t$N(Rv)2 (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)$ $R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above.

If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

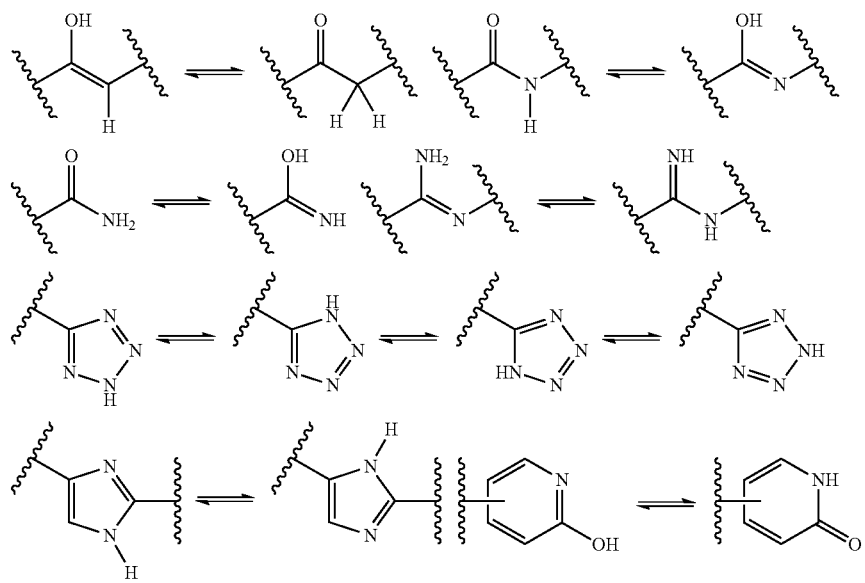

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Heterocyclic Derivative Compounds

Substituted heterocyclic derivative compounds are described herein that are lysine specific demethylase-1 inhibitors. These compounds, and compositions comprising these compounds, are useful for the treatment of cancer and neoplastic disease. The compounds described herein are useful for treating prostate cancer, breast cancer, bladder cancer, lung cancer and/or melanoma and the like.

One embodiment provides a compound having the structure of Formula (I), or a pharmaceutically acceptable salt thereof,

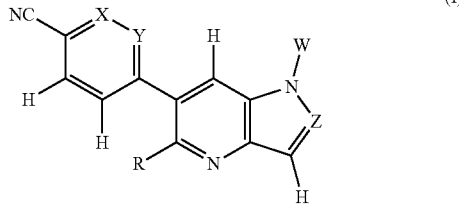

wherein,
X and Y are each independently chosen from C—H, C—F, C—CH3, or N;
Z is chosen from C—H or N;
R is chosen from hydrogen, halogen, aryl, heteroaryl, heterocyclyl, carbocyclyl, alkoxy, cycloalkylalkyloxy, or aralkyloxy
W is -L-G, heterocyclyl, or heteroaryl;
L is alkylene;
G is —N(R1)2, heterocyclyl, or heteroaryl; and
R1 is hydrogen or alkyl.

Another embodiment provides a compound having the structure of Formula (I), or a pharmaceutically acceptable salt thereof, wherein R is chosen from aryl, heteroaryl, heterocyclyl, carbocyclyl, alkoxy, cycloalkylalkyloxy, or aralkyloxy.

Another embodiment provides a compound having the structure of Formula (I), or a pharmaceutically acceptable salt thereof, wherein Z is C—H. Another embodiment provides a compound having the structure of Formula (I), or a pharmaceutically acceptable salt thereof, wherein Z is N. Another embodiment provides a compound having the structure of Formula (I), or a pharmaceutically acceptable salt thereof, wherein X is C—H. Another embodiment provides a compound having the structure of Formula (I), or a pharmaceutically acceptable salt thereof, wherein X is C—F. Another embodiment provides a compound having the structure of Formula (I), or a pharmaceutically acceptable salt thereof, wherein X is C—CH$_3$. Another embodiment provides a compound having the structure of Formula (I), or a pharmaceutically acceptable salt thereof, wherein X is N. Another embodiment provides a compound having the structure of Formula (I), or a pharmaceutically acceptable salt thereof, wherein Y is C—H. Another embodiment provides a compound having the structure of Formula (I), or a pharmaceutically acceptable salt thereof, wherein Y is C—F. Another embodiment provides a compound having the structure of Formula (I), or a pharmaceutically acceptable salt thereof, wherein Y is C—CH$_3$. Another embodiment provides a compound having the structure of Formula (I), or a pharmaceutically acceptable salt thereof, wherein Y is N. Another embodiment provides a compound having the structure of Formula (I), or a pharmaceutically acceptable salt thereof, wherein X is C—H, and Y is C—H. Another embodiment provides a compound having the structure of Formula (I), or a pharmaceutically acceptable salt thereof, wherein X is C—H, Y is C—H, and Z is C—H. Another embodiment provides a compound having the structure of Formula (I), or a pharmaceutically acceptable salt thereof, wherein X is C—H, Y is C—H, and Z is N. Another embodiment provides a compound having the structure of Formula (I), or a pharmaceutically acceptable salt thereof, wherein X is C—H, Y is C—CH$_3$, and Z is C—H. Another embodiment provides a compound having the structure of Formula (I), or a pharmaceutically acceptable salt thereof, wherein X is C—H, Y is C—CH$_3$, and Z is N.

Another embodiment provides a compound having the structure of Formula (I), or a pharmaceutically acceptable salt thereof, wherein W is L-G. Another embodiment provides a compound having the structure of Formula (I), or a pharmaceutically acceptable salt thereof, wherein W is heterocyclyl.

Another embodiment provides a compound having the structure of Formula (I), or a pharmaceutically acceptable salt thereof, wherein W is heteroaryl. Another embodiment provides a compound having the structure of Formula (I), or a pharmaceutically acceptable salt thereof, wherein W is L-G, and the L is chosen from a $C_1$ alkylene, $C_1$-$C_2$ alkylene, $C_1$-$C_4$ alkylene, or $C_2$-$C_5$ alkylene. Another embodiment provides a compound having the structure of Formula (I), or a pharmaceutically acceptable salt thereof, wherein W is L-G, and the L is a $C_1$ alkylene. Another embodiment provides a compound having the structure of Formula (I), or a pharmaceutically acceptable salt thereof, wherein W is L-G, and the G is a heterocyclyl. Another embodiment provides a compound having the structure of Formula (I), or a pharmaceutically acceptable salt thereof, wherein W is L-G, and the G is a heteroaryl. Another embodiment provides a compound having the structure of Formula (I), or a pharmaceutically acceptable salt thereof, wherein W is L-G, and the G is —N(R$^1$)$_2$. Another embodiment provides a compound having the structure of Formula (I), or a pharmaceutically acceptable salt thereof, wherein W is L-G, the L is chosen from a $C_1$ alkylene, $C_1$-$C_2$ alkylene, $C_1$-$C_4$ alkylene, or $C_2$-$C_5$ alkylene, and the G is —N(R$^1$)$_2$. Another embodiment provides a compound having the structure of Formula (I), or a pharmaceutically acceptable salt thereof, wherein W is L-G, and the G is —NH$_2$. Another embodiment provides a compound having the structure of Formula (I), or a pharmaceutically acceptable salt thereof, wherein W is L-G, and the G is —NH(alkyl). Another embodiment provides a compound having the structure of Formula (I), or a pharmaceutically acceptable salt thereof, wherein W is L-G, and the G is —N(alkyl)$_2$.

Another embodiment provides a compound having the structure of Formula (I), or a pharmaceutically acceptable salt thereof, wherein W is L-G, the G is a heterocyclyl and the heterocyclyl is a nitrogen-containing heterocyclyl. Another embodiment provides a compound having the structure of Formula (I), or a pharmaceutically acceptable salt thereof, wherein W is L-G, the G is a heterocyclyl, the heterocyclyl is a nitrogen-containing heterocyclyl and the nitrogen-containing heterocyclyl is a 5- or 6-membered heterocyclyl. Another embodiment provides a compound having the structure of Formula (I), or a pharmaceutically acceptable salt thereof, wherein W is L-G, the G is a heterocyclyl and the heterocyclyl is chosen from:

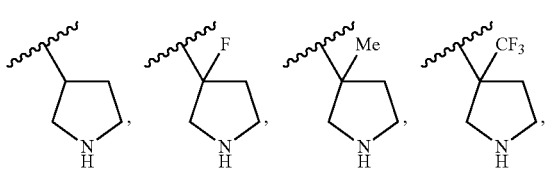

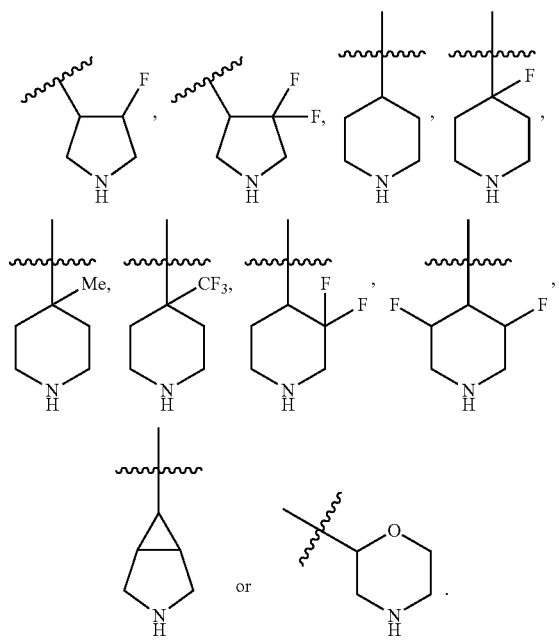

Another embodiment provides a compound having the structure of Formula (I), or a pharmaceutically acceptable salt thereof, wherein W is a heterocyclyl and the heterocyclyl is a nitrogen-containing heterocyclyl. Another embodiment provides a compound having the structure of Formula (I), or a pharmaceutically acceptable salt thereof, wherein W is a heterocyclyl, the heterocyclyl is a nitrogen-containing heterocyclyl and the nitrogen-containing heterocyclyl is a 5- or 6-membered heterocyclyl. Another embodiment provides a compound having the structure of Formula (I), or a pharmaceutically acceptable salt thereof, wherein W is a heterocyclyl and the heterocyclyl is a nitrogen-containing heterocyclyl chosen from:

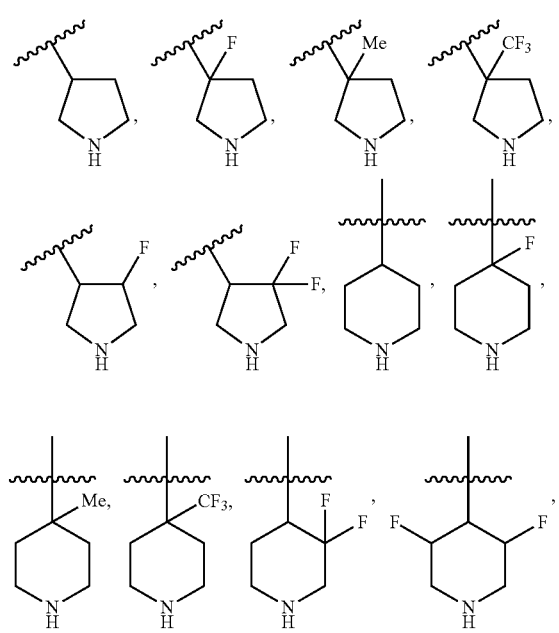

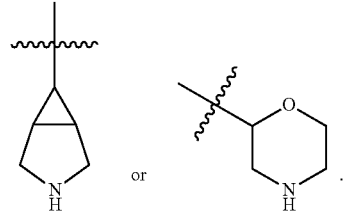

Another embodiment provides a compound having the structure of Formula (I), or a pharmaceutically acceptable salt thereof, wherein G is a nitrogen-containing heterocyclyl, and the heterocyclyl is chosen from:

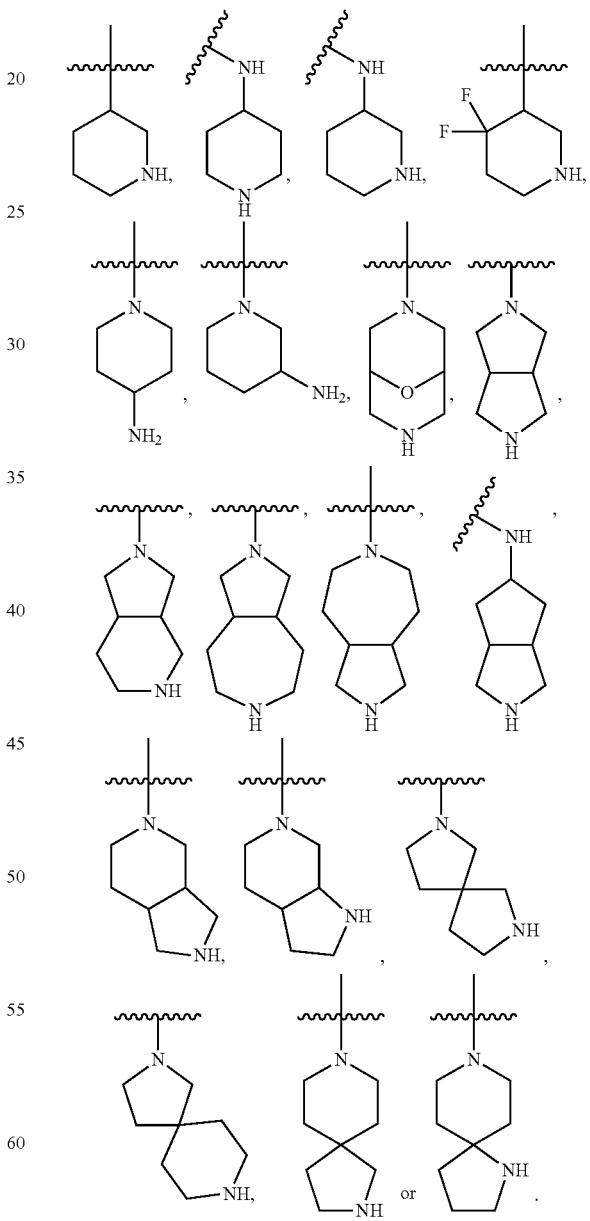

Another embodiment provides a compound having the structure of Formula (I), or a pharmaceutically acceptable salt thereof, wherein the R is an aryl group or a heterocyclyl group. Another embodiment provides a compound having the structure of Formula (I), or a pharmaceutically acceptable salt thereof, wherein the R is an aryl group. Another embodiment provides a compound having the structure of Formula (I), or a pharmaceutically acceptable salt thereof, wherein the aryl group is an optionally substituted phenyl group. Another embodiment provides a compound having the structure of Formula (I), or a pharmaceutically acceptable salt thereof, wherein the optionally substituted phenyl group is chosen from 4-methylphenyl, 4-chlorophenyl, 4-fluorophenyl, 4-cyanophenyl, 4-(methylsulfonyl)phenyl, or 4-trifluoromethylphenyl.

One embodiment provides a compound having the structure of Formula (II), or a pharmaceutically acceptable salt thereof,

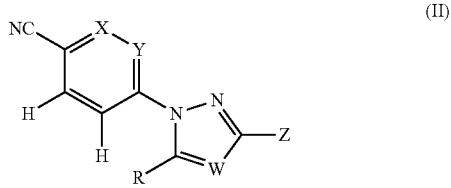

wherein,
X and Y are each independently chosen from C—H, C—F, C—CH$_3$, or N;
W is chosen from C—H, C—F, C—Cl, C—CH$_3$, C—CF$_3$, C—OCH$_3$, C—OCH$_2$CH$_3$, or N;
Z is chosen -G, —CH$_2$-G, —CH$_2$—CH$_2$-G, —N(R$^1$)-G, —N(R$^1$)—CH$_2$-G, —O-G, —O—CH$_2$-G, or —C(O)N(R$^2$)(R$^3$);
G is carbocyclyl, aryl, heterocyclyl or heteroaryl;
R$^1$ is hydrogen or alkyl;
R$^2$ and R$^3$ are independently selected from hydrogen, alkyl, heterocyclyl, heterocyclylalkyl, or optionally, R$^2$ and R$^3$ join to form an N-linked heterocyclyl ring system;
R is chosen from aryl, halogen, heteroaryl, heterocyclyl, carbocyclyl, alkoxy, cycloalkylalkyloxy, or aralkyloxy.

Another embodiment provides a compound having the structure of Formula (II), or a pharmaceutically acceptable salt thereof, wherein X is C—H. Another embodiment provides a compound having the structure of Formula (II), or a pharmaceutically acceptable salt thereof, wherein X is C—F. Another embodiment provides a compound having the structure of Formula (II), or a pharmaceutically acceptable salt thereof, wherein X is C—CH$_3$. Another embodiment provides a compound having the structure of Formula (II), or a pharmaceutically acceptable salt thereof, wherein X is N. Another embodiment provides a compound having the structure of Formula (II), or a pharmaceutically acceptable salt thereof, wherein Y is C—H. Another embodiment provides a compound having the structure of Formula (II), or a pharmaceutically acceptable salt thereof, wherein Y is C—F. Another embodiment provides a compound having the structure of Formula (II), or a pharmaceutically acceptable salt thereof, wherein Y is C—CH$_3$. Another embodiment provides a compound having the structure of Formula (II), or a pharmaceutically acceptable salt thereof, wherein Y is N. Another embodiment provides a compound having the structure of Formula (II), or a pharmaceutically acceptable salt thereof, wherein X is C—H and Y is C—H. Another embodiment provides a compound having the structure of Formula (II), or a pharmaceutically acceptable salt thereof, wherein W is N. Another embodiment provides a compound having the structure of Formula (II), or a pharmaceutically acceptable salt thereof, wherein W is C—H. Another embodiment provides a compound having the structure of Formula (II), or a pharmaceutically acceptable salt thereof, wherein X is C—H and W is N. Another embodiment provides a compound having the structure of Formula (II), or a pharmaceutically acceptable salt thereof, wherein X is C—H and W is C—H. Another embodiment provides a compound having the structure of Formula (II), or a pharmaceutically acceptable salt thereof, wherein X is C—H, Y is C—H, and W is N. Another embodiment provides a compound having the structure of Formula (II), or a pharmaceutically acceptable salt thereof, wherein X is C—H, Y is C—H, and W is C—H.

Another embodiment provides a compound having the structure of Formula (II), or a pharmaceutically acceptable salt thereof, wherein Z is —O—CH$_2$-G. Another embodiment provides a compound having the structure of Formula (II), or a pharmaceutically acceptable salt thereof, wherein Z is —O-G. Another embodiment provides a compound having the structure of Formula (II), or a pharmaceutically acceptable salt thereof, wherein Z is —N(R$^1$)—CH$_2$-G.

Another embodiment provides a compound having the structure of Formula (II), or a pharmaceutically acceptable salt thereof, wherein Z is —N(R$^1$)-G. Another embodiment provides a compound having the structure of Formula (II), or a pharmaceutically acceptable salt thereof, wherein Z is —CH$_2$—CH$_2$-G.

Another embodiment provides a compound having the structure of Formula (II), or a pharmaceutically acceptable salt thereof, wherein Z is —CH$_2$-G. Another embodiment provides a compound having the structure of Formula (II), or a pharmaceutically acceptable salt thereof, wherein Z is -G.

Another embodiment provides a compound having the structure of Formula (II), or a pharmaceutically acceptable salt thereof, wherein Z is —C(O)N(R$_2$)(R$^3$). Another embodiment provides a compound having the structure of Formula (II), or a pharmaceutically acceptable salt thereof, wherein Z is —C(O)N(R$^2$)(R$^3$), and R$^2$ and $^{R3}$ are independently selected from hydrogen, or alkyl. Another embodiment provides a compound having the structure of Formula (II), or a pharmaceutically acceptable salt thereof, wherein Z is —C(O)N(R$^2$)(R$^3$), and R$^2$ and R$^3$ are independently selected from hydrogen, alkyl, or heterocyclyl.

Another embodiment provides a compound having the structure of Formula (II), or a pharmaceutically acceptable salt thereof, wherein Z is —C(O)N(R$^2$)(R$^3$), and R$^2$ and R$^3$ are independently selected from hydrogen, alkyl, or heterocyclylalkyl.

Another embodiment provides a compound having the structure of Formula (II), or a pharmaceutically acceptable salt thereof, wherein Z is —C(O)N(R$^2$)(R$^3$), R$^2$ and R$^3$ are both alkyl, and R$^2$ and R$^3$ join to form an N-linked heterocyclyl ring system. Another embodiment provides a compound having the structure of Formula (II), or a pharmaceutically acceptable salt thereof, wherein Z is —C(O)N(R$^2$)(R$^3$), R$^2$ and R$^3$ are both alkyl, R$^2$ and R$^3$ join to form an N-linked heterocyclyl, and the heterocyclyl is chosen from an optionally substituted piperdinyl, piperizinyl, morpholinyl, or pyrrolidinyl group.

Another embodiment provides a compound having the structure of Formula (II), or a pharmaceutically acceptable salt thereof, wherein Z is —N(R1)-CH$_2$-G, and R1 is hydrogen. Another embodiment provides a compound having the structure of Formula (II), or a pharmaceutically acceptable salt thereof, wherein Z is —N(R$^1$)-G, and R$^1$ is hydrogen.

Another embodiment provides a compound having the structure of Formula (II), or a pharmaceutically acceptable salt thereof, wherein Z is —N(R$^1$)—CH$_2$-G, and R$^1$ is alkyl. Another embodiment provides a compound having the structure of Formula (II), or a pharmaceutically acceptable salt thereof, wherein Z is —N(R$^1$)—CH$_2$-G, R$^1$ is alkyl, and the alkyl is a C$_1$-C$_4$ alkyl. Another embodiment provides a compound having the structure of Formula (II), or a pharmaceutically acceptable salt thereof, wherein Z is —N(R$^1$)-G, and R$^1$ is alkyl. Another embodiment provides a compound having the structure of Formula (II), or a pharmaceutically acceptable salt thereof, wherein Z is —N(R$^1$)-G, R$^1$ is alkyl, and the alkyl is a C$_1$-C$_4$ alkyl.

Another embodiment provides a compound having the structure of Formula (II), or a pharmaceutically acceptable salt thereof, wherein G is a heterocyclyl. Another embodiment provides a compound having the structure of Formula (II), or a pharmaceutically acceptable salt thereof, wherein G is a nitrogen-containing heterocyclyl. Another embodiment provides a compound having the structure of Formula (II), or a pharmaceutically acceptable salt thereof, wherein G is a nitrogen-containing heterocyclyl, and the nitrogen-containing heterocyclyl is a 5- or 6-membered heterocyclyl. Another embodiment provides a compound having the structure of Formula (II), or a pharmaceutically acceptable salt thereof, wherein G is a heterocyclyl, and the heterocyclyl is chosen from:

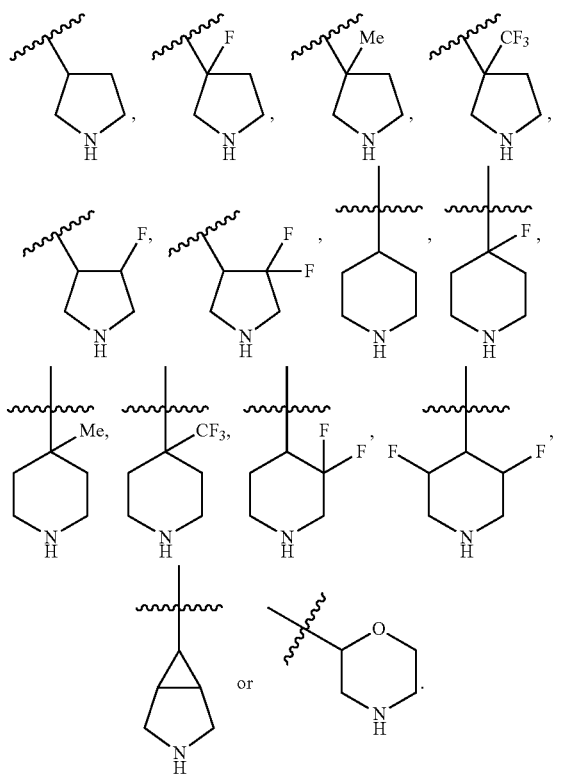

Another embodiment provides a compound having the structure of Formula (II), or a pharmaceutically acceptable salt thereof, wherein G is a nitrogen-containing heterocyclyl, and the heterocyclyl is chosen from:

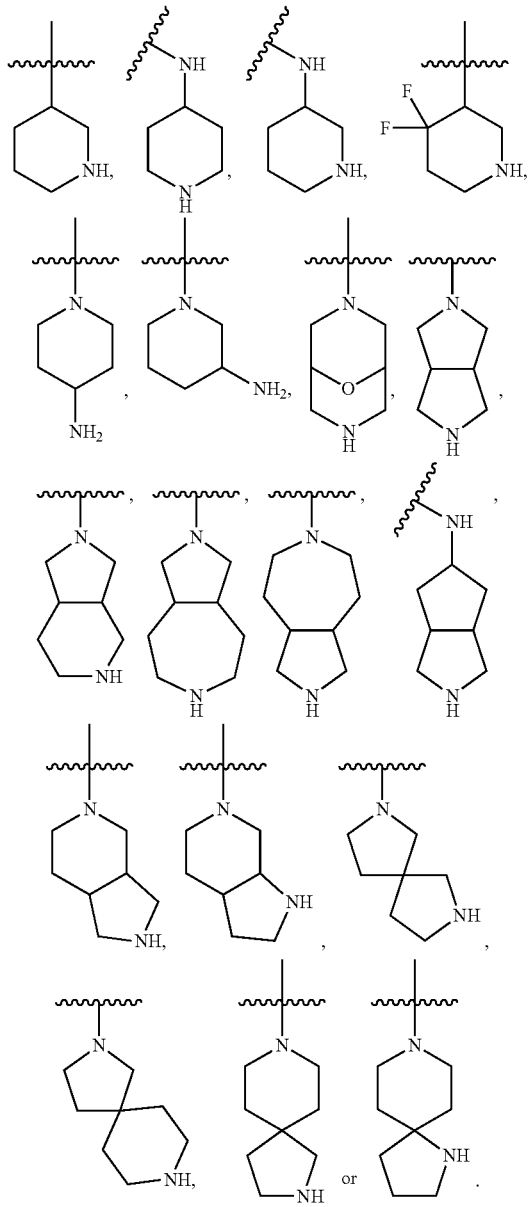

Another embodiment provides a compound having the structure of Formula (II), or a pharmaceutically acceptable salt thereof, wherein G is a heterocyclyl, and the heterocyclyl is chosen from an optionally substituted piperdinyl, piperizinyl, morpholinyl, or pyrrolidinyl group.

Another embodiment provides a compound having the structure of Formula (II), or a pharmaceutically acceptable salt thereof, wherein R is chosen from aryl, heteroaryl, heterocyclyl, carbocyclyl, alkoxy, cycloalkylalkyloxy, or aralkyloxy. Another embodiment provides a compound having the structure of Formula (II), or a pharmaceutically acceptable salt thereof, wherein R is aryl. Another embodiment provides a compound having the structure of Formula (II), or a pharmaceutically acceptable salt thereof, wherein R is aryl, and the aryl group is an optionally substituted phenyl group. Another embodiment provides a compound having the structure of Formula (II), or a pharmaceutically acceptable salt thereof, wherein R is aryl, the aryl group is an optionally substituted phenyl group, and the optionally substituted phenyl group is chosen from 4-methylphenyl, 4-chlorophenyl, 4-fluorophenyl, 4-cyanophenyl, 4-(methylsulfonyl)phenyl, or 4-trifluoromethylphenyl.

One embodiment provides a compound having the structure of Formula (III), or a pharmaceutically acceptable salt thereof,

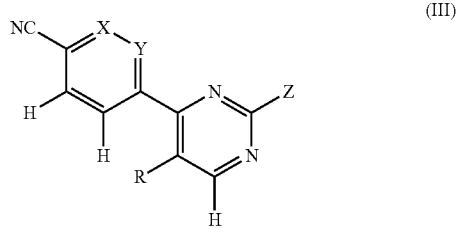

wherein,

X and Y are each independently chosen from C—H, C—F, C—$CH_3$, or N;

Z is chosen -G, —$CH_2$-G, —$CH_2$—$CH_2$-G, —N($R^1$)-G, —N($R^1$)—$CH_2$-G, —O-G, —O—$CH_2$-G, or —C(O)N($R^2$)($R^3$);

G is carbocyclyl, aryl, heterocyclyl or heteroaryl;

$R^1$ is hydrogen or alkyl;

$R^2$ and $R^3$ are independently selected from hydrogen, alkyl, heterocyclyl, heterocyclylalkyl, or optionally, $R^2$ and $R^3$ join to form an N-linked heterocyclyl ring system; and R is chosen from alkoxy, carbocyclylalkyloxy, carbocyclyl, carbocyclylalkyl, aryl, aralkyl, heteroaryl, heterocyclyl, alkynyl, or carbocyclylalkynyl.

Another embodiment provides a compound having the structure of Formula (III), or a pharmaceutically acceptable salt thereof, wherein X is C—H. Another embodiment provides a compound having the structure of Formula (III), or a pharmaceutically acceptable salt thereof, wherein X is C—F. Another embodiment provides a compound having the structure of Formula (III), or a pharmaceutically acceptable salt thereof, wherein X is C—$CH_3$. Another embodiment provides a compound having the structure of Formula (III), or a pharmaceutically acceptable salt thereof, wherein X is N. Another embodiment provides a compound having the structure of Formula (III), or a pharmaceutically acceptable salt thereof, wherein Y is C—H. Another embodiment provides a compound having the structure of Formula (III), or a pharmaceutically acceptable salt thereof, wherein Y is C—F. Another embodiment provides a compound having the structure of Formula (III), or a pharmaceutically acceptable salt thereof, wherein Y is C—$CH_3$. Another embodiment provides a compound having the structure of Formula (III), or a pharmaceutically acceptable salt thereof, wherein Y is N. Another embodiment provides a compound having the structure of Formula (III), or a pharmaceutically acceptable salt thereof, wherein X is C—H and Y is C—H.

Another embodiment provides a compound having the structure of Formula (III), or a pharmaceutically acceptable salt thereof, wherein Z is —O—$CH_2$-G.

Another embodiment provides a compound having the structure of Formula (III), or a pharmaceutically acceptable salt thereof, wherein Z is —O-G.

Another embodiment provides a compound having the structure of Formula (III), or a pharmaceutically acceptable salt thereof, wherein Z is —N($R^1$)—$CH_2$-G. Another embodiment provides a compound having the structure of Formula (III), or a pharmaceutically acceptable salt thereof, wherein Z is —N($R^1$)—$CH_2$-G, and $R^1$ is hydrogen. Another embodiment provides a compound having the structure of Formula (III), or a pharmaceutically acceptable salt thereof, wherein Z is —N($R^1$)—$CH_2$-G, and $R^1$ is alkyl.

Another embodiment provides a compound having the structure of Formula (III), or a pharmaceutically acceptable salt thereof, wherein Z is —N($R^1$)-G. Another embodiment provides a compound having the structure of Formula (III), or a pharmaceutically acceptable salt thereof, wherein Z is —N($R^1$)-G, and $R^1$ is hydrogen. Another embodiment provides a compound having the structure of Formula (III), or a pharmaceutically acceptable salt thereof, wherein Z is —N($R^1$)-G, and $R^1$ is alkyl.

Another embodiment provides a compound having the structure of Formula (III), or a pharmaceutically acceptable salt thereof, wherein Z is —$CH_2$—$CH_2$-G. Another embodiment provides a compound having the structure of Formula (III), or a pharmaceutically acceptable salt thereof, wherein Z is —$CH_2$-G. Another embodiment provides a compound having the structure of Formula (III), or a pharmaceutically acceptable salt thereof, wherein Z is -G. Another embodiment provides a compound having the structure of Formula (III), or a pharmaceutically acceptable salt thereof, wherein Z is —C(O)N($R^2$)($R^3$).

Another embodiment provides a compound having the structure of Formula (III), or a pharmaceutically acceptable salt thereof, wherein Z is —C(O)N($R^2$)($R^3$), and $R^2$ and $R^3$ are independently selected from hydrogen, or alkyl. Another embodiment provides a compound having the structure of Formula (III), or a pharmaceutically acceptable salt thereof, wherein Z is —C(O)N($R^2$)($R^3$), and $R^2$ and $R^3$ are independently selected from hydrogen, alkyl, or heterocyclyl. Another embodiment provides a compound having the structure of Formula (III), or a pharmaceutically acceptable salt thereof, wherein Z is —C(O)N($R^2$)($R^3$), and $R^2$ and $R^3$ are independently selected from hydrogen, alkyl, or heterocyclylalkyl. Another embodiment provides a compound having the structure of Formula (III), or a pharmaceutically acceptable salt thereof, wherein Z is —C(O)N($R^2$)($R^3$), and $R^2$ and $R^3$ join to form an N-linked heterocyclyl ring system. Another embodiment provides a compound having the structure of Formula (III), or a pharmaceutically acceptable salt thereof, wherein Z is —C(O)N($R^2$)($R^3$), $R^2$ and $R^3$ join to form an N-linked heterocyclyl ring system, and the heterocyclyl is chosen from an optionally substituted piperdinyl, piperizinyl, morpholinyl, or pyrrolidinyl group. Another embodiment provides a compound having the structure of Formula (III), or a pharmaceutically acceptable salt thereof, wherein Z is —C(O)N($R^2$)($R^3$), $R^2$ and $R^3$ are both alkyl, and $R^2$ and $R^3$ join to form an N-linked heterocyclyl ring system.

Another embodiment provides a compound having the structure of Formula (III), or a pharmaceutically acceptable salt thereof, wherein G is a heterocyclyl. Another embodiment provides a compound having the structure of Formula (III), or a pharmaceutically acceptable salt thereof, wherein G is a nitrogen-containing heterocyclyl. Another embodiment provides a compound having the structure of Formula (III), or a pharmaceutically acceptable salt thereof, wherein G is a nitrogen-containing heterocyclyl, and the nitrogen-containing heterocyclyl is a 5- or 6-membered heterocyclyl. Another embodiment provides a compound having the structure of Formula (III), or a pharmaceutically acceptable salt thereof, wherein G is a nitrogen-containing heterocyclyl, and the heterocyclyl is chosen from:

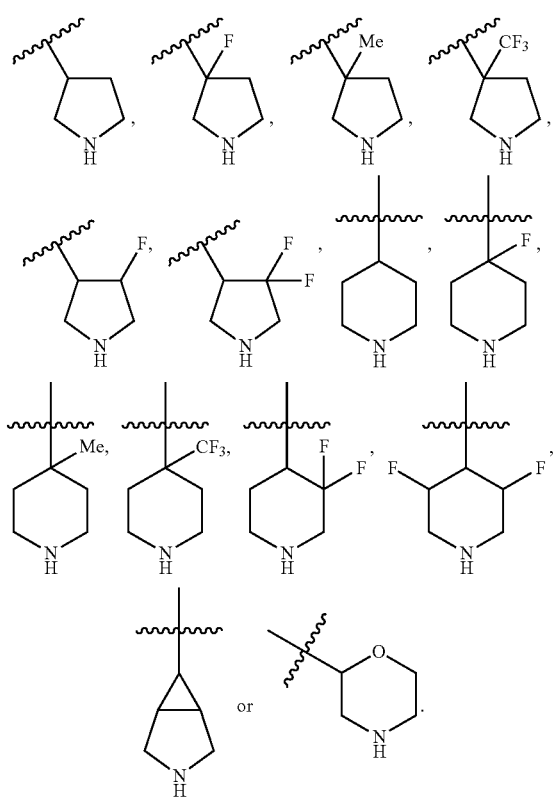

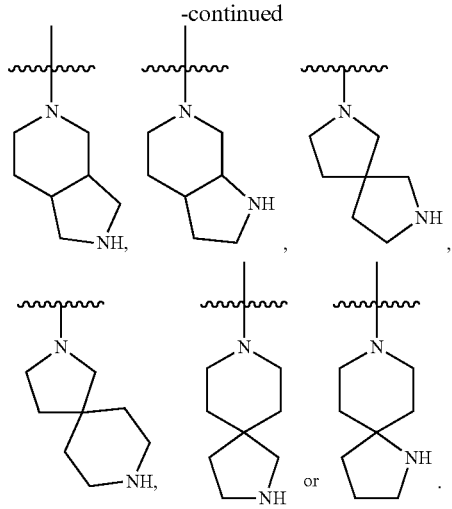

Another embodiment provides a compound having the structure of Formula (III), or a pharmaceutically acceptable salt thereof, wherein G is a nitrogen-containing heterocyclyl, and the heterocyclyl is chosen from:

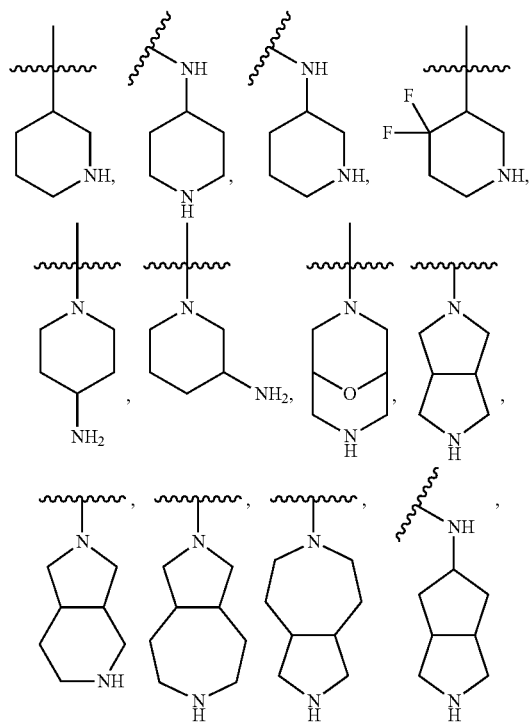

Another embodiment provides a compound having the structure of Formula (III), or a pharmaceutically acceptable salt thereof, wherein G is a heterocyclyl, and the heterocyclyl is chosen from an optionally substituted piperdinyl, piperizinyl, morpholinyl, or pyrrolidinyl group.

Another embodiment provides a compound having the structure of Formula (III), or a pharmaceutically acceptable salt thereof, wherein R is chosen from alkynyl, or carbocyclylalkynyl. Another embodiment provides a compound having the structure of Formula (III), or a pharmaceutically acceptable salt thereof, wherein R is chosen from alkoxy, or carbocyclylalkyloxy. Another embodiment provides a compound having the structure of Formula (III), or a pharmaceutically acceptable salt thereof, wherein R is chosen from heteroaryl, or heterocyclyl. Another embodiment provides a compound having the structure of Formula (III), or a pharmaceutically acceptable salt thereof, wherein R is chosen from carbocyclyl, carbocyclylalkyl, aryl, or aralkyl.

Another embodiment provides a compound having the structure of Formula (III), or a pharmaceutically acceptable salt thereof, wherein R is aryl. Another embodiment provides a compound having the structure of Formula (III), or a pharmaceutically acceptable salt thereof, wherein R is aryl, and the aryl group is an optionally substituted phenyl group. Another embodiment provides a compound having the structure of Formula (III), or a pharmaceutically acceptable salt thereof, wherein R is aryl, and the aryl group is an optionally substituted phenyl group chosen from 4-methylphenyl, 4-chlorophenyl, 4-fluorophenyl, 4-cyanophenyl, 4-(methylsulfonyl)phenyl, or 4-trifluoromethylphenyl.

One embodiment provides a compound having the structure of Formula (IV), or a pharmaceutically acceptable salt thereof,

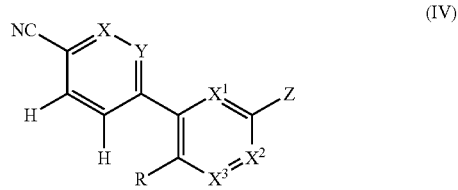

(IV)

wherein,
X and Y are each independently chosen from C—H, C—F, C—CH$_3$, or N;
Z is chosen -G, —CH$_2$-G, —CH$_2$—CH$_2$-G, —N(R$^1$)-G, —N(R$^1$)—CH$_2$-G, —O-G, —O—CH$_2$-G, or —C(O)N(R$^2$)(R$^3$);
X$^1$, X$^2$, and X$^3$ are each independently selected from N or C—R$^4$; provided that at least one of X$^1$, X$^2$, or X$^3$ is N;
G is carbocyclyl, aryl, heterocyclyl or heteroaryl;
R$^1$ is hydrogen or alkyl;
R$^2$ and R$^3$ are independently selected from hydrogen, alkyl, heterocyclyl, heterocyclylalkyl, or optionally, R$^2$ and R$^3$ join to form an N-linked heterocyclyl ring system;
R$^4$ is hydrogen, halogen, C$_1$-C$_3$ alkyl or C$_1$-C$_3$ alkoxy; and
R is aryl, heteroaryl, alkynyl, or cycloalkylalkynylene.

Another embodiment provides a compound, or pharmaceutically acceptable salt thereof, of Formula (IV), wherein R is aryl, or heteroaryl.

Another embodiment provides a compound, or pharmaceutically acceptable salt thereof, of Formula (IV), wherein Formula (IV) is represented by Formula (IVa):

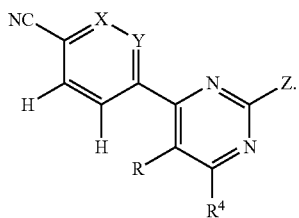

(IVa)

Another embodiment provides a compound, or pharmaceutically acceptable salt thereof, of Formula (IV), wherein Formula (IV) is represented by Formula (IVb):

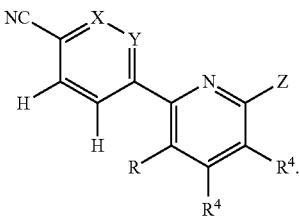

(IVb)

Another embodiment provides a compound, or pharmaceutically acceptable salt thereof, of Formula (IV), wherein Formula (IV) is represented by Formula (IVc):

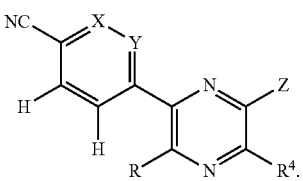

(IVc)

Another embodiment provides a compound, or pharmaceutically acceptable salt thereof, of Formula (IV), wherein Formula (IV) is represented by Formula (IVd):

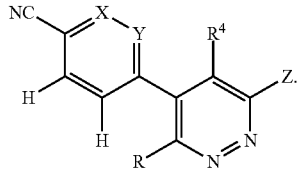

(IVd)

Another embodiment provides a compound, or pharmaceutically acceptable salt thereof, of Formula (IV), wherein Formula (IV) is represented by Formula (IVe):

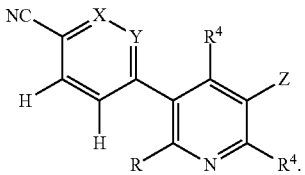

(IVe)

Another embodiment provides a compound, or pharmaceutically acceptable salt thereof, of Formula (IV), wherein Formula (IV) is represented by Formula (IVf):

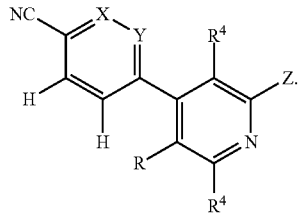

(IVf)

Another embodiment provides a compound, or pharmaceutically acceptable salt thereof, of Formula (IV), wherein Formula (IV) is represented by Formula (IVg):

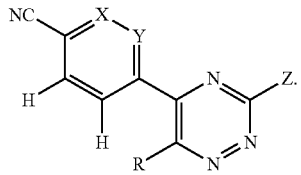

(IVg)

Another embodiment provides a compound, or pharmaceutically acceptable salt thereof, of Formula (IV), wherein X is C—H. Another embodiment provides a compound, or pharmaceutically acceptable salt thereof, of Formula (IV), wherein X is C—F. Another embodiment provides a compound, or pharmaceutically acceptable salt thereof, of Formula (IV), wherein X is C—CH$_3$. Another embodiment provides a compound, or pharmaceutically acceptable salt thereof, of Formula (IV), wherein X is N. Another embodiment provides a compound, or pharmaceutically acceptable salt thereof, of Formula (IV), wherein Y is C—H. Another embodiment provides a compound, or pharmaceutically acceptable salt thereof, of Formula (IV), wherein Y is C—F. Another embodiment provides a compound, or pharmaceutically acceptable salt thereof, of Formula (IV), wherein Y is C—CH₃. Another embodiment provides a compound, or pharmaceutically acceptable salt thereof, of Formula (IV), wherein Y is N. Another embodiment provides a compound, or pharmaceutically acceptable salt thereof, of Formula (IV), wherein X is C—H and Y is C—H.

Another embodiment provides a compound, or pharmaceutically acceptable salt thereof, of Formula (IV), wherein Z is —O—CH₂-G. Another embodiment provides a compound, or pharmaceutically acceptable salt thereof, of Formula (IV), wherein Z is —O-G. Another embodiment provides a compound, or pharmaceutically acceptable salt thereof, of Formula (IV), wherein Z is —N(R¹)—CH₂-G. Another embodiment provides a compound, or pharmaceutically acceptable salt thereof, of Formula (IV), wherein Z is —N(R¹)-G. Another embodiment provides a compound, or pharmaceutically acceptable salt thereof, of Formula (IV), wherein Z is —CH₂—CH₂-G. Another embodiment provides a compound, or pharmaceutically acceptable salt thereof, of Formula (IV), wherein Z is —CH₂-G. Another embodiment provides a compound, or pharmaceutically acceptable salt thereof, of Formula (IV), wherein Z is -G. Another embodiment provides a compound, or pharmaceutically acceptable salt thereof, of Formula (IV), wherein Z is —C(O)N(R²)(R³). Another embodiment provides a compound, or pharmaceutically acceptable salt thereof, of Formula (IV), wherein Z is —C(O)N(R²)(R3), and R² and R³ are independently selected from hydrogen or alkyl. Another embodiment provides a compound, or pharmaceutically acceptable salt thereof, of Formula (IV), wherein Z is —C(O)N(R²)(R³), and R² and R³ are independently selected from heterocyclyl or heterocyclylalkyl. Another embodiment provides a compound, or pharmaceutically acceptable salt thereof, of Formula (IV), wherein Z is —C(O)N(R²)(R³), and R² and R³ join to form an N-linked heterocyclyl ring system.

Another embodiment provides a compound, or pharmaceutically acceptable salt thereof, of Formula (IV), wherein R¹ is hydrogen. Another embodiment provides a compound, or pharmaceutically acceptable salt thereof, of Formula (IV), wherein R¹ is alkyl.

Another embodiment provides a compound, or pharmaceutically acceptable salt thereof, of Formula (IV), wherein R⁴ is hydrogen. Another embodiment provides a compound, or pharmaceutically acceptable salt thereof, of Formula (IV), wherein R⁴ is C₁-C₃ alkoxy.

Another embodiment provides a compound, or pharmaceutically acceptable salt thereof, of Formula (IV), wherein G is a heterocyclyl. Another embodiment provides a compound, or pharmaceutically acceptable salt thereof, of Formula (IV), wherein G is a nitrogen-containing heterocyclyl. Another embodiment provides a compound, or pharmaceutically acceptable salt thereof, of Formula (IV), wherein G is a nitrogen-containing heterocyclyl and the nitrogen-containing heterocyclyl is a 5- or 6-membered heterocyclyl. Another embodiment provides a compound, or pharmaceutically acceptable salt thereof, of Formula (IV), wherein G is a heterocyclyl, and the heterocyclyl is chosen from:

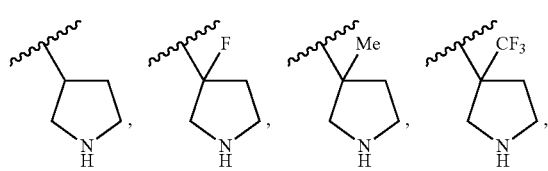

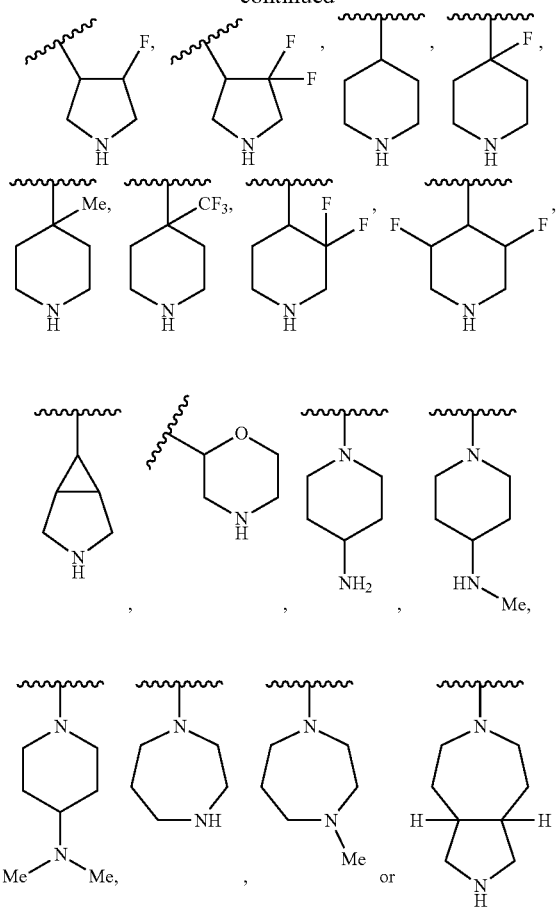

Another embodiment provides a compound, or pharmaceutically acceptable salt thereof, of Formula (IV), wherein G is

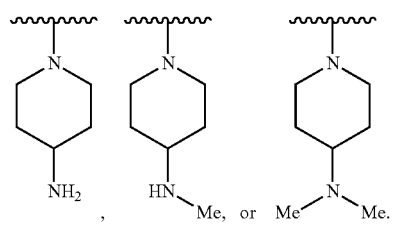

Another embodiment provides a compound having the structure of Formula (IV), or a pharmaceutically acceptable salt thereof, wherein G is a nitrogen-containing heterocyclyl, and the heterocyclyl is chosen from:

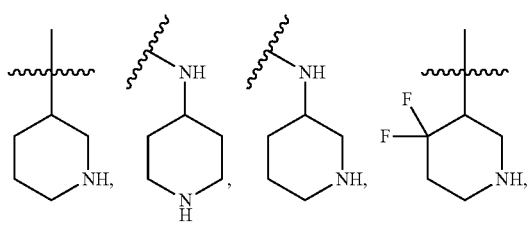

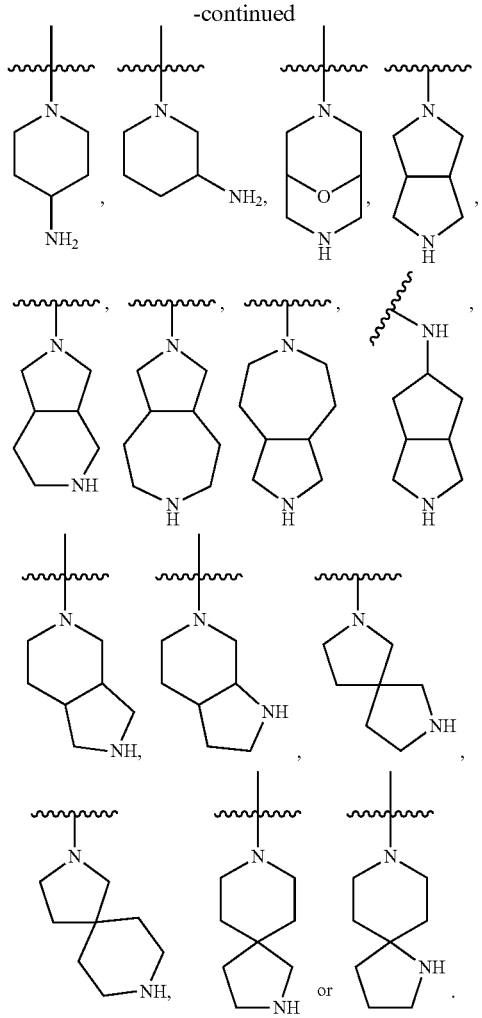

Another embodiment provides a compound, or pharmaceutically acceptable salt thereof, of Formula (IV), wherein R is heteroaryl. Another embodiment provides a compound, or pharmaceutically acceptable salt thereof, of Formula (IV), wherein R is a monocyclic nitrogen-containing heteroaryl.

Another embodiment provides a compound, or pharmaceutically acceptable salt thereof, of Formula (IV), wherein R is a bicyclic nitrogen-containing heteroaryl. Another embodiment provides a compound, or pharmaceutically acceptable salt thereof, of Formula (IV), wherein R is chosen from:

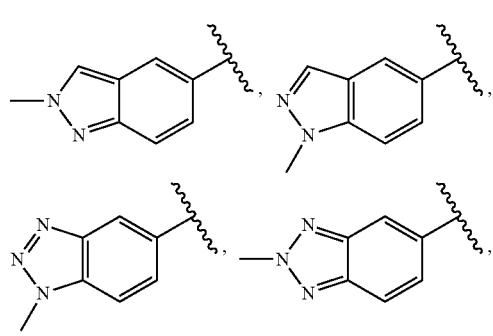

Another embodiment provides a compound, or pharmaceutically acceptable salt thereof, of Formula (IV), wherein R is chosen from:

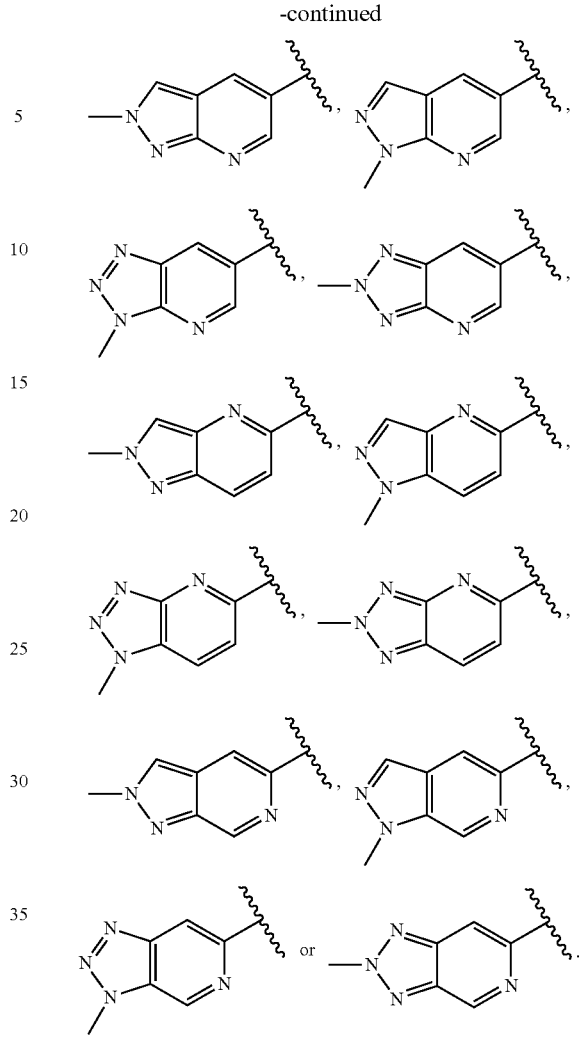

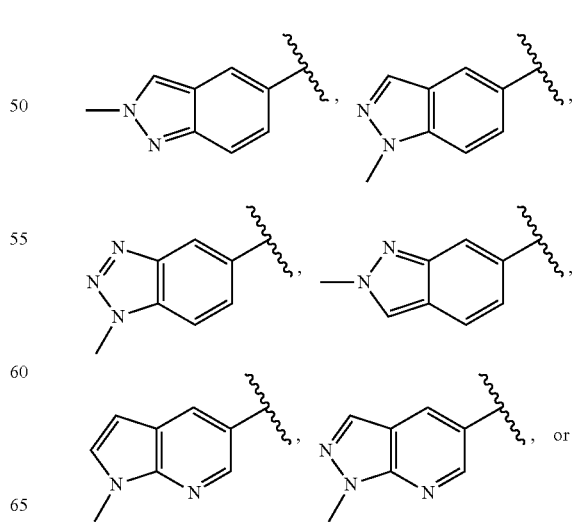

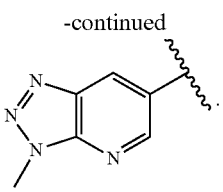

Another embodiment provides a compound, or pharmaceutically acceptable salt thereof, of Formula (IV), wherein R is chosen from:

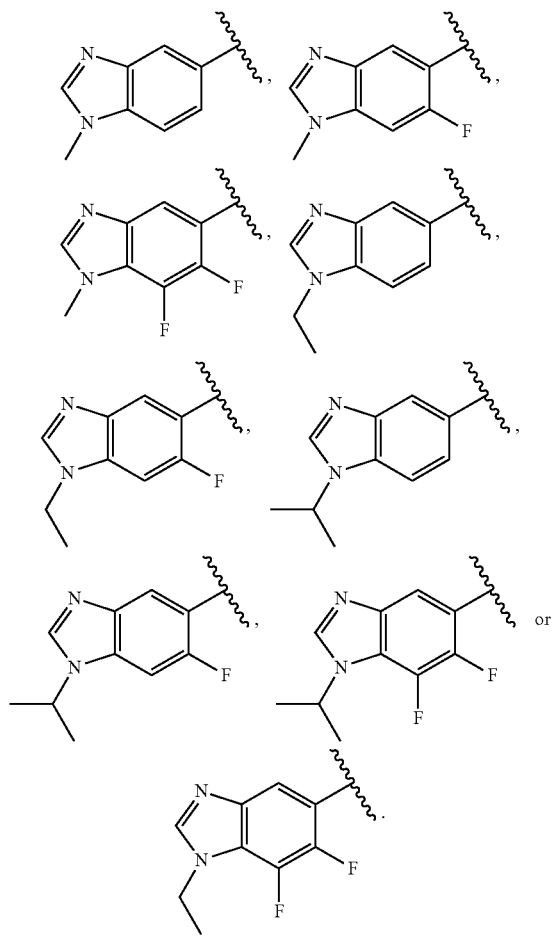

Another embodiment provides a compound, or pharmaceutically acceptable salt thereof, of Formula (IV), wherein R is aryl. Another embodiment provides a compound, or pharmaceutically acceptable salt thereof, of Formula (IV), wherein R is an optionally substituted phenyl group. Another embodiment provides a compound, or pharmaceutically acceptable salt thereof, of Formula (IV), wherein R is an optionally substituted phenyl group chosen from 4-methylphenyl, 4-chlorophenyl, 4-fluorophenyl, 4-cyanophenyl, 4-(methylsulfonyl)phenyl, or 4-trifluoromethylphenyl. Another embodiment provides a compound, or pharmaceutically acceptable salt thereof, of Formula (IV), wherein R is an optionally substituted phenyl group chosen from 4-methoxyphenyl, 3-fluoro-4-methoxyphenyl, or 3-chloro-4-methoxyphenyl.

Another embodiment provides a compound, or pharmaceutically acceptable salt thereof, of Formula (IVc), chosen from:

4-[6-(4-aminopiperidin-1-yl)-3-(2-methyl-2H-indazol-5-yl)pyrazin-2-yl]-2-fluorobenzonitrile,
2-fluoro-4-[3-(2-methyl-2H-indazol-5-yl)-6-[4-(methylamino)piperidin-1-yl]pyrazin-2-yl]benzonitrile,
4-[6-(4-aminopiperidin-1-yl)-3-(1-methyl-1H-indazol-5-yl)pyrazin-2-yl]-2-fluorobenzonitrile,
4-[6-(4-aminopiperidin-1-yl)-3-(2-methyl-2H-indazol-6-yl)pyrazin-2-yl]-2-fluorobenzonitrile,
4-[6-(4-aminopiperidin-1-yl)-3-(1-methyl-1H-1,2,3-benzotriazol-5-yl)pyrazin-2-yl]-2-fluorobenzonitrile,
4-[6-(4-aminopiperidin-1-yl)-3-{3-methyl-3H-[1,2,3]triazolo[4,5-b]pyridin-6-yl}pyrazin-2-yl]-2-fluorobenzonitrile,
4-[6-(4-aminopiperidin-1-yl)-3-{1-methyl-1H-pyrrolo[2,3-b]pyridin-5-yl}pyrazin-2-yl]-2-fluorobenzonitrile,
2-fluoro-4-{6-[4-(methylamino)piperidyl]-3-(1-methylbenzotriazol-5-yl)pyrazin-2-yl}benzenecarbonitrile,
4-{3-[6-(dimethylamino)(3-pyridyl)]-6-[4-(methylamino)piperidyl]pyrazin-2-yl}-2-fluorobenzenecarbonitrile,
4-{3-[2-(dimethylamino)pyrimidin-5-yl]-6-[4-(methylamino)piperidyl]pyrazin-2-yl}-2-fluorobenzenecarbonitrile,
2-fluoro-4-{6-[4-(methylamino)piperidyl]-3-(1-methylpyrazolo[5,4-b]pyridin-5-yl)pyrazin-2-yl}benzenecarbonitrile,
4-{6-[4-(dimethylamino)piperidyl]-3-(2-methyl(2H-indazol-5-yl))pyrazin-2-yl}-2-fluorobenzenecarbonitrile,
2-fluoro-4-[3-(6-fluoro-1-methylbenzimidazol-5-yl)-6-[4-(methylamino)piperidin-1-yl]pyrazin-2-yl]benzonitrile,
4-[3-(6,7-difluoro-1-methylbenzimidazol-5-yl)-6-[4-(methylamino)piperidin-1-yl]pyrazin-2-yl]-2-fluorobenzonitrile,
2-fluoro-4-[6-[4-(methylamino)piperidin-1-yl]-3-(1-propan-2-ylbenzimidazol-5-yl)pyrazin-2-yl]benzonitrile,
2-fluoro-4-[3-[2-(1-hydroxycyclopentyl)ethynyl]-6-[4-(methylamino)piperidin-1-yl]pyrazin-2-yl]benzonitrile,
2-fluoro-4-[6-[4-(methylamino)piperidin-1-yl]-3-(1-methylbenzimidazol-5-yl)pyrazin-2-yl]benzonitrile,
2-fluoro-4-[3-(3-hydroxy-3-methylbut-1-ynyl)-6-[4-(methylamino)piperidin-1-yl]pyrazin-2-yl]benzonitrile,
2-fluoro-4-[3-(6-fluoro-1-propan-2-ylbenzimidazol-5-yl)-6-[4-(methylamino)piperidin-1-yl]pyrazin-2-yl]benzonitrile,
2-fluoro-4-[6-[4-(methylamino)piperidin-1-yl]-3-(1-propan-2-ylbenzimidazol-5-yl)pyrazin-2-yl]benzonitrile,
4-[3-(1-ethyl-6-fluorobenzimidazol-5-yl)-6-[4-(methylamino)piperidin-1-yl]pyrazin-2-yl]-2-fluorobenzonitrile,
4-[6-(4-aminopiperidin-1-yl)-3-(6-fluoro-1-propan-2-ylbenzimidazol-5-yl)pyrazin-2-yl]-2-fluorobenzonitrile,
4-[6-(4-aminopiperidin-1-yl)-3-(1-ethyl-6-fluorobenzimidazol-5-yl)pyrazin-2-yl]-2-fluorobenzonitrile,
4-[6-(4-aminopiperidin-1-yl)-3-(1-propan-2-ylbenzimidazol-5-yl)pyrazin-2-yl]-2-fluorobenzonitrile,
4-[6-(4-aminopiperidin-1-yl)-3-(6,7-difluoro-1-propan-2-ylbenzimidazol-5-yl)pyrazin-2-yl]-2-fluorobenzonitrile,
4-[6-(4-aminopiperidin-1-yl)-3-(1-ethyl-6,7-difluorobenzimidazol-5-yl)pyrazin-2-yl]-2-fluorobenzonitrile, or
4-[6-(4-aminopiperidin-1-yl)-3-(6,7-difluoro-1-methylbenzimidazol-5-yl)pyrazin-2-yl]-2-fluorobenzonitrile.

In some embodiments, the substituted heterocyclic derivative compound described herein has the structure provided in Table 1.

TABLE 1

| Chemical Synthesis Example | Structure | Name |
|---|---|---|
| 1 | 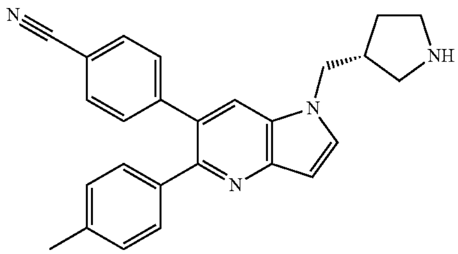 [SMILES: Cc1ccc(-c2nc3ccn(C[C@@H]4CCNC4)c3cc2-c2ccc(C#N)cc2)cc1] | 4-[5-(4-methylphenyl)-1-[[(3R)-pyrrolidin-3-yl]methyl]pyrrolo[3,2-b]pyridin-6-yl]benzonitrile |
| 2 | 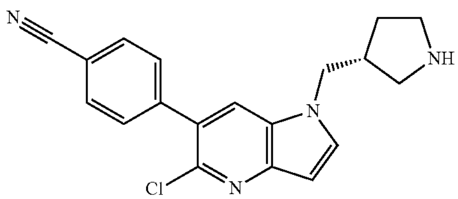 [SMILES: N#Cc1ccc(-c2cc3c(ccn3C[C@@H]3CCNC3)nc2Cl)cc1] | 4-[5-chloro-1-[[(3R)-pyrrolidin-3-yl]methyl]pyrrolo[3,2-b]pyridin-6-yl]benzonitrile |
| 3 | 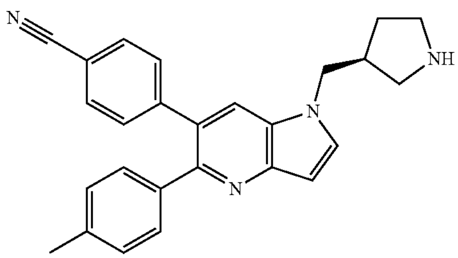 [SMILES: Cc1ccc(-c2nc3ccn(C[C@H]4CCNC4)c3cc2-c2ccc(C#N)cc2)cc1] | 4-[5-(4-methylphenyl)-1-[[(3S)-pyrrolidin-3-yl]methyl]pyrrolo[3,2-b]pyridin-6-yl]benzonitrile |
| 4 | 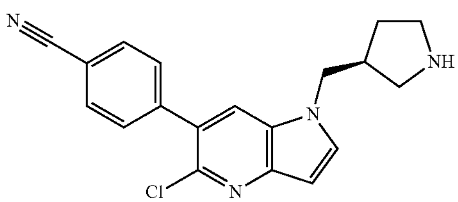 [SMILES: N#Cc1ccc(-c2cc3c(ccn3C[C@H]3CCNC3)nc2Cl)cc1] | 4-[5-chloro-1-[[(3S)-pyrrolidin-3-yl]methyl]pyrrolo[3,2-b]pyridin-6-yl]benzonitrile |
| 5 | 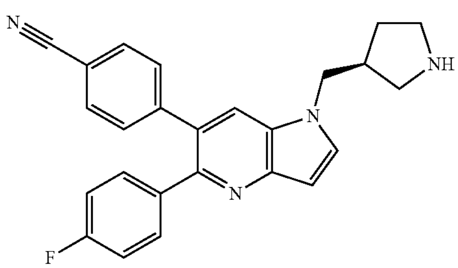 [SMILES: N#Cc1ccc(-c2cc3c(ccn3C[C@H]3CCNC3)nc2-c2ccc(F)cc2)cc1] | 4-[5-(4-fluorophenyl)-1-[[(3S)-pyrrolidin-3-yl]methyl]pyrrolo[3,2-b]pyridin-6-yl]benzonitrile |
| 6 | 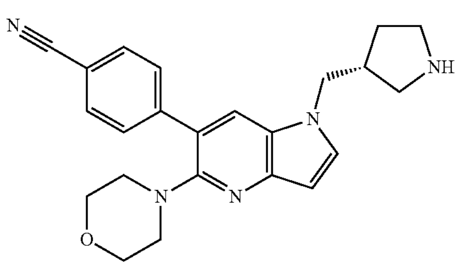 [SMILES: N#Cc1ccc(-c2cc3c(ccn3C[C@@H]3CCNC3)nc2N2CCOCC2)cc1] | 4-[5-morpholin-4-yl-1-[[(3R)-pyrrolidin-3-yl]methyl]pyrrolo[3,2-b]pyridin-6-yl]benzonitrile |

TABLE 1-continued

| Chemical Synthesis Example | Structure | Name |
|---|---|---|
| 7 | 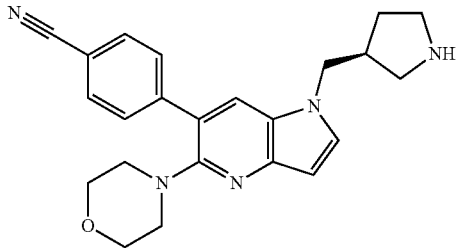 [SMILES: N#Cc1ccc(-c2cc3c(ccn3C[C@H]3CCNC3)nc2N2CCOCC2)cc1] | 4-[5-morpholin-4-yl-1-[[(3S)-pyrrolidin-3-yl]methyl]pyrrolo[3,2-b]pyridin-6-yl]benzonitrile |
| 8 | 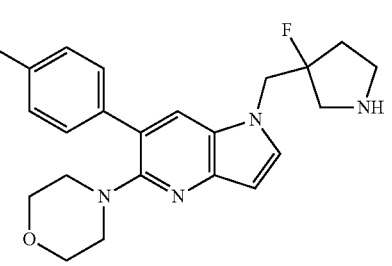 | 4-[1-[(3-fluoropyrrolidin-3-yl)methyl]-5-morpholin-4-ylpyrrolo[3,2-b]pyridin-6-yl]benzonitrile |
| 9 | 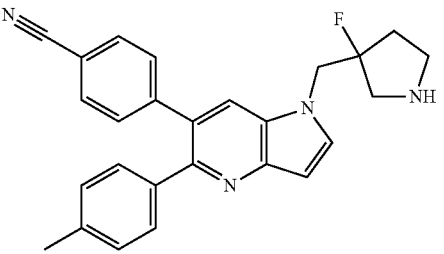 [SMILES: Cc1ccc(-c2nc3ccn(CC4(F)CCNC4)c3cc2-c2ccc(C#N)cc2)cc1] | 4-[1-(3-fluoropyrrolidin-3-yl)methyl]-5-(4-methylphenyl)pyrrolo[3,2-b]pyridin-6-yl]benzonitrile |
| 10 | 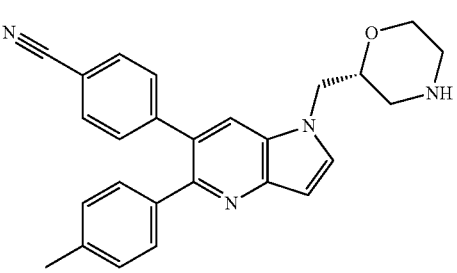 [SMILES: Cc1ccc(-c2nc3ccn(C[C@H]4CNCCO4)c3cc2-c2ccc(C#N)cc2)cc1] | 4-[5-(4-methylphenyl)-1-[[(2R)-morpholin-2-yl]methyl]pyrrolo[3,2-b]pyridin-6-yl]benzonitrile |
| 11 | 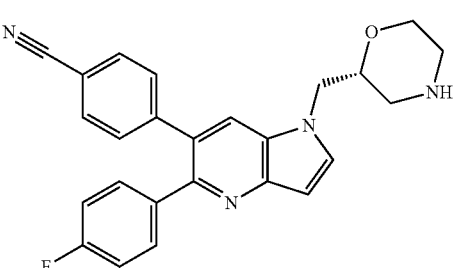 | 4-[5-(4-fluorophenyl)-1-[[(2R)-morpholin-2-yl]methyl]pyrrolo[3,2-b]pyridin-6-yl]benzonitrile |

TABLE 1-continued

| Chemical Synthesis Example | Structure | Name |
|---|---|---|
| 12 | 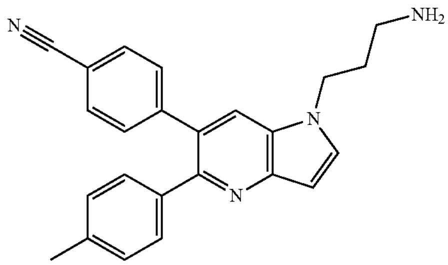 [SMILES: Cc1ccc(-c2nc3ccn(CCCN)c3cc2-c2ccc(C#N)cc2)cc1] | 4-[1-(3-aminopropyl)-5-(4-methylphenyl)pyrrolo[3,2-b]pyridin-6-yl]benzonitrile |
| 13 | 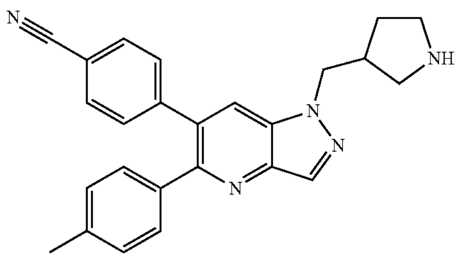 [SMILES: Cc1ccc(-c2nc3cnn(CC4CCNC4)c3cc2-c2ccc(C#N)cc2)cc1] | 4-[5-(4-methylphenyl)-1-(pyrrolidin-3-ylmethyl)pyrazolo[4,3-b]pyridin-6-yl]benzonitrile |
| 14 | 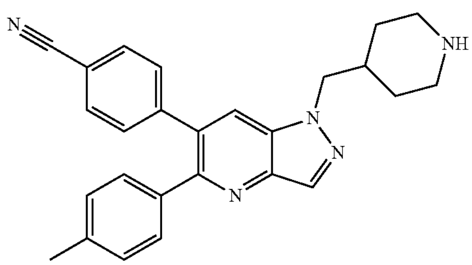 [SMILES: Cc1ccc(-c2nc3cnn(CC4CCNCC4)c3cc2-c2ccc(C#N)cc2)cc1] | 4-[5-(4-methylphenyl)-1-(piperidin-4-ylmethyl)pyrazolo[4,3-b]pyridin-6-yl]benzonitrile |
| 15 | 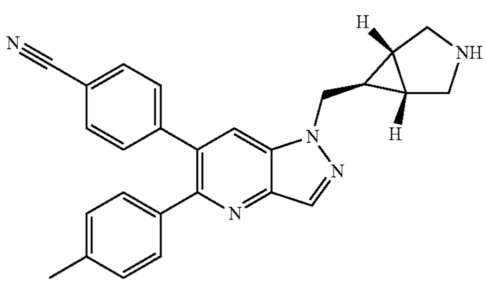 [SMILES: Cc1ccc(-c2nc3cnn(C[C@H]4[C@@H]5CNC[C@@H]54)c3cc2-c2ccc(C#N)cc2)cc1] | 4-[1-[[(1S,5R)-3-azabicyclo[3.1.0]hexan-6-yl]methyl]-5-(4-methylphenyl)pyrazolo[4,3-b]pyridin-6-yl]benzonitrile |
| 16 | 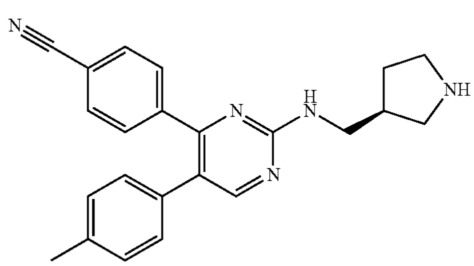 [SMILES: Cc1ccc(-c2cnc(NC[C@H]3CCNC3)nc2-c2ccc(C#N)cc2)cc1] | 4-[5-(4-methylphenyl)-2-{[(3S)-pyrrolidin-3-ylmethyl]amino}pyrimidin-4-yl]benzonitrile |
| 17 | 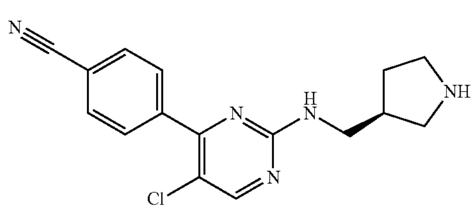 [SMILES: N#Cc1ccc(-c2nc(NC[C@H]3CCNC3)ncc2Cl)cc1] | 4-(5-chloro-2-{[(3S)-pyrrolidin-3-ylmethyl]amino}pyrimidin-4-yl)benzonitrile |

TABLE 1-continued

| Chemical Synthesis Example | Structure | Name |
|---|---|---|
| 18 | 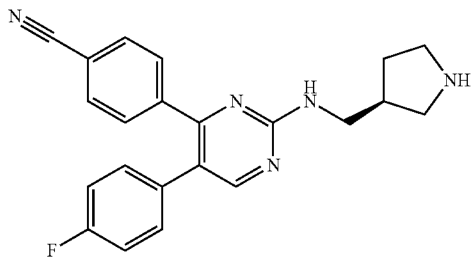 [SMILES: N#Cc1ccc(-c2nc(NC[C@H]3CCNC3)ncc2-c2ccc(F)cc2)cc1] | 4-[5-(4-fluorophenyl)-2-{[(3S)-pyrrolidin-3-ylmethyl]amino}pyrimidin-4-yl]benzonitrile |
| 19 | 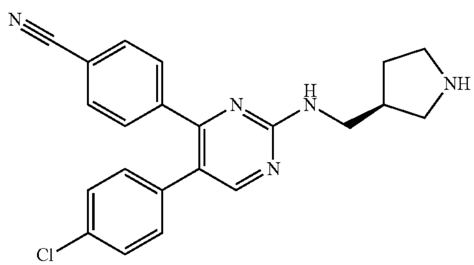 [SMILES: N#Cc1ccc(-c2nc(NC[C@H]3CCNC3)ncc2-c2ccc(Cl)cc2)cc1] | 4-[5-(4-chlorophenyl)-2-{[(3S)-pyrrolidin-3-ylmethyl]amino}pyrimidin-4-yl]benzonitrile |
| 20 | 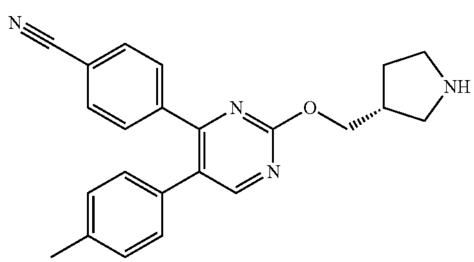 [SMILES: Cc1ccc(-c2cnc(OC[C@@H]3CCNC3)nc2-c2ccc(C#N)cc2)cc1] | 4-[5-(4-methylphenyl)-2-[(3R)-pyrrolidin-3-ylmethoxy]pyrimidin-4-yl]benzonitrile |
| 21 | 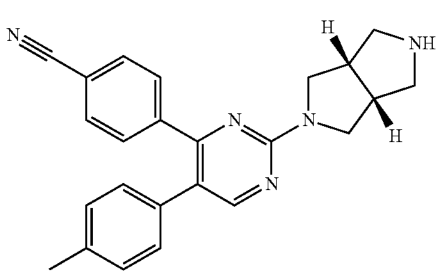 [SMILES: Cc1ccc(-c2cnc(N3C[C@H]4CNC[C@H]4C3)nc2-c2ccc(C#N)cc2)cc1] | 4-{2-[(3aR,6aS)-octahydropyrrolo[3,4-c]pyrrol-2-yl]-5-(4-methylphenyl)pyrimidin-4-yl}benzonitrile |
| 22 | 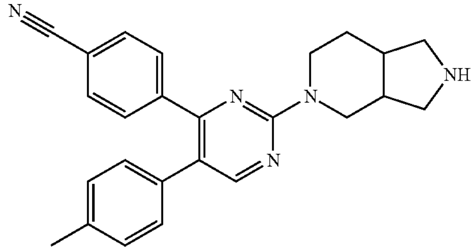 [SMILES: Cc1ccc(-c2cnc(N3CCC4CNCC4C3)nc2-c2ccc(C#N)cc2)cc1] | 4-[5-(4-methylphenyl)-2-{octhydro-1H-pyrrolo[3,4-c]pyridin-5-yl}pyrimidin-4-yl]benzonitrile |

TABLE 1-continued

| Chemical Synthesis Example | Structure | Name |
|---|---|---|
| 23 | 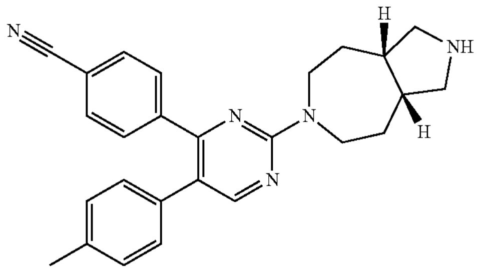 [SMILES: Cc1ccc(-c2cnc(N3CC[C@@H]4CNC[C@@H]4CC3)nc2-c2ccc(C#N)cc2)cc1] | 4-{2-[(3aR,8aS)-decahydropyrrolo[3,4-d]azepin-6-yl]-5-(4-methylphenyl)pyrimidin-4-yl}benzonitrile |
| 24 | 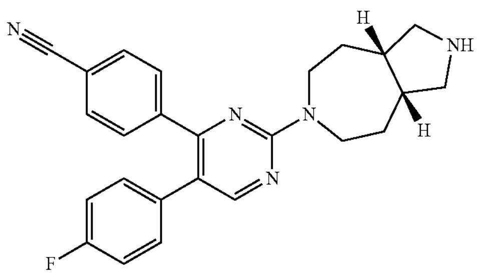 [SMILES: N#Cc1ccc(-c2nc(N3CC[C@@H]4CNC[C@@H]4CC3)ncc2-c2ccc(F)cc2)cc1] | 4-{2-[(3aR,8aS)-decahydropyrrolo[3,4-d]azepin-6-yl]-5-(4-fluorophenyl)pyrimidin-4-yl}benzonitrile |
| 25 | 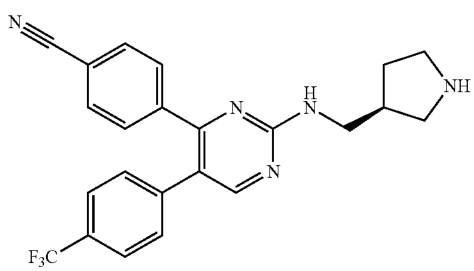 [SMILES: N#Cc1ccc(-c2nc(NC[C@H]3CCNC3)ncc2-c2ccc(C(F)(F)F)cc2)cc1] | 4-(2-{[(3S)-pyrrolidin-3-ylmethyl]amino}-5-[4-(trifluoromethyl)phenyl]pyrimidin-4-yl)benzonitrile |
| 26 | 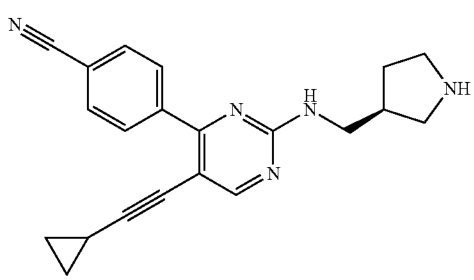 [SMILES: N#Cc1ccc(-c2nc(NC[C@H]3CCNC3)ncc2C#CC2CC2)cc1] | 4-[5-(2-cyclopropylethynyl)-2-{[(3S)-pyrrolidin-3-ylmethyl]amino}pyrimidin-4-yl]benzonitrile |
| 27 | 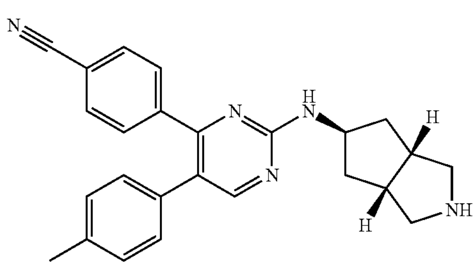 [SMILES: Cc1ccc(-c2cnc(N[C@@H]3C[C@H]4CNC[C@H]4C3)nc2-c2ccc(C#N)cc2)cc1] | 4-(2-{[(3aR,5S,6aS)-octahydrocyclopenta[c]pyrrol-5-yl]amino}-5-(4-methylphenyl)pyrimidin-4-yl)benzonitrile |

TABLE 1-continued

| Chemical Synthesis Example | Structure | Name |
|---|---|---|
| 28 | 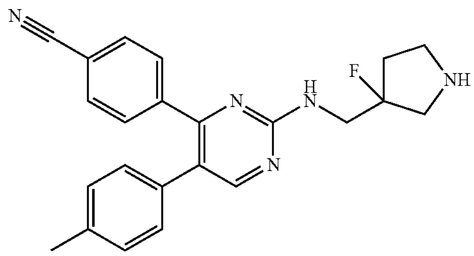 [SMILES: Cc1ccc(-c2cnc(NCC3(F)CCNC3)nc2-c2ccc(C#N)cc2)cc1] | (±)-4-(2-{[(3-fluoropyrrolidin-3-yl)methyl]amino}-5-(4-methylphenyl)pyrimidin-4-yl)benzonitrile |
| 29 | 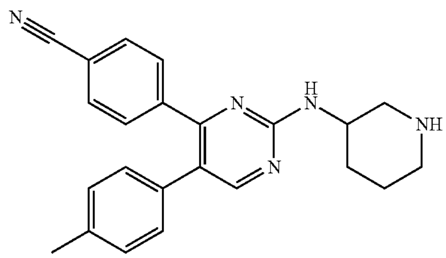 [SMILES: Cc1ccc(-c2cnc(NC3CCCNC3)nc2-c2ccc(C#N)cc2)cc1] | (±)-4-[5-(4-methylphenyl)-2-[(piperidin-3-yl)amino]pyrimidin-4-yl]benzonitrile |
| 30 | 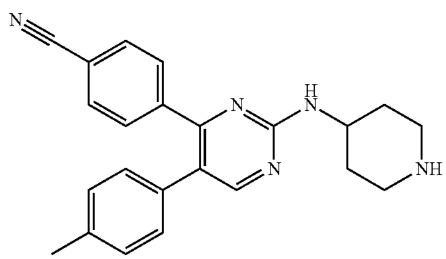 [SMILES: Cc1ccc(-c2cnc(NC3CCNCC3)nc2-c2ccc(C#N)cc2)cc1] | 4-[5-(4-methylphenyl)-2-[(piperidin-4-yl)amino]pyrimidin-4-yl]benzonitrile |
| 31 | 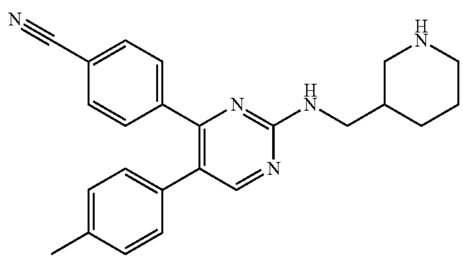 | (±)-4-[5-(4-methylphenyl)-2-[(piperidin-3-ylmethyl)amino]pyrimidin-4-yl]benzonitrile |
| 32 | 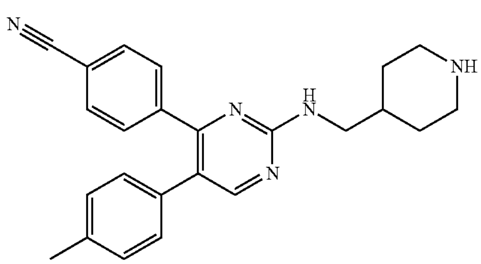 [SMILES: Cc1ccc(-c2cnc(NCC3CCNCC3)nc2-c2ccc(C#N)cc2)cc1] | 4-[5-(4-methylphenyl)-2-[(piperidin-4-ylmethyl)amino]pyrimidin-4-yl]benzonitrile |
| 33 | 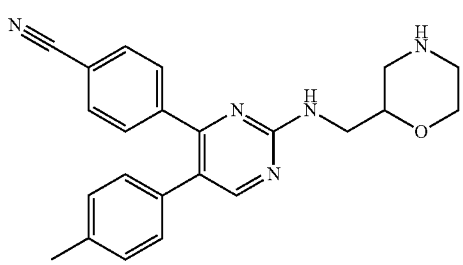 | (±)-4-[5-(4-methylphenyl)-2-[(morpholin-2-ylmethyl)amino]pyrimidin-4-yl]benzonitrile |

TABLE 1-continued

| Chemical Synthesis Example | Structure | Name |
|---|---|---|
| 34 | 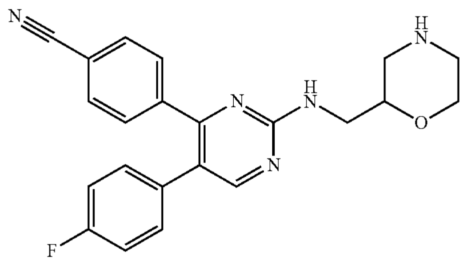 [SMILES: N#Cc1ccc(-c2nc(NCC3CNCCO3)ncc2-c2ccc(F)cc2)cc1] | (±)-4-[5-(4-fluorophenyl)-2-[(morpholin-2-ylmethyl)amino]pyrimidin-4-yl]benzonitrile |
| 35 | 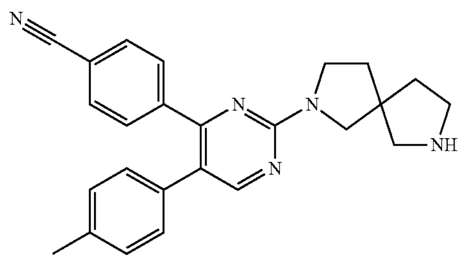 [SMILES: Cc1ccc(-c2cnc(N3CCC4(CCNC4)C3)nc2-c2ccc(C#N)cc2)cc1] | 4-(2-{2,7-diazaspiro[4.4]nonan-2-yl}-5-(4-methylphenyl)pyrimidin-4-yl)benzonitrile |
| 36 | 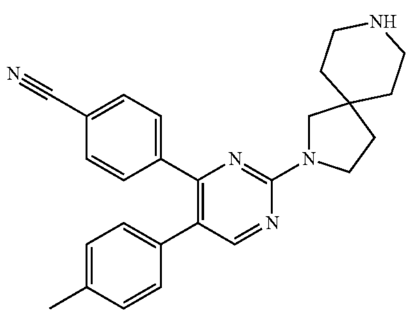 [SMILES: Cc1ccc(-c2cnc(N3CCC4(CCNCC4)C3)nc2-c2ccc(C#N)cc2)cc1] | 4-(2-{2,8-diazaspiro[4.5]decan-2-yl}-5-(4-methylphenyl)pyrimidin-4-yl)benzonitrile |
| 37 | 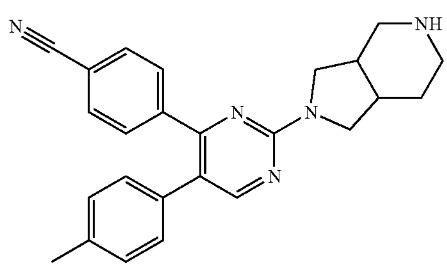 [SMILES: Cc1ccc(-c2cnc(N3CC4CCNCC4C3)nc2-c2ccc(C#N)cc2)cc1] | 4-[5-(4-methylphenyl)-2-{octahydro-1H-pyrrolo[3,4-c]pyridin-2-yl}pyrimidin-4-yl]benzonitrile |
| 38 | 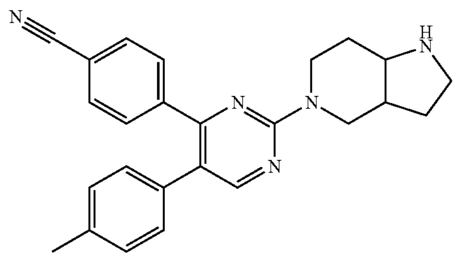 [SMILES: Cc1ccc(-c2cnc(N3CCC4NCCC4C3)nc2-c2ccc(C#N)cc2)cc1] | 4-[5-(4-methylphenyl)-2-{octahydro-1H-pyrrolo[3,2-c]pyridin-5-yl}pyrimidin-4-yl]benzonitrile |

TABLE 1-continued

| Chemical Synthesis Example | Structure | Name |
|---|---|---|
| 39 | 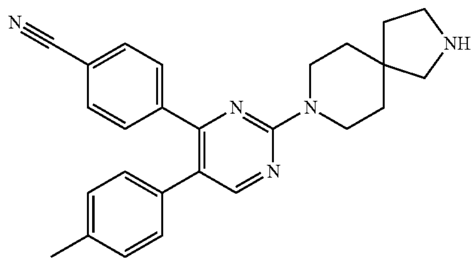 [SMILES: Cc1ccc(-c2cnc(N3CCC4(CCNC4)CC3)nc2-c2ccc(C#N)cc2)cc1] | 4-(2-{2,8-diazaspiro[4.5]decan-8-yl}-5-(4-methylphenyl)pyrimidin-4-yl)benzonitrile |
| 40 | 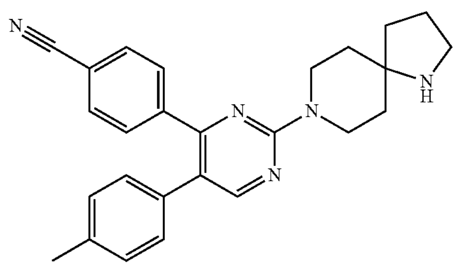 [SMILES: Cc1ccc(-c2cnc(N3CCC4(CCCN4)CC3)nc2-c2ccc(C#N)cc2)cc1] | 4-(2-{1,8-diazaspiro[4.5]decan-8-yl}-5-(4-methylphenyl)pyrimidin-4-yl)benzonitrile |
| 41 | 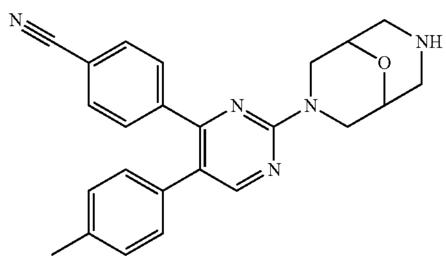 [SMILES: Cc1ccc(-c2cnc(N3CC4CNCC(C3)O4)nc2-c2ccc(C#N)cc2)cc1] | 4-[5-(4-methylphenyl)-2-{9-oxa-3,7-diazabicyclo[3.3.1]nonan-3-yl}pyrimidin-4-yl]benzonitrile |
| 42 | 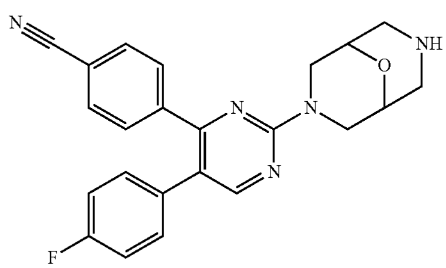 [SMILES: N#Cc1ccc(-c2nc(N3CC4CNCC(C3)O4)ncc2-c2ccc(F)cc2)cc1] | 4-[5-(4-fluorophenyl)-2-{9-oxa-3,7-diazabicyclo[3.3.1]nonan-3-yl}pyrimidin-4-yl]benzonitrile |
| 43 | 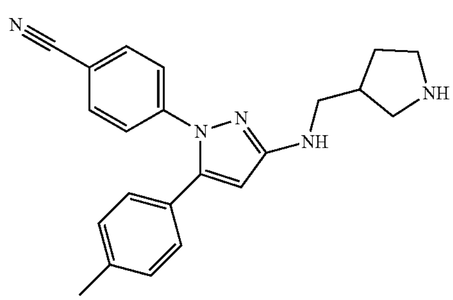 | 4-[5-(4-methylphenyl)-3-(pyrrolidin-3-ylmethylamino)pyrazol-1-yl]benzonitrile |

TABLE 1-continued

| Chemical Synthesis Example | Structure | Name |
|---|---|---|
| 44 | 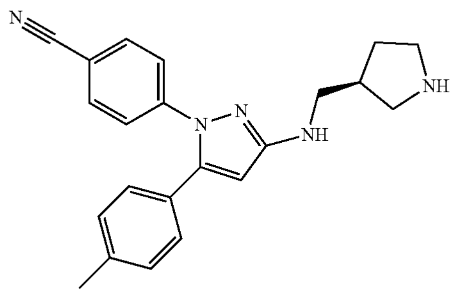 [SMILES: Cc1ccc(-c2cc(NC[C@H]3CCNC3)nn2-c2ccc(C#N)cc2)cc1] | 4-[5-(4-methylphenyl)-3-[[(3S)-pyrrolidin-3-yl]methylamino]pyrazol-1-yl]benzonitrile |
| 45 | 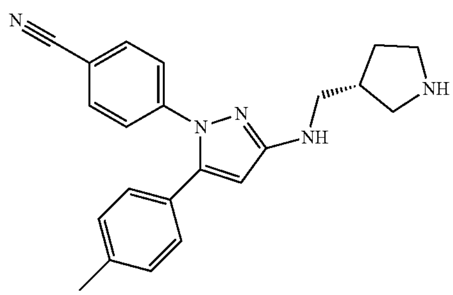 [SMILES: Cc1ccc(-c2cc(NC[C@@H]3CCNC3)nn2-c2ccc(C#N)cc2)cc1] | 4-[5-(4-methylphenyl)-3-[[(3R)-pyrrolidin-3-yl]methylamino]pyrazol-1-yl]benzonitrile |
| 46 | 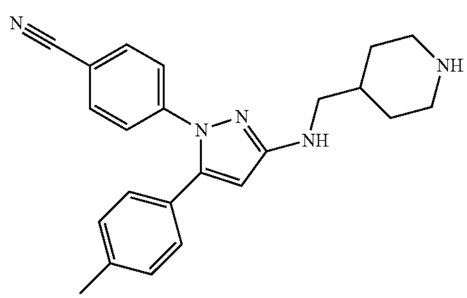 [SMILES: Cc1ccc(-c2cc(NCC3CCNCC3)nn2-c2ccc(C#N)cc2)cc1] | 4-[5-(4-methylphenyl)-3-(piperidin-4-ylmethylamino)pyrazol-1-yl]benzonitrile |
| 47 | 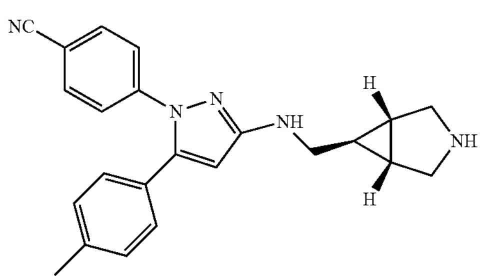 [SMILES: Cc1ccc(-c2cc(NC[C@H]3[C@@H]4CNC[C@@H]43)nn2-c2ccc(C#N)cc2)cc1] | 4-[3-[[(1S,5R)-3-azabicyclo[3.1.0]hexan-6-yl]methylamino]-5-(4-methylphenyl)pyrazol-1-yl]benzonitrile |
| 48 | 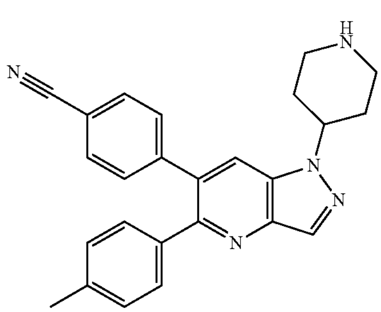 [SMILES: Cc1ccc(-c2nc3cnn(C4CCNCC4)c3cc2-c2ccc(C#N)cc2)cc1] | 4-[5-(4-methylphenyl)-1-piperidin-4-ylpyrazolo[4,3-b]pyridin-6-yl]benzonitrile |

TABLE 1-continued

| Chemical Synthesis Example | Structure | Name |
|---|---|---|
| 49 | 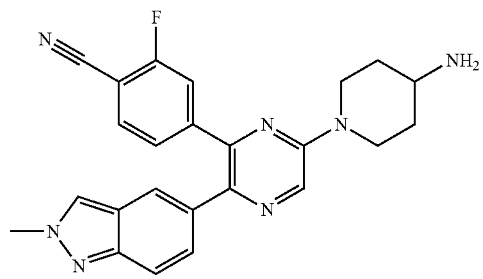 | 4-[6-(4-aminopiperidin-1-yl)-3-(2-methyl-2H-indazol-5-yl)pyrazin-2-yl]-2-fluorobenzonitrile |
| 50 | 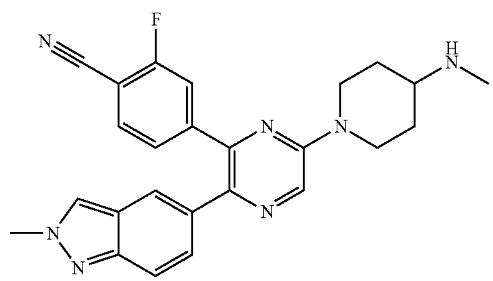 | 2-fluoro-4-[3-(2-methyl-2H-indazol-5-yl)-6-[4-(methylamino)piperidin-1-yl]pyrazin-2-yl]benzonitrile |
| 51 | 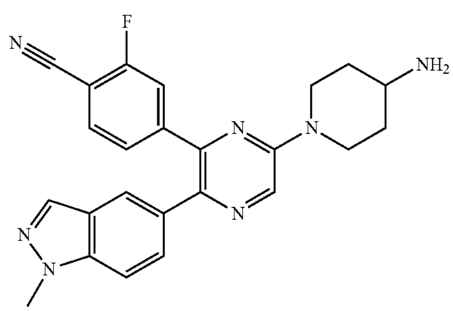 [SMILES: Cn1ncc2cc(-c3ncc(N4CCC(N)CC4)nc3-c3ccc(C#N)c(F)c3)ccc21] | 4-[6-(4-aminopiperidin-1-yl)-3-(1-methyl-1H-indazol-5-yl)pyrazin-2-yl]-2-fluorobenzonitrile |
| 52 | 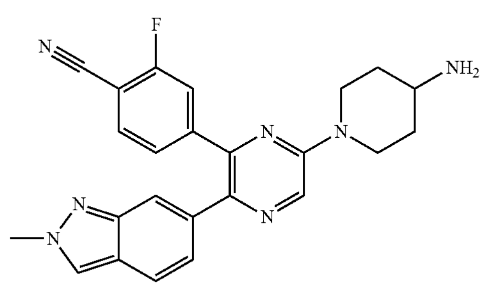 [SMILES: Cn1cc2ccc(-c3ncc(N4CCC(N)CC4)nc3-c3ccc(C#N)c(F)c3)cc2n1] | 4-[6-(4-aminopiperidin-1-yl)-3-(2-methyl-2H-indazol-6-yl)pyrazin-2-yl]-2-fluorobenzonitrile |
| 53 | 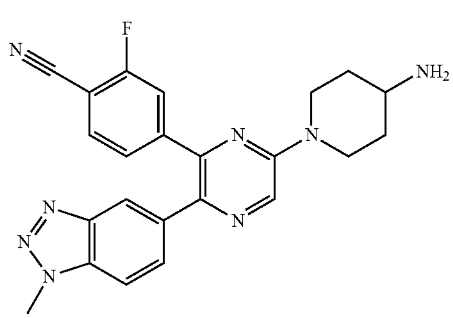 | 4-[6-(4-aminopiperidin-1-yl)-3-(1-methyl-1H-1,2,3-benzotriazol-5-yl)pyrazin-2-yl]-2-fluorobenzonitrile |

TABLE 1-continued

| Chemical Synthesis Example | Structure | Name |
|---|---|---|
| 54 | 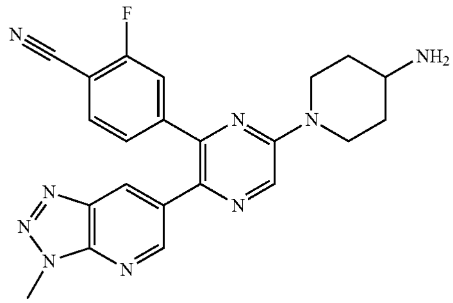 [SMILES: Cn1nnc2cc(-c3ncc(N4CCC(N)CC4)nc3-c3ccc(C#N)c(F)c3)cnc21] | 4-[6-(4-aminopiperidin-1-yl)-3-{3-methyl-3H-[1,2,3]triazolo[4,5-b]pyridin-6-yl}pyrazin-2-yl]-2-fluorobenzonitrile |
| 55 | 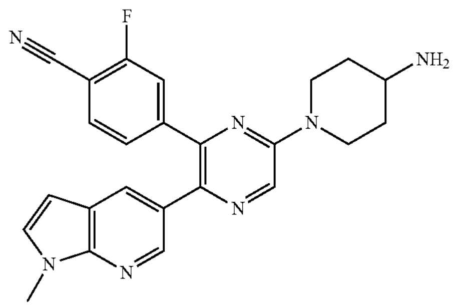 [SMILES: Cn1ccc2cc(-c3ncc(N4CCC(N)CC4)nc3-c3ccc(C#N)c(F)c3)cnc21] | 4-[6-(4-aminopiperidin-1-yl)-3-{1-methyl-1H-pyrrolo[2,3-b]pyridin-5-yl}pyrazin-2-yl]-2-fluorobenzonitrile |
| 56 | 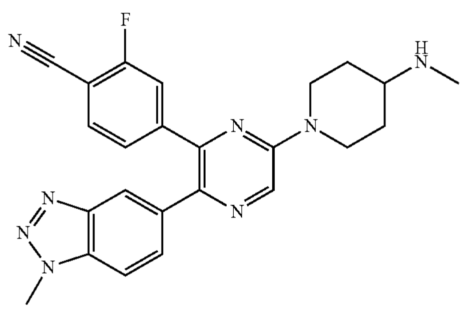 [SMILES: CNC1CCN(c2cnc(-c3ccc4c(c3)nnn4C)c(-c3ccc(C#N)c(F)c3)n2)CC1] | 2-fluoro-4-{6-[4-(methylamino)piperidyl]-3-(1-methylbenzotriazol-5-yl)pyrazin-2-yl}benzenecarbonitrile |
| 57 | 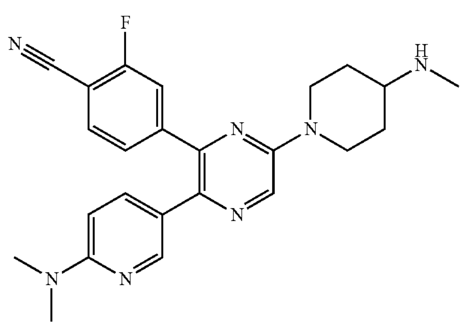 [SMILES: CNC1CCN(c2cnc(-c3ccc(N(C)C)nc3)c(-c3ccc(C#N)c(F)c3)n2)CC1] | 4-{3-[6-(dimethylamino)(3-pyridyl)]-6-[4-(methylamino)piperidyl]pyrazin-2-yl}-2-fluorobenzenecarbonitrile |
| 58 | 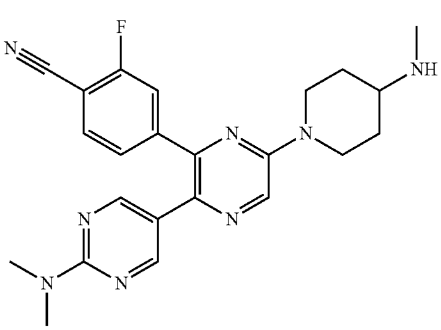 [SMILES: CNC1CCN(c2cnc(-c3cnc(N(C)C)nc3)c(-c3ccc(C#N)c(F)c3)n2)CC1] | 4-{3-[2-(dimethylamino)pyrimidin-5-yl]-6-[4-(methylamino)piperidyl]pyrazin-2-yl}-2-fluorobenzenecarbonitrile |

TABLE 1-continued

| Chemical Synthesis Example | Structure | Name |
|---|---|---|
| 59 | 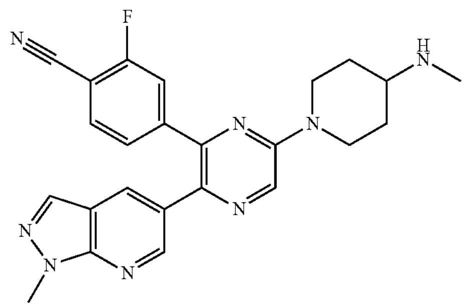 [SMILES: CNC1CCN(c2cnc(-c3cnc4c(cnn4C)c3)c(-c3ccc(C#N)c(F)c3)n2)CC1] | 2-fluoro-4-{6-[4-(mehtylmino)piperidyl]-3-(1-methylpyrazolo[5,4-b]pyridin-5-yl)pyrazin-2-yl}benzenecarbonitrile |
| 60 | 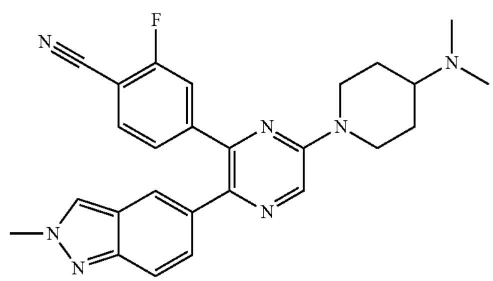 | 4-{6-[4-(dimethylamino)piperidyl]-3-(2-methyl(2H-indazol-5-yl)pyrazin-2-yl}-2-fluorobenzenecarbonitrile |
| 61 | 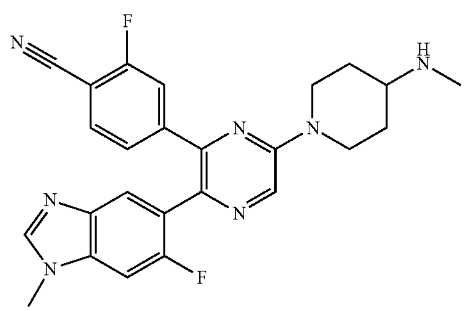 [SMILES: CNC1CCN(c2cnc(-c3cc4ncn(C)c4cc3F)c(-c3ccc(C#N)c(F)c3)n2)CC1] | 2-fluoro-4-[3-(6-fluoro-1-methylbenzimidazol-5-yl)-6-[4-(methylamino)piperidin-1-yl]pyrazin-2-yl]benzonitrile |
| 62 | 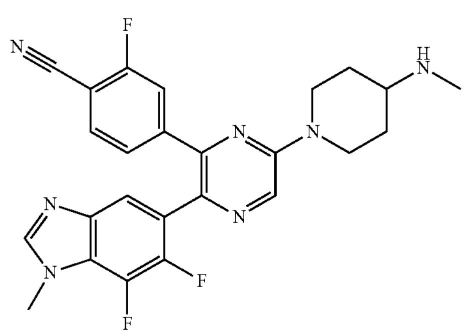 [SMILES: CNC1CCN(c2cnc(-c3cc4ncn(C)c4c(F)c3F)c(-c3ccc(C#N)c(F)c3)n2)CC1] | 4-[3-(6,7-difluoro-1-methylbenzimidazol-5-yl)-6-[4-(methylamino)piperidin-1-yl]pyrazin-2-yl]-2-fluorobenzonitrile |
| 63 | 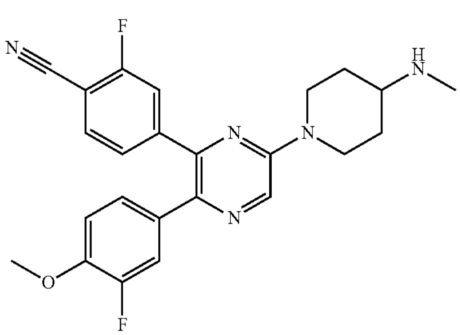 [SMILES: CNC1CCN(c2cnc(-c3ccc(OC)c(F)c3)c(-c3ccc(C#N)c(F)c3)n2)CC1] | 2-fluoro-4-[6-[4-(methylamino)piperidin-1-yl]-3-(1-propan-2-ylbenzimidazol-5-yl)pyrazin-2-yl]benzonitrile |

TABLE 1-continued

| Chemical Synthesis Example | Structure | Name |
|---|---|---|
| 64 | 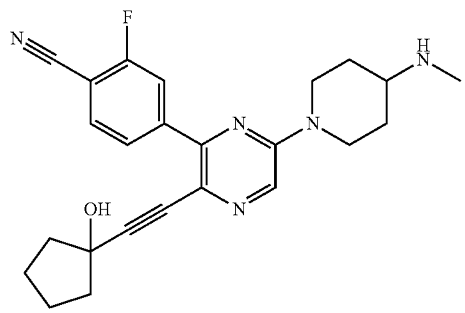 [SMILES: CNC1CCN(c2cnc(C#CC3(O)CCCC3)c(-c3ccc(C#N)c(F)c3)n2)CC1] | 2-fluoro-4-[3-[2-(1-hydroxycyclopentyl)ethynyl]-6-[4-(methylamino)piperidin-1-yl]pyrazin-2-yl]benzonitrile |
| 65 | 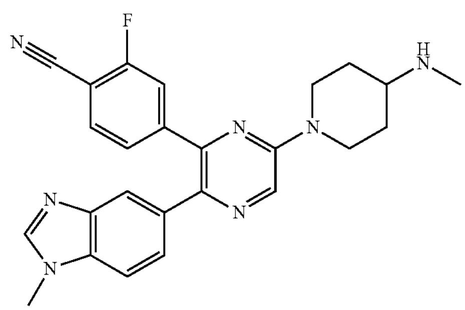 [SMILES: CNC1CCN(c2cnc(-c3ccc4c(c3)ncn4C)c(-c3ccc(C#N)c(F)c3)n2)CC1] | 2-fluoro-4-[6-[4-(methylamino)piperidin-1-yl]-3-(1-methylbenzimidazol-5-yl)pyrazin-2-yl]benzonitrile |
| 66 | 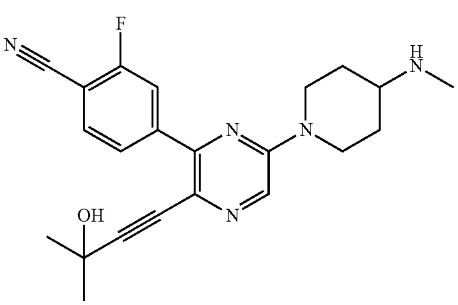 [SMILES: CNC1CCN(c2cnc(C#CC(C)(C)O)c(-c3ccc(C#N)c(F)c3)n2)CC1] | 2-fluoro-4-[3-(3-hydroxy-3-methylbut-1-ynyl)-6-[4-(methylamino)piperidin-1-yl]pyrazin-2-yl]benzonitrile |
| 67 | 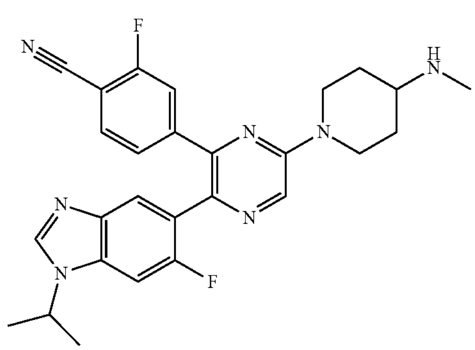 [SMILES: CNC1CCN(c2cnc(-c3cc4ncn(C(C)C)c4cc3F)c(-c3ccc(C#N)c(F)c3)n2)CC1] | 2-fluoro-4-[3-(6-fluoro-1-propan-2-ylbenzimidazol-5-yl)-6-[4-(methylamino)piperidin-1-yl]pyrazin-2-yl]benzonitrile |

TABLE 1-continued

| Chemical Synthesis Example | Structure | Name |
|---|---|---|
| 68 | 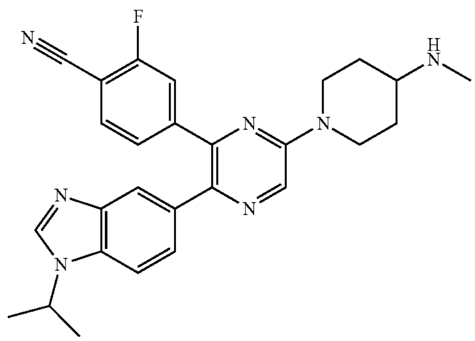 [SMILES: CNC1CCN(c2cnc(-c3ccc4c(c3)ncn4C(C)C)c(-c3ccc(C#N)c(F)c3)n2)CC1] | 2-fluoro-4-[6-[4-(methylamino)piperidin-1-yl]-3-(1-propan-2-ylbenzimidazol-5-yl)pyrazin-2-yl]benzonitrile |
| 69 | 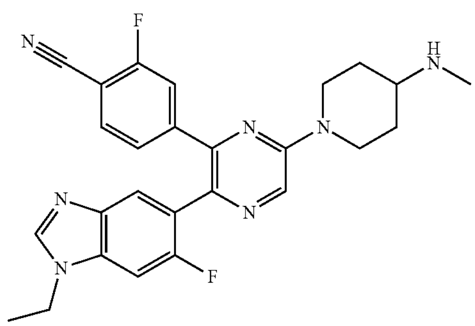 [SMILES: CCn1cnc2cc(-c3ncc(N4CCC(NC)CC4)nc3-c3ccc(C#N)c(F)c3)c(F)cc21] | 4-[3-(1-ethyl-6-fluorobenzimidazol-5-yl)-6-[4-(methylaino)piperidin-1-yl]pyrazin-2-yl]-2-fluorobenzonitrile |
| 70 | 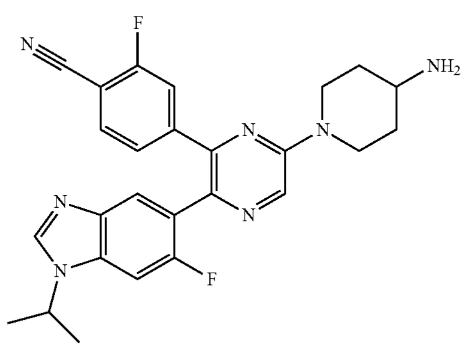 [SMILES: CC(C)n1cnc2cc(-c3ncc(N4CCC(N)CC4)nc3-c3ccc(C#N)c(F)c3)c(F)cc21] | 4-[6-(4-aminopiperidin-1-yl)-3-(6-fluoro-1-propan-2-ylbenzimidazol-5-yl)pyrazin-2-yl]-2-fluorobenzoitrile |
| 71 | 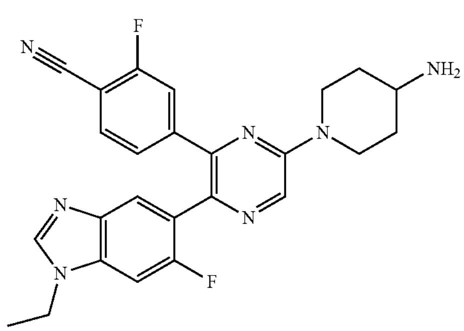 [SMILES: CCn1cnc2cc(-c3ncc(N4CCC(N)CC4)nc3-c3ccc(C#N)c(F)c3)c(F)cc21] | 4-[6-(4-aminopiperidin-1-yl)-3-(1-ethyl-6-fluorobenzimidazol-5-yl)pyrazin-2-yl]-2-fluorobenzonitrile |

TABLE 1-continued

| Chemical Synthesis Example | Structure | Name |
|---|---|---|
| 72 | 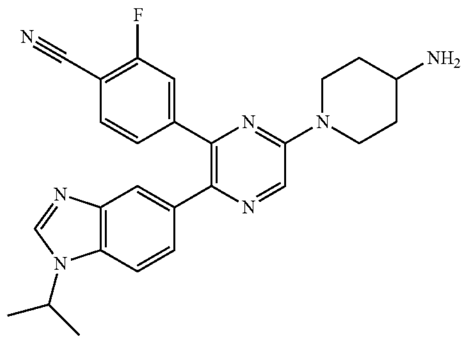 [SMILES: CC(C)n1cnc2cc(-c3ncc(N4CCC(N)CC4)nc3-c3ccc(C#N)c(F)c3)ccc21] | 4-[6-(4-aminopiperidin-1-yl)-3-(1-propan-2-ylbenzimidazol-5-yl)pyrazin-2-yl]-2-fluorobenzonitrile |
| 73 | 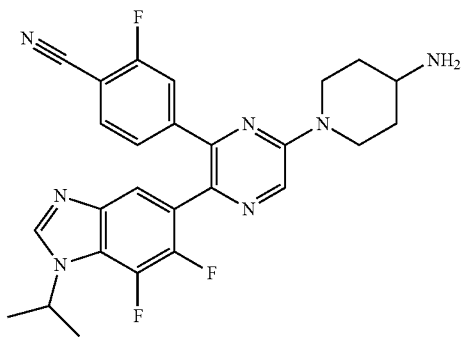 [SMILES: CC(C)n1cnc2cc(-c3ncc(N4CCC(N)CC4)nc3-c3ccc(C#N)c(F)c3)c(F)c(F)c21] | 4-[6-(4-aminopiperidin-1-yl)-3-(6,7-difluoro-1-propan-2-ylbenzimidazol-5-yl)pyrazin-2-yl]-2-fluorobenzonitrile |
| 74 | 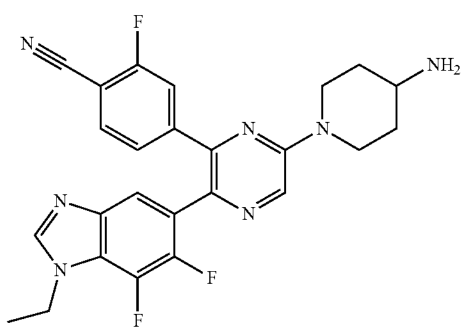 [SMILES: CCn1cnc2cc(-c3ncc(N4CCC(N)CC4)nc3-c3ccc(C#N)c(F)c3)c(F)c(F)c21] | 4-[6-(4-aminopiperidin-1-yl)-3-(1-ethyl-6,7-difluorobenzimidazol-5-yl)pyrazin-2-yl]-2-fluorobenzonitrile |
| 75 | 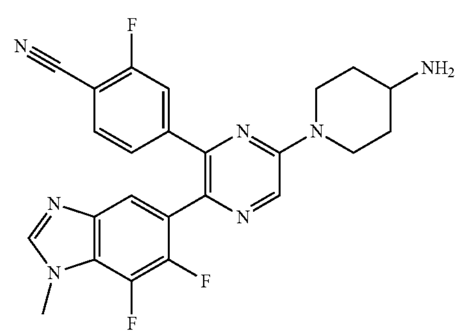 [SMILES: Cn1cnc2cc(-c3ncc(N4CCC(N)CC4)nc3-c3ccc(C#N)c(F)c3)c(F)c(F)c21] | 4-[6-(4-aminopiperidin-1-yl)-3-(6,7-difluoro-1-methylbenzimidazol-5-yl)pyrazin-2-yl]-2-fluorobenzonitrile |

In some embodiments, the substituted heterocyclic derivative compound described herein has the structure provided in Table 2.

TABLE 2

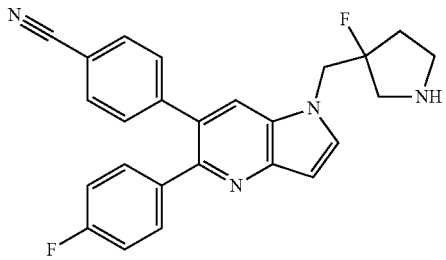 [SMILES: N#Cc1ccc(-c2cc3c(ccn3CC3(F)CCNC3)nc2-c2ccc(F)cc2)cc1]

4-[5-(4-fluorophenyl)-1-[(3-fluoropyrrolidin-3-yl)methyl]pyrrolo[3,2-b]pyridin-6-yl]benzonitrile

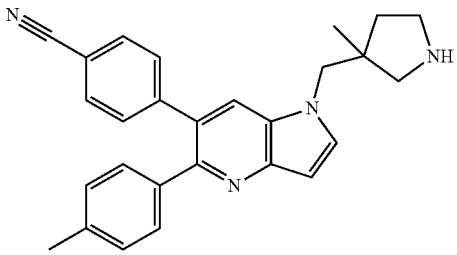 [SMILES: Cc1ccc(-c2nc3ccn(CC4(C)CCNC4)c3cc2-c2ccc(C#N)cc2)cc1]

4-[5-(4-methylphenyl)-1-[(3-methylpyrrolidin-3-yl)methyl]pyrrolo[3,2-b]pyridin-6-yl]benzonitrile

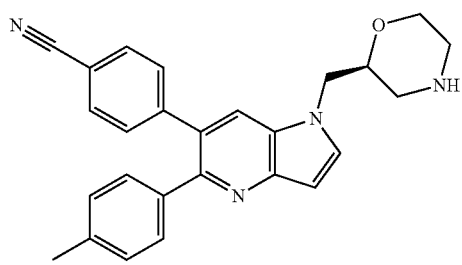 [SMILES: Cc1ccc(-c2nc3ccn(C[C@@H]4CNCCO4)c3cc2-c2ccc(C#N)cc2)cc1]

4-[5-(4-methylphenyl)-1-[[(2S)-morpholin-2-yl]methyl]pyrrolo[3,2-b]pyridin-6-yl]benzonitrile

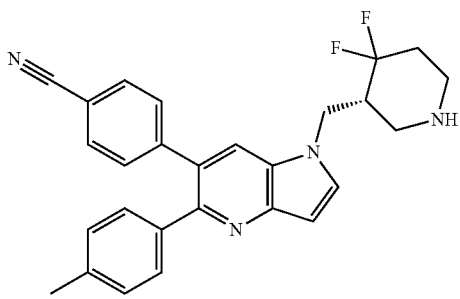 [SMILES: Cc1ccc(-c2nc3ccn(C[C@H]4CNCCC4(F)F)c3cc2-c2ccc(C#N)cc2)cc1]

4-[1-[[(3R)-4,4-difluoropiperidin-3-yl]methyl]-5-(4-methylphenyl)pyrrolo[3,2-b]pyridin-6-yl]benzonitrile

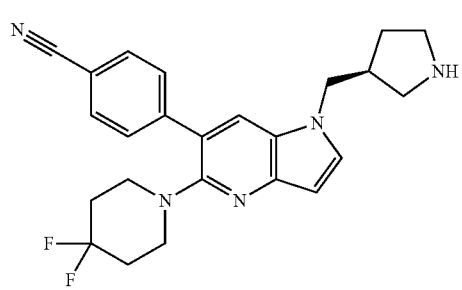

4-[5-(4,4-difluoropiperidin-1-yl)-1-[[(3S)-pyrrolidin-3-yl]methyl]pyrrolo[3,2-b]pyridin-6-yl]benzonitrile

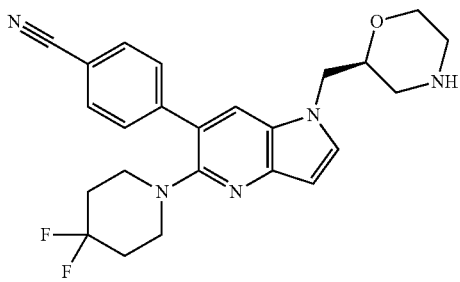 [SMILES: N#Cc1ccc(-c2cc3c(ccn3C[C@@H]3CNCCO3)nc2N2CCC(F)(F)CC2)cc1]

4-[5-(4,4-difluoropiperidin-1-yl)-1-[[(2S)-morpholin-2-yl]methyl]pyrrolo[3,2-b]pyridin-6-yl]benzonitrile

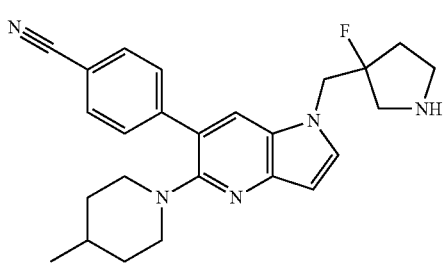 [SMILES: CC1CCN(c2nc3ccn(CC4(F)CCNC4)c3cc2-c2ccc(C#N)cc2)CC1]

4-[1-[(3-fluoropyrrolidin-3-yl)methyl]-5-(4-methylpiperidin-1-yl)pyrrolo[3,2-b]pyridin-6-yl]benzonitrile

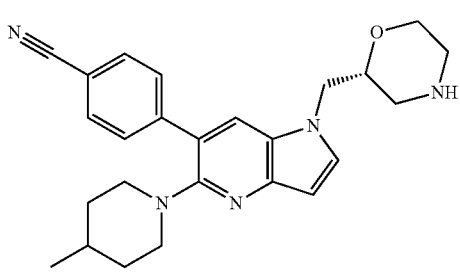

4-[5-(4-methylpiperidin-1-yl)-1-[[(2R)-morpholin-2-yl]methyl]pyrrolo[3,2-b]pyridin-6-yl]benzonitrile TABLE 2-continued

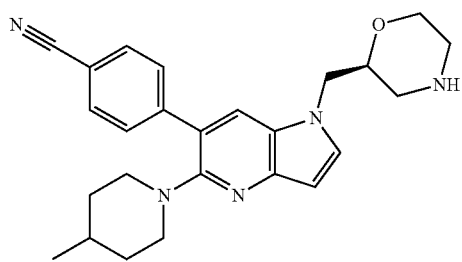 [SMILES: CC1CCN(c2nc3ccn(C[C@@H]4CNCCO4)c3cc2-c2ccc(C#N)cc2)CC1]

4-[5-(4-methylpiperidin-1-yl)-1-[[(2S)-morpholin-2-yl]methyl]pyrrolo[3,2-b]pyridin-6-yl]benzonitrile

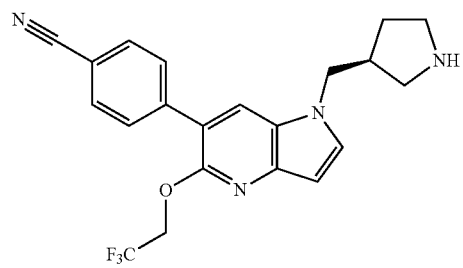 [SMILES: N#Cc1ccc(-c2cc3c(ccn3C[C@H]3CCNC3)nc2OCC(F)(F)F)cc1]

4-[1-[[(3S)-pyrrolidin-3-yl]methyl]-5-(2,2,2-trifluoroethoxy)pyrrolo[3,2-b]pyridin-6-yl]benzonitrile

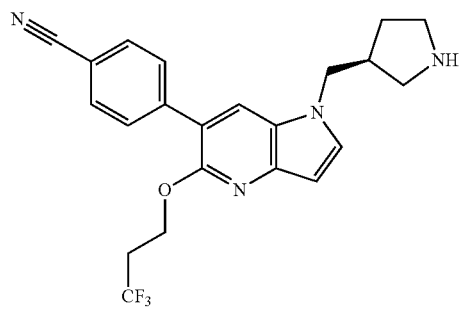 [SMILES: N#Cc1ccc(-c2cc3c(ccn3C[C@H]3CCNC3)nc2OCCC(F)(F)F)cc1]

4-[1-[[(3S)-pyrrolidin-3-yl]methyl]-5-(3,3,3-trifluoropropoxy)pyrrolo[3,2-b]pyridin-6-yl]benzonitrile

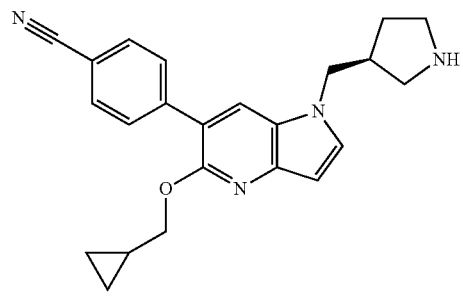 [SMILES: N#Cc1ccc(-c2cc3c(ccn3C[C@H]3CCNC3)nc2OCC2CC2)cc1]

4-[5-(cyclopropylmethoxy)-1-[[(3S)-pyrrolidin-3-yl]methyl]pyrrolo[3,2-b]pyridin-6-yl]benzonitrile

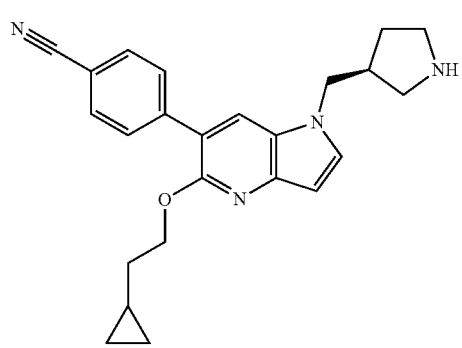 [SMILES: N#Cc1ccc(-c2cc3c(ccn3C[C@H]3CCNC3)nc2OCCC2CC2)cc1]

4-[5-(2-cyclopropylethoxy)-1-[[(3S)-pyrrolidin-3-yl]methyl]pyrrolo[3,2-b]pyridin-6-yl]benzonitrile

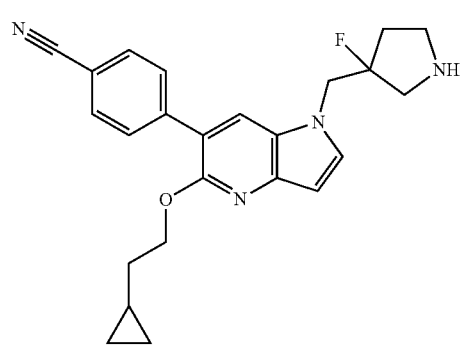 [SMILES: N#Cc1ccc(-c2cc3c(ccn3CC3(F)CCNC3)nc2OCCC2CC2)cc1]

4-[5-(2-cyclopropylethoxy)-1-[(3-fluoropyrrolidin-3-yl)methyl]pyrrolo[3,2-b]pyridin-6-yl]benzonitrile

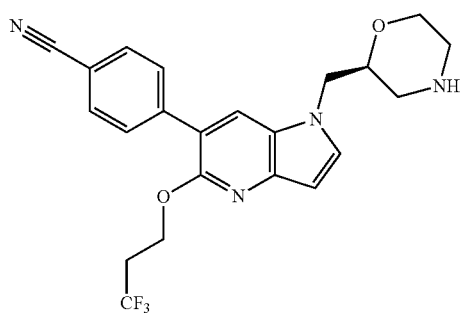

4-[1-[[(2S)-morpholin-2-yl]methyl]-5-(3,3,3-trifluoropropoxy)pyrrolo[3,2-b]pyridin-6-yl]benzonitrile

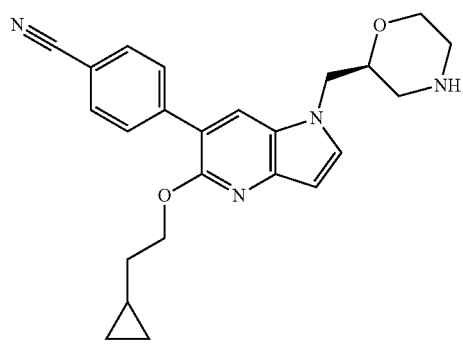 [SMILES: N#Cc1ccc(-c2cc3c(ccn3C[C@@H]3CNCCO3)nc2OCCC2CC2)cc1]

4-[5-(2-cyclopropylethoxy)-1-[[(2S)-morpholin-2-yl]methyl]pyrrolo[3,2-b]pyridin-6-yl]benzonitrile TABLE 2-continued

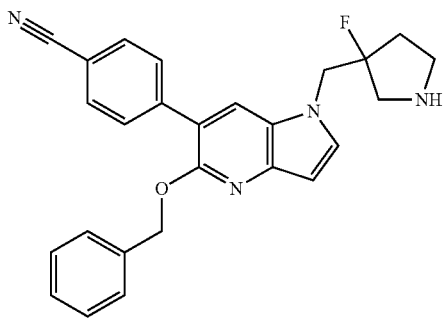 [SMILES: N#Cc1ccc(-c2cc3c(ccn3CC3(F)CCNC3)nc2OCc2ccccc2)cc1]

4-[1-[(3-fluoropyrrolidin-3-yl)methyl]-5-phenylmethoxypyrrolo[3,2-b]pyridin-6-yl]benzonitrile

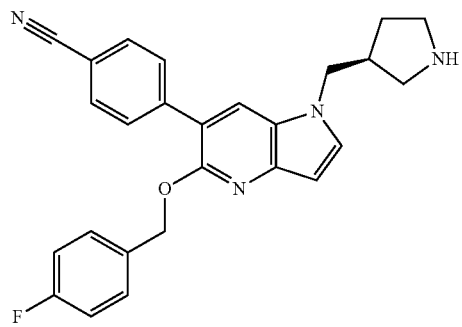 [SMILES: N#Cc1ccc(-c2cc3c(ccn3C[C@H]3CCNC3)nc2OCc2ccc(F)cc2)cc1]

4-[5-[(4-fluorophenyl)methoxy]-1-[[(3S)-pyrrolidin-3-yl]methyl]pyrrolo[3,2-b]pyridin-6-yl]benzonitrile

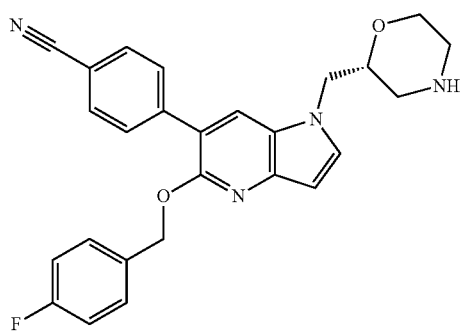 [SMILES: N#Cc1ccc(-c2cc3c(ccn3C[C@H]3CNCCO3)nc2OCc2ccc(F)cc2)cc1]

4-[5-[(4-fluorophenyl)methoxy]-1-[[(2R)-morpholin-2-yl]methyl]pyrrolo[3,2-b]pyridin-6-yl]benzonitrile

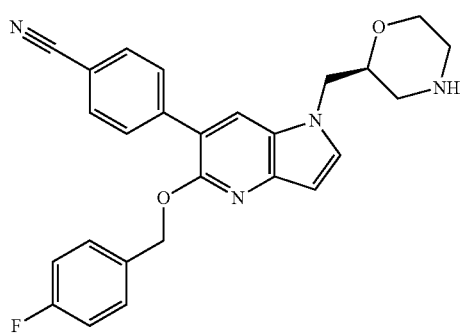 [SMILES: N#Cc1ccc(-c2cc3c(ccn3C[C@@H]3CNCCO3)nc2OCc2ccc(F)cc2)cc1]

4-[5-[(4-fluorophenyl)methoxy]-1-[[(2S)-morpholin-2-yl]methyl]pyrrolo[3,2-b]pyridin-6-yl]benzonitrile

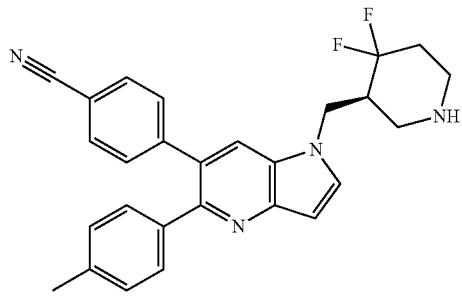 [SMILES: Cc1ccc(-c2nc3ccn(C[C@@H]4CNCCC4(F)F)c3cc2-c2ccc(C#N)cc2)cc1]

4-[1-[[(3S)-4,4-difluoropiperidin-3-yl]methyl]-5-(4-methylphenyl)pyrrolo[3,2-b]pyridin-6-yl]benzonitrile

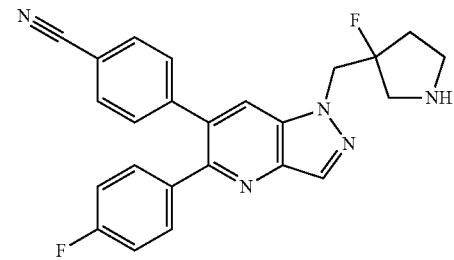 [SMILES: N#Cc1ccc(-c2cc3c(cnn3CC3(F)CCNC3)nc2-c2ccc(F)cc2)cc1]

4-[5-(4-fluorophenyl)-1-[(3-fluoropyrrolidin-3-yl)methyl]pyrazolo[4,3-b]pyridin-6-yl]benzonitrile

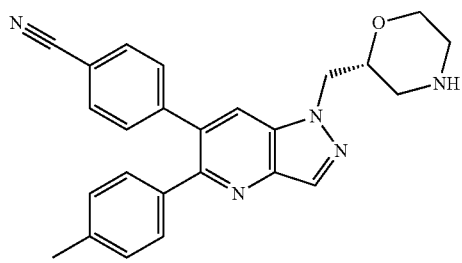

4-[5-(4-methylphenyl)-1-[[(2R)-morpholin-2-yl]methyl]pyrazolo[4,3-b]pyridin-6-yl]benzonitrile

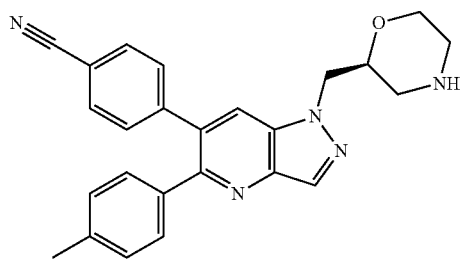 [SMILES: Cc1ccc(-c2nc3cnn(C[C@@H]4CNCCO4)c3cc2-c2ccc(C#N)cc2)cc1]

4-[5-(4-methylphenyl)-1-[[(2S)-morpholin-2-yl]methyl]pyrazolo[4,3-b]pyridin-6-yl]benzonitrile TABLE 2-continued

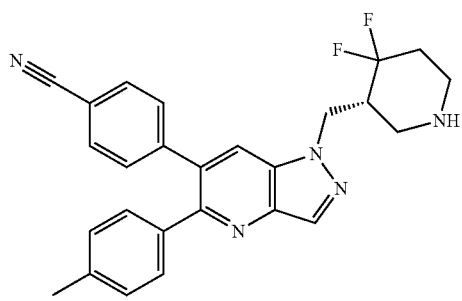 [SMILES: Cc1ccc(-c2nc3cnn(C[C@H]4CNCCC4(F)F)c3cc2-c2ccc(C#N)cc2)cc1]

4-[1-[[(3R)-4,4-difluoropiperidin-3-yl]methyl]-5-(4-methylphenyl)pyrazolo[4,3-b]pyridin-6-yl]benzonitrile

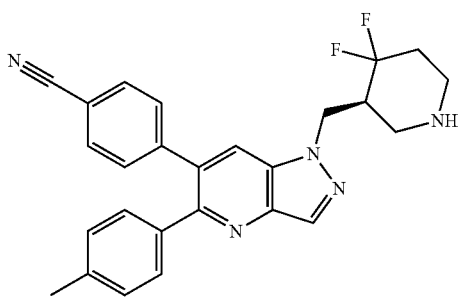 [SMILES: Cc1ccc(-c2nc3cnn(C[C@@H]4CNCCC4(F)F)c3cc2-c2ccc(C#N)cc2)cc1]

4-[1-[[(3S)-4,4-difluoropiperidin-3-yl]methyl]-5-(4-methylphenyl)pyrazolo[4,3-b]pyridin-6-yl]benzonitrile

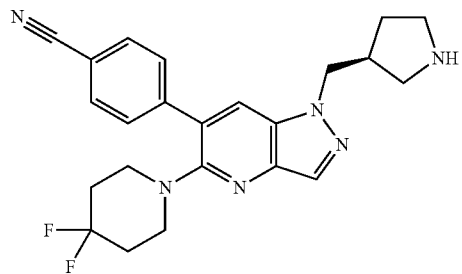 [SMILES: N#Cc1ccc(-c2cc3c(cnn3C[C@H]3CCNC3)nc2N2CCC(F)(F)CC2)cc1]

4-[5-(4,4-difluoropiperidin-1-yl)-1-[[(3S)-pyrrolidin-3-yl]methyl]pyrazolo[4,3-b]pyridin-6-yl]benzonitrile

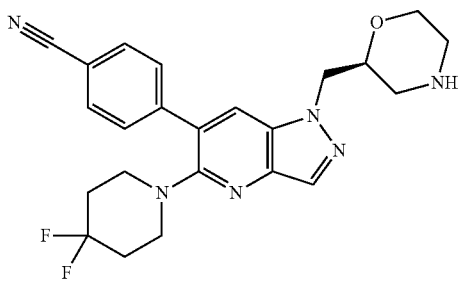 [SMILES: N#Cc1ccc(-c2cc3c(cnn3C[C@@H]3CNCCO3)nc2N2CCC(F)(F)CC2)cc1]

4-[5-(4,4-difluoropiperidin-1-yl)-1-[[(2S)-morpholin-2-yl]methyl]pyrazolo[4,3-b]pyridin-6-yl]benzonitrile

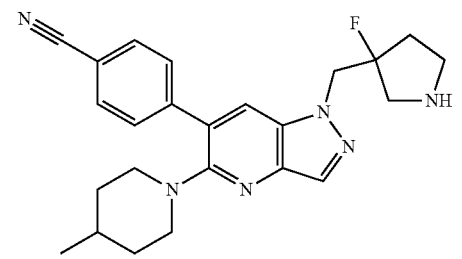 [SMILES: CC1CCN(c2nc3cnn(CC4(F)CCNC4)c3cc2-c2ccc(C#N)cc2)CC1]

4-[1-[(3-fluoropyrrolidin-3-yl)methyl]-5-(4-methylpiperidin-1-yl)pyrazolo[4,3-b]pyridin-6-yl]benzonitrile

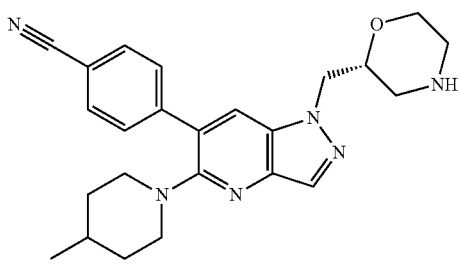 [SMILES: CC1CCN(c2nc3cnn(C[C@H]4CNCCO4)c3cc2-c2ccc(C#N)cc2)CC1]

4-[5-(4-methylpiperidin-1-yl)-1-[[(2R)-morpholin-2-yl]methyl]pyrazolo[4,3-b]pyridin-6-yl]benzonitrile

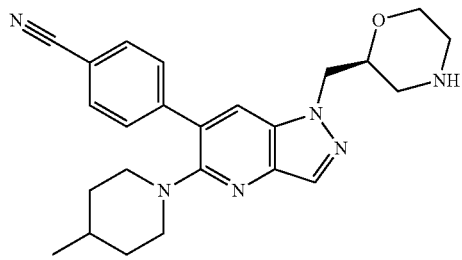 [SMILES: CC1CCN(c2nc3cnn(C[C@@H]4CNCCO4)c3cc2-c2ccc(C#N)cc2)CC1]

4-[5-(4-methylpiperidin-1-yl)-1-[[(2S)-morpholin-2-yl]methyl]pyrazolo[4,3-b]pyridin-6-yl]benzonitrile

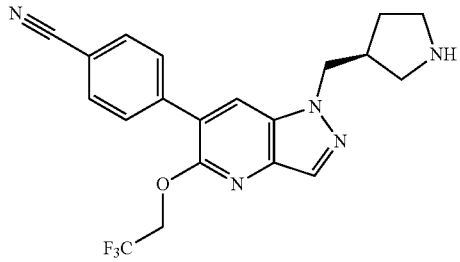

4-[1-[[(3S)-pyrrolidin-3-yl]methyl]-5-(2,2,2-trifluoroethoxy)pyrazolo[4,3-b]pyridin-6-yl]benzonitrile TABLE 2-continued

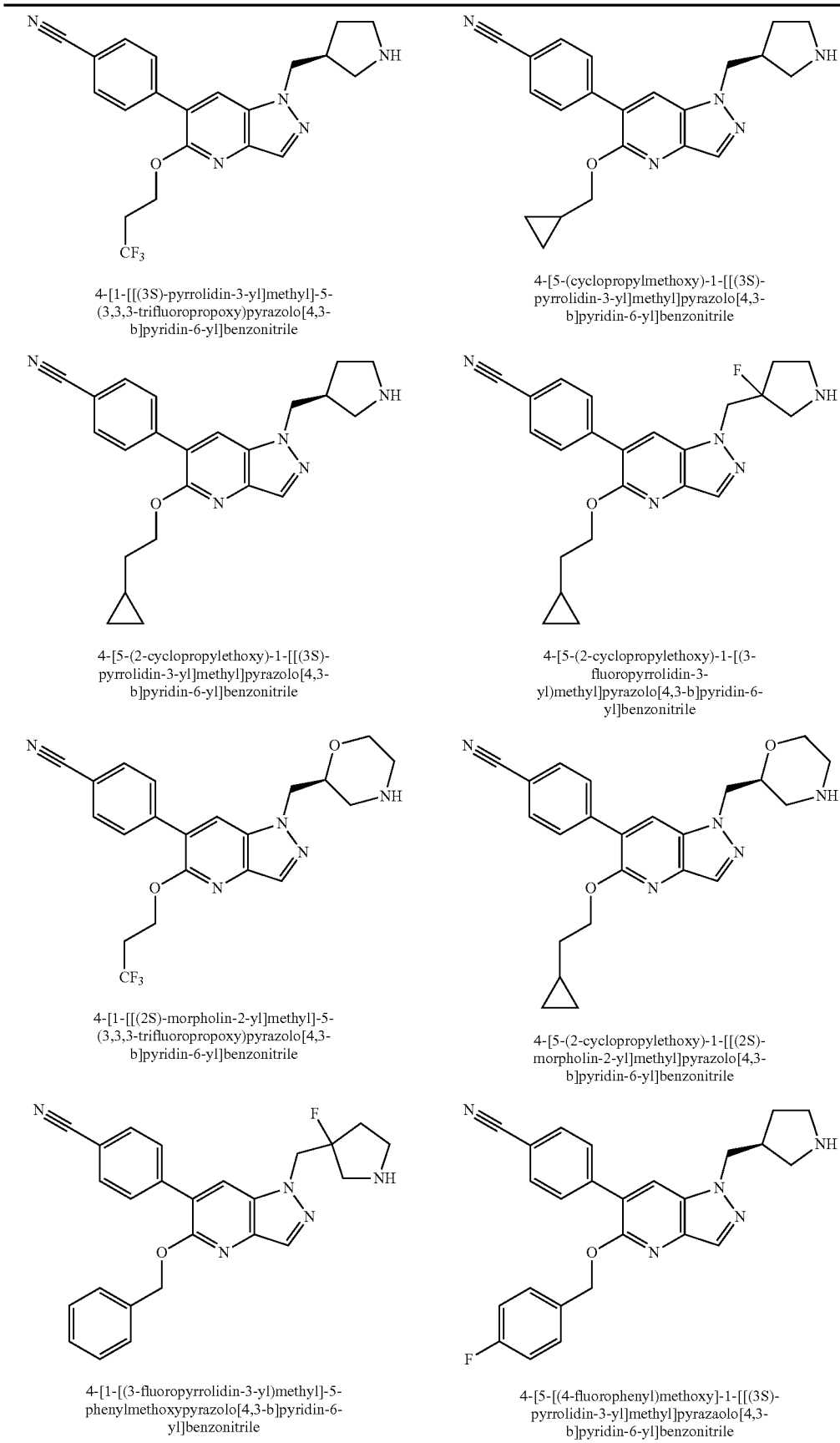

4-[1-[[(3S)-pyrrolidin-3-yl]methyl]-5-(3,3,3-trifluoropropoxy)pyrazolo[4,3-b]pyridin-6-yl]benzonitrile 4-[5-(cyclopropylmethoxy)-1-[[(3S)-pyrrolidin-3-yl]methyl]pyrazolo[4,3-b]pyridin-6-yl]benzonitrile 4-[5-(2-cyclopropylethoxy)-1-[[(3S)-pyrrolidin-3-yl]methyl]pyrazolo[4,3-b]pyridin-6-yl]benzonitrile 4-[5-(2-cyclopropylethoxy)-1-[(3-fluoropyrrolidin-3-yl)methyl]pyrazolo[4,3-b]pyridin-6-yl]benzonitrile 4-[1-[[(2S)-morpholin-2-yl]methyl]-5-(3,3,3-trifluoropropoxy)pyrazolo[4,3-b]pyridin-6-yl]benzonitrile 4-[5-(2-cyclopropylethoxy)-1-[[(2S)-morpholin-2-yl]methyl]pyrazolo[4,3-b]pyridin-6-yl]benzonitrile 4-[1-[(3-fluoropyrrolidin-3-yl)methyl]-5-phenylmethoxypyrazolo[4,3-b]pyridin-6-yl]benzonitrile 4-[5-[(4-fluorophenyl)methoxy]-1-[[(3S)-pyrrolidin-3-yl]methyl]pyrazaolo[4,3-b]pyridin-6-yl]benzonitrile TABLE 2-continued

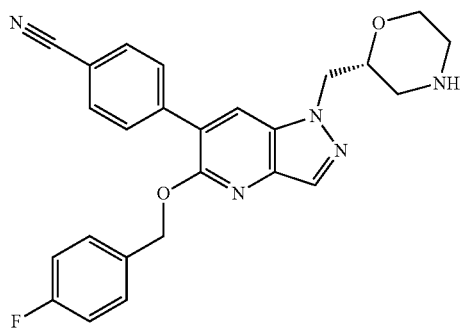 [SMILES: N#Cc1ccc(-c2cc3c(cnn3C[C@H]3CNCCO3)nc2OCc2ccc(F)cc2)cc1]

4-[5-[(4-fluorophenyl)methoxy]-1-[[(2R)-morpholin-2-yl]methyl]pyrazolo[4,3-b]pyridin-6-yl]benzonitrile

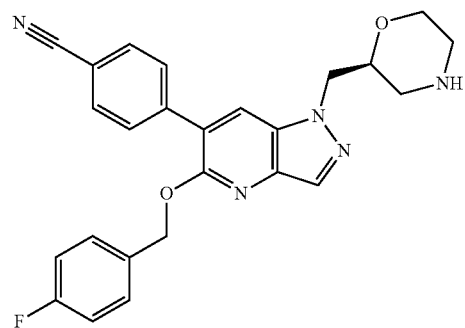 [SMILES: N#Cc1ccc(-c2cc3c(cnn3C[C@@H]3CNCCO3)nc2OCc2ccc(F)cc2)cc1]

4-[5-[(4-fluorophenyl)methoxy]-1-[[(2S)-morpholin-2-yl]methyl]pyrazolo[4,3-b]pyridin-6-yl]benzonitrile

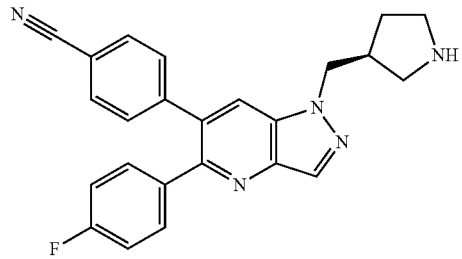 [SMILES: N#Cc1ccc(-c2cc3c(cnn3C[C@H]3CCNC3)nc2-c2ccc(F)cc2)cc1]

4-[5-(4-fluorophenyl)-1-[[(3S)-pyrrolidin-3-yl]methyl]pyrazolo[4,3-b]pyridin-6-yl]benzonitrile

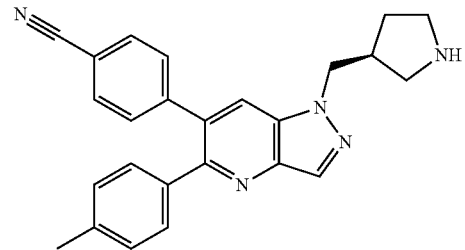 [SMILES: Cc1ccc(-c2nc3cnn(C[C@H]4CCNC4)c3cc2-c2ccc(C#N)cc2)cc1]

4-[5-(4-methylphenyl)-1-[[(3S)-pyrrolidin-3-yl]methyl]pyrazolo[4,3-b]pyridin-6-yl]benzonitrile

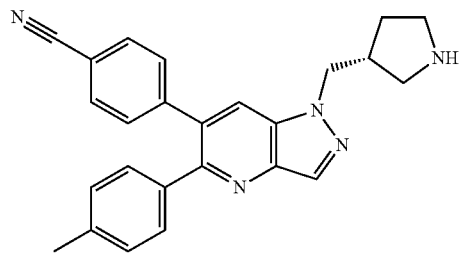 [SMILES: Cc1ccc(-c2nc3cnn(C[C@@H]4CCNC4)c3cc2-c2ccc(C#N)cc2)cc1]

4-[5-(4-methylphenyl)-1-[[(3R)-pyrrolidin-3-yl]methyl]pyrazolo[4,3-b]pyridin-6-yl]benzonitrile

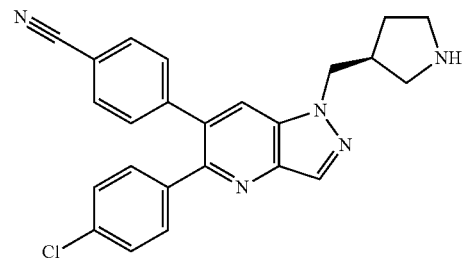 [SMILES: N#Cc1ccc(-c2cc3c(cnn3C[C@H]3CCNC3)nc2-c2ccc(Cl)cc2)cc1]

4-[5-(4-chlorophenyl)-1-[[(3S)-pyrrolidin-3-yl]methyl]pyrazolo[4,3-b]pyridin-6-yl]benzonitrile

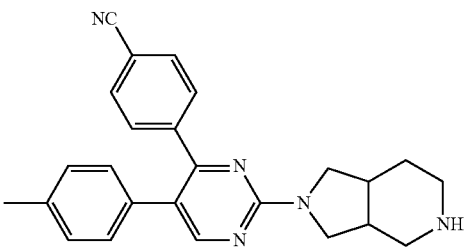 [SMILES: Cc1ccc(-c2cnc(N3CC4CCNCC4C3)nc2-c2ccc(C#N)cc2)cc1]

(±)-4-[5-(4-methylphenyl)-2-{octahydro-1H-pyrrolo[4,3-c]pyridin-2-yl}pyrimidin-4-yl]benzonitrile

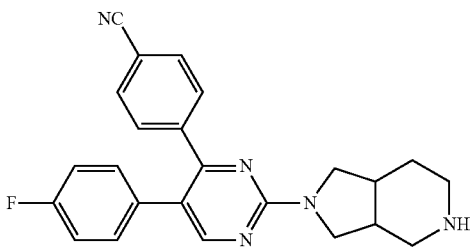 [SMILES: N#Cc1ccc(-c2nc(N3CC4CCNCC4C3)ncc2-c2ccc(F)cc2)cc1]

(±)-4-[5-(4-methylphenyl)-2-{octahydro-1H-pyrrolo[3,4-c]pyridin-2-yl}pyrimidin-4-yl]benzonitrile TABLE 2-continued

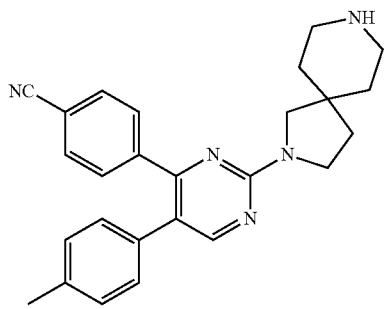 [SMILES: Cc1ccc(-c2cnc(N3CCC4(CCNCC4)C3)nc2-c2ccc(C#N)cc2)cc1]

4-(2-{[2,8-diazaspiro[4.5]decan-2-yl}-5-(4-methylphenyl)pyrimidin-4-yl)benzonitrile

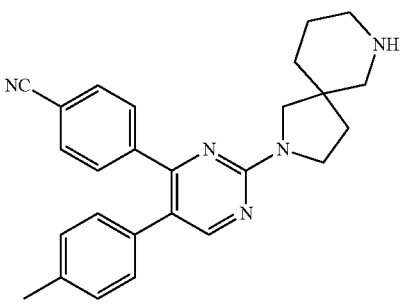 [SMILES: Cc1ccc(-c2cnc(N3CCC4(CCCNC4)C3)nc2-c2ccc(C#N)cc2)cc1]

(±)-4-(2-{2,7-diazaspiro[4.5]decan-2-yl}-5-(4-methylphenyl)pyrimidin-4-yl)benzonitrile

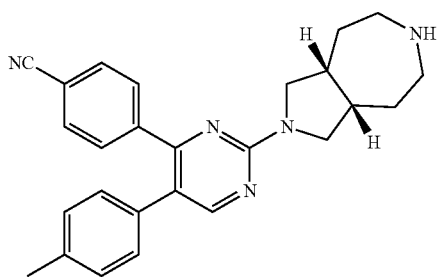 [SMILES: Cc1ccc(-c2cnc(N3C[C@H]4CCNCC[C@H]4C3)nc2-c2ccc(C#N)cc2)cc1]

4-{2-[(3aR,8aS)-decahydropyrrolo[3,4-d]azepin-2-yl]-5-(4-methylphenyl)pyrimidin-4-yl}benzonitrile

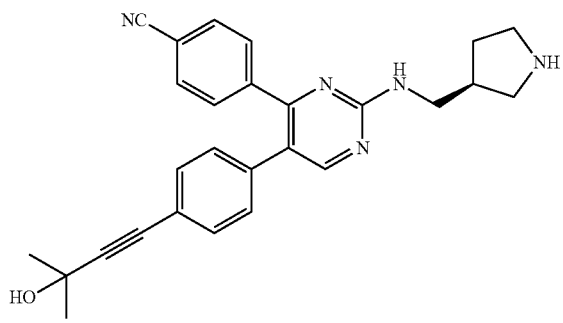 [SMILES: CC(C)(O)C#Cc1ccc(-c2cnc(NC[C@H]3CCNC3)nc2-c2ccc(C#N)cc2)cc1]

4-[5-(3-hydroxy-3-methylbut-1-yn-1-yl)-2-{[(3S)-pyrrolidin-3-ylmethyl]amino}pyrimidin-4-yl]benzonitrile

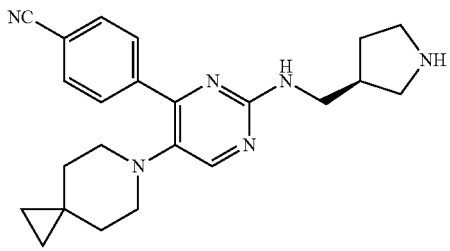 [SMILES: N#Cc1ccc(-c2nc(NC[C@H]3CCNC3)ncc2N2CCC3(CC2)CC3)cc1]

4-(5-{6-azaspiro[2.5]octan-6-yl}-2-{[(3S)-pyrrolidin-3-ylmethyl]amino}pyrimidin-4-yl)benzonitrile

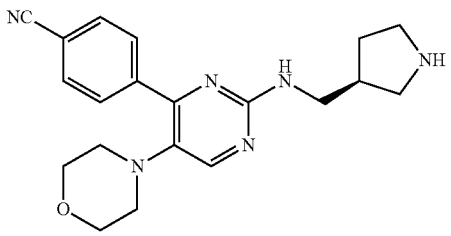 [SMILES: N#Cc1ccc(-c2nc(NC[C@H]3CCNC3)ncc2N2CCOCC2)cc1]

4-[5-(morpholin-4-yl)-2-{[(3S)-pyrrolidin-3-ylmethyl]amino}pyrimidin-4-yl]benzonitrile

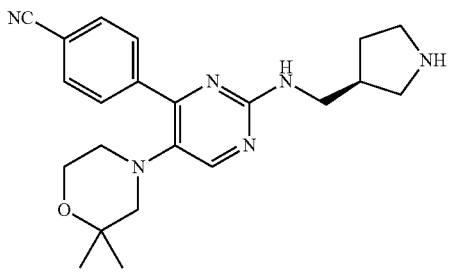 [SMILES: CC1(C)CN(c2cnc(NC[C@H]3CCNC3)nc2-c2ccc(C#N)cc2)CCO1]

4-[5-(2,2-dimethylmorpholin-4-yl)-2-{[(3S)-pyrrolidin-3-ylmethyl]amino}pyrimidin-4-yl]benzonitrile

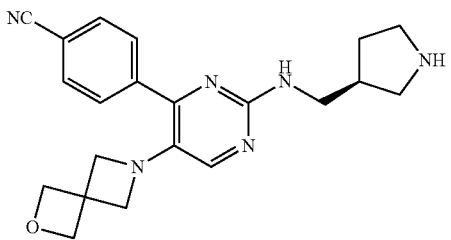 [SMILES: N#Cc1ccc(-c2nc(NC[C@H]3CCNC3)ncc2N2CC3(COC3)C2)cc1]

4-(5-{2-oxa-6-azaspiro[3.3]heptan-6-yl}-2-{[(3S)-pyrrolidin-3-ylmethyl]amino}pyrimidin-4-yl)benzonitrile TABLE 2-continued

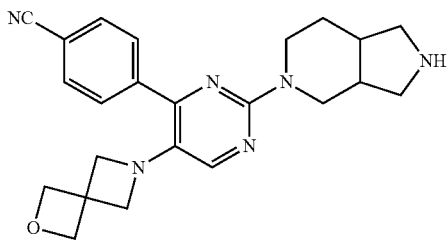 [SMILES: N#Cc1ccc(-c2nc(N3CCC4CNCC4C3)ncc2N2CC3(COC3)C2)cc1]

4-(2-{octahydro-1H-pyrrolo[3,4-c]pyridin-5-yl}-5-{2-oxa-6-azaspiro[3.3]heptan-6-yl}pyrimidin-4-yl)benzonitrile

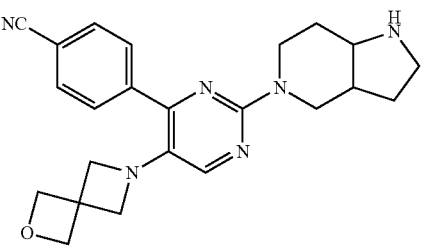 [SMILES: N#Cc1ccc(-c2nc(N3CCC4NCCC4C3)ncc2N2CC3(COC3)C2)cc1]

4-(2-{octahydro-1H-pyrrolo[3,2-c]pyridin-5-yl}-5-{2-oxa-6-azaspiro[3.3]heptan-6-yl}pyrimidin-4-yl)benzonitrile

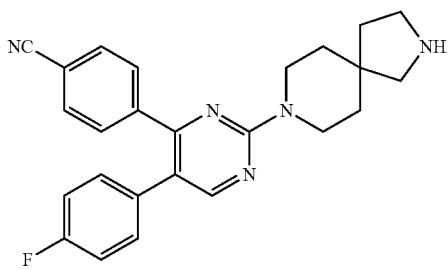 [SMILES: N#Cc1ccc(-c2nc(N3CCC4(CCNC4)CC3)ncc2-c2ccc(F)cc2)cc1]

4-(2-{2,8-diazaspiro[4.5]decan-8-yl}-5-(4-fluorophenyl)pyrimidin-4-yl)benzonitrile

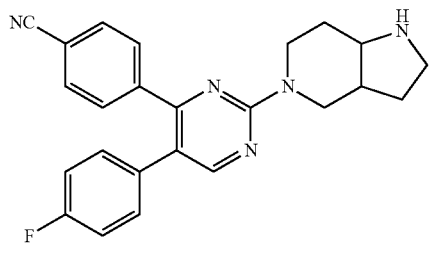 [SMILES: N#Cc1ccc(-c2nc(N3CCC4NCCC4C3)ncc2-c2ccc(F)cc2)cc1]

4-[5-(4-fluorophenyl)-2-{octahydro-1H-pyrrolo[3,2-c]pyridin-5-yl}pyrimidin-4-yl]benzonitrile

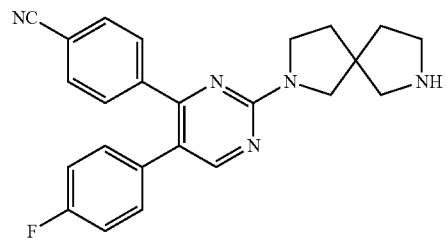 [SMILES: N#Cc1ccc(-c2nc(N3CCC4(CCNC4)C3)ncc2-c2ccc(F)cc2)cc1]

4-(2-{2,7-diazaspiro[4.4]nonan-2-yl}-5-(4-fluorophenyl)pyrimidin-4-yl)benzonitrile

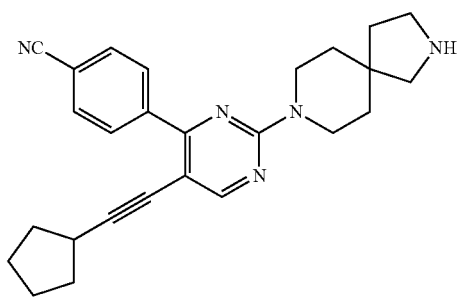 [SMILES: N#Cc1ccc(-c2nc(N3CCC4(CCNC4)CC3)ncc2C#CC2CCCC2)cc1]

4-[5-(2-cyclopentylethynyl)-2-{2,8-diazaspiro[4.5]decan-8-yl}pyrimidin-4-yl]benzonitrile

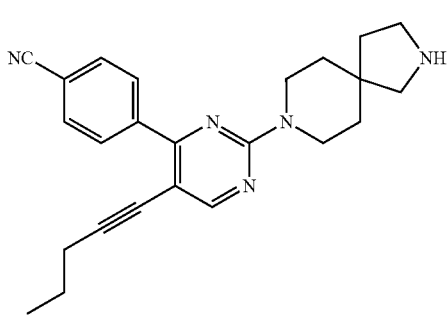 [SMILES: CCCC#Cc1cnc(N2CCC3(CCNC3)CC2)nc1-c1ccc(C#N)cc1]

4-(2-{2,8-diazaspiro[4.5]decan-8-yl}-5-(pent-1-yn-1-yl)pyrimidin-4-yl)benzonitrile

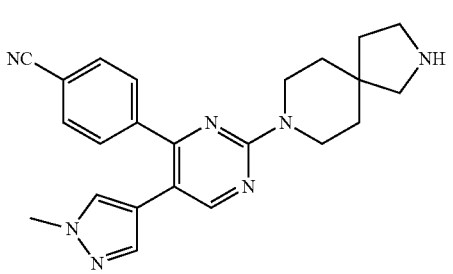 [SMILES: Cn1cc(-c2cnc(N3CCC4(CCNC4)CC3)nc2-c2ccc(C#N)cc2)cn1]

4-(2-{2,8-diazaspiro[4.5]decan-8-yl}-5-(1-methyl-1H-pyrazol-4-yl)pyrimidin-4-yl)benzonitrile

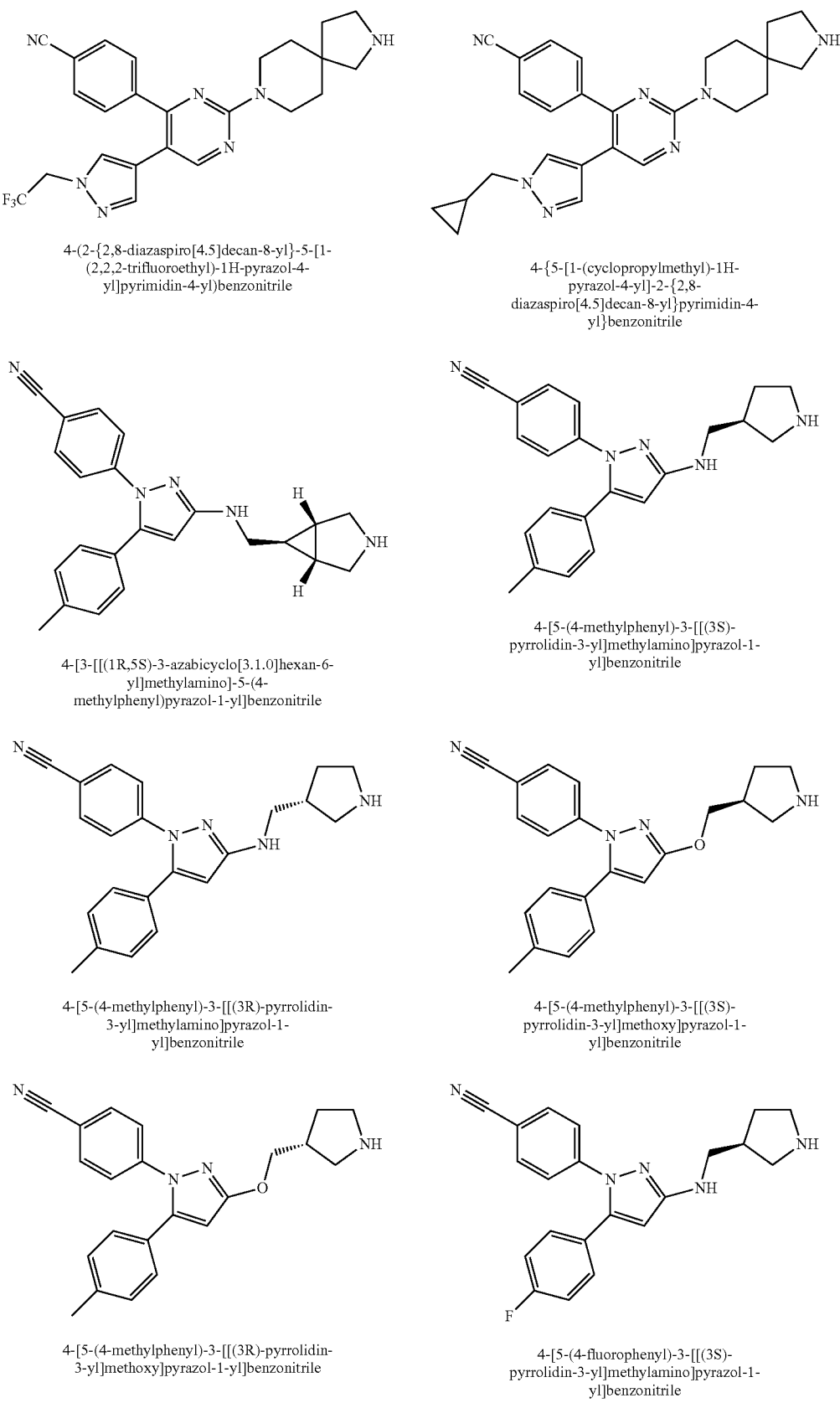

TABLE 2-continued

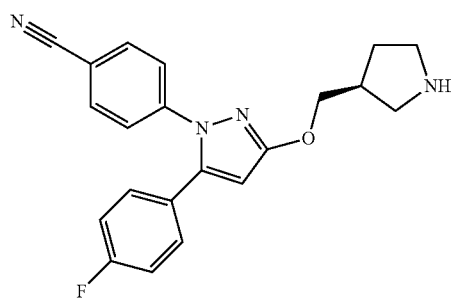 [SMILES: N#Cc1ccc(-n2nc(OC[C@H]3CCNC3)cc2-c2ccc(F)cc2)cc1]

4-[5-(4-fluorophenyl)-3-[[(3S)-pyrrolidin-3-yl]methoxy]pyrazol-1-yl]benzonitrile

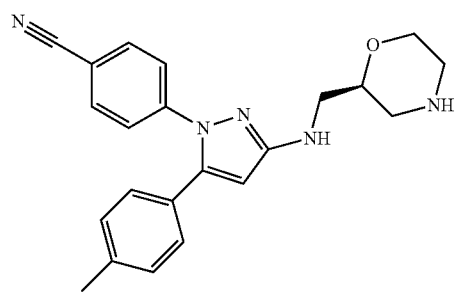 [SMILES: Cc1ccc(-c2cc(NC[C@@H]3CNCCO3)nn2-c2ccc(C#N)cc2)cc1]

4-[5-(4-methylphenyl)-3-[[(2S)-morpholin-2-yl]methylamino]pyrazol-1-yl]benzonitrile

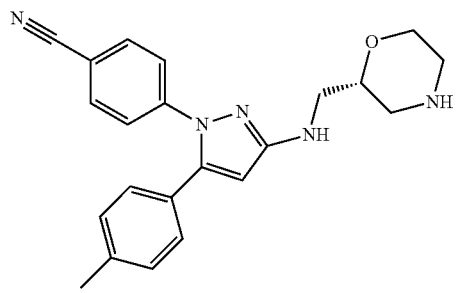 [SMILES: Cc1ccc(-c2cc(NC[C@H]3CNCCO3)nn2-c2ccc(C#N)cc2)cc1]

4-[5-(4-methylphenyl)-3-[[(2R)-morpholin-2-yl]methylamino]pyrazol-1-yl]benzonitrile

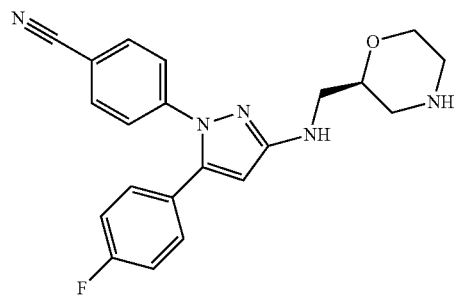 [SMILES: N#Cc1ccc(-n2nc(NC[C@@H]3CNCCO3)cc2-c2ccc(F)cc2)cc1]

4-[5-(4-fluorophenyl)-3-[[(2S)-morpholin-2-yl]methylamino]pyrazol-1-yl]benzonitrile

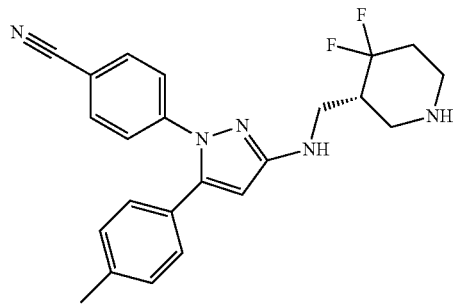 [SMILES: Cc1ccc(-c2cc(NC[C@H]3CNCCC3(F)F)nn2-c2ccc(C#N)cc2)cc1]

4-[3-[[(3R)-4,4-difluoropiperidin-3-yl]methylamino]-5-(4-methylphenyl)pyrazol-1-yl]benzonitrile

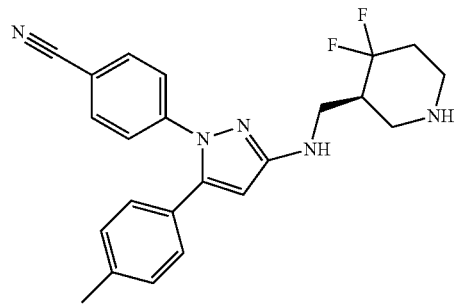 [SMILES: Cc1ccc(-c2cc(NC[C@@H]3CNCCC3(F)F)nn2-c2ccc(C#N)cc2)cc1]

4-[3-[[(3S)-4,4-difluoropiperidin-3-yl]methylamino]-5-(4-methylphenyl)pyrazol-1-yl]benzonitrile

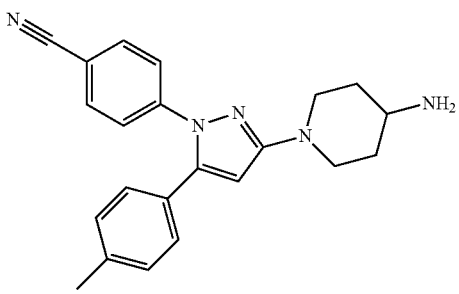 [SMILES: Cc1ccc(-c2cc(N3CCC(N)CC3)nn2-c2ccc(C#N)cc2)cc1]

4-[3-(4-aminopiperidin-1-yl)-5-(4-methylphenyl)pyrazol-1-yl]benzonitrile

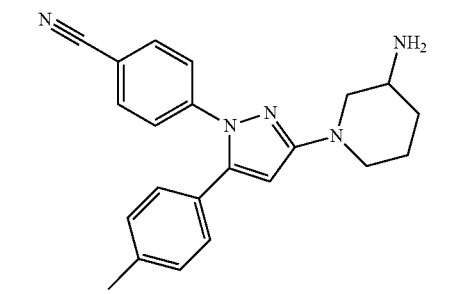 [SMILES: Cc1ccc(-c2cc(N3CCCC(N)C3)nn2-c2ccc(C#N)cc2)cc1]

4-[3-(3-aminopiperidin-1-yl)-5-(4-methylphenyl)pyrazol-1-yl]benzonitrile

TABLE 2-continued

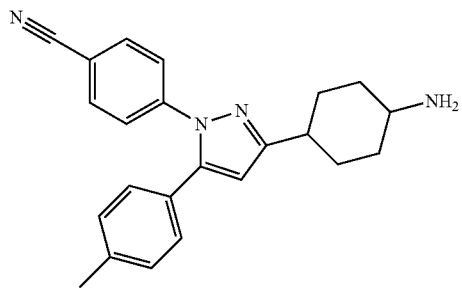 [SMILES: Cc1ccc(-c2cc(C3CCC(N)CC3)nn2-c2ccc(C#N)cc2)cc1]

4-[3-(4-aminocyclohexyl)-5-(4-methylphenyl)pyrazol-1-yl]benzonitrile

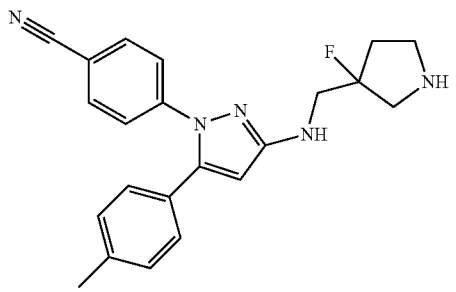 [SMILES: Cc1ccc(-c2cc(NCC3(F)CCNC3)nn2-c2ccc(C#N)cc2)cc1]

4-[3-[(3-fluoropyrrolidin-3-yl)methylamino]-5-(4-methylphenyl)pyrazol-1-yl]benzonitrile

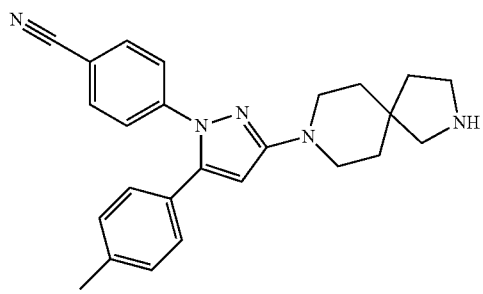 [SMILES: Cc1ccc(-c2cc(N3CCC4(CCNC4)CC3)nn2-c2ccc(C#N)cc2)cc1]

4-[3-(2,8-diazaspiro[4.5]decan-8-yl)-5-(4-methylphenyl)pyrazol-1-yl]benzonitrile

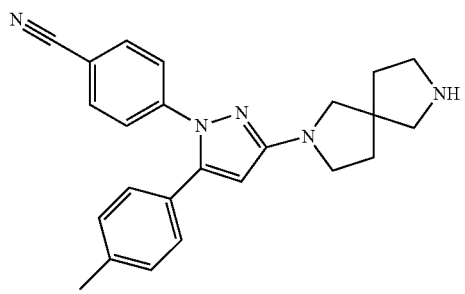 [SMILES: Cc1ccc(-c2cc(N3CCC4(CCNC4)C3)nn2-c2ccc(C#N)cc2)cc1]

4-[3-(2,7-diazaspiro[4.5]nonan-2-yl)-5-(4-methylphenyl)pyrazol-1-yl]benzonitrile

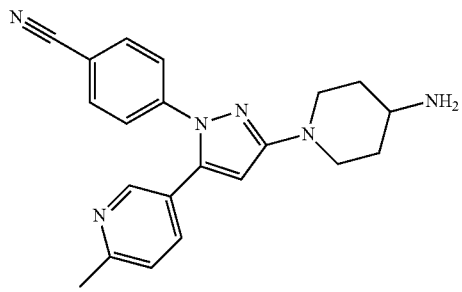

4-(3-(4-aminopiperidin-1-yl)-5-(6-methylpyridin-3-yl)-1H-pyrazol-1-yl)benzonitrile

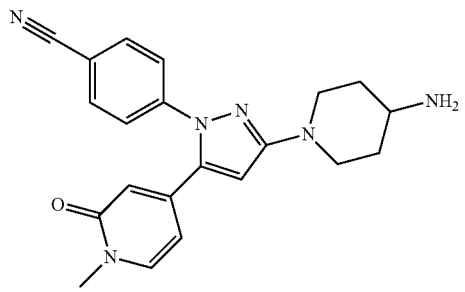 [SMILES: Cn1ccc(-c2cc(N3CCC(N)CC3)nn2-c2ccc(C#N)cc2)cc1=O]

4-(3-(4-aminopiperidin-1-yl)-5-(1-methyl-2-oxo-1,2-dihydropyridin-4-yl)-1H-pyrazol-1-yl)benzonitrile

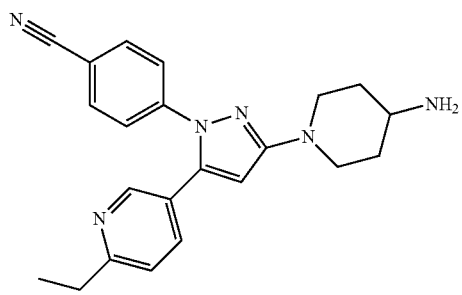 [SMILES: CCc1ccc(-c2cc(N3CCC(N)CC3)nn2-c2ccc(C#N)cc2)cn1]

4-(3-(4-aminopiperidin-1-yl)-5-(6-ethylpyridin-3-yl)-1H-pyrazol-1-yl)benzonitrile

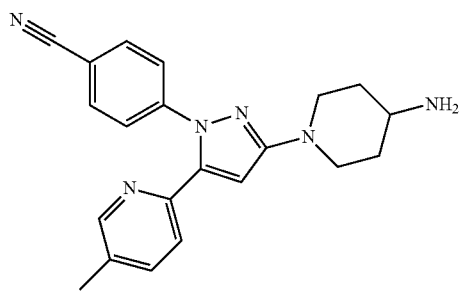

4-(3-(4-aminopiperidin-1-yl)-5-(5-methylpyridin-2-yl)-1H-pyrazol-1-yl)benzonitrile TABLE 2-continued

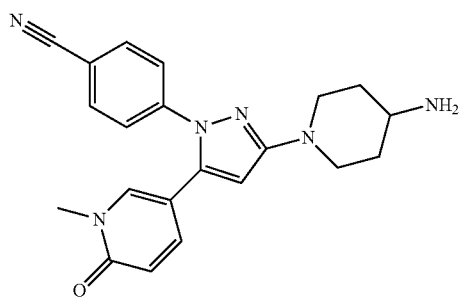 [SMILES: Cn1cc(-c2cc(N3CCC(N)CC3)nn2-c2ccc(C#N)cc2)ccc1=O]

4-(3-(4-aminopiperidin-1-yl)-5-(1-methyl-6-oxo-1,6-dihydropyridin-3-yl)-1H-pyrazol-1-yl)benzonitrile

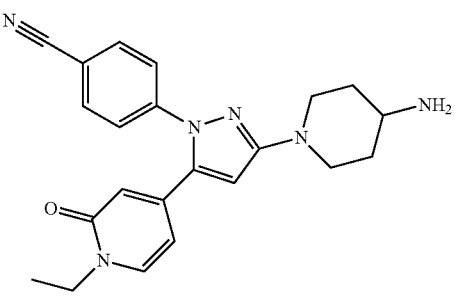 [SMILES: CCn1ccc(-c2cc(N3CCC(N)CC3)nn2-c2ccc(C#N)cc2)cc1=O]

4-(3-(4-aminopiperidin-1-yl)-5-(1-ethyl-2-oxo-1,2-dihydropyridin-4-yl)-1H-pyrazol-1-yl)benzonitrile

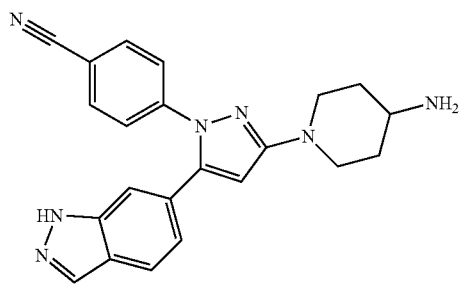 [SMILES: N#Cc1ccc(-n2nc(N3CCC(N)CC3)cc2-c2ccc3cn[nH]c3c2)cc1]

4-(3-(4-aminopiperidin-1-yl)-5-(1H-indazol-6-yl)-1H-pyrazol-1-yl)benzonitrile

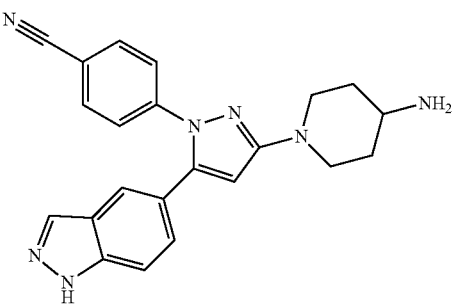 [SMILES: N#Cc1ccc(-n2nc(N3CCC(N)CC3)cc2-c2ccc3[nH]ncc3c2)cc1]

4-(3-(4-aminopiperidin-1-yl)-5-(1H-indazol-5-yl)-1H-pyrazol-1-yl)benzonitrile

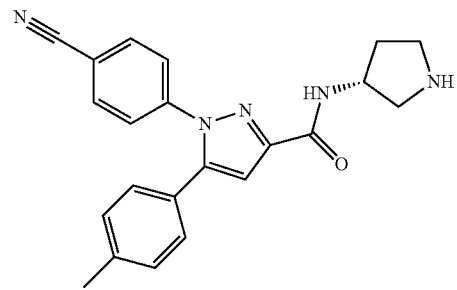 [SMILES: Cc1ccc(-c2cc(C(=O)N[C@@H]3CCNC3)nn2-c2ccc(C#N)cc2)cc1]

1-(4-cyanophenyl)-5-(4-methylphenyl)-N-[(3R)-pyrrolidin-3-yl]pyrazole-3-carboxamide

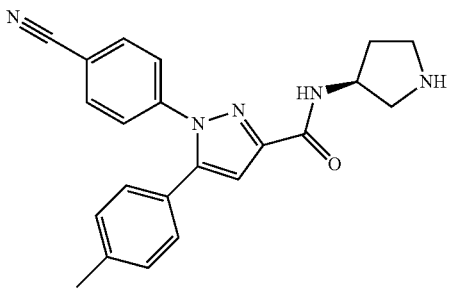 [SMILES: Cc1ccc(-c2cc(C(=O)N[C@H]3CCNC3)nn2-c2ccc(C#N)cc2)cc1]

1-(4-cyanophenyl)-5-(4-methylphenyl)-N-[(3S)-pyrrolidin-3-yl]pyrazole-3-carboxamide

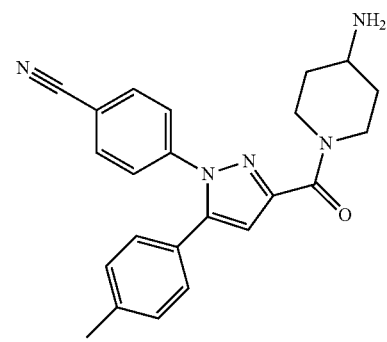 [SMILES: Cc1ccc(-c2cc(C(=O)N3CCC(N)CC3)nn2-c2ccc(C#N)cc2)cc1]

4-[3-(4-aminopiperidine-1-carbonyl)-5-(4-methylphenyl)pyrazol-1-yl]benzonitrile

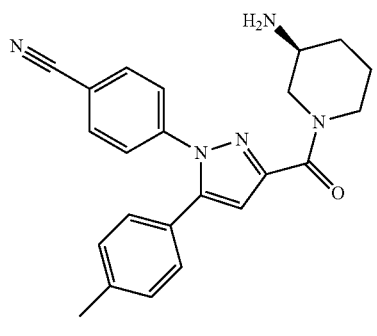 [SMILES: Cc1ccc(-c2cc(C(=O)N3CCC[C@H](N)C3)nn2-c2ccc(C#N)cc2)cc1]

4-[3-[(3S)-3-aminopiperidine-1-carbonyl]-5-(4-methylphenyl)pyrazol-1-yl]benzonitrile TABLE 2-continued

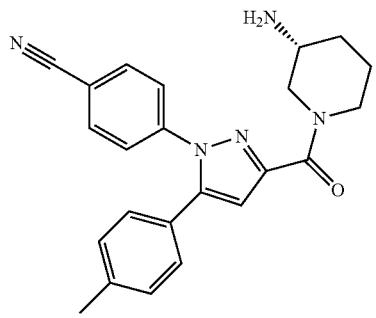 [SMILES: Cc1ccc(-c2cc(C(=O)N3CCC[C@@H](N)C3)nn2-c2ccc(C#N)cc2)cc1]

4-[3-[(3R)-3-aminopiperidine-1-carbonyl]-
5-(4-methylphenyl)pyrazol-1-
yl]benzonitrile

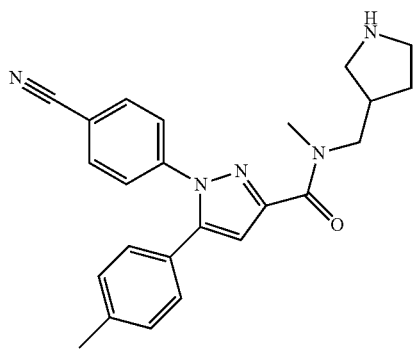 [SMILES: Cc1ccc(-c2cc(C(=O)N(C)CC3CCNC3)nn2-c2ccc(C#N)cc2)cc1]

1-(4-cyanophenyl)-N-methyl-5-(4-
methylphenyl)-N-(pyrrolidin-3-
ylmethyl)pyrazole-3-carboxamide

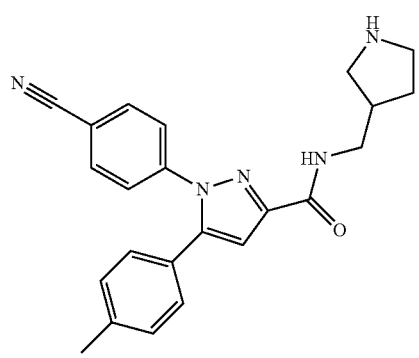 [SMILES: Cc1ccc(-c2cc(C(=O)NCC3CCNC3)nn2-c2ccc(C#N)cc2)cc1]

1-(4-cyanophenyl)-5-(4-methylphenyl)-N-
(pyrrolidin-3-ylmethyl)pyrazole-3-
carboxamide

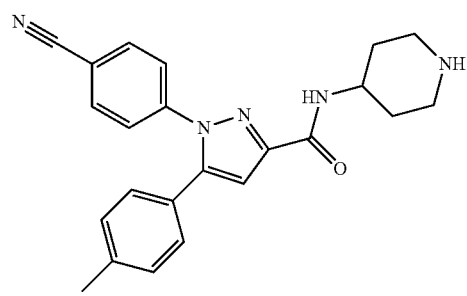 [SMILES: Cc1ccc(-c2cc(C(=O)NC3CCNCC3)nn2-c2ccc(C#N)cc2)cc1]

1-(4-cyanophenyl)-5-(4-methylphenyl)-
N-piperidin-4-ylpyrazole-3-carboxamide

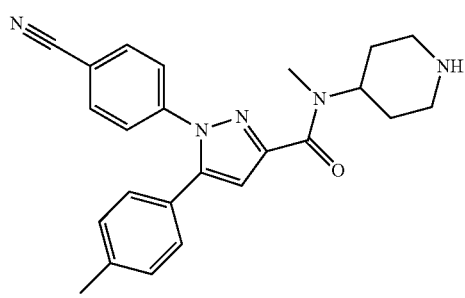 [SMILES: Cc1ccc(-c2cc(C(=O)N(C)C3CCNCC3)nn2-c2ccc(C#N)cc2)cc1]

1-(4-cyanophenyl)-N-methyl-5-(4-
methylphenyl)-N-piperidin-4-ylpyrazole-3-
carboxamide

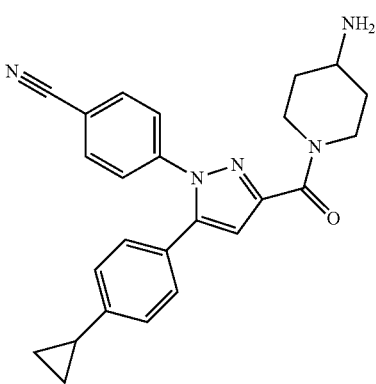 [SMILES: N#Cc1ccc(-n2nc(C(=O)N3CCC(N)CC3)cc2-c2ccc(C3CC3)cc2)cc1]

4-[3-(4-aminopiperidine-1-carbonyl)-5-
(4-cyclopropylphenyl)pyrazol-1-
yl]benzonitrile TABLE 2-continued

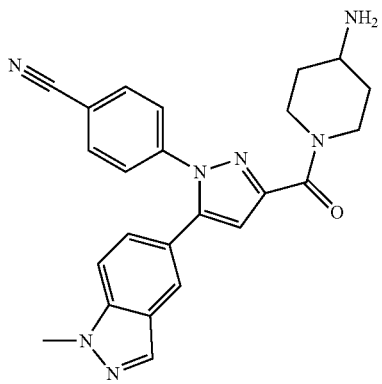 [SMILES: Cn1ncc2cc(-c3cc(C(=O)N4CCC(N)CC4)nn3-c3ccc(C#N)cc3)ccc21]

4-[3-(4-aminopiperidine-1-carbonyl)-5-(1-methylindazol-5-yl)pyrazol-1-yl]benzonitrile

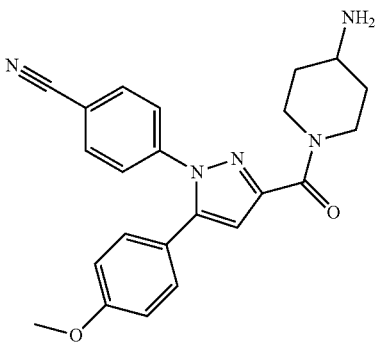 [SMILES: COc1ccc(-c2cc(C(=O)N3CCC(N)CC3)nn2-c2ccc(C#N)cc2)cc1]

4-[3-(4-aminopiperidine-1-carbonyl)-5-(4-methoxyphenyl)-4-methylpyrazol-1-yl]benzonitrile

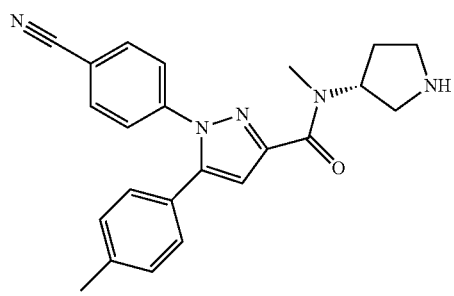 [SMILES: Cc1ccc(-c2cc(C(=O)N(C)[C@@H]3CCNC3)nn2-c2ccc(C#N)cc2)cc1]

1-(4-cyanophenyl)-N-methyl-5-(4-methylphenyl)-N-[(3R)-pyrrolidin-3-yl]pyrazole-3-carboxamide

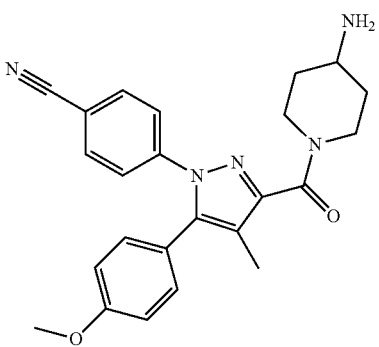 [SMILES: COc1ccc(-c2c(C)c(C(=O)N3CCC(N)CC3)nn2-c2ccc(C#N)cc2)cc1]

4-[3-(4-aminopiperidine-1-carbonyl)-5-(4-methoxyphenyl)-4-methylpyrazol-1-yl]benzonitrile

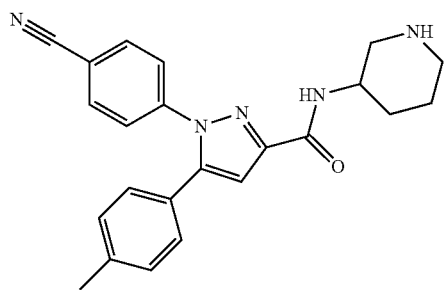 [SMILES: Cc1ccc(-c2cc(C(=O)NC3CCCNC3)nn2-c2ccc(C#N)cc2)cc1]

1-(4-cyanophenyl)-5-(4-methylphenyl)-N-piperidin-3-ylpyrazole-3-carboxamide

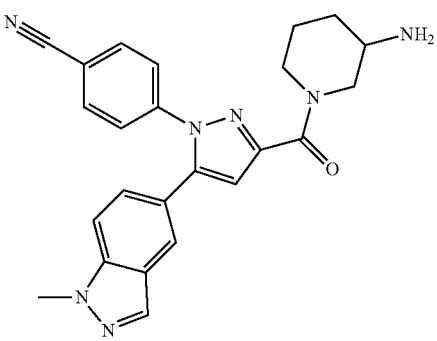 [SMILES: Cn1ncc2cc(-c3cc(C(=O)N4CCCC(N)C4)nn3-c3ccc(C#N)cc3)ccc21]

4-[3-(3-aminopiperidine-1-carbonyl)-5-(1-methylindazol-5-yl)pyrazol-1-yl]benzonitrile TABLE 2-continued

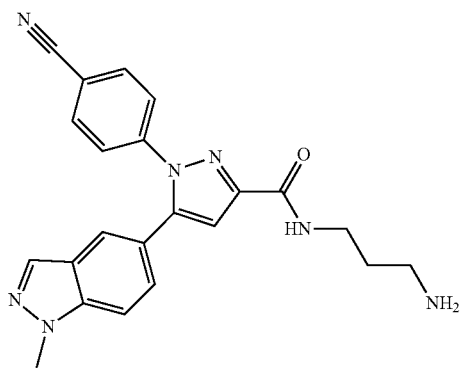 [SMILES: Cn1ncc2cc(-c3cc(C(=O)NCCCN)nn3-c3ccc(C#N)cc3)ccc21]

N-(3-aminopropyl)-1-(4-cyanophenyl)-5-
(1-methylindazol-5-yl)pyrazole-3-
carboxamide

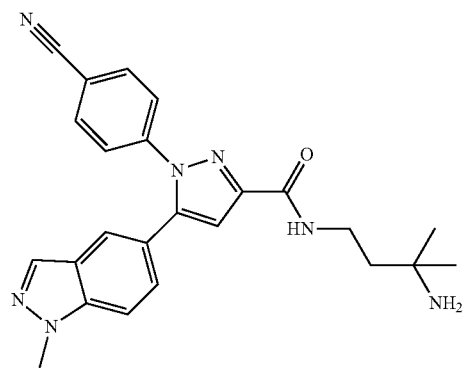 [SMILES: Cn1ncc2cc(-c3cc(C(=O)NCCC(C)(C)N)nn3-c3ccc(C#N)cc3)ccc21]

N-(3-amino-3-methylbutyl)-1-(4-
cyanophenyl)-5-(1-methylindazol-5-
yl)pyrazole-3-carboxamide

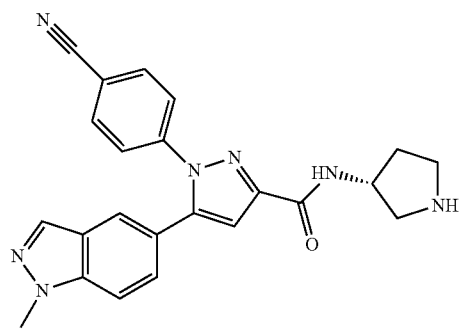 [SMILES: Cn1ncc2cc(-c3cc(C(=O)N[C@@H]4CCNC4)nn3-c3ccc(C#N)cc3)ccc21]

1-(4-cyanophenyl)-5-(1-methylindazole-5-
yl)-N-[(3R)-pyrrolidin-3-yl]pyrazole-3-
carboxamide

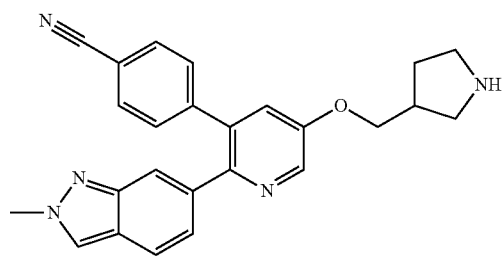 [SMILES: Cn1cc2ccc(-c3ncc(OCC4CCNC4)cc3-c3ccc(C#N)cc3)cc2n1]

4-(2-(2-methyl-2H-indazol-6-yl)-5-
(pyrrolidin-3-ylmethoxy)pyridin-3-
yl)benzonitrile

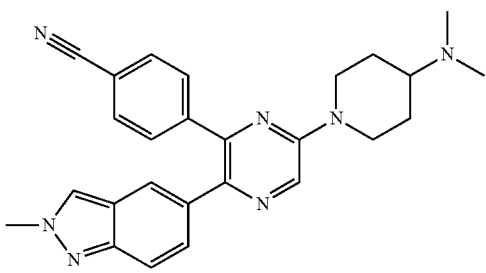

4-(6-(4-(dimethylamino)piperidin-1-yl)-3-
(2-methyl-2H-indazol-5-yl)pyrazin-2-
yl)benzonitrile

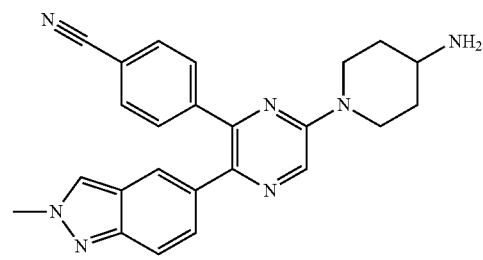 [SMILES: Cn1cc2cc(-c3ncc(N4CCC(N)CC4)nc3-c3ccc(C#N)cc3)ccc2n1]

4-(6-(4-aminopiperidin-1-yl)-3-(2-
methyl-2H-indazol-5-yl)pyrazin-2-
yl)benzonitrile

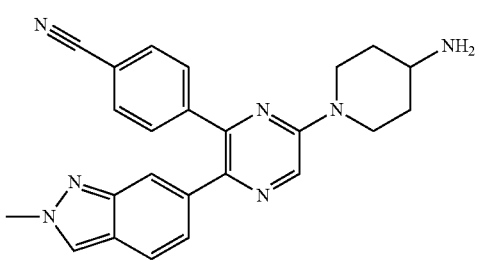 [SMILES: Cn1cc2ccc(-c3ncc(N4CCC(N)CC4)nc3-c3ccc(C#N)cc3)cc2n1]

4-(6-(4-aminopiperidin-1-yl)-3-(2-methyl-
2H-indazol-6-yl)pyrazin-2-yl)benzonitrile

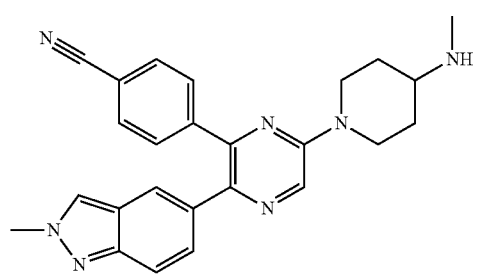

4-(3-(2-methyl-2H-indazol-5-yl)-6-(4-
(methylamino)piperidin-1-yl)pyrazin-2-
yl)benzonitrile TABLE 2-continued

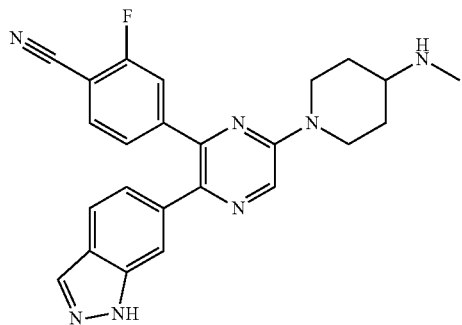 [SMILES: CNC1CCN(c2cnc(-c3ccc4cn[nH]c4c3)c(-c3ccc(C#N)c(F)c3)n2)CC1]

2-fluoro-4-[3-(1H-indazol-6-yl)-6-[4-(methylamino)piperidin-1-yl]pyrazin-2-yl]benzonitrile

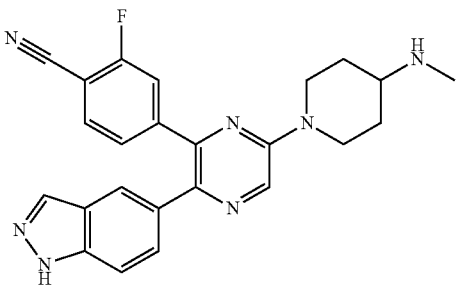 [SMILES: CNC1CCN(c2cnc(-c3ccc4[nH]ncc4c3)c(-c3ccc(C#N)c(F)c3)n2)CC1]

2-fluoro-4-[3-(1H-indazol-5-yl)-6-[4-(methylamino)piperidin-1-yl]pyrazin-2-yl]benzonitrile

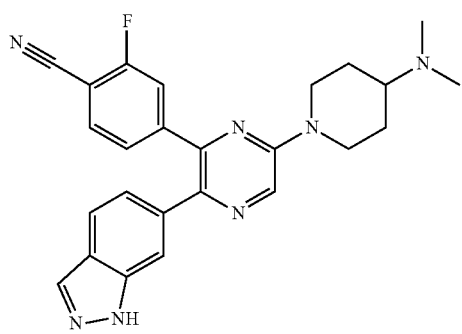 [SMILES: CN(C)C1CCN(c2cnc(-c3ccc4cn[nH]c4c3)c(-c3ccc(C#N)c(F)c3)n2)CC1]

4-{6-[4-(dimethylamino)piperidin-1-yl]-3-(1H-indazol-6-yl)pyrazin-2-yl}-2-fluorobenzonitrile

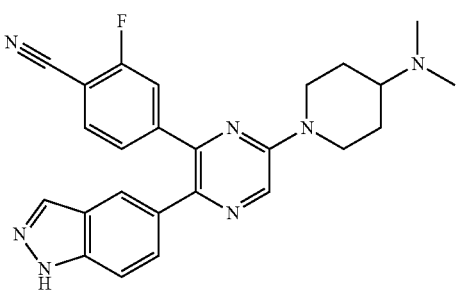 [SMILES: CN(C)C1CCN(c2cnc(-c3ccc4[nH]ncc4c3)c(-c3ccc(C#N)c(F)c3)n2)CC1]

4-{6-[4-(dimethylamino)piperidin-1-yl]-3-(1H-indazol-5-yl)pyrazin-2-yl}-2-fluorobenzonitrile

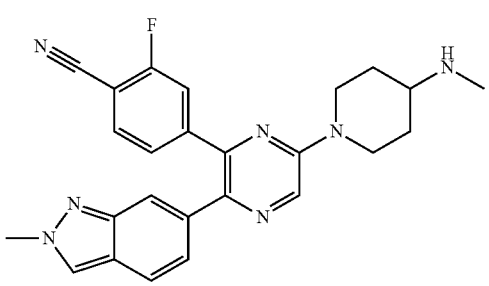

2-fluoro-4-(3-(2-methyl-2H-indazol-6-yl)-6-(4-(methylamino)piperidin-1-yl)pyrazin-2-yl)benzonitrile

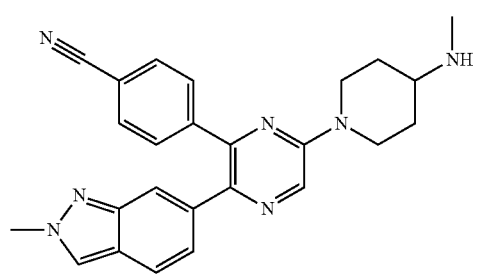

4-(3-(2-methyl-2H-indazol-6-yl)-6-(4-(methylamino)piperidin-1-yl)pyrazin-2-yl)benzonitrile

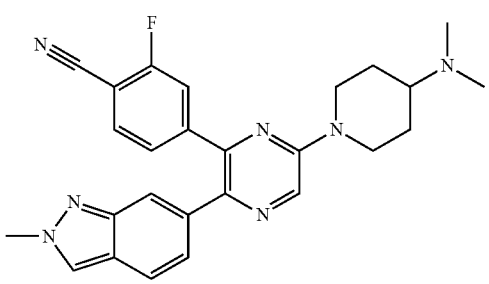

4-(6-(4-(dimethylamino)piperidin-1-yl)-3-(2-methyl-2H-indazol-6-yl)pyrazin-2-yl)-2-fluorobenzonitrile

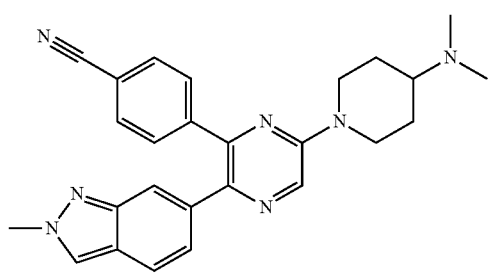

4-(6-(4-(dimethylamino)piperidin-1-yl)-3-(2-methyl-2H-indazol-6-yl)pyrazin-2-yl)benzonitrile TABLE 2-continued

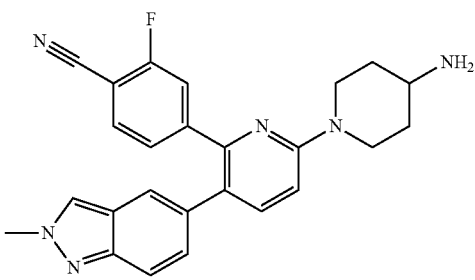

4-(6-(4-aminopiperidin-1-yl)-3-(2-methyl-
2H-indazol-5-yl)pyridin-2-yl)-2-
fluorobenzonitrile

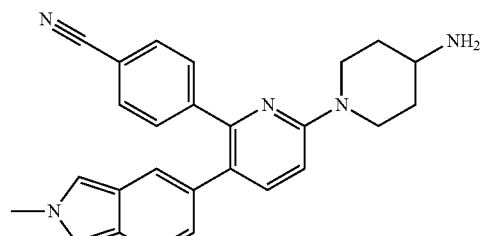

4-(6-(4-aminopiperidin-1-yl)-3-(2-
methyl-2H-indazol-5-yl)pyridin-2-
yl)benzonitrile

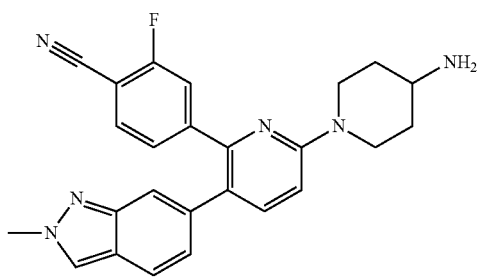 [SMILES: Cn1cc2cc(-c3ccc(N4CCC(N)CC4)nc3-c3ccc(C#N)c(F)c3)ccc2n1]

4-(6-(4-aminopiperidin-1-yl)-3-(2-methyl-
2H-indazol-6-yl)pyridin-2-yl)-2-
fluorobenzonitrile

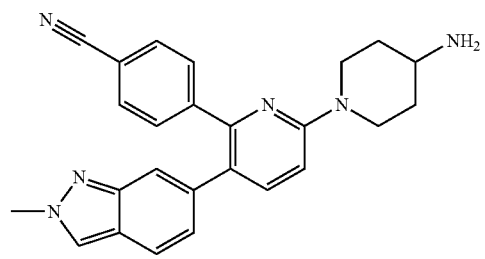 [SMILES: Cn1cc2ccc(-c3ccc(N4CCC(N)CC4)nc3-c3ccc(C#N)cc3)cc2n1]

4-(6-(4-aminopiperidin-1-yl)-3-(2-
methyl-2H-indazol-6-yl)pyridin-2-
yl)benzonitrile

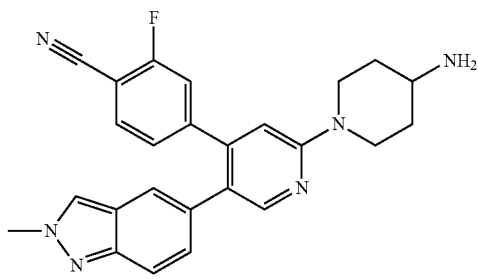 [SMILES: Cn1cc2cc(-c3cnc(N4CCC(N)CC4)cc3-c3ccc(C#N)c(F)c3)ccc2n1]

4-(2-(4-aminopiperidin-1-yl)-5-(2-methyl-
2H-indazol-5-yl)pyridin-4-yl)-2-
fluorobenzonitrile

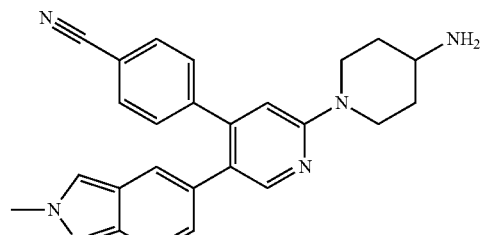

4-(2-(4-aminopiperidin-1-yl)-5-(2-
methyl-2H-indazol-5-yl)pyridin-4-
yl)benzonitrile

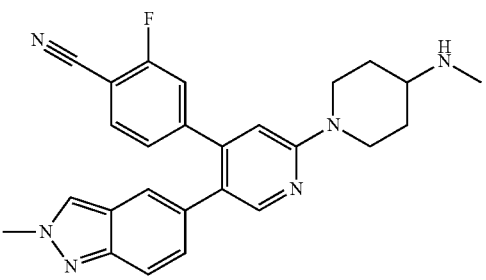

2-fluoro-4-(5-(2-methyl-2H-indazol-5-yl)-
2-(4-(methylamino)piperidin-1-yl)pyridin-
4-yl)benzonitrile

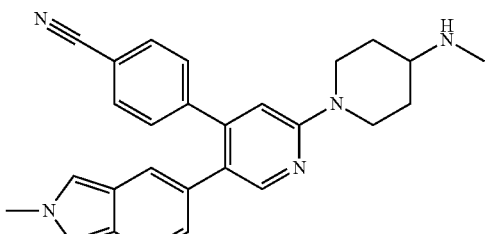

4-(5-(2-methyl-2H-indazol-5-yl)-2-(4-
(methylamino)piperidin-1-yl)pyridin-4-
yl)benzonitrile TABLE 2-continued

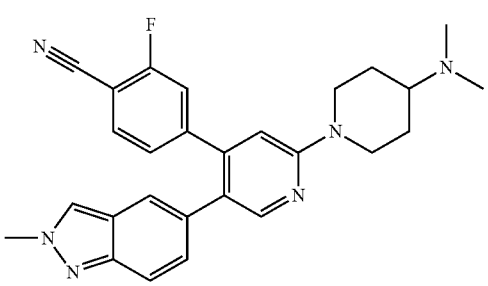

4-(2-(4-(dimethylamino)piperidin-1-yl)-5-
(2-methyl-2H-indazol-5-yl)pyridin-4-yl)-2-
fluorobenzonitrile

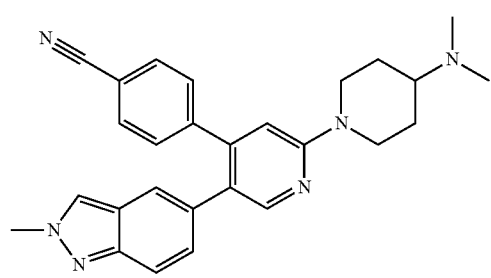

4-(2-(4-(dimethylamino)piperidin-1-yl)-
5-(2-methyl-2H-indazol-5-yl)pyridin-4-
yl)benzonitrile

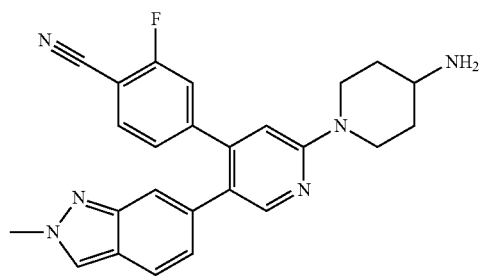 [SMILES: Cn1cc2ccc(-c3cnc(N4CCC(N)CC4)cc3-c3ccc(C#N)c(F)c3)cc2n1]

4-(2-(4-aminopiperidin-1-yl)-5-(2-methyl-
2H-indazol-6-yl)pyridin-4-yl)-2-
fluorobenzonitrile

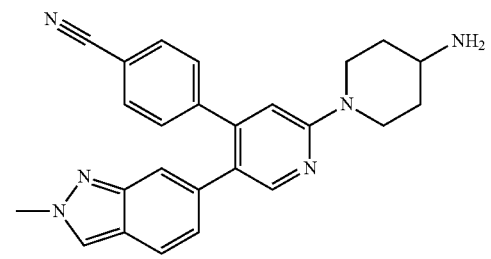 [SMILES: Cn1cc2ccc(-c3cnc(N4CCC(N)CC4)cc3-c3ccc(C#N)cc3)cc2n1]

4-(2-(4-aminopiperidin-1-yl)-5-(2-
methyl-2H-indazol-6-yl)pyridin-4-
yl)benzonitrile

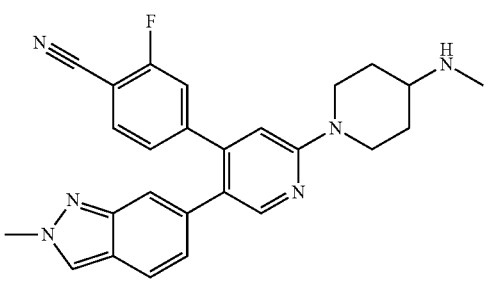

2-fluoro-4-(5-(2-methyl-2H-indazol-6-yl)-
2-(4-(methylamino)piperidin-1-yl)pyridin-
4-yl)benzonitrile

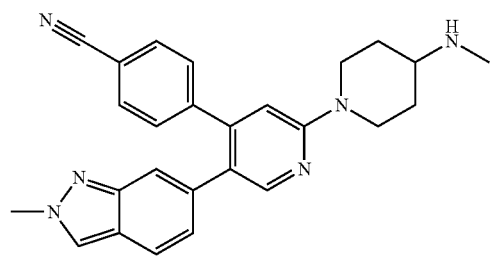

4-(5-(2-methyl-2H-indazol-6-yl)-2-(4-
(methylamino)piperidin-1-yl)pyridin-4-
yl)benzonitrile

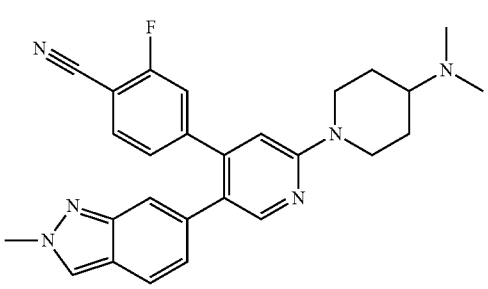

4-(2-(4-(dimethylamino)piperidin-1-yl)-5-
(2-methyl-2H-indazol-6-yl)pyridin-4-yl)-2-
fluorobenzonitrile

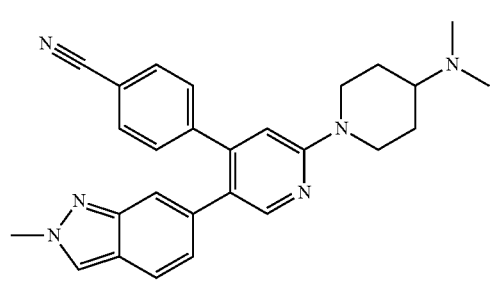

4-(2-(4-(dimethylamino)piperidin-1-yl)-
5-(2-methyl-2H-indazol-6-yl)pyridin-4-
yl)benzonitrile TABLE 2-continued

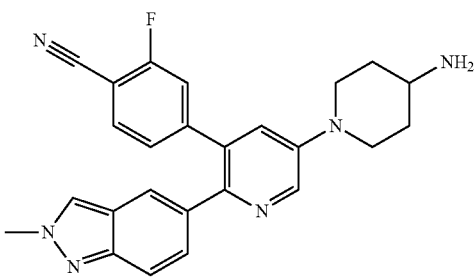 [SMILES: Cn1cc2cc(-c3ncc(N4CCC(N)CC4)cc3-c3ccc(C#N)c(F)c3)ccc2n1]

4-(5-(4-aminopiperidin-1-yl)-2-(2-methyl-
2H-indazol-5-yl)pyridin-3-yl)-2-
fluorobenzonitrile

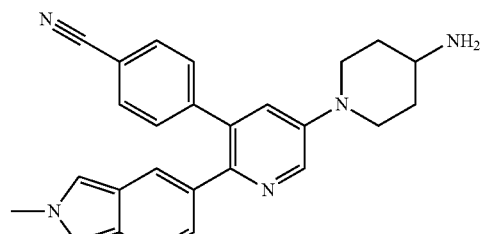

4-(5-(4-aminopiperidin-1-yl)-2-(2-
methyl-2H-indazol-5-yl)pyridin-3-
yl)benzonitrile

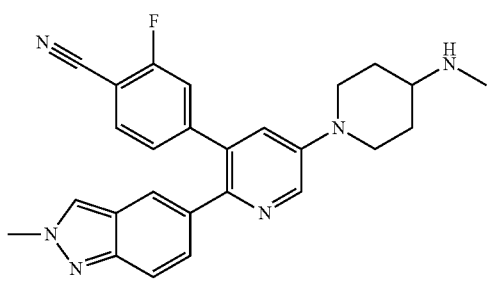

2-fluoro-4-(2-(2-methyl-2H-indazol-5-yl)-
5-(4-(methylamino)piperidin-1-yl)pyridin-
3-yl)benzonitrile

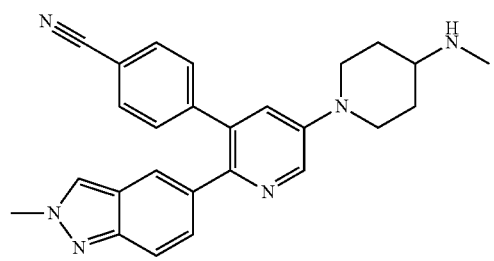

4-(2-(2-methyl-2H-indazol-5-yl)-5-(4-
(methylamino)piperidin-1-yl)pyridin-3-
yl)benzonitrile

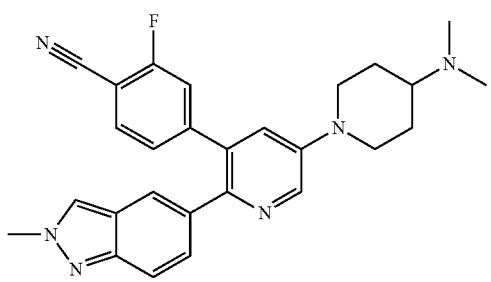

4-(5-(4-(dimethylamino)piperidin-1-yl)-2-
(2-methyl-2H-indazol-5-yl)pyridin-3-yl)-2-
fluorobenzonitrile

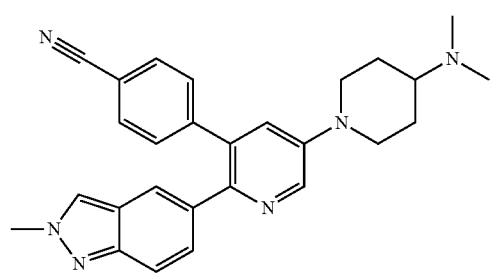

4-(5-(4-(dimethylamino)piperidin-1-yl)-
2-(2-methyl-2H-indazol-5-yl)pyridin-3-
yl)benzonitrile

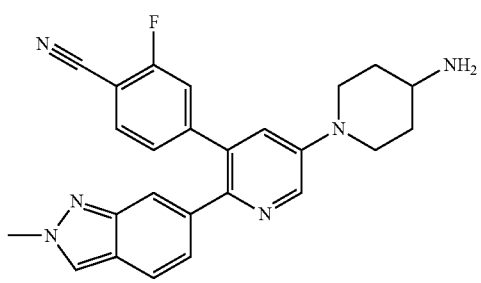 [SMILES: Cn1cc2ccc(-c3ncc(N4CCC(N)CC4)cc3-c3ccc(C#N)c(F)c3)cc2n1]

4-(5-(4-aminopiperidin-1-yl)-2-(2-methyl-
2H-indazol-6-yl)pyridin-3-yl)-2-
fluorobenzonitrile

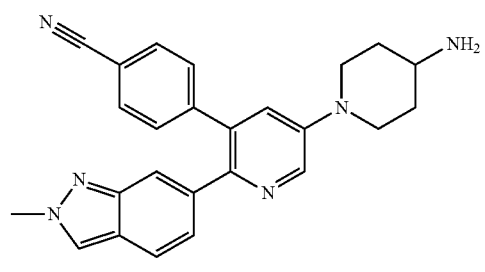

4-(5-(4-aminopiperidin-1-yl)-2-(2-
methyl-2H-indazol-6-yl)pyridin-3-
yl)benzonitrile TABLE 2-continued

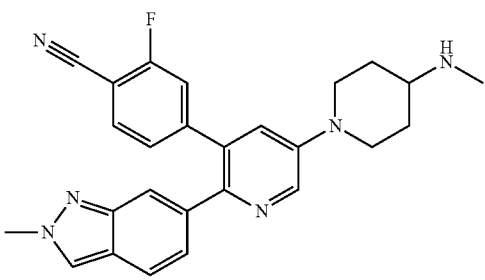

2-fluoro-4-(2-(2-methyl-2H-indazol-6-yl)-
5-(4-(methylamino)piperidin-1-yl)pyridin-
3-yl)benzonitrile

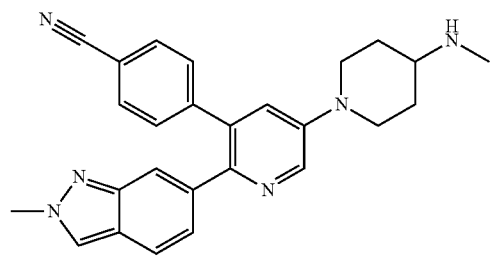

4-(2-(2-methyl-2H-indazol-6-yl)-5-(4-
(methylamino)piperidin-1-yl)pyridin-3-
yl)benzonitrile

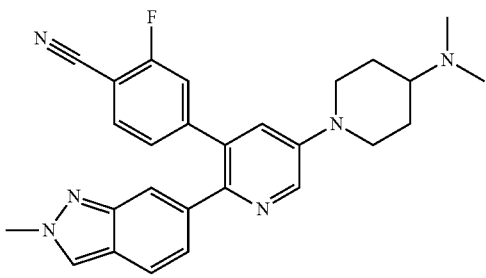

4-(5-(4-(dimethylamino)piperidin-1-yl)-2-
(2-methyl-2H-indazol-6-yl)pyridin-3-yl)-2-
fluorobenzonitrile

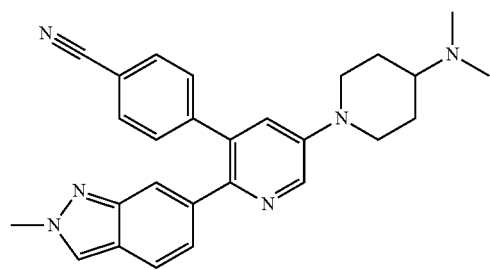

4-(5-(4-(dimethylamino)piperidin-1-yl)-
2-(2-methyl-2H-indazol-6-yl)pyridin-3-
yl)benzonitrile

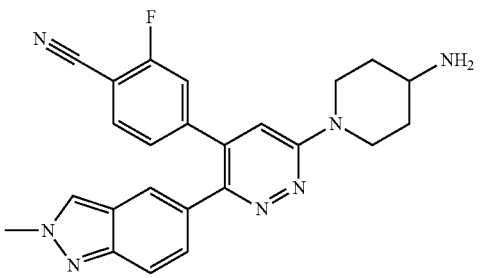 [SMILES: Cn1cc2cc(-c3nnc(N4CCC(N)CC4)cc3-c3ccc(C#N)c(F)c3)ccc2n1]

4-(6-(4-aminopiperidin-1-yl)-3-(2-methyl-
2H-indazol-5-yl)pyridazin-4-yl)-2-
fluorobenzonitrile

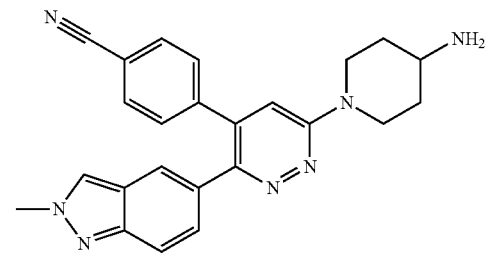

4-(6-(4-aminopiperidin-1-yl)-3-(2-
methyl-2H-indazol-5-yl)pyridazin-4-
yl)benzonitrile

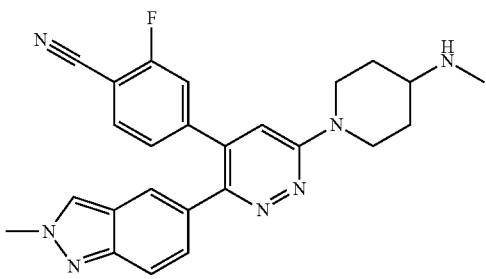

2-fluoro-4-(3-(2-methyl-2H-indazol-5-yl)-
6-(4-(methylamino)piperidin-1-
yl)pyridazin-4-yl)benzonitrile

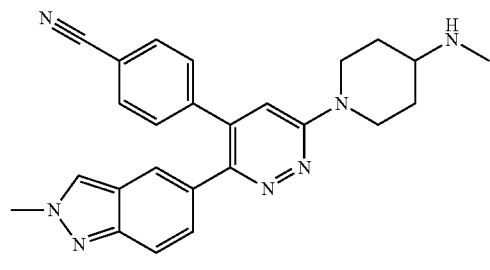

4-(3-(2-methyl-2H-indazol-5-yl)-6-(4-
(methylamino)piperidin-1-yl)pyridazin-
4-yl)benzonitrile TABLE 2-continued

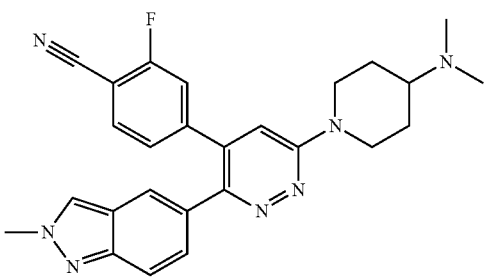

4-(6-(4-(dimethylamino)piperidin-1-yl)-3-
(2-methyl-2H-indazol-5-yl)pyridazin-4-yl)-
2-fluorobenzonitrile

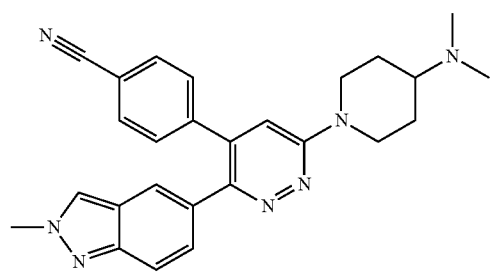

4-(6-(4-(dimethylamino)piperidin-1-yl)-
3-(2-methyl-2H-indazol-5-yl)pyridazin-
4-yl)benzonitrile

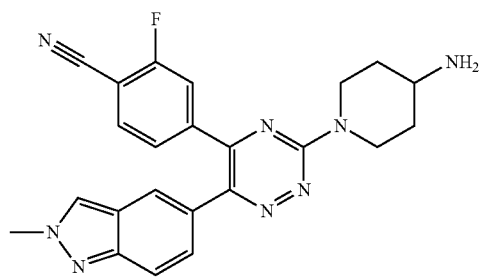 [SMILES: Cn1cc2cc(-c3nnc(N4CCC(N)CC4)nc3-c3ccc(C#N)c(F)c3)ccc2n1]

4-(3-(4-aminopiperidin-1-yl)-6-(2-methyl-
2H-indazol-5-yl)-1,2,4-triazin-5-yl)-2-
fluorobenzonitrile

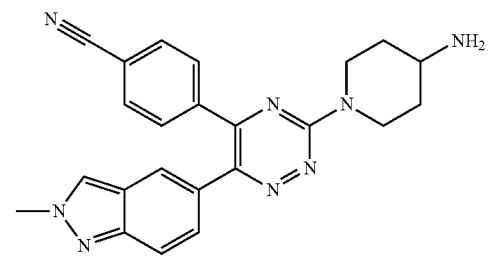

4-(3-(4-aminopiperidin-1-yl)-6-(2-
methyl-2H-indazol-5-yl)-1,2,4-triazin-5-
yl)benzonitrile

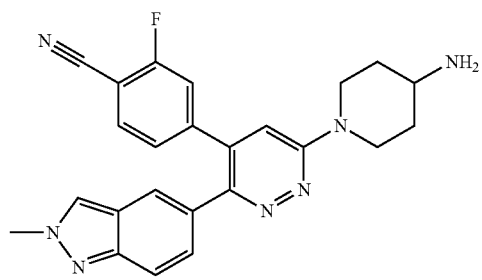 [SMILES: Cn1cc2cc(-c3nnc(N4CCC(N)CC4)cc3-c3ccc(C#N)c(F)c3)ccc2n1]

4-(6-(4-aminopiperidin-1-yl)-3-(2-methyl-
2H-indazol-5-yl)pyridazin-4-yl)-2-
fluorobenzonitrile

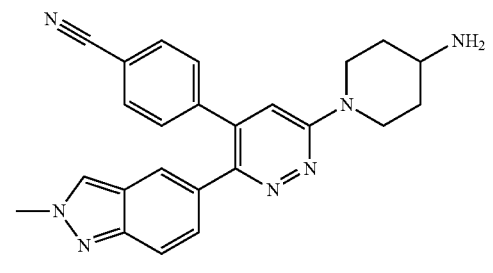

4-(6-(4-aminopiperidin-1-yl)-3-(2-
methyl-2H-indazol-5-yl)pyridazin-4-
yl)benzonitrile

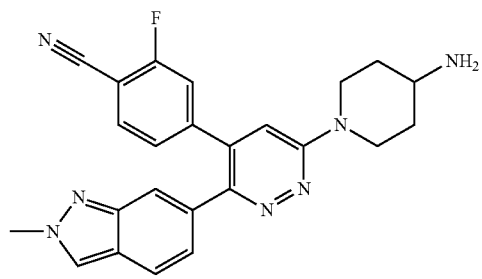 [SMILES: Cn1cc2ccc(-c3nnc(N4CCC(N)CC4)cc3-c3ccc(C#N)c(F)c3)cc2n1]

4-(6-(4-aminopiperidin-1-yl)-3-(2-methyl-
2H-indazol-6-yl)pyridazin-4-yl)-2-
fluorobenzonitrile

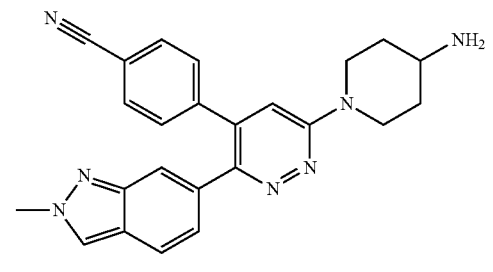

4-(6-(4-aminopiperidin-1-yl)-3-(2-
methyl-2H-indazol-6-yl)pyridazin-4-
yl)benzonitrile TABLE 2-continued

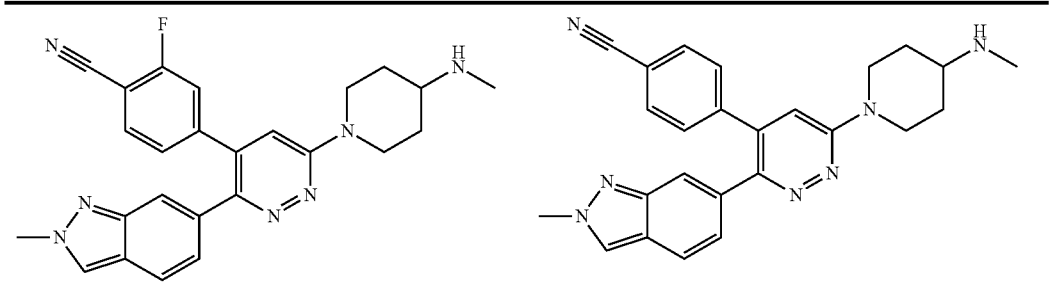

2-fluoro-4-(3-(2-methyl-2H-indazol-6-yl)-
6-(4-(methylamino)piperidin-1-
yl)pyridazin-4-yl)benzonitrile

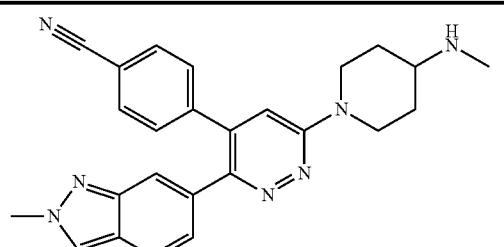

4-(3-(2-methyl-2H-indazol-6-yl)-6-(4-
(methylamino)piperidin-1-yl)pyridazin-
4-yl)benzonitrile

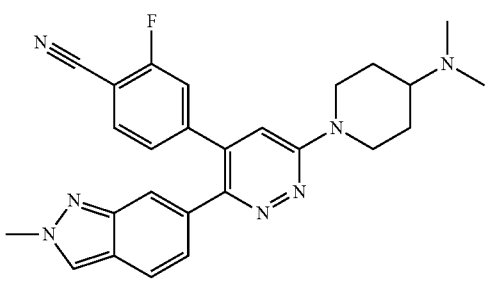

4-(6-(4-(dimethylamino)piperidin-1-yl)-3-
(2-methyl-2H-indazol-6-yl)pyridazin-4-yl)-
2-fluorobenzonitrile

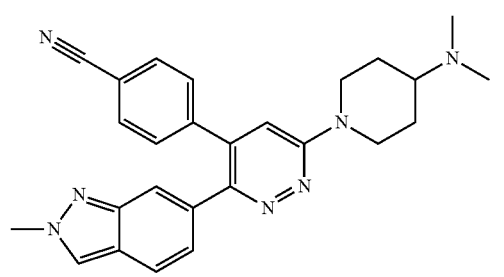

4-(6-(4-(dimethylamino)piperidin-1-yl)-
3-(2-methyl-2H-indazol-6-yl)pyridazin-
4-yl)benzonitrile

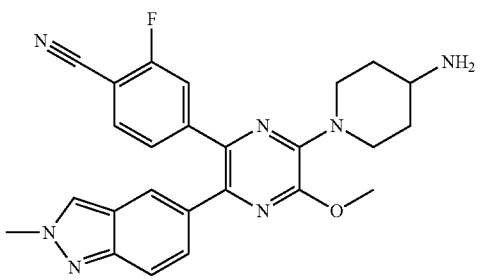 [SMILES: COc1nc(-c2ccc3nn(C)cc3c2)c(-c2ccc(C#N)c(F)c2)nc1N1CCC(N)CC1]

4-(6-(4-aminopiperidin-1-yl)-5-methoxy-3-
(2-methyl-2H-indazol-5-yl)pyrazin-2-yl)-
2-fluorobenzonitrile

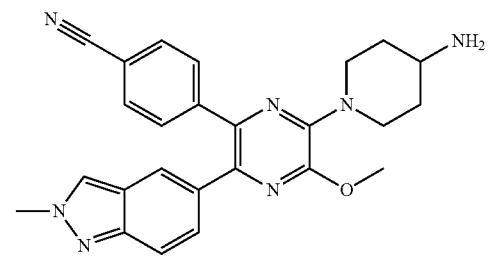 [SMILES: COc1nc(-c2ccc3nn(C)cc3c2)c(-c2ccc(C#N)cc2)nc1N1CCC(N)CC1]

4-(6-(4-aminopiperidin-1-yl)-5-methoxy-
3-(2-methyl-2H-indazol-5-yl)pyrazin-2-
yl)benzonitrile

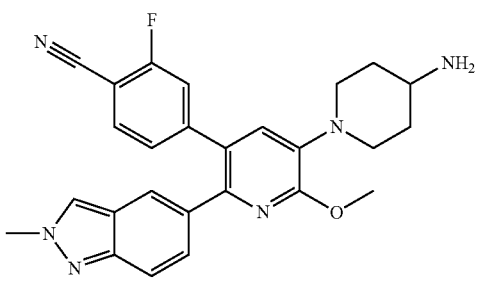 [SMILES: COc1nc(-c2ccc3nn(C)cc3c2)c(-c2ccc(C#N)c(F)c2)cc1N1CCC(N)CC1]

4-(5-(4-aminopiperidin-1-yl)-6-methoxy-2-
(2-methyl-2H-indazol-5-yl)pyridin-3-yl)-2-
fluorobenzonitrile

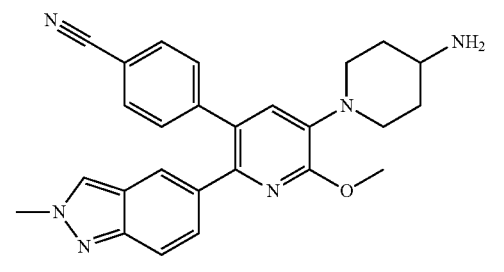 [SMILES: COc1nc(-c2ccc3nn(C)cc3c2)c(-c2ccc(C#N)cc2)cc1N1CCC(N)CC1]

4-(5-(4-aminopiperidin-1-yl)-6-methoxy-
2-(2-methyl-2H-indaozl-5-yl)pyridin-3-
yl)benzonitrile TABLE 2-continued

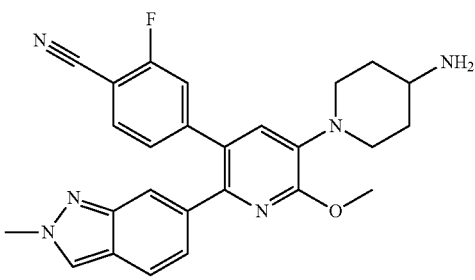 [SMILES: COc1nc(-c2ccc3cn(C)nc3c2)c(-c2ccc(C#N)c(F)c2)cc1N1CCC(N)CC1]

4-(5-(4-aminopiperidin-1-yl)-6-methoxy-2-
(2-methyl-2H-indazol-6-yl)pyridin-3-yl)-2-
fluorobenzonitrile

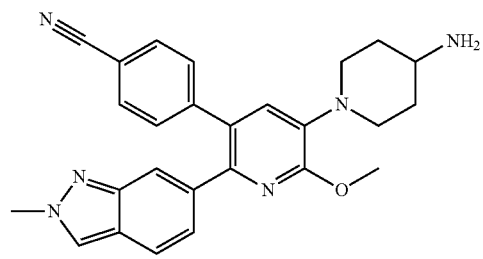 [SMILES: COc1nc(-c2ccc3cn(C)nc3c2)c(-c2ccc(C#N)cc2)cc1N1CCC(N)CC1]

4-(5-(4-aminopiperidin-1-yl)-6-methoxy-
2-(2-methyl-2H-indazol-6-yl)pyridin-3-
yl)benzonitrile

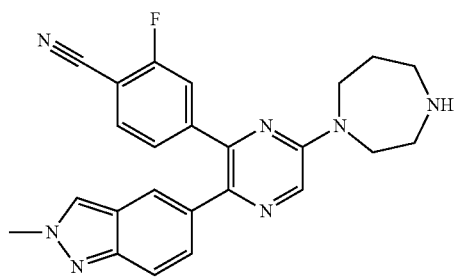 [SMILES: Cn1cc2cc(-c3ncc(N4CCCNCC4)nc3-c3ccc(C#N)c(F)c3)ccc2n1]

4-(6-(1,4-diazepan-1-yl)-3-(2-methyl-2H-
indazol-5-yl)pyrazin-2-yl)-2-
fluorobenzonitrile

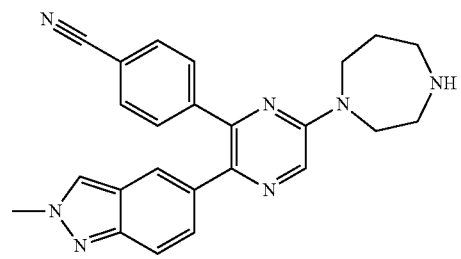 [SMILES: Cn1cc2cc(-c3ncc(N4CCCNCC4)nc3-c3ccc(C#N)cc3)ccc2n1]

4-(6-(1,4-diazepan-1-yl)-3-(2-methyl-
2H-indazol-5-yl)pyrazin-2-
yl)benzonitrile

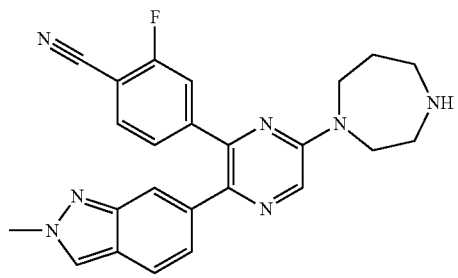 [SMILES: Cn1cc2ccc(-c3ncc(N4CCCNCC4)nc3-c3ccc(C#N)c(F)c3)cc2n1]

4-(6-(1,4-diazepan-1-yl)-3-(2-methyl-2H-
indazol-6-yl)pyrazin-2-yl)-2-
fluorobenzonitrile

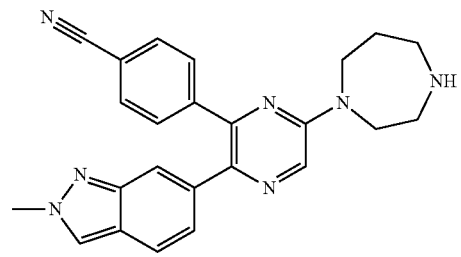 [SMILES: Cn1cc2ccc(-c3ncc(N4CCCNCC4)nc3-c3ccc(C#N)cc3)cc2n1]

4-(6-(1,4-diazepan-1-yl)-3-(2-methyl-
2H-indazol-6-yl)pyrazin-2-
yl)benzonitrile

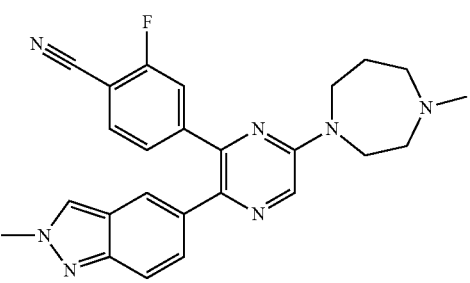

2-fluoro-4-(6-(4-methyl-1,4-diazepan-1-
yl)-3-(2-methyl-2H-indazol-5-yl)pyrazin-
2-yl)benzonitrile

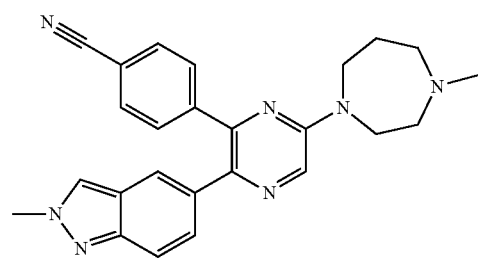

4-(6-(4-methyl-1,4-diazepan-1-yl)-3-(2-
methyl-2H-indazol-5-yl)pyrazin-2-
yl)benzonitrile TABLE 2-continued

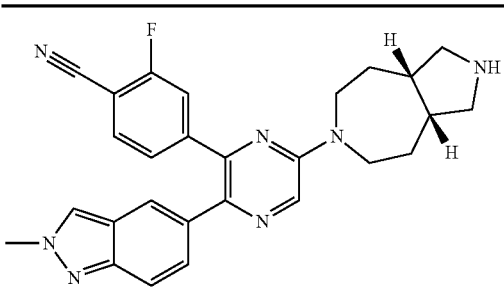

2-fluoro-4-(3-(2-methyl-2H-indazol-5-yl)-
6-((3aR,8aS)-octahydropyrrolo[3,4-
d]azepin-6(7H)-yl)pyrazin-2-
yl)benzonitrile

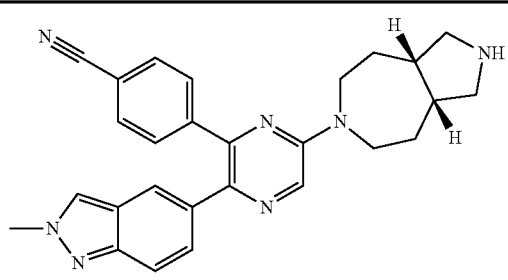

4-(3-(2-methyl-2H-indazol-5-yl)-6-
((3aR,8aS)-octahydropyrrolo[3,4-
d]azepin-6(7H)-yl)pyrazin-2-
yl)benzonitrile

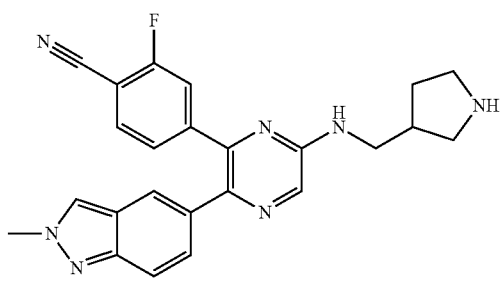 [SMILES: Cn1cc2cc(-c3ncc(NCC4CCNC4)nc3-c3ccc(C#N)c(F)c3)ccc2n1]

2-fluoro-4-(3-(2-methyl-2H-indazol-5-yl)-
6-(pyrrolidin-4-ylmethylamino)pyrazin-2-
yl)benzonitrile

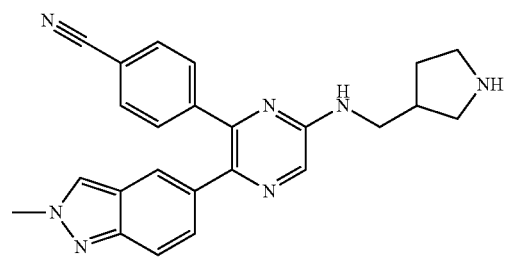 [SMILES: Cn1cc2cc(-c3ncc(NCC4CCNC4)nc3-c3ccc(C#N)cc3)ccc2n1]

4-(3-(2-methyl-2H-indazol-5-yl)-6-
(pyrrolidin-3-ylmethylamino)pyrazin-2-
yl)benzonitrile

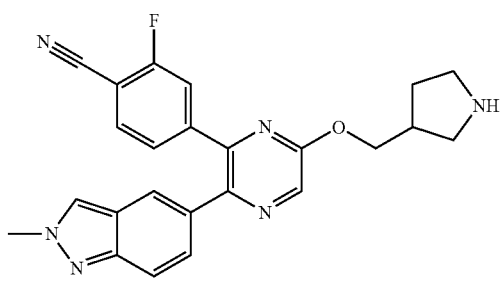

2-fluoro-4-(3-(2-methyl-2H-indazol-5-yl)-
6-(pyrrolidin-3-ylmethoxy)pyrazin-2-
yl)benzonitrile

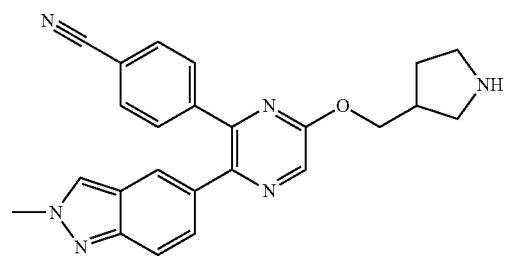 [SMILES: Cn1cc2cc(-c3ncc(OCC4CCNC4)nc3-c3ccc(C#N)cc3)ccc2n1]

4-(3-(2-methyl-2H-indazol-5-yl)-6-
(pyrrolidin-3-ylmethoxy)pyrazin-2-
yl)benzonitrile

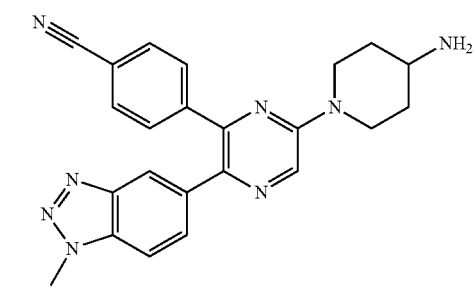 [SMILES: Cn1nnc2cc(-c3ncc(N4CCC(N)CC4)nc3-c3ccc(C#N)cc3)ccc21]

4-(6-(4-aminopiperidin-1-yl)-3-(1-methyl-
1H-benzo[d][1,2,3]triazol-5-yl)pyrazin-2-
yl)benzonitrile

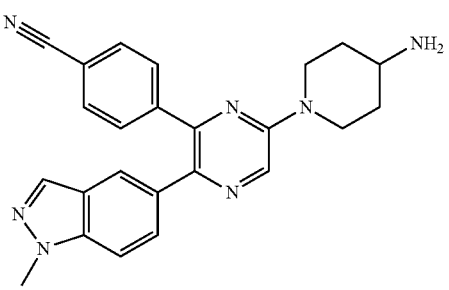 [SMILES: Cn1ncc2cc(-c3ncc(N4CCC(N)CC4)nc3-c3ccc(C#N)cc3)ccc21]

4-(6-(4-aminopiperidin-1-yl)-3-(1-
methyl-1H-indazol-5-yl)pyrazin-2-
yl)benzonitrile TABLE 2-continued

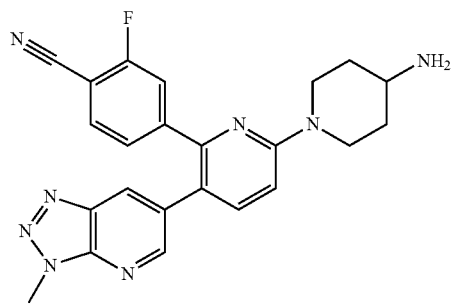

4-(6-(4-aminopiperidin-1-yl)-3-(3-methyl-
3H-[1,2,3]triazolo[4,5-b]pyridin-6-
yl)pyridin-2-yl)-2-fluorobenzonitrile

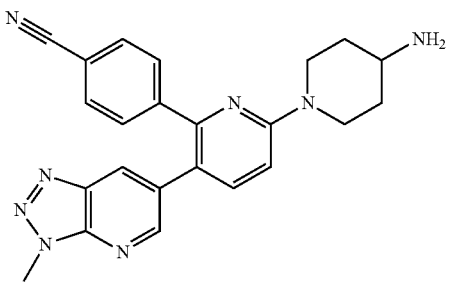 [SMILES: Cn1nnc2cc(-c3ccc(N4CCC(N)CC4)nc3-c3ccc(C#N)cc3)cnc21]

4-(6-(4-aminopiperidin-1-yl)-3-(3-
methyl-3H-[1,2,3]triazolo[4,5-b]pyridin-
6-yl)pyridin-2-yl)-2-fluorobenzonitrile

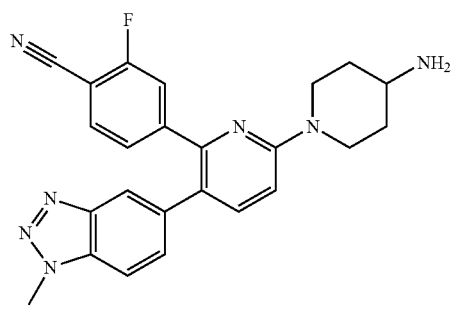

4-(6-(4-aminopiperidin-1-yl)-3-(1-methyl-
1H-benzo[d][1,2,3]triazol-5-yl)pyridin-2-
yl)-2-fluorobenzonitrile

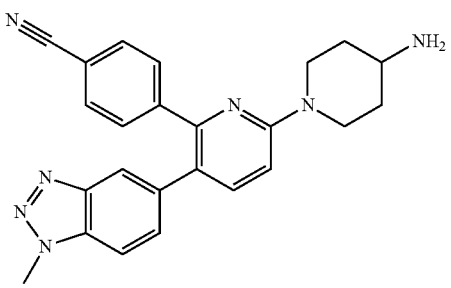 [SMILES: Cn1nnc2cc(-c3ccc(N4CCC(N)CC4)nc3-c3ccc(C#N)cc3)ccc21]

4-(6-(4-aminopiperidin-1-yl)-3-(1-
methyl-1H-benzo[d][1,2,3]triazol-5-
yl)pyridin-2-yl)benzonitrile

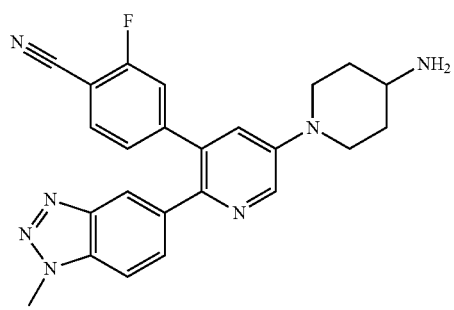

4-(5-(4-aminopiperidin-1-yl)-2-(1-methyl-
1H-benzo[d][1,2,3]triazol-5-yl)pyridin-3-
yl)-2-fluorobenzonitrile

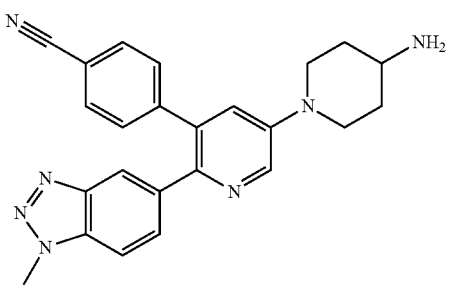 [SMILES: Cn1nnc2cc(-c3ncc(N4CCC(N)CC4)cc3-c3ccc(C#N)cc3)ccc21]

4-(5-(4-aminopiperidin-1-yl)-2-(1-
methyl-1H-benzo[d][1,2,3]triazol-5-
yl)pyridin-3-yl)benzonitrile

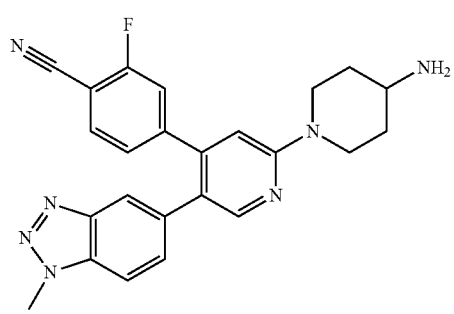 [SMILES: Cn1nnc2cc(-c3cnc(N4CCC(N)CC4)cc3-c3ccc(C#N)c(F)c3)ccc21]

4-(2-(4-aminopiperidin-1-yl)-5-(1-methyl-
1H-benzo[d][1,2,3]triazol-5-yl)pyridin-4-
yl)-2-fluorobenzonitrile

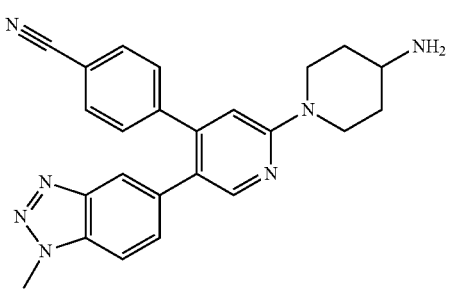 [SMILES: Cn1nnc2cc(-c3cnc(N4CCC(N)CC4)cc3-c3ccc(C#N)cc3)ccc21]

4-(2-(4-aminopiperidin-1-yl)-5-(1-
methyl-1H-benzo[d][1,2,3]triazol-5-
yl)pyridin-4-yl)benzonitrile TABLE 2-continued

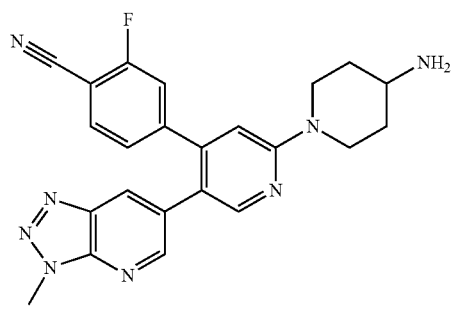 [SMILES: Cn1nnc2cc(-c3cnc(N4CCC(N)CC4)cc3-c3ccc(C#N)c(F)c3)cnc21]

4-(2-(4-aminopiperidin-1-yl)-5-(3-methyl-
3H-[1,2,3]triazolo[4,5-b]pyridin-6-
yl)pyridin-4-yl)-2-fluorobenzonitrile

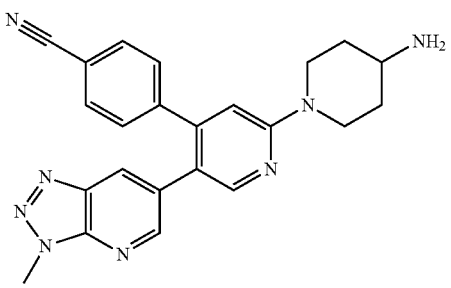 [SMILES: Cn1nnc2cc(-c3cnc(N4CCC(N)CC4)cc3-c3ccc(C#N)cc3)cnc21]

4-(2-(4-aminopiperidin-1-yl)-5-(3-
methyl-3H[1,2,3]triazolo[4,5-b]pyridin-
6-yl)pyridin-4-yl)benzonitrile

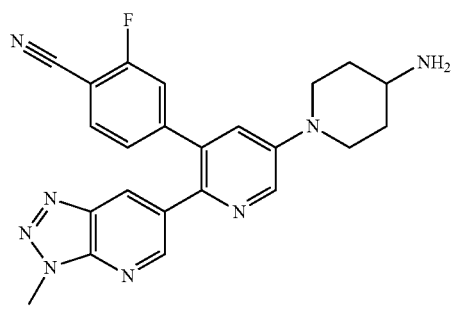

4-(5-(4-aminopiperidin-1-yl)-2-(3-methyl-
3H-[1,2,3]triazolo[4,5-b]pyridin-6-
yl)pyridin-3-yl)-2-fluorobenzonitrile

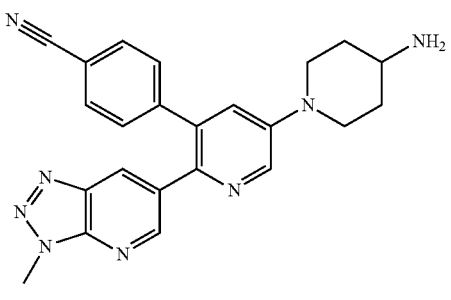 [SMILES: Cn1nnc2cc(-c3ncc(N4CCC(N)CC4)cc3-c3ccc(C#N)cc3)cnc21]

4-(5-(4-aminopiperidin-1-yl)-2-(3-
methyl-3H-[1,2,3]triazolo[4,5-b]pyridin-
6-yl)pyridin-3-yl)benzonitrile

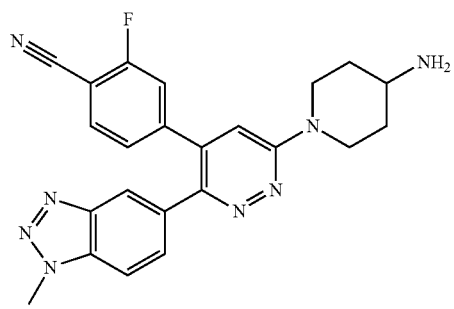

4-(6-(4-aminopiperidin-1-yl)-3-(1-methyl-
1H-benzo[d][1,2,3]triazol-5-yl)pyridazin-
4-yl)-2-fluorobenzonitrile

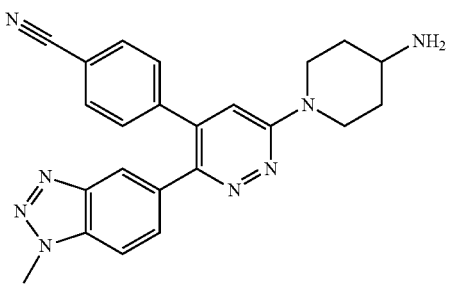 [SMILES: Cn1nnc2cc(-c3nnc(N4CCC(N)CC4)cc3-c3ccc(C#N)cc3)ccc21]

4-(6-(4-aminopiperidin-1-yl)-3-(1-
methyl-1H-benzo[d][1,2,3]triazol-5-
yl)pyridazin-4-yl)benzonitrile

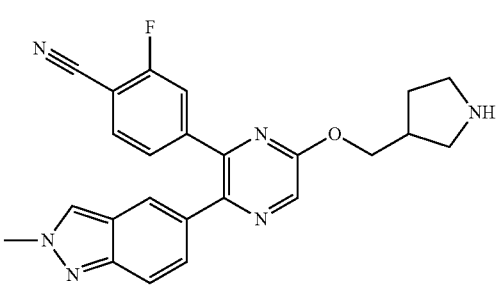 [SMILES: Cn1cc2cc(-c3ncc(OCC4CCNC4)nc3-c3ccc(C#N)c(F)c3)ccc2n1]

2-fluoro-4-(3-(2-methyl-2H-indazol-5-yl)-
6-(pyrrolidin-3-ylmethoxy)pyrazin-2-
yl)benzonitrile

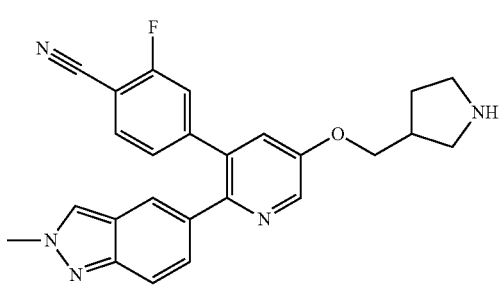 [SMILES: Cn1cc2cc(-c3ncc(OCC4CCNC4)cc3-c3ccc(C#N)c(F)c3)ccc2n1]

2-fluoro-4-(2-(2-methyl-2H-indazol-5-
yl)-5-(pyrrolidin-3-ylmethoxy)pyridin-3-
yl)benzonitrile TABLE 2-continued

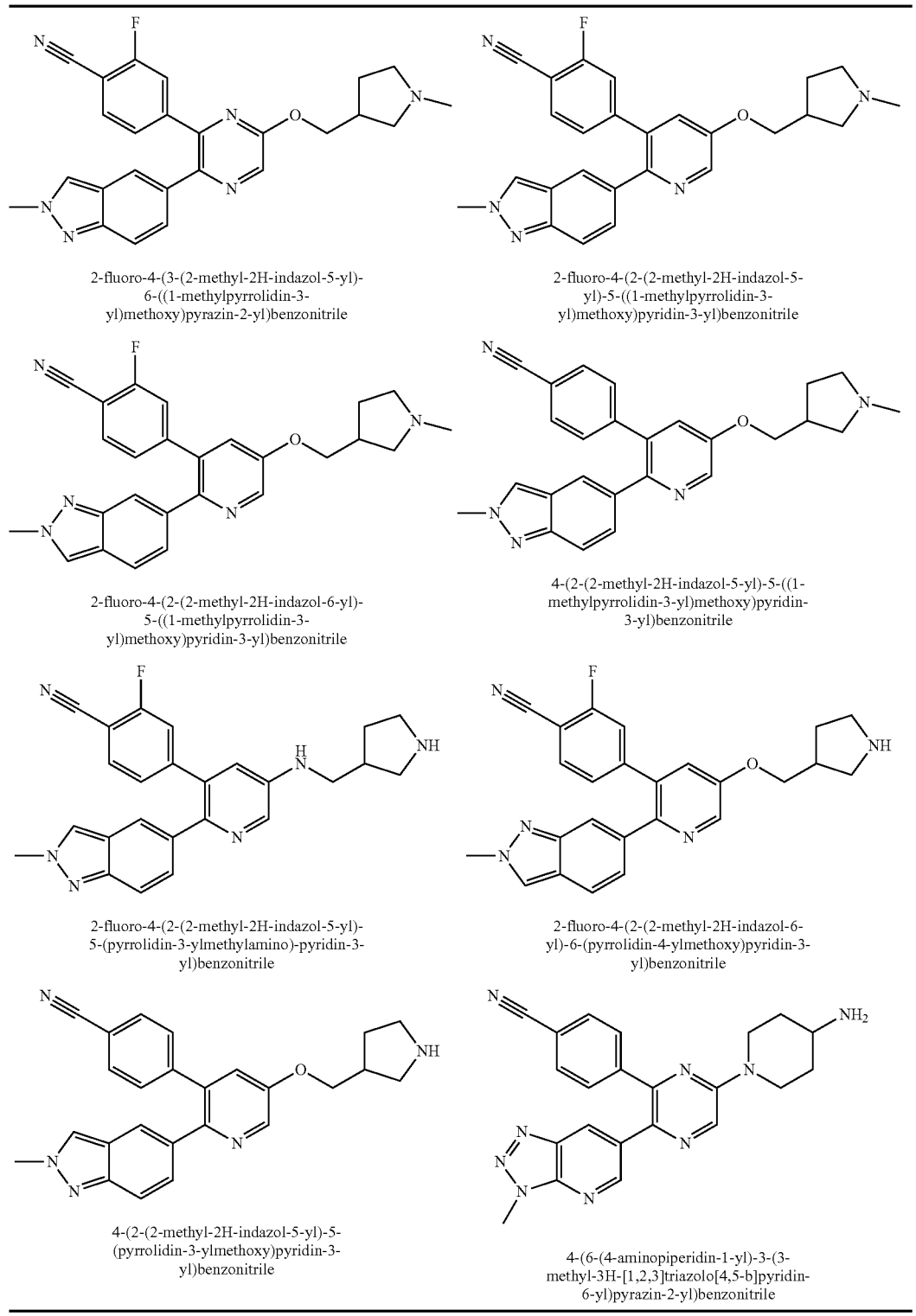

2-fluoro-4-(3-(2-methyl-2H-indazol-5-yl)-6-((1-methylpyrrolidin-3-yl)methoxy)pyrazin-2-yl)benzonitrile 2-fluoro-4-(2-(2-methyl-2H-indazol-5-yl)-5-((1-methylpyrrolidin-3-yl)methoxy)pyridin-3-yl)benzonitrile 2-fluoro-4-(2-(2-methyl-2H-indazol-6-yl)-5-((1-methylpyrrolidin-3-yl)methoxy)pyridin-3-yl)benzonitrile 4-(2-(2-methyl-2H-indazol-5-yl)-5-((1-methylpyrrolidin-3-yl)methoxy)pyridin-3-yl)benzonitrile 2-fluoro-4-(2-(2-methyl-2H-indazol-5-yl)-5-(pyrrolidin-3-ylmethylamino)-pyridin-3-yl)benzonitrile 2-fluoro-4-(2-(2-methyl-2H-indazol-6-yl)-6-(pyrrolidin-4-ylmethoxy)pyridin-3-yl)benzonitrile 4-(2-(2-methyl-2H-indazol-5-yl)-5-(pyrrolidin-3-ylmethoxy)pyridin-3-yl)benzonitrile 4-(6-(4-aminopiperidin-1-yl)-3-(3-methyl-3H-[1,2,3]triazolo[4,5-b]pyridin-6-yl)pyrazin-2-yl)benzonitrile Preparation of the Substituted Heterocyclic Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is P. H. Stahl & C. G. Wermuth "Handbook of Pharmaceutical Salts", Verlag Helvetica Chimica Acta, Zurich, 2002.

The substituted heterocyclic derivative compounds are prepared by the general synthetic routes described below in Schemes 1-6.

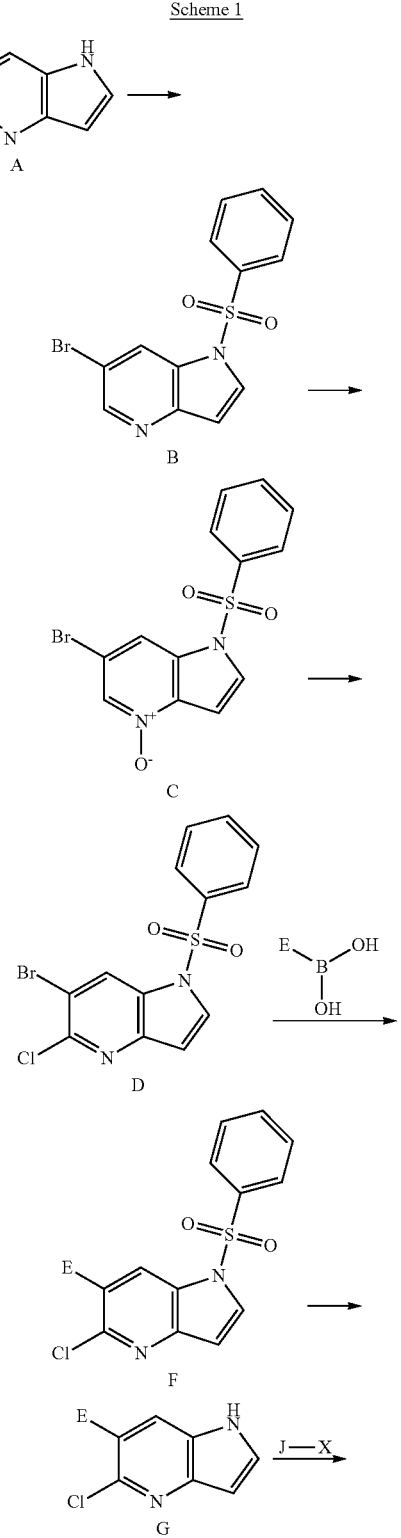

Scheme 1

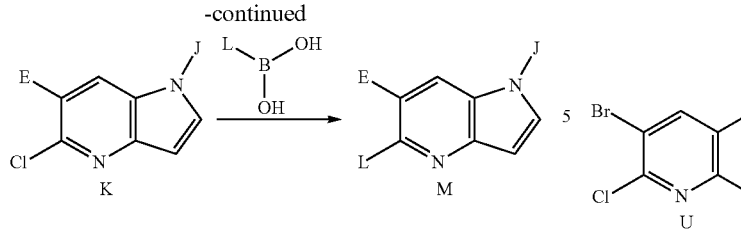

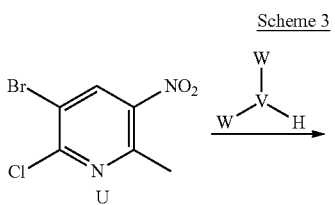

Scheme 3

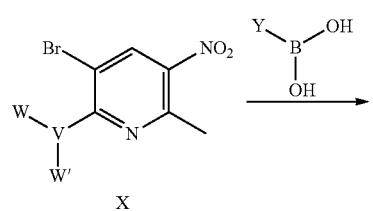

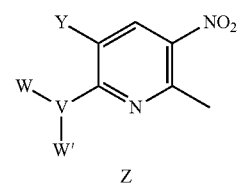

Referring to Scheme 1, Compound A is protected through the use of phenyl sulphonyl group. Compound B is oxidized and chlorinated to produce compound D. For example, chlorination can occur through the formation of the pyridine N-oxide compound C followed by treatment with an appropriate chlorinating agent, such as $POCl_3$. Compound D is converted to compound F via a palladium-mediated cross coupling reaction with a suitable coupling partner, such as boronic acid $E-B(OH)_2$. Compound F is selectively deprotected under basic conditions to form compound G. Alkylation of compound G is carried out with alkyl halides under basic conditions to form compound K. Compound K is subjected to a palladium-mediated cross coupling reaction with a suitable coupling partner, such as boronic acid $L-B(OH)_2$, to give compound M.

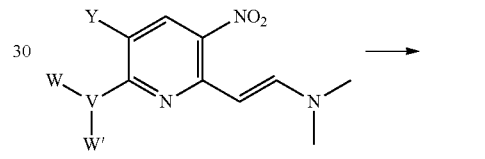

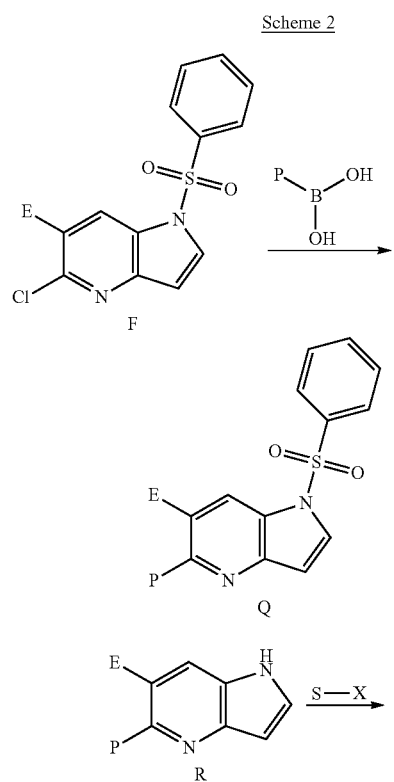

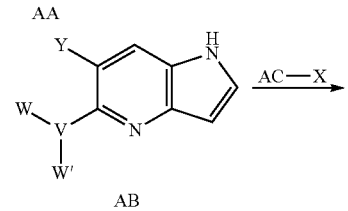

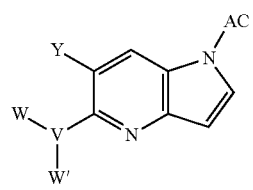

Referring to Scheme 2, Compound F is converted to compound Q via a palladium-mediated cross coupling reaction with a suitable coupling partner, such as boronic acid $P—B(OH)_2$. Compound Q is deprotected under basic hydrolysis conditions to form compound R. Alkylation of compound R is carried out with an alkyl halide under basic conditions to form compound T.

Referring to Scheme 3, nucleophilic substitution upon chloride compound U is carried out with a nucleophile, WW'—VH, such as amines WW'—NH, or alcohols W—OH, under basic conditions to form compound X. For example, compound U can be treated with DIEA and amines WW'—NH. The biaryl compound Z is prepared from aryl halide compound X via a palladium-mediated cross coupling reaction with a suitable coupling partner, such as boronic acid Y—$B(OH)_2$. Compound Z is converted to compound AA by condensation with N,N-dimethylformamide dimethyl acetal. Compound AB is obtained from compound AA by reduction of the nitro group and cyclocondensation to form the indole ring system. Alkylation of compound AB is carried out with an alkyl halide AC-X under basic conditions to form compound AD.

Scheme 4

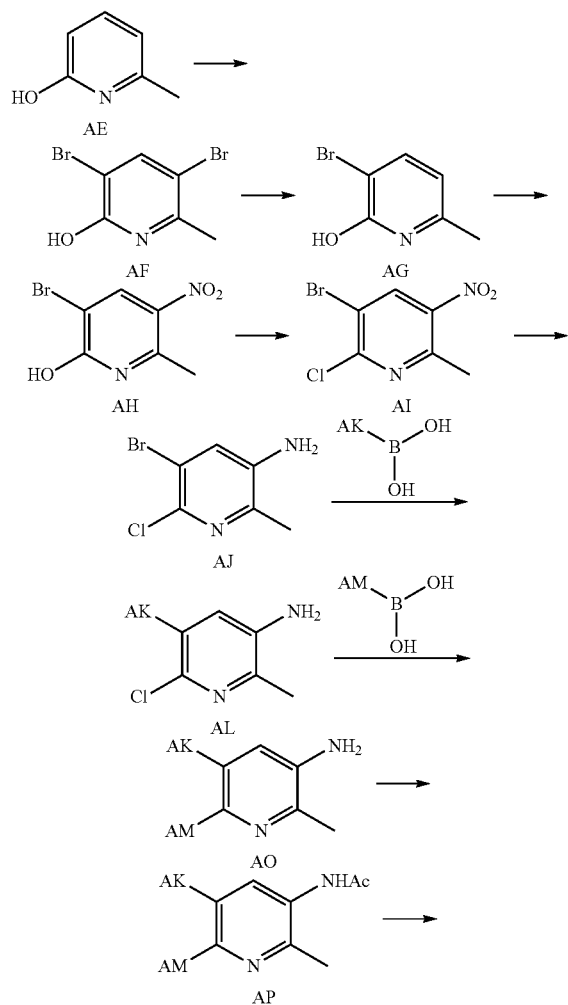

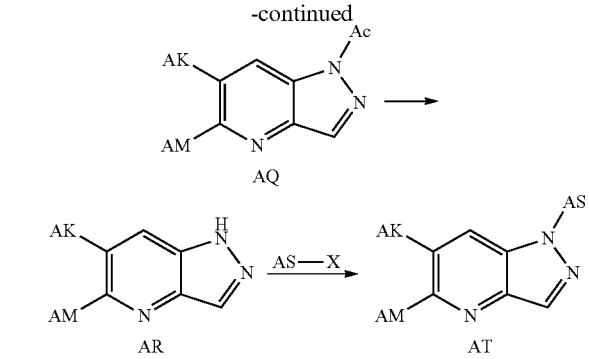

Referring to Scheme 4, Compound AE is brominated to produce compound AF. Compound AF is selectively reduced by halogen-lithium exchange, such as using one equivalent of n-LiBu, followed by aqueous acidic quench. Compound AG is converted to AH using nitration condition such as aqueous $HNO_3$. Compound AH is chlorinated to produce compound AI. For example, chlorination can occur through the use of phosphoryl chloride. Compound AJ is obtained from selective reduction, such as with iron in acetic acid, of compound AI. Compound AJ is converted to compound AL via a palladium-mediated cross coupling reaction with a suitable coupling partner, such as boronic acid AK-$B(OH)_2$. Compound AO is prepared from aryl halide compound AL via a palladium-mediated cross coupling reaction with a suitable coupling partner, such as boronic acid AM-$B(OH)_2$. Compound AO is acylated to give compound AP. This can be achieved by using acetic anhydride in presence of pyridine. Compound AQ was obtained from the treatment of compound AP with isoamyl nitrite and acetic acid. Compound AQ was hydrolyzed under basic conditions to form compound AR. Alkylation of compound AR is carried out with alkyl halide AS-C under basic conditions to form compound AT.

Scheme 5

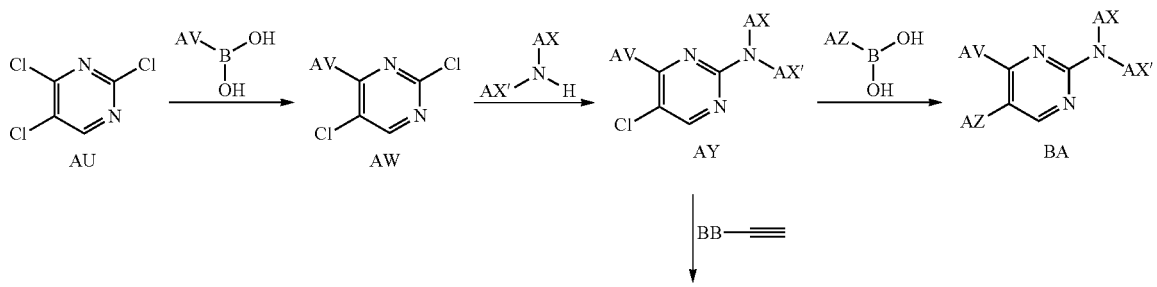

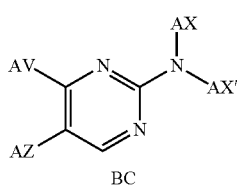

Referring to Scheme 5, compound AW can be made by employing palladium-catalyzed cross-coupling reaction of compound AU with a suitable coupling partner, such as boronic acid AV—B(OH)$_2$, at temperature up to 100° C. Nucleophilic substitution reaction of compound AW with amine AX—NH-AX' under basic conditions at 100° C. furnished AY. Palladium catalyzed cross-coupling of the AY with a suitable coupling partner, such as boronic acid AZ—B(OH)$_2$, at elevated temperature up to 120° C. afforded pyrimidine BA. Alternatively, subjecting compound AY to Sonogashira cross-coupling conditions with a terminal alkyne, such as BB-CCH, affords compound BC.

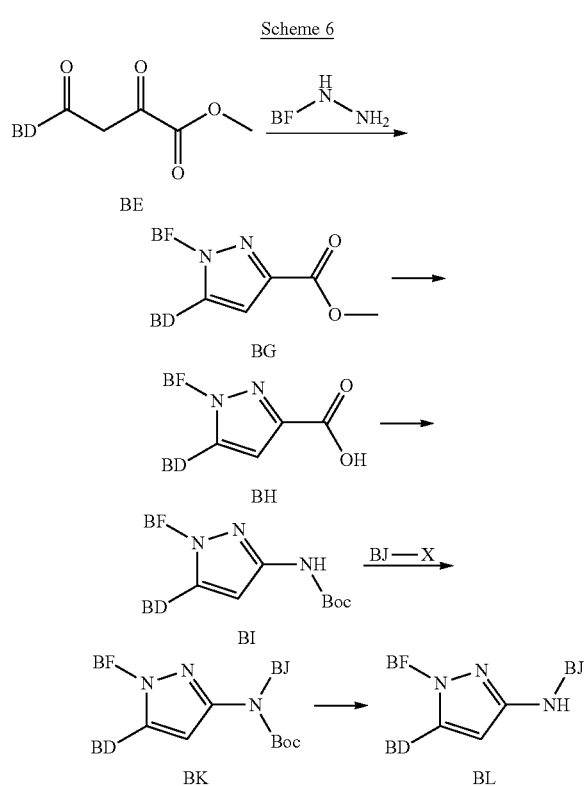

Referring to Scheme 6, compound BE is condensed with monosubstitued hydrazine BF—NHNH2 to form compound BG. Compound BG is hydrolyzed under basic conditions to produce compound BH. Compound BH is converted to compound BI by Curtius rearrangement using diphenyl phosphorazidate (DPPA). Alkylation of compound BI is carried out with a variety of electrophiles, such as alkyl halides, alkyl mesylates, tosylates or the like, under basic conditions to form compound BK. Compound BK is deprotected under acidic conditions to form compound BL.

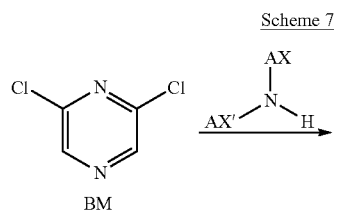

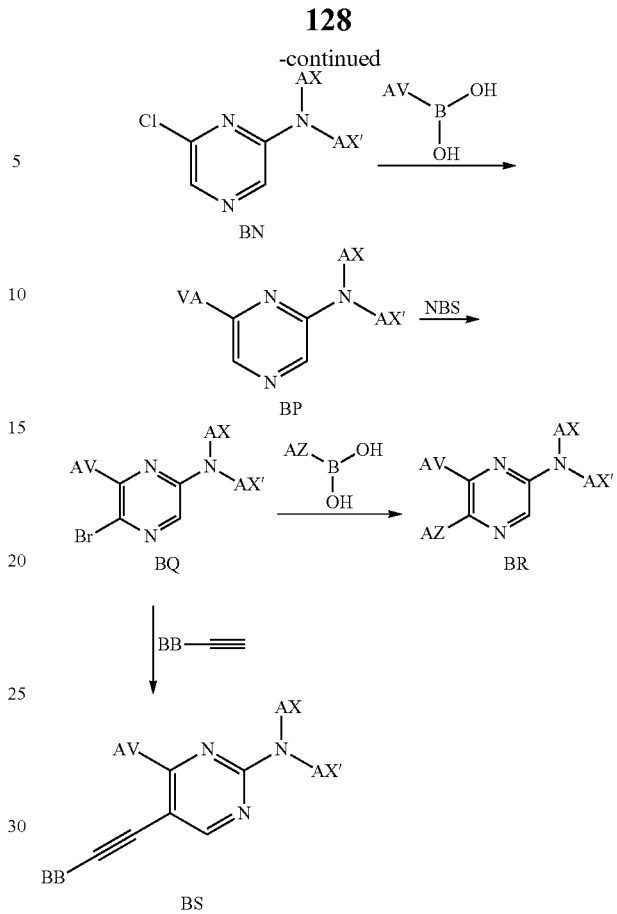

Referring to Scheme 7, compound BN is prepared from the nucleophilic substitution reaction of compound BM with amine AX—NH-AX' under basic conditions. Employing palladium-catalyzed cross-coupling reaction of compound BN with a suitable coupling partner, such as boronic acid AV—B(OH)$_2$ provides compound BP. Treatment with an N-bromosuccinimide (NBS) affords compound BQ. Palladium catalyzed cross-coupling of the BQ with a suitable coupling partner, such as boronic acid AZ—B(OH)$_2$ affords pyrazine BR. Alternatively, subjecting compound BQ (or AY) to Sonogashira cross-coupling conditions with a terminal alkyne, such as BB-CCH, affords compound BS.

In each of the above reaction procedures or schemes, the various substituents may be selected from among the various substituents otherwise taught herein.

Pharmaceutical Compositions

In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)), the disclosure of which is hereby incorporated herein by reference in its entirety.

Accordingly, provided herein is a pharmaceutical composition comprising at least one substituted heterocyclic derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, and a pharmaceutically acceptable excipient.

One embodiment provides a pharmaceutical composition comprising a compound of Formula (II), or a pharmaceutically acceptable salt thereof, and a pharmaceutically acceptable excipient.

One embodiment provides a pharmaceutical composition comprising a compound of Formula (III), or a pharmaceutically acceptable salt thereof, and a pharmaceutically acceptable excipient.

One embodiment provides a pharmaceutical composition comprising a compound of Formula (IV), or a pharmaceutically acceptable salt thereof, and a pharmaceutically acceptable excipient.

In certain embodiments, the substituted heterocyclic derivative compound as described by Formula (I), (II), (III), or (IV) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21st Ed. Mack Pub. Co., Easton, Pa. (2005)).

The dose of the composition comprising at least one substituted heterocyclic derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Biology

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell. Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can modify histones at various sites.

There are a total of six classes of histones (HI, H2A, H2B, H3, H4, and H5) organized into two groups: core histones (H2A, H2B, H3, and H4) and linker histones (HI and H5). The basic unit of chromatin is the nucleosome, which consists of about 147 base pairs of DNA wrapped around the core histone octamer, consisting of two copies each of the core histones H2A, H2B, H3, and H4.

Basic nucleosome units are then further organized and condensed by the aggregation and folding of nucleosomes to form a highly condensed chromatin structure. A range of different states of condensation are possible, and the tightness of chromatin structure varies during the cell cycle, being most compact during the process of cell division.

Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

Histone methylation is one of the most important chromatin marks; these play important roles in transcriptional regulation, DNA-damage response, heterochromatin formation and maintenance, and X-chromosome inactivation. A recent discovery also revealed that histone methylation affects the splicing outcome of pre-mRNA by influencing the recruitment of splicing regulators. Histone methylation includes mono-, di-, and tri-methylation of lysines, and mono-, symmetric di-, and asymmetric di-methylation of arginines. These modifications can be either an activating or repressing mark, depending on the site and degree of methylation.

Histone Demethylases

A "demethylase" or "protein demethylase," as referred to herein, refers to an enzyme that removes at least one methyl group from polypeptide. Demethylases comprise a JmjC domain, and can be a methyl-lysine or methyl-arginine demethylase. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found used a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.
LSD-1

Lysine-specific demethylase 1 (LSD1) is a histone lysine demethylase that specifically demethylates monomethylated and dimethylated histone H3 at K4 and also demethylates dimethylated histone H3 at K9. Although the main target of LSD1 appears to be mono- and di-methylated histone lysines, specifically H3K4 and H3K9, there is evidence in the literature that LSD 1 can demethylate methylated lysines on non-histone proteins like p53, E2F1, Dnmt1 and STAT3.

LSD 1 has a fair degree of structural similarity and amino acid identity/homology to polyamine oxidases and monoamine oxidases, all of which (i. e., MAO-A, MAO-B and LSD1) are flavin dependent amine oxidases which catalyze the oxidation of nitrogen-hydrogen bonds and/or nitrogen-carbon bonds. LSD1 also includes an N-terminal SWRIM domain. There are two transcript variants of LSD1 produced by alternative splicing.
Methods of Use In some embodiments, the compounds disclosed herein are capable of inhibiting LSD1 activity in a biological sample by contacting the biological sample with a substituted heterocyclic compound as disclosed herein. In some embodiments, a substituted heterocyclic compound as disclosed herein is capable of modulating the level of histone 4 lysine 3 methylation in the biological sample. In some embodiments, a substituted heterocyclic compound as disclosed herein is capable of modulating histone-3 lysine-9 methylation levels in the biological sample.

In some embodiments, a substituted heterocyclic compound as disclosed herein inhibits LSD1 activity to a greater extent than MAO-A and/or MAO-B.

One embodiment provides a method of regulating gene transcription in a cell comprising inhibiting lysine-specific demethylase 1 activity by exposing the lysine-specific demethylase 1 enzyme to a compound of Formula (I).

One embodiment provides a method of regulating gene transcription in a cell comprising inhibiting lysine-specific demethylase 1 activity by exposing the lysine-specific demethylase 1 enzyme to a compound of Formula (II).

One embodiment provides a method of regulating gene transcription in a cell comprising inhibiting lysine-specific demethylase 1 activity by exposing the lysine-specific demethylase 1 enzyme to a compound of Formula (III).

One embodiment provides a method of regulating gene transcription in a cell comprising inhibiting lysine-specific demethylase 1 activity by exposing the lysine-specific demethylase 1 enzyme to a compound of Formula (IV).
Methods of Treatment Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation.

One embodiment provides a method of treating cancer in a patient in need thereof, comprising administering to the patient a compound of Formula (I), or a pharmaceutically acceptable salt thereof.

One embodiment provides a method of treating cancer in a patient in need thereof, comprising administering to the patient a compound of Formula (II), or a pharmaceutically acceptable salt thereof.

One embodiment provides a method of treating cancer in a patient in need thereof, comprising administering to the patient a compound of Formula (III), or a pharmaceutically acceptable salt thereof.

One embodiment provides a method of treating cancer in a patient in need thereof, comprising administering to the patient a compound of Formula (IV), or a pharmaceutically acceptable salt thereof.

In a further embodiment is the method for treating cancer in a subject wherein the cancer is selected from prostate cancer, breast cancer, bladder cancer, lung cancer or melanoma.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1A: 1-(benzenesulfonyl)-6-bromopyrrolo[3,2-b]pyridine

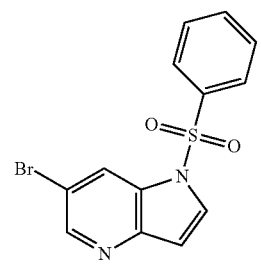 [SMILES: O=S(=O)(c1ccccc1)n1ccc2ncc(Br)cc21]

To a solution of NaH (1.13 g, 28.05 mmol, 60%) in THF (50 mL) at 0° C. was added 6-bromo-1H-pyrrolo[3,2-b] pyridine (5 g, 25.5 mmol) in small portions. The reaction mixture was stirred for 15 minutes. A THF (40 mL) solution of benzenesulfonyl chloride (4.86 g, 25.5 mmol) was then added dropwise at 0° C. The resulting solution was stirred at RT for 18 h. The reaction mixture was quenched by adding 50 mL of H₂O. The mixture was concentrated and the resulting solution was extracted with EtOAc (3×). The organic layers were combined, dried (Na₂SO₄) and concentrated in vacuo to give 8.54 g (99%) of the title compound as a beige solid. ¹H NMR (400 MHz, DMSO-d₆) δ 7.01 (d, J=3.79 Hz, 1H), 7.60-7.69 (m, 2H), 7.71-7.81 (m, 1H), 8.09-8.16 (m, 2H), 8.22 (d, J=3.79 Hz, 1H), 8.45-8.51 (m, 1H), 8.64 (d, J=2.02 Hz, 1H). [M+H] Calc'd for C₁₃H₉BrN₂O₂S, 337, 339; Found, 337, 339.

Preparation 1B: 6-bromo-1-(phenylsulfonyl)-1H-pyrrolo[3,2-b]pyridine-4-oxide

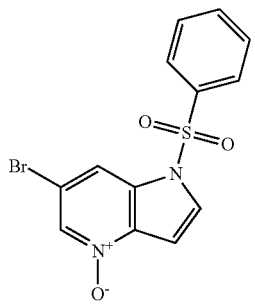 [SMILES: O=S(=O)(c1ccccc1)n1ccc2c1cc(Br)c[n+]2[O-]]

To a stirred solution of 6-bromo-1-(phenylsulfonyl)-1H-pyrrolo[3,2-b]pyridine (8.54 g, 25.4 mmol) in DCM (120 mL) at 0° C. was added 3-chloroperbenzoic acid (77 wt %, 6.83 g, 30.49 mmol). The reaction mixture was stirred overnight at rt. The solution was washed with saturated aqueous NaHCO₃ (2×). The organics were dried (Na₂SO₄4) and concentrated in vacuo. The residue was chromatographed (0-15%, MeOH:DCM) to afford 6.34 g (71%) of the title compound as a white solid. ¹H NMR (400 MHz, DMSO-d₆) δ 7.05-7.09 (m, 1H), 7.64-7.71 (m, 2H), 7.76-7.84 (m, 1H), 8.08 (s, 1H), 8.12-8.18 (m, 3H), 8.57 (d, J=1.26 Hz, 1H). [M+H] Calc'd for C₁₃H₉BrN₂O₃S, 354, 356; Found, 354, 356.

Preparation 1C: 1-(benzenesulfonyl)-6-bromo-5-chloropyrrolo[3,2-b]pyridine

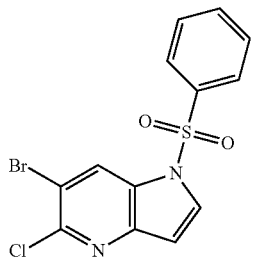 [SMILES: O=S(=O)(c1ccccc1)n1ccc2nc(Cl)c(Br)cc21]

A solution of phosphorus oxychloride (1.43 mL, 15.3 mmol) in DCM (8 mL) was added dropwise to a mixture of 6-bromo-1-(phenylsulfonyl)-1H-pyrrolo[3,2-b]pyridine-4-oxide (4.50 g, 12.8 mmol) and triethylamine (2.13 mL, 15.3 mmol) in DCM (40 mL) at 0° C. The reaction mixture was stirred at 0° C. for 1 h and then at rt for 3 h. The mixture was quenched with water (100 mL). The organic layer was separated, washed with a saturated solution of NaHCO₃, brine, dried (Na₂SO₄) and concentrated in vacuo. The residue was chromatographed (0-5%, MeOH:DCM) to afford 2.23 g (47%) of the title compound as a white solid. ¹H NMR (400 MHz, DMSO-d₆) δ 7.00 (d, J=3.79 Hz, 1H), 7.61-7.69 (m, 2H), 7.74-7.80 (m, 1H), 8.14 (d, J=7.33 Hz, 2H), 8.31 (d, J=3.79 Hz, 1H), 8.65 (s, 1H). [M+H] Calc'd for C₁₃H₈BrClN₂O₂S, 373, 375; Found, 373, 375.

Preparation 1D: 4-[1-(benzenesulfonyl)-5-chloropyrrolo[3,2-b]pyridin-6-yl]benzonitrile

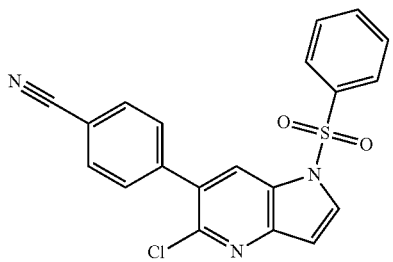 [SMILES: N#Cc1ccc(-c2cc3c(ccn3S(=O)(=O)c3ccccc3)nc2Cl)cc1]

To a mixture of 1-(benzenesulfonyl)-6-bromo-5-chloropyrrolo[3,2-b]pyridine (2.23 g, 6.04 mmol), Pd(dppf)Cl₂ (0.25 g, 0.30 mmol), aqueous sodium carbonate (2.0 M, 10 mL) in dioxane (40 mL), was added 4-cyanophenylboronic acid (0.98 g, 6.64 mmol). The reaction mixture was stirred and heated at reflux for 30 min. Solvent was evaporated. The residue was taken in water and extracted with DCM (3×). The organic layers were combined, washed with brine, dried (Na₂SO₄) and concentrated in vacuo. The residue was chromatographed (0-5%, MeOH:DCM) to give 1.79 g (75%) of the title compound as a white solid. ¹H NMR (400 MHz, DMSO-d₆) δ 7.06 (d, J=3.79 Hz, 1H), 7.60-7.67 (m, 2H), 7.73-7.79 (m, 3H), 8.01 (d, J=8.34 Hz, 2H), 8.12 (d, J=7.58 Hz, 2H), 8.31 (s, 1H), 8.35 (d, J=3.79 Hz, 1H). [M+H] Calc'd for C₂₀H₁₂ClN₃O₂S, 394; Found, 394.

Preparation 1E: 4-(5-chloro-1H-pyrrolo[3,2-b]pyridin-6-yl)benzonitrile

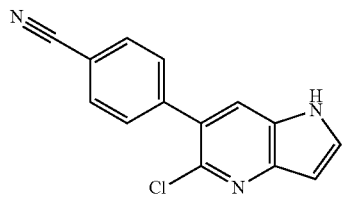 [SMILES: N#Cc1ccc(-c2cc3[nH]ccc3nc2Cl)cc1]

To a mixture of 4-[1-(benzenesulfonyl)-5-chloropyrrolo[3,2-b]pyridin-6-yl]benzonitrile (1.18 g, 3.00 mmol) in MeOH:THF (3:2, 50 mL) was added NaOH (2.5 N, 12 mL). The reaction mixture was stirred at rt for 15 min. The reaction was acidified (2 N HCl) and extracted with DCM (3×). The organics were combined and washed with brine, dried (Na₂SO₄) and concentrated in vacuo. The residue was triturated in DCM (20 mL) and filtered to give 580 mg (76%) of the title compound as a yellow solid. ¹H NMR (400 MHz, DMSO-d₆) δ 6.60 (br. s., 1H), 7.72 (d, J=8.34 Hz, 2H), 7.81 (t, J=2.91 Hz, 1H), 7.85 (s, 1H), 7.95 (d, J=8.34 Hz, 2H), 11.68 (br. s., 1H). [M+H] Calc'd for C₁₄H₈ClN₃, 254; Found, 254.

Preparation 1F: tert-butyl (3S)-3-[[5-chloro-6-(4-cyanophenyl)pyrrolo[3,2-b]pyridin-1-yl]methyl]pyrrolidine-1-carboxylate

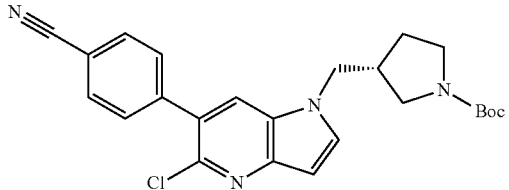 [SMILES: CC(C)(C)OC(=O)N1CC[C@@H](Cn2ccc3nc(Cl)c(-c4ccc(C#N)cc4)cc32)C1]

(R)—N-boc-3-bromomethylpyrrolidine (96 mg, 0.37 mmol) was added to a mixture of 4-(5-chloro-1H-pyrrolo[3,2-b]pyridin-6-yl)benzonitrile (100 mg, 0.33 mmol) and cesium carbonate (214 mg, 0.65 mmol) in DMF (3 mL). The reaction mixture was stirred at 90° C. overnight. (R)—N-Boc-3-bromomethylpyrrolidine (96 mg, 0.37 mmol) was added and the reaction was stirred at 90° C. for 2 h. DMF was concentrated in vacuo. The residue was taken in DCM and the insoluble solids were filtered off. The filtrate was loaded on silica column and chromatographed (0-100%, EtOAc:Hexanes) to give 125 mg (77%) of the title compound as a colorless oil. $^1$H NMR (400 MHz, DMSO-$d_6$) δ 1.25-1.45 (m, 9H), 1.59 (br. s., 1H), 1.76 (br. s., 1H), 2.67 (br. s., 2H), 2.89-3.05 (m, 1H), 3.08-3.30 (m, 2H), 4.18-4.39 (m, 2H), 6.63 (d, J=3.03 Hz, 1H), 7.75 (d, J=8.34 Hz, 2H), 7.87 (d, J=3.28 Hz, 1H), 7.97 (d, J=8.34 Hz, 2H), 8.21 (d, J=2.78 Hz, 1H). [M+H] Calc'd for $C_{24}H_{25}ClN_3O_2$, 437; Found, 437.

Preparation 1G: tert-butyl (3S)-3-[[6-(4-cyanophenyl)-5-(4-methylphenyl)pyrrolo[3,2-b]pyridin-1-yl]methyl]pyrrolidine-1-carboxylate

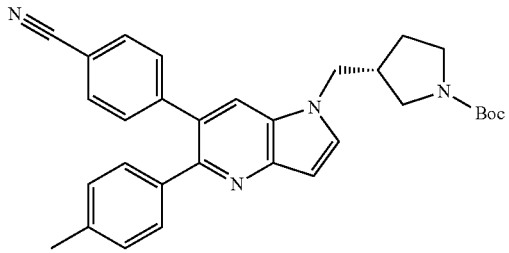 [SMILES: Cc1ccc(-c2nc3ccn(C[C@@H]4CCN(C(=O)OC(C)(C)C)C4)c3cc2-c2ccc(C#N)cc2)cc1]

To a mixture of tert-butyl (3S)-3-[[5-chloro-6-(4-cyanophenyl)pyrrolo[3,2-b]pyridin-1-yl]methyl]pyrrolidine-1-carboxylate (100 mg, 0.23 mmol), Pd(dppf)Cl$_2$ (10 mg, 0.012 mmol), aqueous sodium carbonate (2.0 M, 1.0 mL, 2.00 mmol) in dioxane (2 mL), was added 4-methyphenyl-boronic acid (50 mg, 0.36 mmol). The reaction mixture was stirred and heated in the microwave at 143° C. for 1 h. Solvent was evaporated in vacuo. The residue was taken in DCM and filtered. The filtrate was chromatographed (0-90%, EtOAc:Hexanes) to give 90 mg (79%) of the title compound as a beige solid. [M+H] Calc'd for $C_{31}H_{32}N_4O_2$, 493; Found, 493.

Example 1: 4-[5-(4-methylphenyl)-1-[[(3R)-pyrrolidin-3-yl]methyl]pyrrolo[3,2-b]pyridin-6-yl]benzonitrile

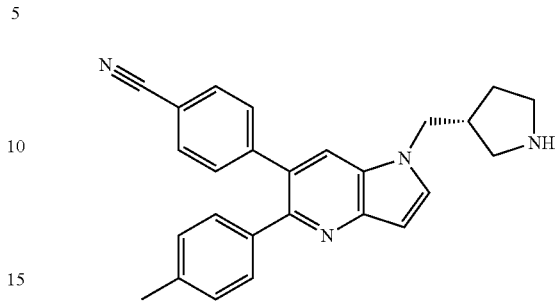

To a mixture of tert-butyl (3S)-3-[[6-(4-cyanophenyl)-5-(4-methylphenyl)pyrrolo[3,2-b]pyridin-1-yl]methyl]pyrrolidine-1-carboxylate (90 mg, 0.18 mmol) in DCM (2 mL) was added TFA (2 mL). The reaction was stirred for 30 min. Solvent was evaporated in vacuo. The residue was chromatographed (0-20%, MeOH:DCM) to give 56 mg (78%) of the TFA salt of the title compound as a beige solid. $^1$H NMR (400 MHz, DMSO-$d_6$) δ 1.61-1.77 (m, 1H), 1.84-2.01 (m, 1H), 2.29 (s, 3H), 2.76-3.01 (m, 3H), 3.02-3.16 (m, 1H), 3.24-3.37 (m, 2H), 4.29-4.49 (m, 2H), 6.72 (d, J=3.03 Hz, 1H), 7.05-7.14 (m, 2H), 7.14-7.20 (m, 2H), 7.42 (d, J=8.34 Hz, 2H), 7.80 (d, J=8.34 Hz, 2H), 7.91 (br. s., 1H), 8.23 (br. s., 1H), 8.60-8.85 (m, 2H). [M+H] Calc'd for $C_{26}H_{24}N_4$, 393; Found, 393.

Example 2: 4-[5-chloro-1-[[(3R)-pyrrolidin-3-yl]methyl]pyrrolo[3,2-b]pyridin-6-yl]benzonitrile

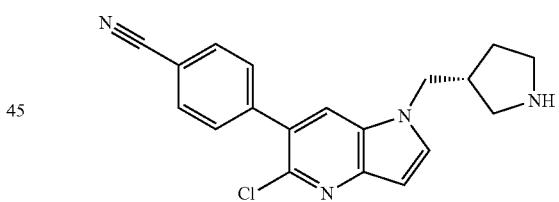

To a mixture of tert-butyl (3S)-3-[[5-chloro-6-(4-cyanophenyl)pyrrolo[3,2-b]pyridin-1-yl]methyl]pyrrolidine-1-carboxylate (50 mg, 0.11 mmol) in DCM (3 mL) was added TFA (1 mL). The reaction was stirred for 2 h. Solvent was evaporated in vacuo. The residue was chromatographed (0-20%, MeOH:DCM) to give 35 mg (96%) of the TFA salt of the title compound as a yellow glassy solid. $^1$H NMR (400 MHz, DMSO-$d_6$) δ 1.56-1.71 (m, 1H), 1.90 (td, J=12.69, 7.20 Hz, 1H), 2.72-2.93 (m, 3H), 3.05-3.15 (m, 1H), 3.21-3.30 (m, 1H), 4.32 (dd, J=7.20, 4.42 Hz, 2H), 6.66 (d, J=3.28 Hz, 1H), 7.74 (d, J=8.34 Hz, 2H), 7.90 (d, J=3.03 Hz, 1H), 7.99 (d, J=8.34 Hz, 2H), 8.24 (s, 1H), 8.62 (br. s., 2H). [M+H] Calc'd for $C_{19}H_{17}ClN_4$, 337; Found, 337.

Preparation 3A: 4-[1-(benzenesulfonyl)-5-(4-methylphenyl)pyrrolo[3,2-b]pyridin-6-yl]benzonitrile

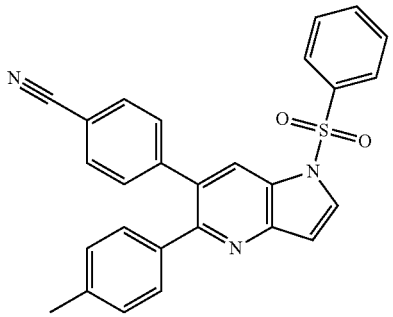 [SMILES: Cc1ccc(-c2nc3ccn(S(=O)(=O)c4ccccc4)c3cc2-c2ccc(C#N)cc2)cc1]

To a mixture of 4-[1-(benzenesulfonyl)-5-chloropyrrolo[3,2-b]pyridin-6-yl]benzonitrile (300 mg, 0.76 mmol), Pd(dppf)Cl2 (31 mg, 0.038 mmol), aqueous sodium carbonate (2.0 M, 1.15 mL, 2.28 mmol) in dioxane (7 mL) was added 4-methyphenylboronic acid (310 mg, 2.28 mmol). The reaction mixture was stirred and heated at 135° C. for 3 h in the microwave. Solvent was evaporated in vacuo. The residue was taken in water and extracted with DCM. The organics were combined and washed with brine, dried (Na2SO4) and concentrated in vacuo. The residue was chromatographed (0-5%, MeOH:DCM) to give 260 mg (47%) of the title compound as a beige solid. [M+H] Calc'd for $C_{27}H_{19}N_3O_2S$, 450; Found, 450.

Preparation 3B: 4-[5-(4-methylphenyl)-1H-pyrrolo[3,2-b]pyridin-6-yl]benzonitrile

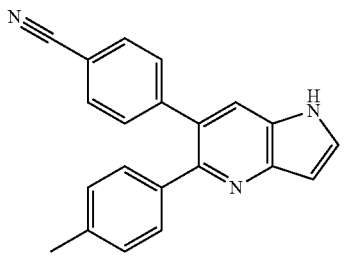 [SMILES: Cc1ccc(-c2nc3cc[nH]c3cc2-c2ccc(C#N)cc2)cc1]

To a mixture of 4-[1-(benzenesulfonyl)-5-(4-methylphenyl)pyrrolo[3,2-b]pyridin-6-yl]benzonitrile (260 mg, 0.58 mmol) in MeOH:THF (2:1, 15 mL) was added NaOH (2.5 N, 3 mL). The reaction mixture was stirred at rt for 3 h. The reaction was neutralized using aqueous HCl and the solvent was evaporated. The residue was taken in water and extracted with DCM. The organics were combined and washed with brine, dried (Na$_2$SO$_4$) and concentrated in vacuo. The residue was chromatographed (0-5%, MeOH:DCM). The relevant fractions were combined and concentrated to afford 90 mg (49%) of the title compound as a beige solid. [M+H] Calc'd for $C_{21}H_{15}N_3$, 310; Found, 310.

Preparation 3C: tert-butyl (3R)-3-[[6-(4-cyanophenyl)-5-(4-methylphenyl)pyrrolo[3,2-b]pyridin-1-yl]methyl]pyrrolidine-1-carboxylate

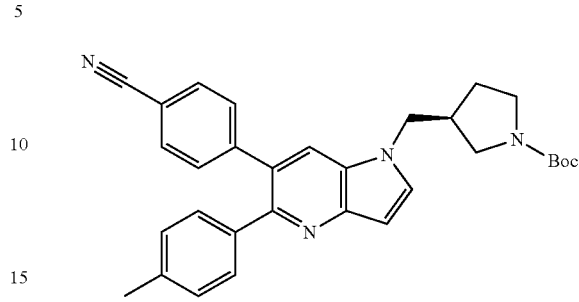

(S)—N-Boc-3-bromomethylpyrrolidine (137 mg, 0.52 mmol) was added to a mixture of 4-[5-(4-methylphenyl)-1H-pyrrolo[3,2-b]pyridin-6-yl]benzonitrile (80 mg, 0.26 mmol) and cesium carbonate (422 mg, 1.30 mmol) in DMF (3 mL). The reaction mixture was stirred at 90° C. overnight. The DMF was removed in vacuo. The residue was taken in DCM, and the insoluble solids were filtered off. The filtrate was loaded on silica column and chromatographed (0-10%, MeOH:DCM) to give 45 mg (35%) of the title compound as a colorless oil. [M+H] Calc'd for $C_{31}H_{32}N_4O_2$, 493; Found, 493.

Example 3: 4-[5-(4-methylphenyl)-1-[[(3S)-pyrrolidin-3-yl]methyl]pyrrolo[3,2-b]pyridin-6-yl]benzonitrile

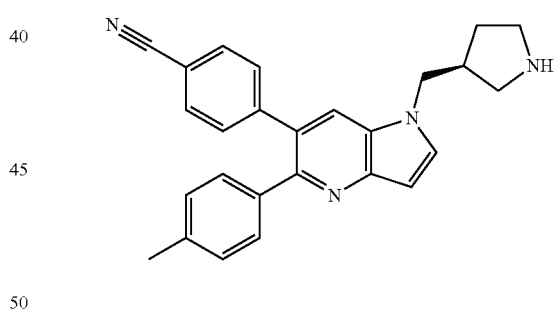

To tert-butyl (3R)-3-[[6-(4-cyanophenyl)-5-(4-methylphenyl)pyrrolo[3,2-b]pyridin-1-yl]methyl]pyrrolidine-1-carboxylate (45 mg, 0.09 mmol) in ethanol (2 mL) was added HCl in dioxane (4 N, 1 mL). The reaction was stirred for 2 h and the solvent was evaporated. The residue was chromatographed (0-20%, MeOH:DCM) to give 30 mg (84%) of the HCl salt of the title compound as a beige solid. $^1$H NMR (400 MHz, DMSO-d$_6$) δ 1.60-1.77 (m, 1H), 1.89-2.01 (m, 1H), 2.32 (s, 3H), 2.80-3.02 (m, 3H), 3.24-3.37 (m, 2H), 4.48 (br. s., 2H), 6.82 (br. s., 1H), 7.12-7.29 (m, 4H), 7.45 (d, J=8.34 Hz, 2H), 7.84 (d, J=8.08 Hz, 2H), 8.18 (s, 1H), 8.63 (s, 1H), 9.02 (br. s., 1H), 9.28 (br. s., 1H). [M+H] Calc'd for $C_{26}H_{24}N_4$, 393; Found, 393.

Preparation 4A: tert-butyl (3R)-3-[[5-chloro-6-(4-cyanophenyl)pyrrolo[3,2-b]pyridin-1-yl]methyl]pyrrolidine-1-carboxylate

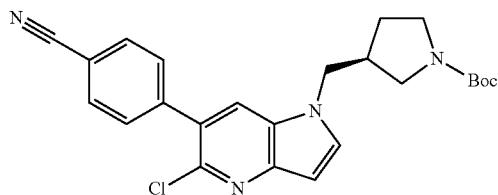 [SMILES: CC(C)(C)OC(=O)N1CC[C@H](Cn2ccc3nc(Cl)c(-c4ccc(C#N)cc4)cc32)C1]

The title compound was prepared in 25% yield from (S)—N-boc-3-bromomethylpyrrolidine and was added to a mixture of 4-(5-chloro-1H-pyrrolo[3,2-b]pyridin-6-yl)benzonitrile according to the procedure for the preparation 3C. [M+H] Calc'd for $C_{24}H_{25}ClN_3O_2$, 437; Found, 437.

Example 4: 4-[5-chloro-1-[[(3S)-pyrrolidin-3-yl]methyl]pyrrolo[3,2-b]pyridin-6-yl]benzonitrile

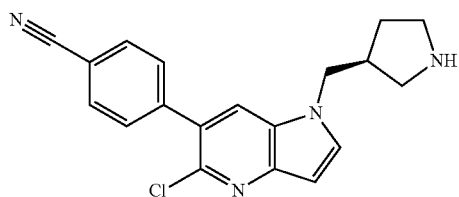 [SMILES: N#Cc1ccc(-c2cc3c(ccn3C[C@H]3CCNC3)nc2Cl)cc1]

The title compound was prepared as the HCl salt in 90% yield from tert-butyl (3R)-3-[[5-chloro-6-(4-cyanophenyl)pyrrolo[3,2-b]pyridin-1-yl]methyl]pyrrolidine-1-carboxylate according to the procedure for the preparation of Example 3. $^1$H NMR (400 MHz, DMSO-$d_6$) δ 1.56-1.71 (m, 1H), 1.84-1.95 (m, 1H), 2.71-2.92 (m, 2H), 3.04-3.23 (m, 3H), 4.23-4.39 (m, 2H), 6.66 (d, J=3.28 Hz, 1H), 7.74 (d, J=8.59 Hz, 2H), 7.90 (d, J=3.28 Hz, 1H), 7.99 (d, J=8.59 Hz, 2H), 8.24 (s, 1H), 8.63 (br. s., 1H), 8.73 (br. s., 1H). [M+H] Calc'd for $C_{19}H_{17}ClN_4$, 337; Found, 337.

Preparation 5A: 4-[1-(benzenesulfonyl)-5-(4-fluorophenyl)pyrrolo[3,2-b]pyridin-6-yl]benzonitrile

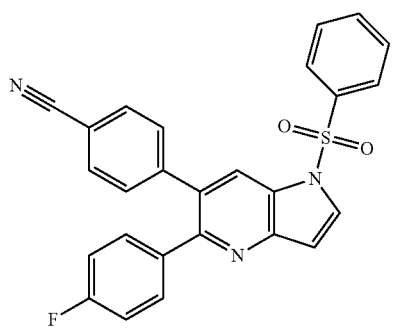 [SMILES: N#Cc1ccc(-c2cc3c(ccn3S(=O)(=O)c3ccccc3)nc2-c2ccc(F)cc2)cc1]

To a mixture of 4-[1-(benzenesulfonyl)-5-chloropyrrolo[3,2-b]pyridin-6-yl]benzonitrile (1 g, 2.54 mmol), Pd(dppf)Cl$_2$ (100 mg, 0.13 mmol), aqueous sodium carbonate (2.0 M, 3.31 mL, 7.62 mmol) in dioxane (10 mL), was added 4-fluoro-phenylboronic acid (1.42 g, 10.16 mmol). The reaction mixture was stirred and heated at 143° C. for 4 h in the microwave. This crude reaction was used without purification in the next step. [M+H] Calc'd for $C_{26}H_{16}FN_3O_2S$, 454; Found, 454.

Preparation 5B: 4-[5-(4-fluorophenyl)-1H-pyrrolo[3,2-b]pyridin-6-yl]benzonitrile

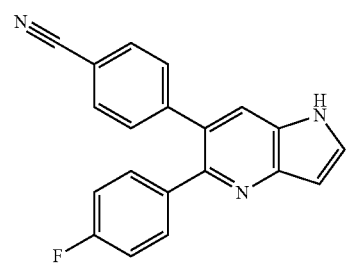 [SMILES: N#Cc1ccc(-c2cc3[nH]ccc3nc2-c2ccc(F)cc2)cc1]

To a mixture of crude 4-[1-(benzenesulfonyl)-5-(4-fluorophenyl)pyrrolo[3,2-b]pyridin-6-yl]benzonitrile (2.54 mmol) was added in MeOH (10 mL) and NaOH (2.5N, 6 mL). The reaction mixture was stirred at RT for 5 h. The reaction was extracted with DCM. The organics were combined and washed with brine, dried (Na$_2$SO$_4$) and concentrated in vacuo. The residue was chromatographed (0-5%, MeOH:DCM). The relevant fractions were combined and concentrated to afford 480 mg (60%) of the title compound as a beige solid. [M+H] Calc'd for $C_{20}H_{12}FN_3$, 314; Found, 314.

Preparation 5C: tert-butyl (3R)-3-[[6-(4-cyanophenyl)-5-(4-fluorophenyl)pyrrolo[3,2-b]pyridin-1-yl]methyl]pyrrolidine-1-carboxylate

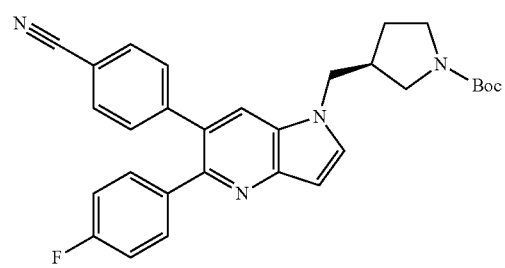 [SMILES: CC(C)(C)OC(=O)N1CC[C@H](Cn2ccc3nc(-c4ccc(F)cc4)c(-c4ccc(C#N)cc4)cc32)C1]

The title compound was prepared in 100% yield from 4-[5-(4-fluorophenyl)-1H-pyrrolo[3,2-b]pyridin-6-yl]benzonitrile and (R)—N-boc-3-bromomethylpyrrolidine according to the procedure for the preparation 3C. [M+H] Calc'd for $C_{30}H_{29}FN_4O_2$, 497; Found, 497.

Example 5: 4-[5-(4-fluorophenyl)-1-[[(3S)-pyrrolidin-3-yl]methyl]pyrrolo[3,2-b]pyridin-6-yl]benzonitrile

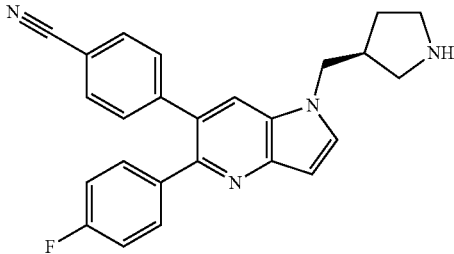 [SMILES: N#Cc1ccc(-c2cc3c(ccn3C[C@H]3CCNC3)nc2-c2ccc(F)cc2)cc1]

The title compound was prepared as the HCl salt in 14% yield from tert-butyl N-[3-[6-(4-cyanophenyl)-5-(4-methylphenyl)pyrrolo[3,2-b]pyridin-1-yl]propyl]carbamate according to the procedure for the preparation of Example 3. $^1$H NMR (400 MHz, DMSO-d$_6$): δ ppm 1.68-1.92 (m, 2H) 1.96-2.23 (m, 2H) 2.99-3.18 (m, 1H) 3.25-3.34 (m, 1H) 3.95 (d, J=7.07 Hz, 1H) 4.67 (br. s., 2H) 6.78 (d, J=3.03 Hz, 1H) 7.16 (t, J=8.08 Hz, 2H) 7.26-7.38 (m, 2H) 7.44 (d, J=8.34 Hz, 3H) 7.83 (d, J=8.34 Hz, 2H) 8.04 (br. s., 1H) 8.38 (br. s., 1H) 8.95-9.34 (m, 2H). [M+H] Calc'd for C$_{25}$H$_{21}$FN$_4$, 397; Found, 397.

Preparation 6A: 4-(3-bromo-6-methyl-5-nitropyridin-2-yl)morpholine

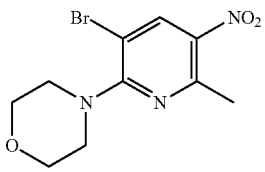 [SMILES: Cc1nc(N2CCOCC2)c(Br)cc1[N+](=O)[O-]]

To a mixture of 3-bromo-2-chloro-6-methyl-5-nitropyridine (2.00 g, 8.0 mmol) and morpholine (700 µL, 8.0 mmol) in DCM (20 mL), was added DIEA (1.40 mL, 8.0 mmol). The reaction mixture was stirred at rt for 16 h. Solvent was evaporated. The residue was chromatographed (0-5%, MeOH:DCM) to give 2.21 g (92%) of the title compound as a yellow solid. $^1$H NMR (400 MHz, DMSO-d$^6$) δ 2.66 (s, 3H), 3.57-3.63 (m, 4H), 3.70-3.75 (m, 4H), 8.54 (s, 1H). Calc'd for C$_{10}$H$_{12}$BrN$_3$O$_3$, 303, 305; Found, 303, 305.

Preparation 6B: 4-(6-methyl-2-morpholin-4-yl-5-nitropyridin-3-yl)benzonitrile

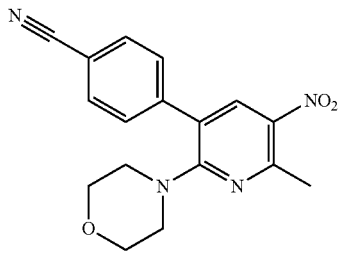 [SMILES: Cc1nc(N2CCOCC2)c(-c2ccc(C#N)cc2)cc1[N+](=O)[O-]]

To a mixture of 3-bromo-6-methyl-2-morpholine-5-nitropyridine (2.21 g, 7.34 mmol), Pd(dppf)Cl$_2$ (0.31 g, 0.37 mmol) and aqueous sodium carbonate (2.0 M, 5 mL) in dioxane (15 mL) was added 4-cyanophenylboronic acid (1.30 g, 8.08 mmol). The reaction mixture was stirred and heated at 110° C. for 1 h. Solvent was evaporated, the residue was taken in water and extracted with DCM (3×). The organic layers were combined, washed with brine, dried (Na$_2$SO$_4$) and concentrated in vacuo. The residue was chromatographed (0-5%, MeOH:DCM) to afford 2.15 g (90%) of the title compound as a yellow solid. [M+H] Calc'd for C$_{17}$H$_{16}$N$_4$O$_3$, 325; Found, 325.

Preparation 6C: 4-[6-[(E)-2-(dimethylamino)ethenyl]-2-morpholin-4-yl-5-nitropyridin-3-yl]benzonitrile

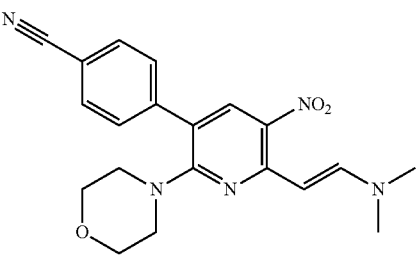 [SMILES: CN(C)/C=C/c1nc(N2CCOCC2)c(-c2ccc(C#N)cc2)cc1[N+](=O)[O-]]

To 3-(4-cyanonphenyl)-6-methyl-2-morphiline-5-nitropyridine (2.15 g, 7.14 mmol) in DMF (12 mL) was added N,N-dimethylformamide dimethyl acetal (5.6 mL, 42.8 mmol). The reaction mixture was stirred at rt for 30 min and heated at 100° C. for 3 h. Solvent was removed in vacuo to give 2.7 g (99%) of the title compound as a burgundy red solid. This residue was used without purification in the next step. [M+H] Calc'd for C20H21N5O3, 380; Found, 380.

Preparation 6D: 4-(5-morpholin-4-yl-1H-pyrrolo[3,2-b]pyridin-6-yl)benzonitrile

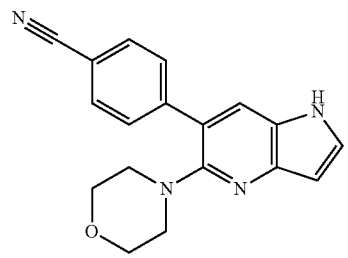 [SMILES: N#Cc1ccc(-c2cc3[nH]ccc3nc2N2CCOCC2)cc1]

4-[6-[(E)-2-(dimethylamino)ethenyl]-2-morpholin-4-yl-5-nitropyridin-3-yl]benzonitrile (2.7 g, 7.14 mmol) was dissolved in MeOH:DCM (200 mL, 1:10). Pd/C (10% w, 330 mg, 0.72 mmol) was added under nitrogen. Nitrogen atmosphere was displaced by hydrogen and the reaction was stirred at rt for 3 h. The reaction mixture was filtered through Celite and concentrated in vacuo. The residue was chromatographed (0-10%, MeOH:DCM) to give 1.41 g (65%) of the title compound as a beige solid. $^1$H NMR (400 MHz, DMSO-d$_6$) δ 2.83-2.99 (m, 4H), 3.47-3.62 (m, 4H), 6.46 (t, J=2.15 Hz, 1H), 7.58 (t, J=2.91 Hz, 1H), 7.65 (s, 1H), 7.85-7.98 (m, 4H), 11.25 (br. s., 1H). [M+H] Calc'd for $C_{18}H_{16}N_4O$, 305; Found, 305.

Preparation 6E: tert-butyl (3S)-3-[[6-(4-cyanophenyl)-5-morpholin-4-ylpyrrolo[3,2-b]pyridin-1-yl]methyl]pyrrolidine-1-carboxylate

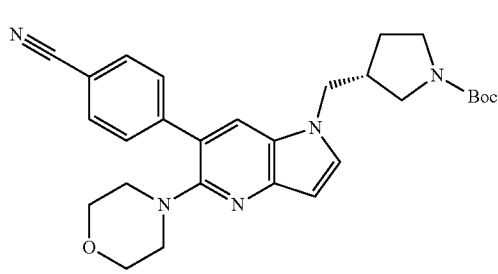 [SMILES: CC(C)(C)OC(=O)N1CC[C@@H](Cn2ccc3nc(N4CCOCC4)c(-c4ccc(C#N)cc4)cc32)C1]

To a solution of 4-(5-morpholin-4-yl-1H-pyrrolo[3,2-b]pyridin-6-yl)benzonitrile (100 mg, 0.33 mmol) in DMF (3 mL) was added (R)—N-boc-3-bromomethylpyrrolidine (96 mg, 0.37 mmol) followed by cesium carbonate (214 mg, 0.65 mmol) and the mixture was stirred at 90° C. overnight. (R)—N-Boc-3-bromomethylpyrrolidine (96 mg, 0.37 mmol) was added and the reaction was stirred at 90° C. for 2 h. The DMF was removed in vacuo. The residue was taken in DCM and the insoluble solids were filtered off. The filtrate was loaded on silica column and chromatographed (0-100%, EtOAc:Hexanes) to afford 125 mg (77%) of the title compound as a light yellow oil. [M+H] Calc'd for C28H33N5O3, 488; Found, 488.

Example 6: 4-[5-morpholin-4-yl-1-[[(3R)-pyrrolidin-3-yl]methyl]pyrrolo[3,2-b]pyridin-6-yl]benzonitrile

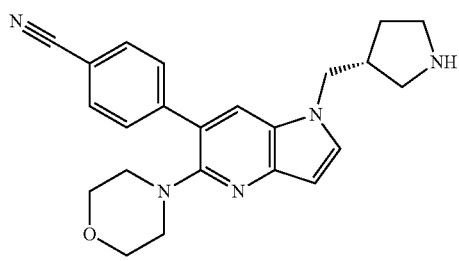 [SMILES: N#Cc1ccc(-c2cc3c(ccn3C[C@@H]3CCNC3)nc2N2CCOCC2)cc1]

To tert-butyl (3S)-3-[[6-(4-cyanophenyl)-5-morpholin-4-ylpyrrolo[3,2-b]pyridin-1-yl]methyl]pyrrolidine-1-carboxylate (125 mg, 0.26 mmol) in ethanol (4 mL) was added HCl in dioxane (4 N, 3 mL). The reaction was stirred for 2 h. Solvent was evaporated in vacuo. The residue was chromatographed (0-20%, MeOH:DCM) to give 71 mg (70%) of the HCl salt of the title compound as a light yellow solid (HCl salt). $^1$H NMR (400 MHz, DMSO-d$_6$) δ 2.73-2.87 (m, 2H), 2.86-2.97 (m, 4H), 3.05-3.15 (m, 3H), 3.22-3.30 (m, 2H), 3.54 (d, J=4.55 Hz, 4H), 4.23-4.32 (m, 2H), 6.49 (d, J=3.03 Hz, 1H), 7.70 (d, J=3.03 Hz, 1H), 7.91-7.99 (m, 4H), 8.01 (s, 1H), 9.07 (br. s., 1H). [M+H] Calc'd for $C_{23}H_{25}N_5O$, 388; Found, 388.

Preparation 7A: tert-butyl (3R)-3-[[6-(4-cyanophenyl)-5-morpholin-4-ylpyrrolo[3,2-b]pyridin-1-yl]methyl]pyrrolidine-1-carboxylate

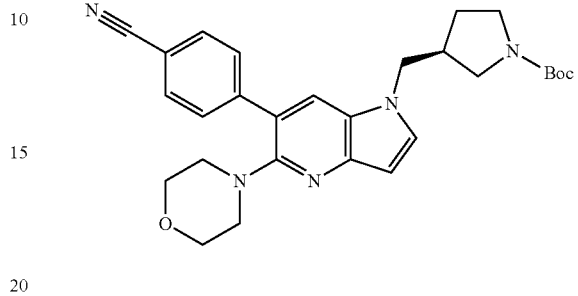

The title compound was prepared in 58% yield from (S)—N-boc-3-bromomethylpyrrolidine and 4-(5-morpholin-4-yl-1H-pyrrolo[3,2-b]pyridin-6-yl)benzonitrile according to the procedure for preparation 6E. $^1$H NMR (400 MHz, DMSO-d$_6$) δ 1.33 (s, 9H), 1.50-1.67 (m, 1H), 1.67-1.88 (m, 1H), 2.61-2.77 (m, 2H), 2.90 (br. s., 4H), 2.95-3.23 (m, 3H), 3.54 (br. s., 4H), 4.23 (d, J=7.58 Hz, 2H), 6.46 (d, J=2.80 Hz, 1H), 7.63 (d, J=2.78 Hz, 1H), 7.83-8.05 (m, 5H). [M+H] Calc'd for $C_{28}H_{33}N_5O_3$, 488; Found, 488.

Example 7: 4-[5-morpholin-4-yl-1-[[(3S)-pyrrolidin-3-yl]methyl]pyrrolo[3,2-b]pyridin-6-yl]benzonitrile

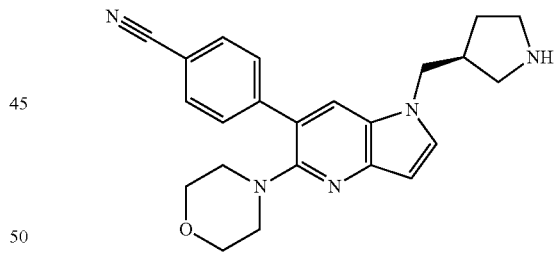

To tert-butyl (3R)-3-[[6-(4-cyanophenyl)-5-morpholin-4-ylpyrrolo[3,2-b]pyridin-1-yl]methyl]pyrrolidine-1-carboxylate (116 mg, 0.19 mmol) in ethanol (4 mL) was added HCl in dioxane (4 N, 3 mL). The reaction was stirred for 2 h. Solvent was evaporated in vacuo to give 81 mg (99%) of the HCl salt of the title compound as a light yellow solid. $^1$H NMR (400 MHz, DMSO-d$_6$) δ 1.53-1.73 (m, 1H), 1.83-1.97 (m, 1H), 2.72-2.91 (m, 2H), 2.92-3.03 (m, 4H), 3.06-3.20 (m, 2H), 3.21-3.38 (m, 1H), 3.48-3.59 (m, 4H), 4.25-4.39 (m, 2H), 6.58 (br. s., 1H), 7.82 (br. s., 1H), 7.89-8.02 (m, 4H), 8.22 (br. s., 1H), 8.98 (br. s., 1H), 9.25 (br. s., 1H). [M+H] Calc'd for $C_{23}H_{25}N_5O$, 388; Found, 388.

Preparation 8A: tert-butyl 3-[[6-(4-cyanophenyl)-5-morpholin-4-ylpyrrolo[3,2-b]pyridin-1-yl]methyl]-3-fluoropyrrolidine-1-carboxylate

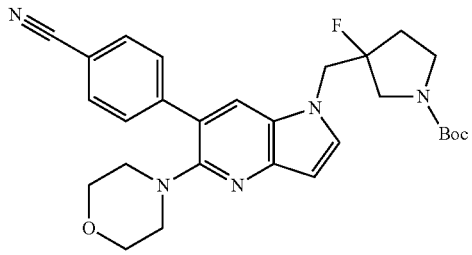 [SMILES: CC(C)(C)OC(=O)N1CCC(F)(Cn2ccc3nc(N4CCOCC4)c(-c4ccc(C#N)cc4)cc32)C1]

The title compound was prepared in 79% yield from 1-N-boc-3-bromomethyl-3-fluoro-pyrrolidine and 4-(5-morpholin-4-yl-1H-pyrrolo[3,2-b]pyridin-6-yl)benzonitrile according to the procedure for preparation 6E. [M+H] Calc'd for C28H32FN5O3, 506; Found, 506.

Example 8: 4-[1-[(3-fluoropyrrolidin-3-yl)methyl]-5-morpholin-4-ylpyrrolo[3,2-b]pyridin-6-yl]benzonitrile

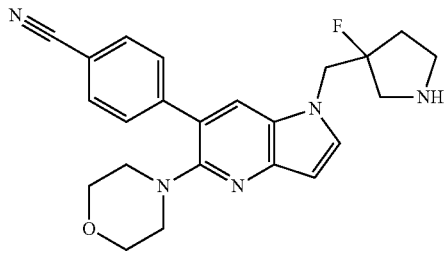 [SMILES: N#Cc1ccc(-c2cc3c(ccn3CC3(F)CCNC3)nc2N2CCOCC2)cc1]

The HCL salt of the title compound was prepared in 88% yield from tert-butyl 3-[[6-(4-cyanophenyl)-5-morpholin-4-ylpyrrolo[3,2-b]pyridin-1-yl]methyl]-3-fluoropyrrolidine-1-carboxylate according to the procedure for the preparation of Example 6. $^1$H NMR (400 MHz, DMSO-d$_6$) δ 1.93-2.39 (m, 2H), 2.89-3.03 (m, 4H), 3.21-3.34 (m, 2H), 3.35-3.48 (m, 2H), 3.50-3.60 (m, 4H), 4.73-4.87 (m, 2H), 6.60 (d, J=2.78 Hz, 1H), 7.68 (br. s., 1H), 7.87-8.02 (m, 4H), 8.09 (br. s., 1H), 9.44 (br. s., 1H), 9.66 (br. s., 1H). [M+H] Calc'd for C23H24FN5O, 406; Found, 406.

Preparation 9A: tert-butyl 3-[[6-(4-cyanophenyl)-5-(4-methylphenyl)pyrrolo[3,2-b]pyridin-1-yl]methyl]-3-fluoropyrrolidine-1-carboxylate

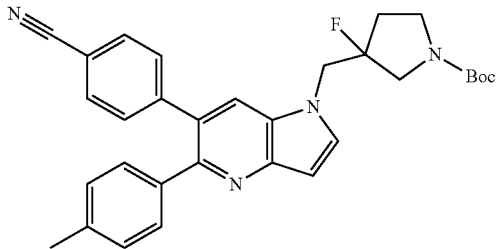 [SMILES: Cc1ccc(-c2nc3ccn(CC4(F)CCN(C(=O)OC(C)(C)C)C4)c3cc2-c2ccc(C#N)cc2)cc1]

The title compound was prepared in 41% yield from 1-N-boc-3-bromomethyl-3-fluoro-pyrrolidine and 4-[5-(4-methylphenyl)-1H-pyrrolo[3,2-b]pyridin-6-yl]benzonitrile according to the procedure for preparation 3C. [M+H] Calc'd for C31H31FN4O2, 511; Found, 511.

Example 9: 4-[1-[(3-fluoropyrrolidin-3-yl)methyl]-5-(4-methylphenyl)pyrrolo[3,2-b]pyridin-6-yl]benzonitrile

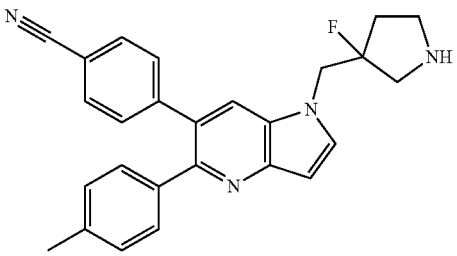

The HCl salt of the title compound was prepared in 66% yield from tert-butyl 3-[[6-(4-cyanophenyl)-5-(4-methylphenyl)pyrrolo[3,2-b]pyridin-1-yl]methyl]-3-fluoropyrrolidine-1-carboxylate according to the procedure for the preparation of Example 3. $^1$H NMR (400 MHz, DMSO-d$_6$) δ 2.08 (br. s., 1H), 2.23-2.31 (m, 1H), 2.32 (s, 3H), 3.33 (d, J=5.05 Hz, 4H), 4.77-5.15 (m, 2H), 6.90 (br. s., 1H), 7.17-7.29 (m, 4H), 7.43 (d, J=8.34 Hz, 2H), 7.84 (d, J=8.34 Hz, 2H), 8.13 (br. s., 1H), 8.65 (br. s., 1H), 9.67 (br. s., 1H), 9.98 (br. s., 1H). [M+H] Calc'd for C26H23FN4, 411; Found, 411.

Preparation 10A: tert-butyl (2S)-2-[[6-(4-cyanophenyl)-5-(4-methylphenyl)pyrrolo[3,2-b]pyridin-1-yl]methyl]morpholine-4-carboxylate

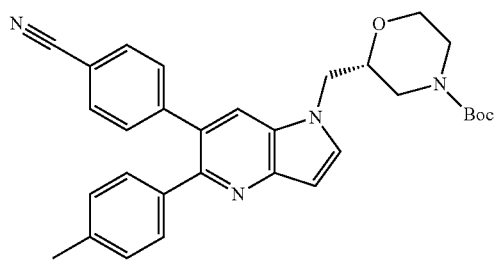 [SMILES: Cc1ccc(-c2nc3ccn(C[C@H]4CN(C(=O)OC(C)(C)C)CCO4)c3cc2-c2ccc(C#N)cc2)cc1]

Tert-butyl (2R)-2-(bromomethyl)morpholine-4-carboxylate (145 mg, 0.52 mmol) was added to a mixture of 4-[5-(4-methylphenyl)-1H-pyrrolo[3,2-b]pyridin-6-yl]benzonitrile (80 mg, 0.26 mmol) and cesium carbonate (422 mg, 1.30 mmol) in DMF (3 mL). The reaction mixture was stirred at 90° C. overnight. The insoluble solids were filtered off and DMF was concentrated in vacuo to give 282 mg (100%) of the title compound as a brown semisolid. This residue was used without purification in the next step. [M+H] Calc'd for C31H32N4O3, 509; Found, 509.

Example 10: 4-[5-(4-methylphenyl)-1-[[(2R)-morpholin-2-yl]methyl]pyrrolo[3,2-b]pyridin-6-yl]benzonitrile

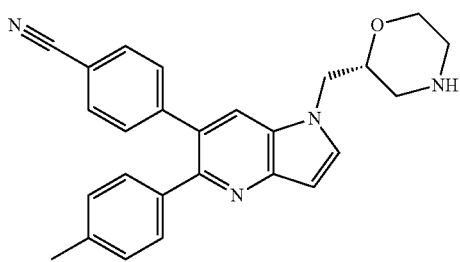

The title compound was prepared as the HCl salt in 36% yield from tert-butyl (2S)-2-[[6-(4-cyanophenyl)-5-(4-methylphenyl)pyrrolo[3,2-b]pyridin-1-yl]methyl]morpholine-4-carboxylate according to the procedure for the preparation of Example 3. $^1$H NMR (400 MHz, DMSO-$d_6$): δ ppm 2.20-2.40 (m, 3H) 2.76 (d, J=11.37 Hz, 1H) 2.91 (d, J=12.13 Hz, 1H) 3.06-3.24 (m, 2H) 3.37 (d, J=11.87 Hz, 2H) 3.94 (d, J=9.60 Hz, 2H) 4.13 (br. s., 1H) 4.43-4.74 (m, 2H) 6.84 (br. s., 1H) 7.14-7.34 (m, 4H) 7.39-7.54 (m, 2H) 7.85 (d, J=8.34 Hz, 2H) 8.06 (br. s., 1H) 8.49-8.75 (m, 1H) 9.25-9.67 (m, 2H). [M+H] Calc'd for $C_{26}H_{24}N_4O$, 409; Found, 409.

Preparation 11A: tert-butyl (2S)-2-[[6-(4-cyanophenyl)-5-(4-fluorophenyl)pyrrolo[3,2-b]pyridin-1-yl]methyl]morpholine-4-carboxylate

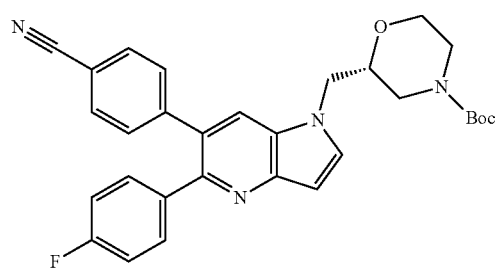 [SMILES: CC(C)(C)OC(=O)N1CCO[C@@H](Cn2ccc3nc(-c4ccc(F)cc4)c(-c4ccc(C#N)cc4)cc32)C1]

The title compound was prepared in 100% yield from 4-[5-(4-fluorophenyl)-1H-pyrrolo[3,2-b]pyridin-6-yl]benzonitrile and tert-butyl (2R)-2-(bromomethyl)morpholine-4-carboxylate according to the procedure for the preparation 10A. [M+H] Calc'd for $C_{30}H_{29}FN_4O_3$, 513; Found, 513.

Example 11: 4-[5-(4-fluorophenyl)-1-[[(2R)-morpholin-2-yl]methyl]pyrrolo[3,2-b]pyridin-6-yl]benzonitrile

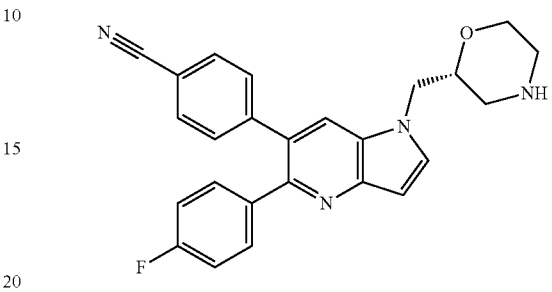

The title compound was prepared as the HCl salt in 27% yield from tert-butyl (2S)-2-[[6-(4-cyanophenyl)-5-(4-fluorophenyl)pyrrolo[3,2-b]pyridin-1-yl]methyl]morpholine-4-carboxylate according to the procedure for the preparation of Example 3. $^1$H NMR (400 MHz, DMSO-$d_6$) δ ppm 2.71-2.81 (m, 1H) 2.92 (d, J=11.62 Hz, 1H) 3.15 (d, J=13.14 Hz, 1H) 3.35 (d, J=12.88 Hz, 1H) 3.94 (d, J=9.09 Hz, 2H) 4.11 (br. s., 1H) 4.39-4.72 (m, 2H) 6.80 (br. s., 1H) 7.12-7.29 (m, 2H) 7.29-7.53 (m, 4H) 7.71-7.92 (m, 2H) 7.92-8.10 (m, 1H) 8.45 (br. s., 1H) 9.13-9.55 (m, 2H). [M+H] Calc'd for $C_{25}H_{21}FN_4O$, 413; Found, 413.

Preparation 12A: tert-butyl N-[3-[6-(4-cyanophenyl)-5-(4-methylphenyl)pyrrolo[3,2-b]pyridin-1-yl]propyl]carbamate

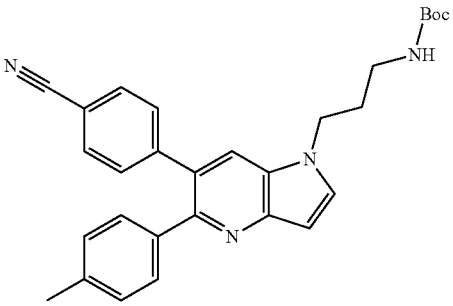 [SMILES: Cc1ccc(-c2nc3ccn(CCCNC(=O)OC(C)(C)C)c3cc2-c2ccc(C#N)cc2)cc1]

The title compound was prepared in 100% yield from 4-[5-(4-methylphenyl)-1H-pyrrolo[3,2-b]pyridin-6-yl]benzonitrile and tert-butyl N-(3-bromopropyl)carbamate according to the procedure for the preparation 10A. [M+H] Calc'd for $C_{29}H_{30}N_4O_2$, 466; Found, 466.

Example 12: 4-[1-(3-aminopropyl)-5-(4-methylphenyl)pyrrolo[3,2-b]pyridin-6-yl]benzonitrile

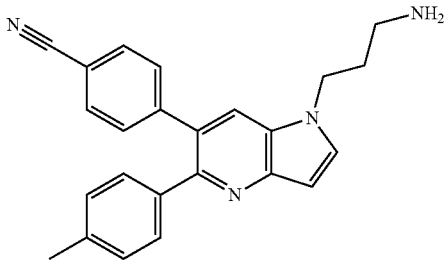

The title compound was prepared as the HCl salt in 20% yield from tert-butyl N-[3-[6-(4-cyanophenyl)-5-(4-methylphenyl)pyrrolo[3,2-b]pyridin-1-yl]propyl]carbamate according to the procedure for the preparation of Example 3. $^1$H NMR (400 MHz, DMSO-d$_6$): δ ppm 2.05-2.21 (m, 2H) 2.32 (s, 3H) 2.78 (d, J=5.81 Hz, 2H) 4.51 (br. s., 2H) 6.82 (br. s., 2H) 7.09-7.31 (m, 4H) 7.46 (d, J=8.34 Hz, 2H) 7.84 (d, J=8.34 Hz, 2H) 7.98 (br. s., 2H) 8.16 (br. s., 1H) 8.62 (s, 1H). [M+H] Calc'd for C$_{24}$H$_{22}$N$_4$, 366; Found, 366.

Preparation 13A: 3,5-dibromo-6-methylpyridin-2-ol

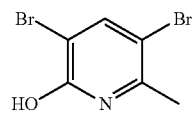

To a 1-L three-necked reaction flask packed with aluminum foil was added a solution of 2-hydroxy-6-methylpyridine (27.4 g, 0.25 mol) in dry acetonitrile (300 mL). NBS (89 g, 0.5 mol) was added portion-wise to the mixture over 20 min at 0° C. As the suspension was difficult to stir, additional dry acetonitrile (200 ml) was added and stirring continued at 30° C. for 1.5 h. The suspension was filtered. The filter cake was thoroughly washed with methanol (50 mL×3) and dried to give 58.6 g (88%) of the title compound as a white solid. $^1$H NMR (400 MHz, CDCl$_3$) δ 7.90 (s, 1H), 2.46 (s, 3H). [M+H] Calc'd for C$_6$H$_5$Br$_2$NO, 268, 270; Found, 268, 270.

Preparation 13B: 3-bromo-6-methylpyridin-2-ol

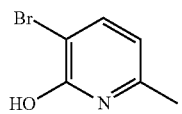

In a 2-L three-necked reaction flask (flame-dried), 3,5-dibromo-6-methylpyridin-2-ol (51.6 g, 193 mmol) in dry THF (500 mL) was stirred under N$_2$ at room temperature. The mixture was cooled to −67° C. n-BuLi (178 mL, 445 mmol) was added dropwise over 1 h at a temperature maintained below −60° C. The mixture was stirred for 1.5 h at −60° C. Saturated aqueous NH$_4$Cl (100 mL) was added dropwise over 1 h at a temperature between −65° C. and −40° C. The reaction mixture was stirred at −40° C. for 15 min, allowed to reach 25° C. and then stirred overnight. The mixture was concentrated to remove THF and the aqueous layer was extracted with EtOAc (300 mL×3). The combined organic layers were washed with brine (200 mL×2), dried over Na$_2$SO$_4$, filtered, concentrated and purified by column chromatography on silica gel (10-50%, EtOAc:PE) to give 6.07 g (17%) of the title compound as an off-white solid. $^1$H NMR (400 MHz, CDCl$_3$) δ 12.94 (s, 1H), 7.72 (d, J=7.2 Hz, 1H), 5.99 (d, J=7.2 Hz, 1H), 2.37 (t, J=8.4 Hz, 3H). [M+H] Calc'd for C$_6$H$_6$BrNO, 189, 191; Found, 189, 191.

Preparation 13C: 3-bromo-6-methyl-5-nitropyridin-2-ol

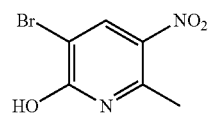

In a 500-mL round-bottomed flask, a 65% aqueous HNO$_3$ was stirred at 0° C. and 3-bromo-6-methylpyridin-2-ol (5.7 g, 30.3 mmol) was introduced dropwise. The reaction mixture was stirred at room temperature for 3.5 h. After pouring the mixture into ice water (200 mL), the aqueous layer was extracted with EtOAc (300 mL×2). The combined organic layers were washed with water, brine (200 mL×2), dried over Na$_2$SO$_4$, filtered, concentrated and purified by column chromatography on silica gel (25%, EtOAc:PE) to give 4.7 g (67%) of the title compound as an off-white solid. $^1$H NMR (400 MHz, CDCl$_3$) δ 12.85 (s, 3H), 8.66 (s, 1H), 2.86 (s, 1H). [M+H] Calc'd for C$_6$H$_5$BrN$_2$O$_3$, 235, 237; Found, 235, 237.

Preparation 13D: 3-bromo-2-chloro-6-methyl-5-nitropyridine

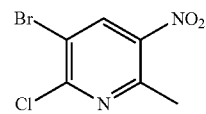

In a 500-mL single round-bottomed flask, POCl$_3$ (12 g, 78.1 mmol) was added dropwise to 3-bromo-6-methyl-5-nitropyridin-2-ol (4 g, 15.87 mmol). This mixture was then stirred at reflux for 7 h. The reaction mixture was cooled to 30° C., poured into ice water and stirred for 10 min. Saturated NaHCO$_3$ solution (30 mL) was then added. The aqueous layer was extracted with EtOAc (200 mL×3). The combined organic layers were washed with water, brine (200 mL×2), dried over Na$_2$SO$_4$, filtered and concentrated to give 2.8 g (65%) of the title compound as a yellow solid. $^1$H NMR (400 MHz, CDCl$_3$) δ 8.55 (s, 1H), 2.83 (s, 3H).

Preparation 13E: 5-bromo-6-chloro-2-methylpyridin-3-amine

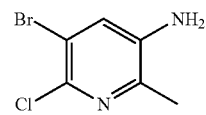

To a solution of 3-bromo-2-chloro-6-methyl-5-nitropyridine (2.2 g, 8.7 mmol) in EtOH (100 mL) was added Fe (4.8 g, 85.7 mmol) and HOAc (300 mL). The mixture was stirred at 30° C. for 13 h. The solids were filtered and the filtrate was concentrated in vacuo to remove EtOH and most of HOAc. The remaining aqueous was extracted with DCM (100 mL×3). The combined organic layers were washed with water, brine (100 mL×2), dried over $Na_2SO_4$, filtered and concentrated to give 1.66 g (86%) of the title compound as a brown solid. [M+H] Calc'd for $C_6H_6BrClN_2$, 221, 223; Found, 221, 223.

Preparation 13F: 4-(5-amino-2-chloro-6-methylpyridin-3-yl)benzonitrile

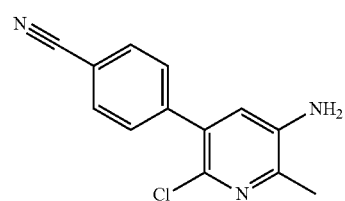 [SMILES: Cc1nc(Cl)c(-c2ccc(C#N)cc2)cc1N]

To a solution of 5-bromo-6-chloro-2-methylpyridin-3-amine (1.66 g, 7.48 mmol) in dioxane (50 mL) was added 4-cyanophenylboronic acid (1.2 g, 8.97 mmol), $Na_2CO_3$ (2.5 g, 23.6 mmol), Pd(dppf)Cl$_2$ (306 mg, 0.37 mmol) and a few drops of water. The mixture was degassed with $N_2$ for 5 min and heated to 70° C. for 13 h. The solids were filtered and the filtrate was concentrated in vacuo. The residue was purified by silica gel chromatography (15-25%, EtOAc:PE) to afford 1.42 g (79%) of the title compound as a brown solid. [M+H] Calc'd for $C_{13}H_{10}ClN_3$, 244; Found, 244.

Preparation 13G: 4-[5-amino-6-methyl-2-(4-methylphenyl)pyridin-3-yl]benzonitrile

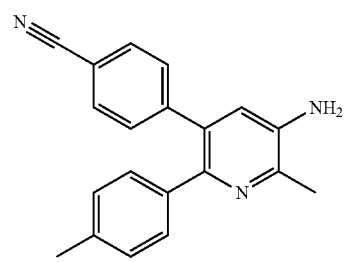 [SMILES: Cc1ccc(-c2nc(C)c(N)cc2-c2ccc(C#N)cc2)cc1]

To a solution of 4-(5-amino-2-chloro-6-methylpyridin-3-yl)benzonitrile (1.4 g, 5.76 mmol) in dioxane (50 mL) was added 4-(5-amino-2-chloro-6-methylpyridin-3-yl)benzonitrile (1.1 g, 8.15 mmol), $Na_2CO_3$ (2.2 g, 20.7 mmol), Pd(dppf)Cl$_2$ (0.8 g, 1.09 mmol) and a few drops of water. The mixture was degassed with $N_2$ for 5 min and heated to 110° C. for 14 h. The solids were filtered and the filtrate was concentrated in vacuo. The residue was purified by silica gel chromatography (15-25%, EtOAc:PE) to afford 1.3 g (76%) of the title compound as a light yellow solid. $^1$H NMR (400 MHz, CDCl$_3$) δ 7.54 (d, J=8.0 Hz, 2H), 7.26 (d, J=6.0 Hz, 2H), 7.12 (d, J=8.0 Hz, 2H), 7.02 (d, J=8.0 Hz, 2H), 6.96 (s, 1H), 3.77 (s, 2H), 2.56 (s, 3H), 2.30 (s, 3H). [M+H] Calc'd for $C_{20}H_{17}N_3$, 300; Found, 300.

Preparation 13H: N-[5-(4-cyanophenyl)-2-methyl-6-(4-methylphenyl)pyridin-3-yl]acetamide

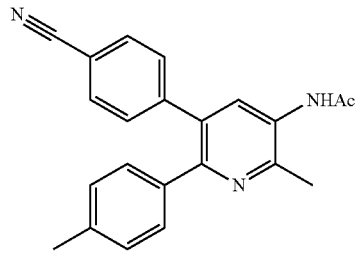 [SMILES: CC(=O)Nc1cc(-c2ccc(C#N)cc2)c(-c2ccc(C)cc2)nc1C]

To a solution of 4-[5-amino-6-methyl-2-(4-methylphenyl)pyridin-3-yl]benzonitrile (1.3 g, 4.35 mmol) in DCM (50 mL) was added pyridine (1.4 mL, 15 mmol) and Ac2O (1.3 mL, 13 mmol). The mixture was stirred at 30° C. for 16 h. To the reaction mixture was added saturated aqueous sodium bicarbonate solution in portions. The reaction mixture was stirred for 10 min. The aqueous layer was extracted with DCM (100 mL×3). The combined organic layers were washed with water, brine, dried over $Na_2SO_4$, filtered and concentrated in vacuo to give 1.3 g (86%) of the title compound as a yellow oil. [M+H] Calc'd for $C_{22}H_{19}N_3O$, 342; Found, 342.

Preparation 13I: 4-[1-acetyl-5-(4-methylphenyl)pyrazolo[4,3-b]pyridin-6-yl]benzonitrile

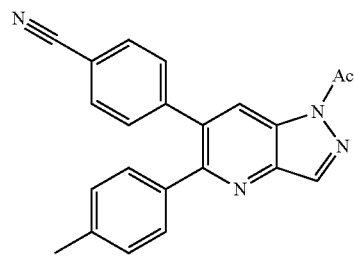 [SMILES: CC(=O)n1ncc2nc(-c3ccc(C)cc3)c(-c3ccc(C#N)cc3)cc21]

To a solution of N-[5-(4-cyanophenyl)-2-methyl-6-(4-methylphenyl)pyridin-3-yl]acetamide (1.3 g, 3.81 mmol) in toluene (20 mL) was added tert-butyl nitrite (630 mg, 6.1 mmol), Ac2O (1.1 mL, 11.5 mmol) and KOAc (452 mg, 4.6 mmol). The mixture was heated at 80° C. for 2 h, and then cooled to room temperature. 10% NaHCO3 (150 mL) was added and the mixture was extracted with EtOAc (100 ml×3). The combined organic layers were washed with water, NaHCO3, brine, dried over Na2SO4, filtered and concentrated in vacuo to give 0.8 g (60%) of the title compound as brown solid. [M+H] Calc'd for C22H16N4O, 353; Found, 353.

Preparation 13J: 4-[5-(4-methylphenyl)-1H-pyrazolo[4,3-b]pyridin-6-yl]benzonitrile

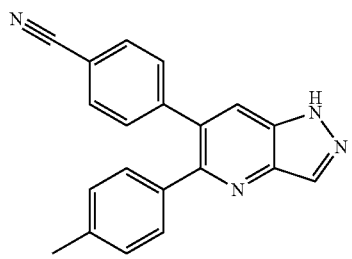 [SMILES: Cc1ccc(-c2nc3cn[nH]c3cc2-c2ccc(C#N)cc2)cc1]

To 4-[1-acetyl-5-(4-methylphenyl)pyrazolo[4,3-b]pyridin-6-yl]benzonitrile (0.8 g, 2.27 mmol) in THF/MeOH (30 mL, 2:1) was added NaOH (2.3 M, 3 mL). The resulting mixture was stirred at room temperature for 1 h. The solvent was removed in vacuo. The residue was taken in water (30 mL) and the aqueous was extracted with EtOAc (20 mL×3). The combined organic layers were washed with water, brine, dried over $Na_2SO_4$ and concentrated. The crude product was further purified by column chromatography (33%, EtOAc: PE) to give 0.41 g (58%) of the title compound as a yellow solid. $^1$H NMR (400 MHz, $CD_3OD$): δ 8.29 (s, 1H), 8.07 (s, 1H), 7.65 (d, J=8.0 Hz, 2H), 7.42 (d, J=8.0 Hz, 2H), 7.19 (d, J=8.0 Hz, 2H), 7.12 (d, J=8.0 Hz, 2H), 2.33 (s, 3H). [M+H] Calc'd for $C_{20}H_{14}N_4$, 311; Found, 311.

Preparation 13K: tert-butyl 3-[[6-(4-cyanophenyl)-5-(4-methylphenyl)pyrazolo[4,3-b]pyridin-1-yl]methyl]pyrrolidine-1-carboxylate

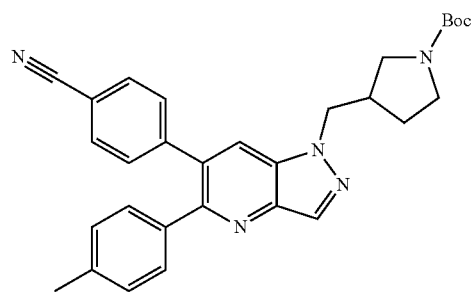 [SMILES: Cc1ccc(-c2nc3cnn(CC4CCN(C(=O)OC(C)(C)C)C4)c3cc2-c2ccc(C#N)cc2)cc1]

To a solution of 4-[5-(4-methylphenyl)-1H-pyrazolo[4,3-b]pyridin-6-yl]benzonitrile (100 mg, 0.32 mmol) and tert-butyl 3-[(4-ethylphenyl)sulfonyloxymethyl]pyrrolidine-1-carboxylate (185 mg, 0.52 mmol) in DMF (5 mL) was added potassium carbonate (209 mg, 0.96 mmol). The mixture was then stirred at RT overnight. The mixture was diluted with EtOAc (20 mL) and water (20 mL). The aqueous layer was extracted with EtOAc (30 mL×3). The combined organic layers were washed with water (20 mL×2), brine, dried over $Na_2SO_4$, filtered, and concentrated. The residue was purified by prep-HPLC to give 66 mg (43%) of the title compound as a white solid. $^1$H NMR (CDCl$_3$, 400 MHz): δ 8.32 (s, 1H), 7.71 (s, 1H), 7.57 (d, J=8.4 Hz, 2H), 7.35 (d, J=5.6 Hz, 2H), 7.18 (d, J=8.0 Hz, 2H), 7.07 (d, J=8.0 Hz, 2H), 4.41 (d, J=7.2 Hz, 2H), 3.48-3.43 (m, 2H), 3.34-3.32 (m, 1H), 3.18 (t, J=4.8 Hz, 1H), 2.90-2.91 (m, 1H), 2.33 (s, 3H), 2.00-1.98 (m, 1H), 1.75-1.73 (m, 1H), 1.42 (s, 9H). [M+H] Calc'd for $C_{30}H_{31}N_5O_2$, 494; Found, 494.

Example 13: 4-[5-(4-methylphenyl)-1-(pyrrolidin-3-ylmethyl)pyrazolo[4,3-b]pyridin-6-yl]benzonitrile

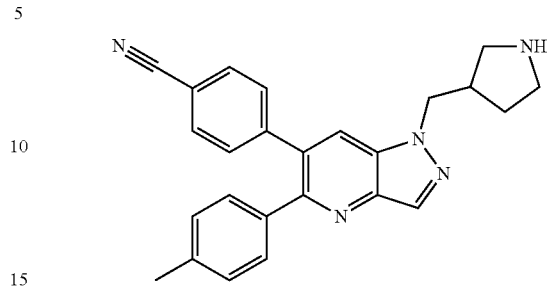

A solution of hydrochloric acid in dioxane (4 M, 3 mL) was added to 4-[5-(4-methylphenyl)-1-(pyrrolidin-3-ylmethyl)pyrazolo[4,3-b]pyridin-6-yl]benzonitrile (66 mg, 0.13 mmol). The mixture was then stirred at room temperature for 30 min. The resulting mixture was concentrated to afford 49 mg (94%) of the title compound as a white solid. $^1$H NMR ($CD_3OD$, 400 MHz): δ 9.10 (s, 1H), 8.54 (s, 1H), 7.73 (d, J=8.0 Hz, 2H), 7.56 (d, J=8.0 Hz, 2H), 7.35 (d, J=8.0 Hz, 2H), 7.28 (d, J=8.0 Hz, 2H), 4.87-4.85 (m, 2H), 3.62-3.49 (m, 3H), 3.29-3.17 (m, 2H), 2.39 (s, 3H), 2.28-2.24 (m, 1H), 1.99-1.93 (m, 1H). [M+H] Calc'd for $C_{25}H_{23}N_5$, 394; Found, 394.

Preparation 14A: tert-butyl 4-[[6-(4-cyanophenyl)-5-(4-methylphenyl)pyrazolo[4,3-b]pyridin-1-yl]methyl]piperidine-1-carboxylate

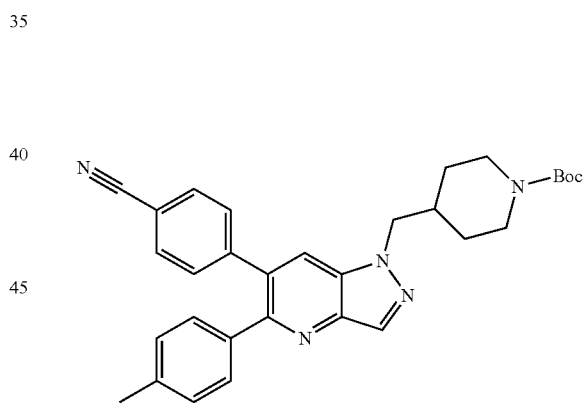

To a solution of 4-[5-(4-methylphenyl)-1H-pyrazolo[4,3-b]pyridin-6-yl]benzonitrile (80 mg, 0.26 mmol) and tert-butyl 4-(bromomethyl)piperidine-1-carboxylate (138 mg, 0.49 mmol) in DMF (3 mL) was added potassium carbonate (120 mg, 0.55 mmol). The mixture was stirred at RT overnight. The mixture was diluted with EtOAc (20 mL) and water (20 mL). The aqueous layer was extracted with EtOAc (30 mL×3). The combined organic layers were washed with water (20 mL×2), brine, dried over $Na_2SO_4$, filtered and concentrated to give the title compound as yellow oil. This oil was used without purification in the next step. [M+H] Calc'd for $C_{31}H_{33}N_5O_2$, 508; Found, 508.

Example 14: 4-[5-(4-methylphenyl)-1-(piperidin-4-ylmethyl)pyrazolo[4,3-b]pyridin-6-yl]benzonitrile

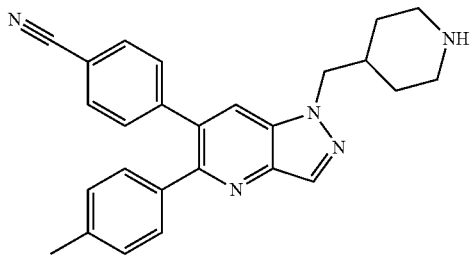 [SMILES: Cc1ccc(-c2nc3cnn(CC4CCNCC4)c3cc2-c2ccc(C#N)cc2)cc1]

To tert-butyl 4-[[6-(4-cyanophenyl)-5-(4-methylphenyl)pyrazolo[4,3-b]pyridin-1-yl]methyl]piperidine-1-carboxylate (76 mg, 0.15 mmol) was added hydrochloric acid in dioxane (4 M, 4 mL) at 0° C. The mixture was warmed to room temperature and stirred for 30 min. The reaction mixture was concentrated and the residue was purified by prep-HPLC to afford 25 mg (41%) of the title compound as white solid. 1H NMR (D20, 400 MHz): δ 8.18 (s, 1H), 8.06 (s, 1H), 7.45 (d, J=8.4 Hz, 2H), 7.16 (d, J=8.0 Hz, 2H), 6.94 (s, 4H), 4.33 (d, J=6.8 Hz, 2H), 3.31 (d, J=13.2 Hz, 2H), 2.83 (t, J=10.4 Hz, 2H), 2.24-2.23 (m, 1H), 2.14 (s, 3H), 1.69 (d, J=11.6 Hz, 2H), 1.47-1.29 (m, 2H). Calc'd for C26H25N5, 408; Found, 408.

Preparation 15A: tert-butyl (1S,5R)-6-[[6-(4-cyanophenyl)-5-(4-methylphenyl)pyrazolo[4,3-b]pyridin-1-yl]methyl]-3-azabicyclo[3.1.0]hexane-3-carboxylate

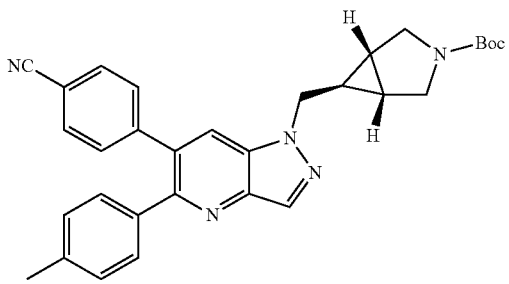 [SMILES: Cc1ccc(-c2nc3cnn(C[C@H]4[C@@H]5CN(C(=O)OC(C)(C)C)C[C@@H]54)c3cc2-c2ccc(C#N)cc2)cc1]

A mixture of 4-[5-(4-methylphenyl)-1H-pyrazolo[4,3-b]pyridin-6-yl]benzonitrile (100 mg, 0.32 mmol), tert-butyl (1S,5R)-6-(chloromethyl)-3-azabicyclo[3.1.0]hexane-3-carboxylate (115 mg, 0.49 mmol) and K$_2$CO$_3$ (150 mg, 0.69 mmol) in DMF (8 mL) was stirred at 60° C. overnight. The mixture was cooled down to room temperature, diluted with water (50 mL) and ethyl acetate (50 mL). The solution was extracted with ethyl acetate (30 mL×3). The combined organic layers were washed with water (50 mL×3), brine (50 mL), dried over Na$_2$SO$_4$, filtered and concentrated. The residue was purified by pre-HPLC to give 62 mg (38%) of the title compound as a white solid. $^1$H NMR (CDCl$_3$, 400 MHz): δ 8.35 (s, 1H), 7.76 (s, 1H), 7.61 (d, J=7.8 Hz, 2H), 7.36 (d, J=8.2 Hz, 2H), 7.21 (d, J=7.4 Hz, 2H), 7.09 (d, J=7.8 Hz, 2H), 4.41-4.35 (m, 2H), 3.63-3.61 (m, 1H), 3.50-3.48 (m, 1H), 3.37-3.36 (m, 2H), 2.35 (s, 3H), 1.62-1.67 (m, 2H), 1.40 (s, 9H), 1.26-1.14 (m, 1H). [M+H] Calc'd for C$_{31}$H$_{31}$N$_5$O$_2$, 506; Found, 506.

Example 15: 4-[1-[[(1S,5R)-3-azabicyclo[3.1.0]hexan-6-yl]methyl]-5-(4-methylphenyl)pyrazolo[4,3-b]pyridin-6-yl]benzonitrile

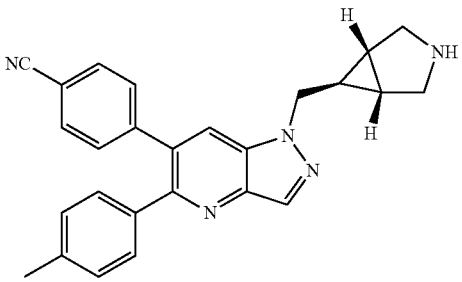 [SMILES: Cc1ccc(-c2nc3cnn(C[C@H]4[C@@H]5CNC[C@@H]54)c3cc2-c2ccc(C#N)cc2)cc1]

To a solution of tert-butyl (1S,5R)-6-[[6-(4-cyanophenyl)-5-(4-methylphenyl)pyrazolo[4,3-b]pyridin-1-yl]methyl]-3-azabicyclo[3.1.0]hexane-3-carboxylate (62 mg, 0.12 mmol) in DCM (5 mL) was added hydrochloric acid in dioxane (4 M, 2 mL). The mixture was then stirred at room temperature for 30 min. The resulting mixture was concentrated to give 35 mg (72%) of the title compound as the HCl salt as a yellow oil. $^1$H NMR (CD$_3$OD, 400 MHz): δ 8.85 (s, 1H), 8.45 (s, 1H), 7.72 (d, J=6.9 Hz, 2H), 7.54 (d, J=7.4 Hz, 2H), 7.24-7.31 (m, 4H), 4.64 (d, J=6.4 Hz, 2H), 3.61-3.59 (m, 4H), 2.38 (s, 3H), 2.08-2.10 (m, 2H), 1.72-1.74 (m, 1H). [M+H] Calc'd for C$_{26}$H$_{23}$N$_5$, 406; Found, 406.

Preparation 16A: 4-(2,5-dichloropyrimidin-4-yl)benzonitrile

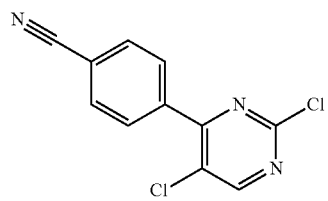 [SMILES: N#Cc1ccc(-c2nc(Cl)ncc2Cl)cc1]

To a 100 mL pressure vessel charged with 2,4,5-trichloropyrimidine (1.83 g, 10 mmol) in dioxane (20 mL) was added (4-cyanophenyl)boronic acid (1.47 g, 10 mmol), PdCl$_2$(dppf) (146 mg, 0.2 mmol), and Na$_2$CO$_3$ (10 mL, 2M). The mixture was purged with N$_2$ for 5 min and sealed. The reaction was kept at 70° C. for 1 h with vigorous stirring. Water was added and the heterogeneous mixture was filtered. The filter cake was taken up in ethanol, stirred for 10 min, filtered, and dried in vacuo to afford the title compound (2.2 g, 89%) as off-white crystals. [M+H] calc'd for C$_{11}$H$_5$N$_3$Cl$_2$, 250; found 250.

Preparation 16B: tert-butyl (3R)-3-({[5-chloro-4-(4-cyanophenyl)pyrimidin-2-yl]amino}methyl)pyrrolidine-1-carboxylate

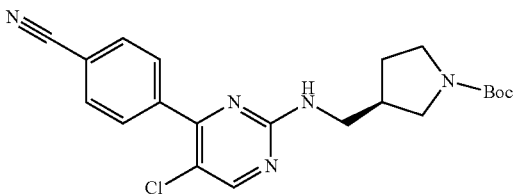 [SMILES: CC(C)(C)OC(=O)N1CC[C@H](CNc2ncc(Cl)c(-c3ccc(C#N)cc3)n2)C1]

To a vial containing 4-(2,5-dichloropyrimidin-4-yl)benzonitrile (496 mg, 2 mmol) in ethanol (5 mL), was added tert-butyl (3S)-3-(aminomethyl)pyrrolidine-1-carboxylate (400 mg, 2 mmol), and DIEA (694 μL, 4 mmol). The reaction was stirred at 100° C. for 16 h. The reaction was concentrated in vacuo, and the residue purified by column chromatography (0-50% gradient of EtOAc in hexanes) to afford the title compound (743 mg, 90%) as a yellow amorphous solid. [M+H] calc'd for $C_{21}H_{24}N_5O_2Cl$, 414; found 414.

Example 16: 4-[5-(4-methylphenyl)-2-{[(3S)-pyrrolidin-3-ylmethyl]amino}pyrimidin-4-yl]benzonitrile

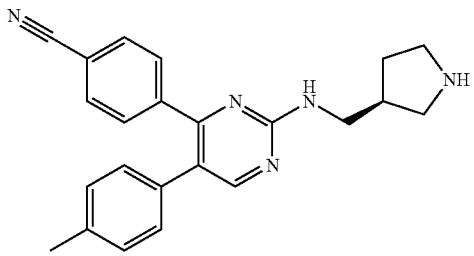 [SMILES: Cc1ccc(-c2cnc(NC[C@H]3CCNC3)nc2-c2ccc(C#N)cc2)cc1]

To a microwave vial charged with tert-butyl (3R)-3-({[5-chloro-4-(4-cyanophenyl)pyrimidin-2-yl]amino}methyl)pyrrolidine-1-carboxylate (206 mg, 0.5 mmol) in dioxane (3 mL) was added (4-methylphenyl)boronic acid (136 mg, 1 mmol), PdCl2(dppf) (36 mg, 0.05 mmol), and Na2CO3 (1 mL, 2M). The mixture was purged with N2 for 2 min and sealed. The reaction was irradiated in the microwave at 120° C. for 2 h or kept at 120° C. on a heating block for 16 h. Water was added, and the mixture was extracted with EtOAc (3×). The combined organic layers were dried over Na2SO4 and concentrated in vacuo. The residue was purified by column chromatography (0-50% gradient of EtOAc in hexanes) to afford a yellow amorphous foam that was further purified by prep-HPLC (75%-95% gradient of ACN in water with 0.1% HCO2H) to afford tert-butyl (3R)-3-({[4-(4-cyanophenyl)-5-(4-methylphenyl)pyrimidin-2-yl]amino}methyl)pyrrolidine-1-carboxylate as a yellow amorphous foam. The foam was dissolved in DCM (2 mL) followed by dropwise addition of TFA (2 mL). The reaction was stirred at ambient temperature for 30 min and concentrated in vacuo to afford the TFA salt of the title compound (109 mg, 47%) as an off-white amorphous foam. 1H NMR (400 MHz, CDCl3) δ 1.79-1.95 (m, 1H), 2.12-2.29 (m, 1H), 2.35 (s, 3H), 2.78-2.93 (m, 1H), 3.12-3.26 (m, 1H), 3.26-3.49 (m, 3H), 3.49-3.61 (m, 1H), 3.61-3.70 (m, 1H), 5.76-6.01 (m, 1H), 6.88-7.02 (m, 2H), 7.08-7.18 (m, 2H), 7.47-7.62 (m, 4H), 8.09-8.29 (m, 1H), 8.29-8.39 (m, 1H). [M+H] calc'd for C23H23N5, 370; found 370.

Example 17: 4-(5-chloro-2-{[(3S)-pyrrolidin-3-ylmethyl]amino}pyrimidin-4-yl)benzonitrile

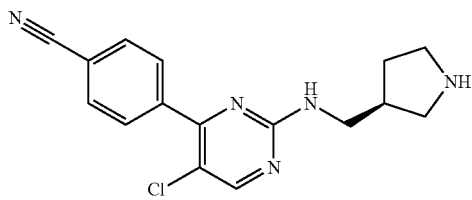 [SMILES: N#Cc1ccc(-c2nc(NC[C@H]3CCNC3)ncc2Cl)cc1]

tert-butyl (3R)-3-({[5-chloro-4-(4-cyanophenyl)pyrimidin-2-yl]amino}methyl)pyrrolidine-1-carboxylate dissolved in DCM (2 mL) was added TFA (2 mL) dropwise. The reaction was stirred at ambient temperature for 30 min and concentrated in vacuo to afford the TFA salt of the title compound (59 mg, 47%) as an off-white amorphous foam. $^1$H NMR (400 MHz, CDCl$_3$-d): δ ppm 1.68-2.08 (m, 1H), 2.12-2.49 (m, 1H), 2.66-3.11 (m, 1H), 3.37-3.90 (m, 6H), 7.67-8.13 (m, 4H), 8.44-8.83 (s, 1H), 9.45-10.14 (br. s., 2H). [M+H] calc'd for $C_{16}H_{16}N_5Cl$, 314; found 314.

Example 18: 4-[5-(4-fluorophenyl)-2-{[(3S)-pyrrolidin-3-ylmethyl]amino}pyrimidin-4-yl]benzonitrile

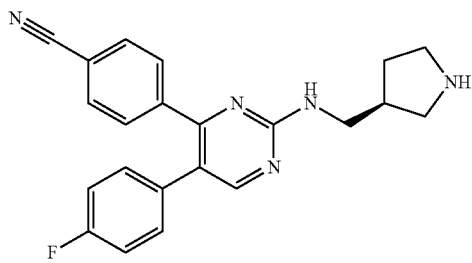

The TFA salt of the title compound was prepared in 34% yield using tert-butyl (3R)-3-({[5-chloro-4-(4-cyanophenyl)pyrimidin-2-yl]amino}methyl)pyrrolidine-1-carboxylate and (4-fluorophenyl)boronic acid according to the procedure for the preparation of Example 16. $^1$H NMR (400 MHz, DMSO-d$_6$): δ ppm 1.59-1.85 (m, 1H), 1.97-2.17 (m, 1H), 2.59-2.72 (m, 1H), 2.82-3.01 (m, 1H), 3.06-3.36 (m, 2H), 3.37-3.50 (m, 2H), 7.15 (d, J=7.07 Hz, 4H), 7.40-7.56 (m, 2H), 7.67-7.79 (m, 1H), 7.79-7.88 (m, 2H), 8.38 (s, 1H), 8.54-8.78 (m, 2H). [M+H] calc'd for $C_{22}H_{20}N_5F$, 374; found 374.

159

Example 19: 4-[5-(4-chlorophenyl)-2-{[(3S)-pyrrolidin-3-ylmethyl]amino}pyrimidin-4-yl]benzonitrile

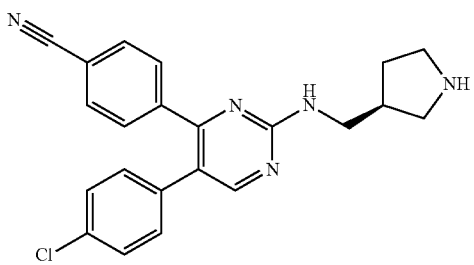 [SMILES: N#Cc1ccc(-c2nc(NC[C@H]3CCNC3)ncc2-c2ccc(Cl)cc2)cc1]

The TFA salt of the title compound was prepared in 31% yield using tert-butyl (3R)-3-({[5-chloro-4-(4-cyanophenyl)pyrimidin-2-yl]amino}methyl)pyrrolidine-1-carboxylate and (4-chlorophenyl)boronic acid, pinacol ester according to the procedure for the preparation of Example 16. $^1$H NMR (400 MHz, DMSO-d$_6$): δ ppm 1.62-1.83 (m, 1H), 1.94-2.17 (m, 1H), 2.62-2.74 (m, 1H), 2.86-3.02 (m, 1H), 3.13 (m, 1H), 3.27 (m, 2H), 3.43 (m, 2H), 7.07-7.19 (m, 2H), 7.29-7.43 (m, 2H), 7.44-7.56 (m, 2H), 7.62-7.75 (m, 1H), 7.77-7.89 (m, 2H), 8.40 (s, 1H), 8.60 (br. s., 1H). [M+H] calc'd for C$_{22}$H$_{20}$N$_5$Cl, 390; found 390.

Preparation 20A: tert-butyl (3R)-3-({[5-chloro-4-(4-cyanophenyl)pyrimidin-2-yl]oxy}methyl)pyrrolidine-1-carboxylate

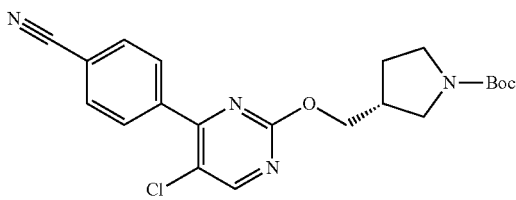 [SMILES: CC(C)(C)OC(=O)N1CC[C@@H](COc2ncc(Cl)c(-c3ccc(C#N)cc3)n2)C1]

To a round-bottom flask charged with tert-butyl (3R)-3-(hydroxymethyl)pyrrolidine-1-carboxylate (664 mg, 3.3 mmol) in DMF (10 mL) at 0° C. was added NaH (144 mg, 3.6 mmol, 60%). The reaction was allowed to stir for 30 min at ambient temperature before adding 4-(2,5-dichloropyrimidin-4-yl)benzonitrile (744 mg, 3 mmol) at 0° C. The reaction was allowed to warm to ambient temperature and stirred for 16 h. The reaction was quenched with saturated NH$_4$Cl and taken up in EtOAc. The organic layers were sequentially washed with water (3×) and brine, dried over Na$_2$SO$_4$, and concentrated in vacuo. The residue was purified by column chromatography (0-40% gradient of EtOAc in hexanes) to afford the title compound (655 mg, 53%) as a yellow amorphous solid. [M+H] calc'd for C$_{21}$H$_{23}$N$_4$O$_3$Cl, 415; found 415.

160

Example 20: 4-[5-(4-methylphenyl)-2-[(3R)-pyrrolidin-3-ylmethoxy]pyrimidin-4-yl]benzonitrile

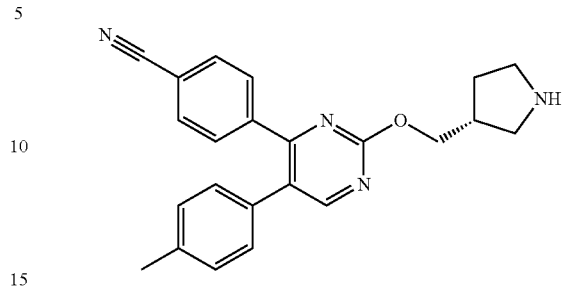

To a microwave vial charged with tert-butyl (3R)-3-({[5-chloro-4-(4-cyanophenyl)pyrimidin-2-yl]oxy}methyl)pyrrolidine-1-carboxylate (103 mg, 0.25 mmol) in dioxane (3 mL) was added (4-methylphenyl)boronic acid (68 mg, 0.5 mmol), PdCl$_2$(dppf) (36 mg, 0.05 mmol), and Na$_2$CO$_3$ (1 mL, 2M). The mixture was purged with N$_2$ for 2 min and sealed. The reaction was irradiated in the microwave at 120° C. for 2 h. Water was added and the mixture extracted with EtOAc (3×). The combined organic layers were dried over Na$_2$SO$_4$ and concentrated in vacuo. The residue was purified by column chromatography (0-40% gradient of EtOAc in hexanes) to afford a yellow amorphous foam that was further purified by prep-HPLC (75%-95% gradient of ACN in water with 0.1% HCO$_2$H) to afford tert-butyl (3R)-3-({[4-(4-cyanophenyl)-5-(4-methylphenyl)pyrimidin-2-yl]oxy}methyl)pyrrolidine-1-carboxylate as a yellow amorphous foam. The foam was dissolved in DCM (2 mL) and followed by dropwise addition of TFA (2 mL). The reaction was stirred at ambient temperature for 30 min and concentrated in vacuo to afford the TFA salt of the title compound (35 mg, 30%) as an off-white amorphous foam. $^1$H NMR (400 MHz, DMSO-d$_6$): δ ppm 1.70-1.96 (m, 1H), 2.05-2.23 (m, 1H), 2.31 (s, 3H), 2.76-2.91 (m, 1H), 3.00-3.13 (m, 1H), 3.13-3.24 (m, 1H), 3.25-3.35 (m, 1H), 3.35-3.48 (m, 1H), 4.34-4.52 (m, 2H), 7.01-7.13 (m, 2H), 7.18 (d, J=8.08 Hz, 2H), 7.55 (d, J=8.34 Hz, 2H), 7.83 (d, J=8.34 Hz, 2H), 8.67 (s, 1H), 8.69-8.87 (m, 2H). [M+H] calc'd for C$_{23}$H$_{22}$N$_4$O, 371; found 371.

Preparation 21A: tert-butyl (3aR,6aS)-5-[5-chloro-4-(4-cyanophenyl)pyrimidin-2-yl]-octahydropyrrolo[3,4-c]pyrrole-2-carboxylate

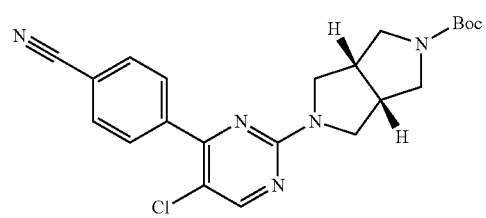 [SMILES: CC(C)(C)OC(=O)N1C[C@@H]2CN(c3ncc(Cl)c(-c4ccc(C#N)cc4)n3)C[C@@H]2C1]

To a vial containing 4-(2,5-dichloropyrimidin-4-yl)benzonitrile (144 mg, 0.58 mmol) in ethanol (2 mL) was added tert-butyl (3aR,6aS)-octahydropyrrolo[3,4-c]pyrrole-2-carboxylate (123 mg, 0.58 mmol), and DIEA (144 µL, 1.2 mmol). The reaction was stirred at 100° C. for 1 h. The reaction was concentrated in vacuo and the residue purified by column chromatography (0-50% gradient of EtOAc in

Example 21: 4-{2-[(3aR,6aS)-octahydropyrrolo[3,4-c]pyrrol-2-yl]-5-(4-methylphenyl)pyrimidin-4-yl}benzonitrile

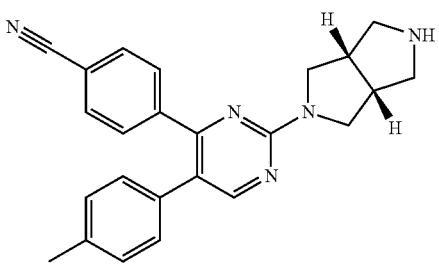 [SMILES: Cc1ccc(-c2cnc(N3C[C@H]4CNC[C@H]4C3)nc2-c2ccc(C#N)cc2)cc1]

The TFA salt of the title compound was prepared in 33% yield using tert-butyl (3aR,6aS)-5-[5-chloro-4-(4-cyanophenyl)pyrimidin-2-yl]-octahydropyrrolo[3,4-c]pyrrole-2-carboxylate and (4-methylphenyl)boronic acid according to the procedure for the preparation of Example 16. $^1$H NMR (400 MHz, DMSO-$d_6$): δ ppm 2.29 (s, 3H), 2.98-3.27 (m, 4H), 3.46 (m, 2H), 3.60-3.70 (m, 2H), 3.72-3.83 (m, 2H), 7.01 (d, J=8.08 Hz, 2H), 7.13 (d, J=7.83 Hz, 2H), 7.52 (d, J=8.34 Hz, 2H), 7.81 (d, J=8.08 Hz, 2H), 8.44 (s, 1H), 8.78-8.98 (m, 2H). [M+H] calc'd for $C_{24}H_{23}N_5$, 382; found 382.

Example 22: 4-[5-(4-methylphenyl)-2-{octahydro-1H-pyrrolo[3,4-c]pyridin-5-yl}pyrimidin-4-yl]benzonitrile

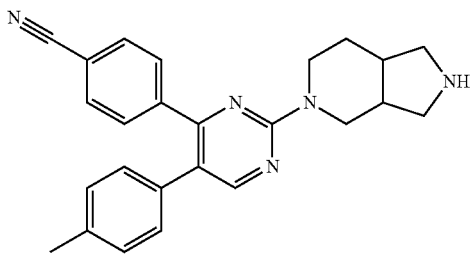

The TFA salt of the title compound was prepared in 37% yield starting from tert-butyl octahydro-1H-pyrrolo[3,4-c]pyridine-2-carboxylate according to the procedure for the preparation of Example 21. $^1$H NMR (400 MHz, METHANOL-$d_4$): δ ppm 1.53-1.70 (m, 1H), 1.84-1.99 (m, 1H), 2.32 (s, 3H), 2.59-2.75 (m, 2H), 2.99-3.11 (m, 1H), 3.18-3.28 (m, 1H), 3.37-3.48 (m, 3H), 3.68-3.82 (m, 1H), 4.41-4.61 (m, 2H), 6.94-7.06 (d, J=8.08 Hz, 2H), 7.13 (d, J=8.08 Hz, 2H), 7.54-7.59 (d, J=8.08 Hz, 2H), 7.63 (d, J=8.08 Hz, 3H), 8.38 (s, 1H). [M+H] calc'd for $C_{25}H_{25}N_5$, 396; found 396.

Example 23: 4-{2-[(3aR,8aS)-decahydropyrrolo[3,4-d]azepin-6-yl]-5-(4-methylphenyl)pyrimidin-4-yl}benzonitrile

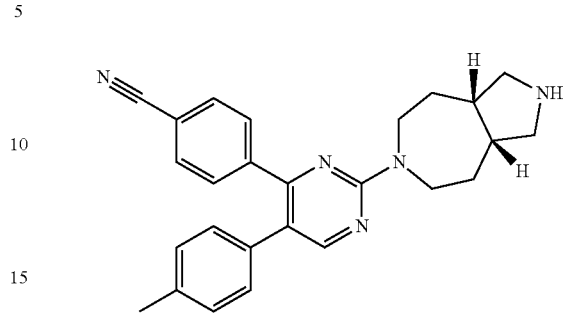

The TFA salt of the title compound was prepared in 28% yield starting from tert-butyl (3aR,8aS)-decahydropyrrolo[3,4-d]azepine-2-carboxylate according to the procedure for the preparation of Example 21. $^1$H NMR (400 MHz, DMSO-$d_6$): δ ppm 1.62-1.79 (m, 2H), 1.82-1.99 (m, 2H), 2.29 (s, 3H), 2.55-2.65 (m, 2H), 2.76-2.95 (m, 2H), 3.28-3.40 (m, 2H), 3.40-3.54 (m, 2H), 4.25-4.43 (m, 2H), 7.00 (d, J=8.08 Hz, 2H), 7.13 (d, J=7.83 Hz, 2H), 7.51 (d, J=8.59 Hz, 2H), 7.80 (d, J=8.59 Hz, 2H), 8.43 (s, 1H), 8.53-8.64 (m, 1H), 8.64-8.79 (m, 1H). [M+H] calc'd for $C_{26}H_{27}N_5$, 410; found 410.

Example 24: 4-{2-[(3aR,8aS)-decahydropyrrolo[3,4-d]azepin-6-yl]-5-(4-fluorophenyl)pyrimidin-4-yl}benzonitrile

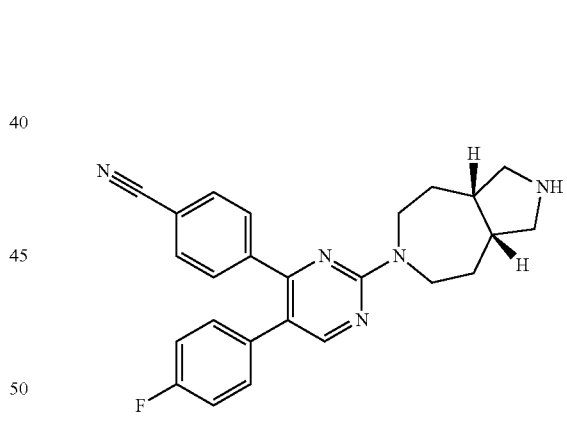

The TFA salt of the title compound was prepared in 32% yield using tert-butyl (3aR,8aS)-6-[5-chloro-4-(4-cyanophenyl)pyrimidin-2-yl]-decahydropyrrolo[3,4-d]azepine-2-carboxylate and (4-fluorophenyl)boronic acid according to the procedure for the preparation of Example 21. $^1$H NMR (400 MHz, DMSO-$d_6$): δ ppm 1.62-1.79 (m, 2H), 1.82-1.99 (m, 2H), 2.50-2.62 (m, 2H), 2.77-2.93 (m, 2H), 3.30-3.42 (m, 4H), 3.42-3.55 (m, 2H), 4.26-4.42 (m, 2H), 7.14-7.20 (m, 4H), 7.50 (d, J=8.34 Hz, 2H), 7.81 (d, J=8.34 Hz, 2H), 8.40-8.52 (m, 1H), 8.52-8.64 (m, 1H), 8.67-8.79 (m, 1H). [M+H] calc'd for $C_{25}H_{24}N_5F$, 414; found 414.

Example 25: 4-(2-{[(3S)-pyrrolidin-3-ylmethyl]amino}-5-[4-(trifluoromethyl)phenyl]pyrimidin-4-yl)benzonitrile

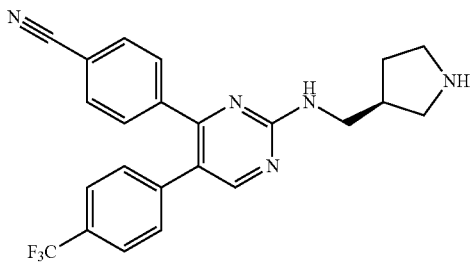

The TFA salt of the title compound was prepared in 46% yield using tert-butyl (3R)-3-({[5-chloro-4-(4-cyanophenyl)pyrimidin-2-yl]amino}methyl)pyrrolidine-1-carboxylate and (4-trifluoromethylphenyl)boronic acid according to the procedure for the preparation of Example 16. $^1$H NMR (400 MHz, DMSO-$d_6$): δ ppm 1.65-1.81 (m, 1H), 2.00-2.14 (m, 1H), 2.59-2.73 (m, 1H), 2.89-2.99 (m, 1H), 3.09-3.20 (m, 1H), 3.21-3.37 (m, 2H), 3.38-3.50 (m, 2H), 7.35 (d, J=8.08 Hz, 2H), 7.44-7.57 (m, 2H), 7.67 (d, J=8.08 Hz, 2H), 7.80 (d, J=8.34 Hz, 2H), 8.46 (s, 1H), 8.65 (br. s., 2H). [M+H] calc'd for $C_{23}H_{20}N_5F_3$, 424; found 424.

Example 26: 4-[5-(2-cyclopropylethynyl)-2-{[(3S)-pyrrolidin-3-ylmethyl]amino}pyrimidin-4-yl]benzonitrile

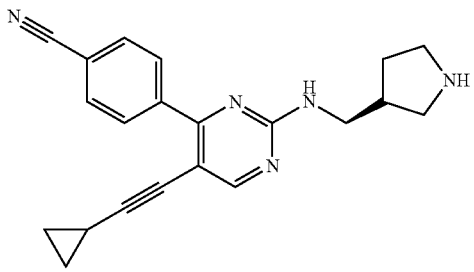

To a vial charged with tert-butyl (3R)-3-({[5-chloro-4-(4-cyanophenyl)pyrimidin-2-yl]amino}methyl)pyrrolidine-1-carboxylate (103 mg, 0.25 mmol) in ACN (3 mL) was added cyclopropane acetylene (33 mg, 0.5 mmol), PdCl$_2$(ACN)$_2$ (2.6 mg, 0.01 mmol), XPhos (4 mg, 0.02), and K$_2$CO$_3$ (103 mg, 0.75 mmol). The mixture was purged with N$_2$ for 2 min and sealed. The reaction was kept at 100° C. for 16 h. Water was added and the mixture was extracted with EtOAc (3×). The combined organic layers were dried over Na$_2$SO$_4$ and concentrated in vacuo. The residue was purified by column chromatography (0-50% gradient of EtOAc in hexanes) to afford a yellow amorphous residue. The residue was dissolved in DCM (2 mL) followed by dropwise addition of TFA (2 mL). The reaction was stirred at ambient temperature for 30 min and concentrated in vacuo. The residue was further purified by prep-HPLC (5%-95% gradient of ACN in water with 0.1% HCO2H) to afford the formic acid salt of the title compound as a yellow amorphous foam (3 mg, 3%). $^1$H NMR (400 MHz, CD$_3$OD): δ ppm 0.58-0.75 (m, 2H), 0.80-0.96 (m, 2H), 1.36-1.53 (m, 1H), 1.72-1.93 (m, 1H), 2.10-2.31 (m, 1H), 2.66-2.82 (m, 1H), 2.95-3.09 (m, 1H), 3.51-3.62 (m, 5H), 7.76-7.90 (m, 2H), 8.14-8.27 (m, 2H), 8.34-8.45 (m, 1H). [M+H] calc'd for $C_{21}H_{21}N_5$, 344; found 344.

Example 27: 4-(2-{[(3aR,5S,6aS)-octahydrocyclopenta[c]pyrrol-5-yl]amino}-5-(4-methylphenyl)pyrimidin-4-yl)benzonitrile

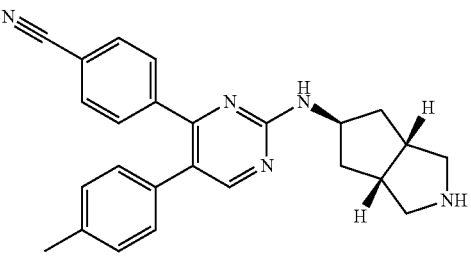 [SMILES: Cc1ccc(-c2cnc(N[C@@H]3C[C@H]4CNC[C@H]4C3)nc2-c2ccc(C#N)cc2)cc1]

To a vial containing tert-butyl (3aR,5S,6aS)-5-{[5-chloro-4-(4-cyanophenyl)pyrimidin-2-yl]amino}-octahydrocyclopenta[c]pyrrole-2-carboxylate (250.0 mg, 0.57 mmol), prepared according to the procedure for preparation 16B, in dioxane (3 mL) was added (4-methylphenyl)boronic acid (155.0 mg, 1.14 mmol), Pd(dppf)Cl$_2$ (80.0 mg, 0.11 mmol), and Na$_2$CO$_3$ (1 mL, 2 M). The mixture was purged with N$_2$ for 2 min and sealed. The reaction mixture was irradiated in the microwave at 130° C. for 4 hrs. Water was added, and the mixture was extracted with EtOAc (3×). The combined organic layers were dried with Na$_2$SO$_4$ and concentrated in vacuo. The residue was purified by column chromatography (petroleum ether:ethyl acetate=5:1) to afford a crude residue. HCl (5 mL, 4 M in dioxane) was added the mixture and for stirred at 30° C. for 1 h. The mixture was concentrated in vacuo and purified by prep-HPLC to afford the title compound (40.0 mg, yield 33.7%) as a light-yellow foam. $^1$H NMR (Methanol-$d_4$, 400 MHz): δ 1.87-1.84 (m, 4H), 2.32 (s, 3H), 2.63-2.59 (m, 2H), 2.80-2.70 (m, 2H), 3.12-3.07 (m, 2H), 4.47-4.40 (m, 1H), 6.98 (d, J=8.0 Hz, 2H), 7.12 (d, J=8.0 Hz, 2H), 7.54 (d, J=8.4 Hz, 2H), 7.62 (d, J=8.4 Hz, 2H), 8.29 (s, 1H). [M+H] calc'd for $C_{25}H_{25}N_5$, 396; found 396.

Example 28: (+)-4-(2-{[(3-fluoropyrrolidin-3-yl)methyl]amino}-5-(4-methylphenyl)pyrimidin-4-yl)benzonitrile

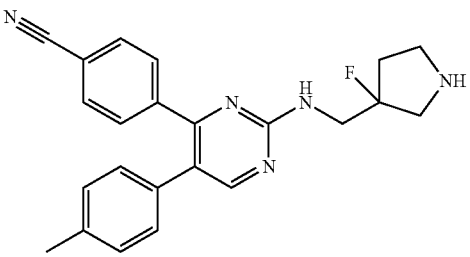 [SMILES: Cc1ccc(-c2cnc(NCC3(F)CCNC3)nc2-c2ccc(C#N)cc2)cc1]

The title compound was prepared in 29% yield using (+)-tert-butyl-3-({[5-chloro-4-(4-cyanophenyl)pyrimidin-2-yl]amino}methyl)-3-fluoropyrrolidine-1-carboxylate and (4-methylphenyl)boronic acid according to the procedure for the preparation of Example 27. ¹H NMR (Methanol-d₄, 400 MHz): δ 2.00-2.15 (m, 2H), 2.34 (s, 3H), 3.17-2.96 (m, 4H), 3.95 (d, J=19.2 Hz, 2H), 7.02 (d, J=8.8 Hz, 2H), 7.14 (d, J=8.8 Hz, 2H), 7.57 (d, J=8.8 Hz, 2H), 7.65 (d, J=8.8 Hz, 2H), 8.35 (s, 1H). [M+H] calc'd for C₂₃H₂₂N₅F, 388; found 388.

Example 29: (+)-4-[5-(4-methylphenyl)-2-[(piperidin-3-yl)amino]pyrimidin-4-yl]benzonitrile

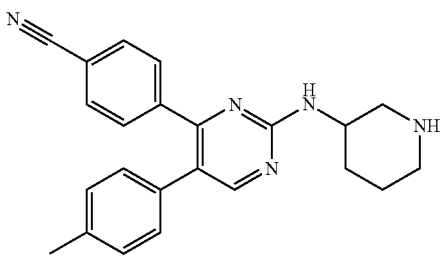 [SMILES: Cc1ccc(-c2cnc(NC3CCCNC3)nc2-c2ccc(C#N)cc2)cc1]

The title compound was prepared in 29% yield using tert-butyl 3-{[5-chloro-4-(4-cyanophenyl)pyrimidin-2-yl]amino}piperidine-1-carboxylate and (4-methylphenyl)boronic acid according to the procedure for the preparation of Example 27. ¹H NMR (CDCl₃, 400 MHz): δ 8.34 (s, 1H), 7.56-7.50 (m, 4H), 7.11 (d, J=8.0 Hz, 2H), 6.97 (d, J=8.0 Hz, 2H), 5.53-5.51 (m, 1H), 4.11-4.07 (m, 1H), 3.31-3.27 (m, 1H), 2.95-2.85 (m, 1H), 2.79-2.67 (m, 2H), 2.36 (s, 3H), 2.05-1.95 (m, 1H), 1.83-1.79 (m, 2H), 1.70-1.60 (m, 2H). [M+H] calc'd for C₂₃H₂₃N₅, 370; found 370.

Example 30: 4-[5-(4-methylphenyl)-2-[(piperidin-4-yl)amino]pyrimidin-4-yl]benzonitrile

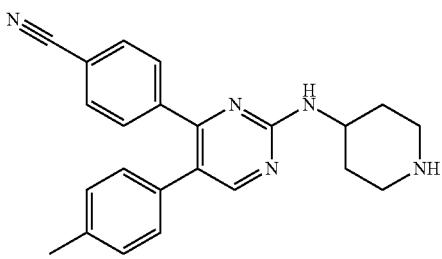 [SMILES: Cc1ccc(-c2cnc(NC3CCNCC3)nc2-c2ccc(C#N)cc2)cc1]

The title compound was prepared in 17% yield using tert-butyl-4-{[5-chloro-4-(4-cyanophenyl)pyrimidin-2-yl]amino}piperidine-1-carboxylate and (4-methylphenyl)boronic acid according to the procedure for the preparation of Example 27. ¹H NMR (Methanol-d₄, 400 MHz): δ 8.31 (s, 1H), 7.64 (d, J=8.4 Hz, 2H), 7.55 (d, J=8.4 Hz, 2H), 7.13 (d, J=8.0 Hz, 2H), 7.05 (d, J=8.0 Hz, 2H), 4.03-4.01 (m, 1H), 3.14-3.10 (m, 2H), 2.77-2.71 (m, 2H), 2.34 (s, 3H), 2.10-2.07 (m, 2H), 1.58-1.52 (m, 2H). [M+H] calc'd for C₂₃H₂₃N₅, 370; found 370.

Example 31: (+)-4-[5-(4-methylphenyl)-2-[(piperidin-3-ylmethyl)amino]pyrimidin-4-yl]benzonitrile

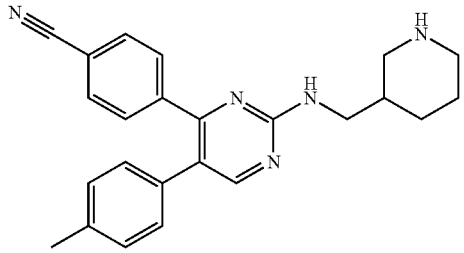

The title compound was prepared in 18% yield using (+)-tert-butyl-3-({[5-chloro-4-(4-cyanophenyl)pyrimidin-2-yl]amino}methyl)piperidine-1-carboxylate and (4-methylphenyl)boronic acid according to the procedure for the preparation of Example 27. ¹H NMR (Methanol-d₄, 400 MHz): δ 8.29 (s, 1H), 7.63 (d, J=8.4 Hz, 2H), 7.55 (d, J=8.4 Hz, 2H), 7.12 (d, J=8.0 Hz, 2H), 6.99 (d, J=8.0 Hz, 2H), 3.35-3.31 (m, 2H), 3.14-3.11 (m, 1H), 3.00-2.97 (m, 1H), 2.57-2.56 (m, 1H), 2.40-2.32 (m, 4H), 1.93-1.91 (m, 2H), 1.75-1.72 (m, 1H), 1.54-1.47 (m, 2H). [M+H] calc'd for C₂₄H₂₅N₅, 384; found 384.

Example 32: 4-[5-(4-methylphenyl)-2-[(piperidin-4-ylmethyl)amino]pyrimidin-4-yl]benzonitrile

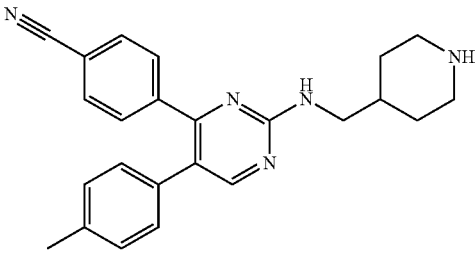 [SMILES: Cc1ccc(-c2cnc(NCC3CCNCC3)nc2-c2ccc(C#N)cc2)cc1]

The title compound was prepared in 35% yield using tert-butyl-4-({[5-chloro-4-(4-cyanophenyl)pyrimidin-. 2-yl]amino}methyl)piperidine-1-carboxylate and (4-methylphenyl)boronic acid according to the procedure for the preparation of Example 27. ¹H NMR (Methanol-d₄, 400 MHz): δ 8.29 (s, 1H), 7.64 (d, J=8.0 Hz, 2H), 7.56 (d, J=8.0 Hz, 2H), 7.13 (d, J=8.0 Hz, 2H), 7.00 (d, J=8.0 Hz, 2H), 3.39-3.36 (m, 2H), 3.09-3.05 (m, 2H), 2.63-2.59 (m, 2H), 2.34 (s, 3H), 1.83-1.79 (m, 3H), 1.31-1.23 (m, 2H). [M+H] calc'd for C₂₄H₂₅N₅, 384; found 384.

Example 33: (+)-4-[5-(4-methylphenyl)-2-[(morpholin-2-ylmethyl)amino]pyrimidin-4-yl]benzonitrile

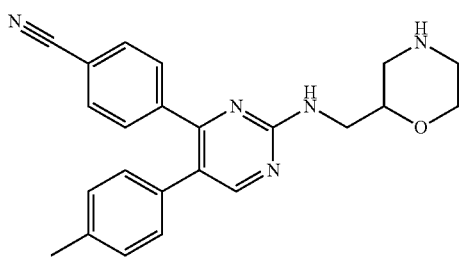 [SMILES: Cc1ccc(-c2cnc(NCC3CNCCO3)nc2-c2ccc(C#N)cc2)cc1]

The TFA salt of the title compound was prepared in 19% yield using (+)-tert-butyl 2-({[5-chloro-4-(4-cyanophenyl)pyrimidin-2-yl]amino}methyl)morpholine-4-carboxylate and (4-methylphenyl)boronic acid according to the procedure for the preparation of Example 21. $^1$H NMR (400 MHz, DMSO-d$_6$): δ ppm 2.28 (s, 3H), 2.75-2.91 (m, 1H), 2.92-3.09 (m, 1H), 3.10-3.17 (m, 1H), 3.24-3.34 (m, 1H), 3.36-3.59 (m, 2H), 3.62-3.77 (m, 1H), 3.86-3.94 (m, 1H), 3.94-4.02 (m, 1H), 7.00 (d, J=8.08 Hz, 2H), 7.12 (d, J=7.83 Hz, 2H), 7.42-7.53 (m, 2H), 7.55-7.65 (m, 1H), 7.80 (d, J=8.08 Hz, 2H), 8.37 (s, 1H), 8.64-8.94 (m, 2H). [M+H] calc'd for C$_{22}$H$_{22}$N$_5$O, 386; found 386.

Example 34: (+)-4-[5-(4-fluorophenyl)-2-[(morpholin-2-ylmethyl)amino]pyrimidin-4-yl]benzonitrile

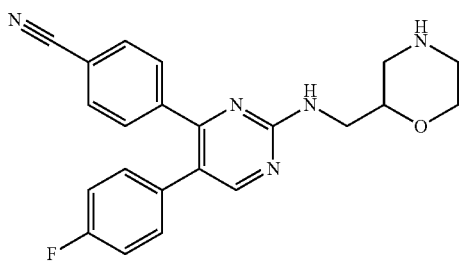 [SMILES: N#Cc1ccc(-c2nc(NCC3CNCCO3)ncc2-c2ccc(F)cc2)cc1]

The TFA salt of the title compound was prepared in 44% yield using (+)-tert-butyl 2-({[5-chloro-4-(4-cyanophenyl)pyrimidin-2-yl]amino}methyl)morpholine-4-carboxylate and (4-fluorophenyl)boronic acid according to the procedure for the preparation of Example 21. $^1$H NMR (400 MHz, DMSO-d$_6$): δ ppm 2.74-2.93 (m, 1H), 2.93-3.10 (m, 1H), 3.17-3.22 (m, 1H), 3.24-3.34 (m, 1H), 3.36-3.59 (m, 2H), 3.61-3.77 (m, 1H), 3.84-3.95 (m, 1H), 3.96-4.00 (m, 1H), 7.16 (d, J=7.07 Hz, 4H), 7.40-7.59 (m, 2H), 7.60-7.74 (m, 1H), 7.81 (d, J=8.34 Hz, 2H), 8.40 (s, 1H), 8.65-8.98 (m, 2H). [M+H] calc'd for C$_{22}$H$_{20}$N$_5$OF, 390; found 390.

Example 35: 4-(2-{2,7-diazaspiro[4.4]nonan-2-yl}-5-(4-methylphenyl)pyrimidin-4-yl)benzonitrile

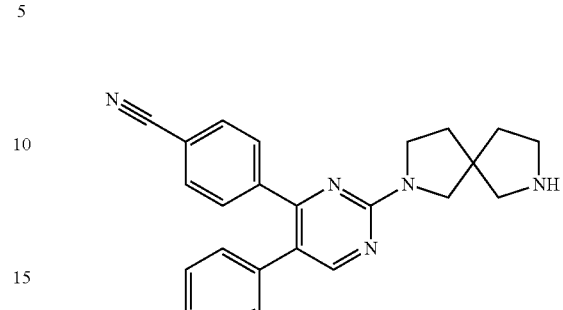

The TFA salt of the title compound was prepared in 24% yield starting tert-butyl 2,7-diazaspiro[4.4]nonane-2-carboxylate according to the procedure for the preparation of Example 21. $^1$H NMR (400 MHz, DMSO-d$_6$): δ ppm 1.88-2.17 (m, 4H), 2.28 (s, 3H), 3.08-3.41 (m, 4H), 3.55-3.63 (m, 1H), 3.63-3.73 (m, 3H), 7.00 (d, J=8.08 Hz, 2H), 7.12 (d, J=7.83 Hz, 2H), 7.51 (d, J=8.08 Hz, 2H), 7.80 (d, J=8.34 Hz, 2H), 8.45 (s, 1H), 8.74-9.01 (br. s., 2H). [M+H] calc'd for C$_{25}$H$_{25}$N$_5$, 396; found 396.

Example 36: 4-(2-{2,8-diazaspiro[4.5]decan-2-yl}-5-(4-methylphenyl)pyrimidin-4-yl)benzonitrile

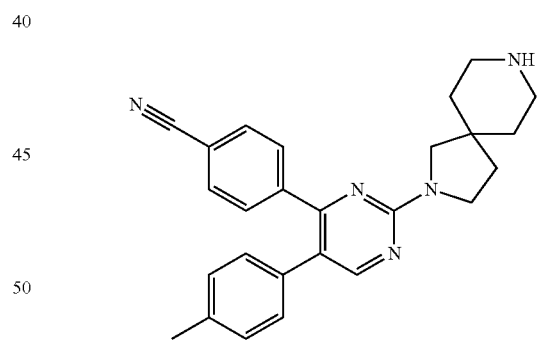

The TFA salt of the title compound was prepared in 42% yield using tert-butyl 2-[5-chloro-4-(4-cyanophenyl)pyrimidin-2-yl]-2,8-diazaspiro[4.5]decane-8-carboxylate and (4-methylphenyl)boronic acid according to the procedure for the preparation of Example 21. $^1$H NMR (400 MHz, DMSO-d$_6$): δ ppm 1.65-1.82 (m, 4H), 1.90-1.99 (m, 2H), 2.28 (m, 3H), 3.13 (br. s., 4H), 3.52 (s, 2H), 3.66 (t, J=6.95 Hz, 2H), 7.00 (s, 2H), 7.12 (d, J=7.83 Hz, 2H), 7.52 (d, J=8.34 Hz, 2H), 7.80 (d, J=8.59 Hz, 2H), 8.29-8.54 (m, 3H). [M+H] calc'd for C$_{26}$H$_{27}$N$_5$, 410; found 410.

Example 37: 4-[5-(4-methylphenyl)-2-{octahydro-1H-pyrrolo[3,4-c]pyridin-2-yl}pyrimidin-4-yl]benzonitrile

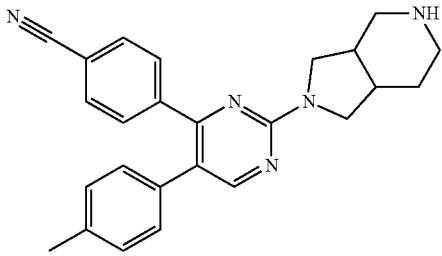

The TFA salt of the title compound was prepared in 42% yield using tea-butyl-2-[5-chloro-4-(4-cyanophenyl)pyrimidin-2-yl]-octahydro-1H-pyrrolo[3,4-c]pyridine-5-carboxylate and (4-methylphenyl)boronic acid according to the procedure for the preparation of Example 21. $^1$H NMR (400 MHz, DMSO-$d_6$): δ ppm 1.60-1.79 (m, 1H), 1.84-2.01 (m, 1H), 2.28 (s, 3H), 2.50-2.62 (m, 2H), 2.96-3.20 (m, 3H), 3.20-3.35 (m, 1H), 3.53-3.76 (m, 4H), 7.01 (d, J=8.08 Hz, 2H), 7.13 (d, J=7.83 Hz, 2H), 7.52 (d, J=8.34 Hz, 2H), 7.80 (d, J=8.34 Hz, 2H), 8.42 (s, 1H), 8.47-8.69 (m, 1H). [M+H] calc'd for $C_{25}H_{25}N_5$, 396; found 396.

Example 38: 4-[5-(4-methylphenyl)-2-{octahydro-1H-pyrrolo[3,2-c]pyridin-5-yl}pyrimidin-4-yl]benzonitrile

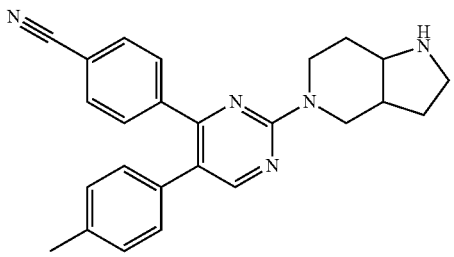 [SMILES: Cc1ccc(-c2cnc(N3CCC4NCCC4C3)nc2-c2ccc(C#N)cc2)cc1]

The TFA salt of the title compound was prepared in 48% yield starting tert-butyl octahydro-1H-pyrrolo[3,2-c]pyridine-1-carboxylate according to the procedure for the preparation of Example 21. $^1$H NMR (400 MHz, METHANOL-$d_4$): δ ppm 1.77-2.00 (m, 2H), 2.05-2.23 (m, 2H), 2.32 (s, 3H), 2.56-2.69 (m, 1H), 3.42-3.55 (m, 3H), 3.79-3.88 (m, 1H), 3.90-4.02 (m, 1H), 4.30-4.40 (m, 1H), 4.40-4.52 (m, 1H), 6.99 (d, J=8.08 Hz, 2H), 7.13 (d, J=7.83 Hz, 2H), 7.52-7.59 (d, J=8.14 Hz, 2H), 7.63 (d, J=8.34 Hz, 2H), 8.34-8.44 (m, 1H). [M+H] calc'd for $C_{25}H_{25}N_5$, 396; found 396.

Example 39: 4-(2-{2,8-diazaspiro[4.5]decan-8-yl}-5-(4-methylphenyl)pyrimidin-4-yl)benzonitrile

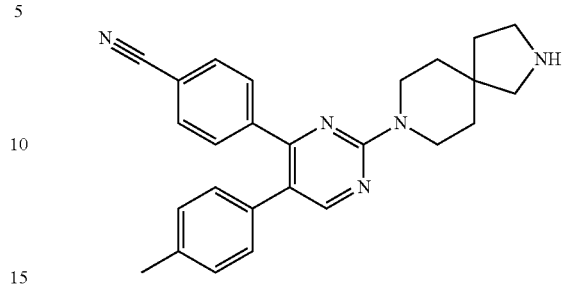

The TFA salt of the title compound was prepared in 62% yield starting tert-butyl 2,8-diazaspiro[4.5]decane-2-carboxylate according to the procedure for the preparation of Example 21. $^1$H NMR (400 MHz, DMSO-$d_6$): δ ppm 1.50-1.71 (m, 4H), 1.84-1.94 (m, 2H), 2.28 (s, 3H), 3.02-3.11 (m, 2H), 3.23-3.38 (m, 2H), 3.73-3.95 (m, 4H), 7.01 (d, J=8.08 Hz, 2H), 7.13 (d, J=8.08 Hz, 2H), 7.51 (d, J=8.34 Hz, 2H), 7.80 (d, J=8.34 Hz, 2H), 8.43 (s, 1H), 8.84 (br. s., 2H). [M+H] calc'd for $C_{26}H_{27}N_5$, 410; found 410.

Example 40: 4-(2-{1,8-diazaspiro[4.5]decan-8-yl}-5-(4-methylphenyl)pyrimidin-4-yl)benzonitrile

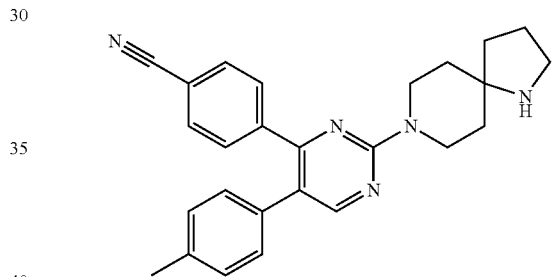

The TFA salt of the title compound was prepared in 64% yield tert-butyl 1,8-diazaspiro[4.5]decane-1-carboxylate according to the procedure for the preparation of Example 21. $^1$H NMR (400 MHz, DMSO-$d_6$): δ ppm 1.77-1.92 (m, 4H), 1.93-2.08 (m, 4H), 2.29 (s, 3H), 3.20-3.35 (m, 2H), 3.45-3.58 (m, 2H), 4.27-4.41 (m, 2H), 7.02 (d, J=7.83 Hz, 2H), 7.13 (d, J=7.83 Hz, 2H), 7.52 (d, J=8.34 Hz, 2H), 7.81 (d, J=8.34 Hz, 2H), 8.46 (s, 1H) 8.64-8.79 (m, 1H). [M+H] calc'd for $C_{26}H_{27}N_5$, 410; found 410.

Example 41: 4-[5-(4-methylphenyl)-2-{9-oxa-3,7-diazabicyclo[3.3.1]nonan-3-yl}pyrimidin-4-yl]benzonitrile

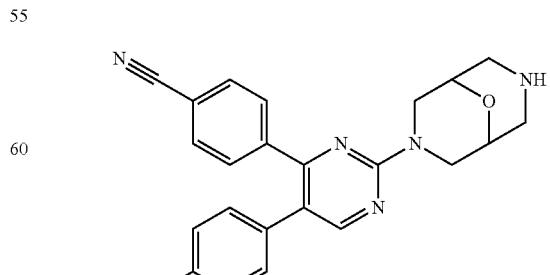

The HCl salt of the title compound was prepared in 26% yield using tert-butyl-7-[5-chloro-4-(4-cyanophenyl)pyrimidin-2-yl]-9-oxa-3,7-diazabicyclo[3.3.1]nonane-3-carboxylate and (4-methylphenyl)boronic acid according to the procedure for the preparation of Example 21. $^1$H NMR (400 MHz, DMSO-$d_6$): δ ppm 2.30 (s, 3H), 3.27-3.44 (m, 4H), 3.44-3.55 (m, 1H), 3.62-3.75 (m, 1H), 4.27 (m, 2H), 4.25-4.33 (m, 4H), 4.57 (d, J=13.39 Hz, 2H), 7.04 (d, J=8.08 Hz, 2H), 7.17 (d, J=7.83 Hz, 2H), 7.56 (d, J=8.59 Hz, 2H), 7.83 (d, J=8.59 Hz, 2H), 8.13-8.38 (m, 1H), 8.52-8.64 (m, 1H), 9.43 (br. s., 1H). [M+H] calc'd for $C_{24}H_{23}N_5O$, 398; found 398.

Example 42: 4-[5-(4-fluorophenyl)-2-{9-oxa-3,7-diazabicyclo[3.3.1]nonan-3-yl}pyrimidin-4-yl]benzonitrile

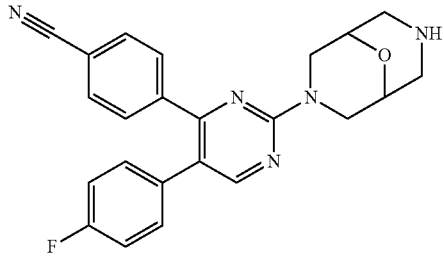 [SMILES: N#Cc1ccc(-c2nc(N3CC4CNCC(C3)O4)ncc2-c2ccc(F)cc2)cc1]

The HCl salt of the title compound was prepared in 20% yield using tert-butyl-7-[5-chloro-4-(4-cyanophenyl)pyrimidin-2-yl]-9-oxa-3,7-diazabicyclo[3.3.1]nonane-3-carboxylate and (4-fluorophenyl)boronic acid according to the procedure for the preparation of Example 21. $^1$H NMR (400 MHz, DMSO-$d_6$): δ ppm 3.25-3.44 (m, 4H), 3.44-3.53 (m, 2H), 3.66-3.69 (m, 2H), 4.28 (br. s., 2H), 4.57 (d, J=13.39 Hz, 2H), 7.17-7.25 (m, 4H), 7.54 (d, J=8.59 Hz, 2H), 7.85 (d, J=8.59 Hz, 2H), 8.13-8.31 (m, 1H), 8.60 (s, 1H), 9.20-9.41 (m, 1H). [M+H] calc'd for $C_{23}H_{20}N_5OF$, 402; found 402.

Preparation 43A: methyl 1-(4-cyanophenyl)-5-(4-methylphenyl)pyrazole-3-carboxylate

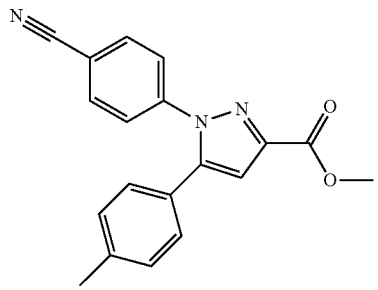 [SMILES: COC(=O)c1cc(-c2ccc(C)cc2)n(-c2ccc(C#N)cc2)n1]

A mixture of methyl 4-(4-methylphenyl)-2,4-dioxobutanoate (1.0 g, 4.55 mmol) and 4-hydrazinylbenzonitrile (0.85 g, 5.0 mmol) in AcOH (20 mL) was stirred at 118° C. for 16 h. The solvent was removed in vacuo and the residue was purified by column chromatography (0-80%, EtOAc:PE) to give 1.3 g (90%) the title compound as yellow solid. $^1$H NMR (CDCl$_3$, 400 MHz): δ 7.65 (d, J=8.0 Hz, 2H), 7.48 (d, J=8.0 Hz, 2H), 7.18 (d, J=8.0 Hz, 2H), 7.10 (d, J=8.0 Hz, 2H), 7.02 (s, 1H), 3.99 (s, 3H), 2.39 (s, 3H). [M+H] Calc'd for $C_{19}H_{15}N_3O_2$, 318; Found, 318.

Preparation 43B: 1-(4-cyanophenyl)-5-(4-methylphenyl)pyrazole-3-carboxylic acid

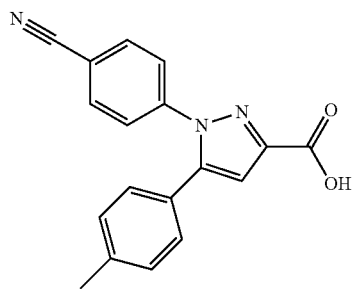 [SMILES: Cc1ccc(-c2cc(C(=O)O)nn2-c2ccc(C#N)cc2)cc1]

A mixture of methyl 1-(4-cyanophenyl)-5-(4-methylphenyl)pyrazole-3-carboxylate (1.3 g, 4.1 mmol) and LiOH (0.3 g, 12.3 mmol) in MeOH/H$_2$O (20 mL/20 mL) was stirred at room temperature for 3 h. MeOH was removed in vacuo and H$_2$O (20 mL) was added. The pH of the solution was adjusted to 4 using HCl (0.6 M) solution. The mixture was extracted with DCM (80 mL×3), washed with brine (50 mL×2) and dried over Na$_2$SO$_4$. The solvent was evaporated in vacuo to give 1.1 g (88%) of the title compound as yellow solid. $^1$H NMR (Methanol-$d_4$, 400 MHz): δ 7.78 (d, J=8.4 Hz, 2H), 7.52 (d, J=8.8 Hz, 2H), 7.21 (d, J=8.0 Hz, 2H), 7.15 (d, J=8.0 Hz, 2H), 7.02 (s, 1H), 2.35 (s, 3H). [M+H] Calc'd for $C_{18}H_{13}N_3O_2$, 304; Found, 304.

Preparation 43C: tert-butyl N-[1-(4-cyanophenyl)-5-(4-methylphenyl)pyrazol-3-yl]carbamate

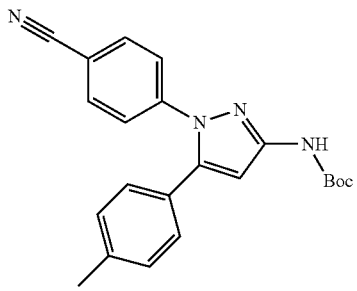 [SMILES: Cc1ccc(-c2cc(NC(=O)OC(C)(C)C)nn2-c2ccc(C#N)cc2)cc1]

A mixture of 1-(4-cyanophenyl)-5-(4-methylphenyl)pyrazole-3-carboxylic acid (1.1 g, 3.63 mmol), DPPA (1.2 g, 4.36 mmol) and TEA (0.44 g, 4.36 mmol) in dioxane/t-BuOH (20 mL/20 mL) was stirred at 110° C. for 16 h. The solvent was removed in vacuo and the crude residue was purified by column chromatography (0-50%, EtOAc:PE) to give 0.3 g (22%) of the title compound as yellow solid. $^1$H NMR (CDCl$_3$, 400 MHz): δ 7.58-7.56 (d, J=8.0 Hz, 2H), 7.36-7.34 (d, J=8.0 Hz, 2H), 7.18-7.13 (m, 5H), 6.81 (br. S., 1H), 2.38 (s, 3H), 1.54 (s, 9H). [M+H] Calc'd for $C_{22}H_{22}N_4O_2$, 375; Found, 375.

Preparation 43D: tert-butyl 3-[[[1-(4-cyanophenyl)-5-(4-methylphenyl)pyrazol-3-yl]-[(2-methylpropan-2-yl)oxycarbonyl]amino]methyl]pyrrolidine-1-carboxylate

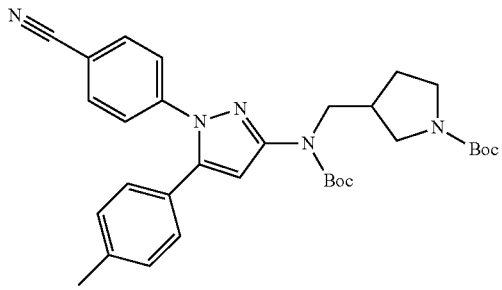 [SMILES: Cc1ccc(-c2cc(N(CC3CCN(C(=O)OC(C)(C)C)C3)C(=O)OC(C)(C)C)nn2-c2ccc(C#N)cc2)cc1]

A mixture of tert-butyl N-[1-(4-cyanophenyl)-5-(4-methylphenyl)pyrazol-3-yl]carbamate (80 mg, 0.21 mmol), tert-butyl 3-[(4-methylphenyl)sulfonyloxymethyl]pyrrolidine-1-carboxylate (92 mg, 0.25 mmol) and $Cs_2CO_3$ (210 mg, 0.64 mmol) in DMF (6 mL) was refluxed at 90° C. for 16 h. The mixture was extracted with EtOAc (20 mL×3). The combined organic layers were washed with brine (20 mL×2) and dried over $Na_2SO_4$. The solvent was removed in vacuo and the crude residue was purified by prep-HPLC to give 76 mg (63%) of the title compound as a yellow oil. $^1$H NMR ($CDCl_3$, 400 MHz): δ 7.57 (d, J=8.4 Hz, 2H), 7.37 (d, J=8.4 Hz, 2H), 7.19-7.12 (m, 4H), 6.80 (brs, 1H), 4.05-3.95 (m, 2H), 3.51 (m, 2H), 3.38-3.26 (m, 1H), 3.17 (dd, J1=8.0 Hz, J2=12.0 Hz, 1H), 2.75 (m, 1H), 2.39 (s, 3H), 2.03-1.93 (m, 1H), 1.78-1.68 (m, 1H), 1.57 (s, 9H), 1.45 (s, 9H). [M+H] Calc'd for $C_{32}H_{39}N_5O_4$, 558; Found, 558.

Example 43: 4-[5-(4-methylphenyl)-3-(pyrrolidin-3-ylmethylamino)pyrazol-1-yl]benzonitrile

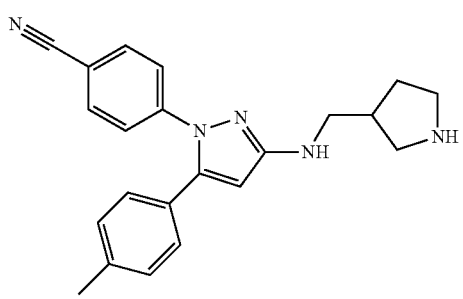 [SMILES: Cc1ccc(-c2cc(NCC3CCNC3)nn2-c2ccc(C#N)cc2)cc1]

To a solution of tert-butyl 3-[[[1-(4-cyanophenyl)-5-(4-methylphenyl)pyrazol-3-yl]-[(2-methylpropan-2-yl)oxycarbonyl]amino]methyl]pyrrolidine-1-carboxylate (76 mg, 0.09 mmol) in DCM (2 mL) was added HCl/dioxane (4 M, 5 mL) dropwise at 0° C.~−10° C. The mixture was stirred at RT for 2 h and concentrated in vacuo. The crude residue was purified by prep-HPLC to give 24 mg (39%) of the title compound as a yellow oil. $^1$H NMR (Methanol-$d_4$, 400 MHz): δ 8.53 (brs, 1H), 7.63 (d, J=8.0 Hz, 2H), 7.35 (d, J=8.0 Hz, 2H), 7.20 (d, J=8.0 Hz, 2H), 7.13 (d, J=8.0 Hz, 2H), 5.94 (s, 1H), 3.46-3.38 (m, 2H), 3.38-3.32 (m, 2H), 3.30-3.25 (m, 1H), 3.12 (dd, J1=8.0 Hz, J2=12.0 Hz, 1H), 2.78 (m, 1H), 2.36 (s, 3H), 2.27-2.17 (m, 1H), 1.86 (m, 1H). [M+H] Calc'd for $C_{22}H_{23}N_5$, 358; Found, 358.

Preparation 44A: tert-butyl (3S)-3-[[[1-(4-cyanophenyl)-5-(4-methylphenyl)pyrazol-3-yl]-[(2-methylpropan-2-yl)oxycarbonyl]amino]methyl]pyrrolidine-1-carboxylate

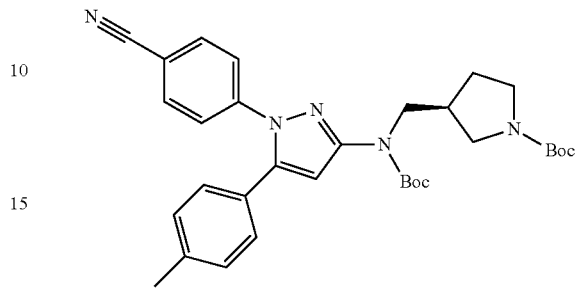

The title compound was prepared in 34% from tert-butyl N-[1-(4-cyanophenyl)-5-(4-methylphenyl)pyrazol-3-yl]carbamate and tert-butyl (3S)-3-[(4-methylphenyl)sulfonyloxymethyl]pyrrolidine-1-carboxylate according to the procedure for preparation 43D. $^1$H NMR ($CDCl_3$, 400 MHz) δ 7.57 (d, J=8.4 Hz, 2H), 7.37 (d, J=8.4 Hz, 2H), 7.21-7.09 (m, 4H), 6.82 (br. s., 1H), 4.07-3.91 (m, 2H), 3.58-3.41 (m, 2H), 3.32 (m, 1H), 3.16 (br. s., 1H), 2.75 (m, 1H), 2.38 (s, 3H), 1.98 (m, 1H), 1.73 (m, 1H), 1.60-1.53 (s, 9H), 1.45 (s, 9H). [M+H] Calc'd for $C_{32}H_{39}N_5O_4$, 558; Found, 558.

Example 44: 4-[5-(4-methylphenyl)-3-[[(3S)-pyrrolidin-3-yl]methylamino]pyrazol-1-yl]benzonitrile

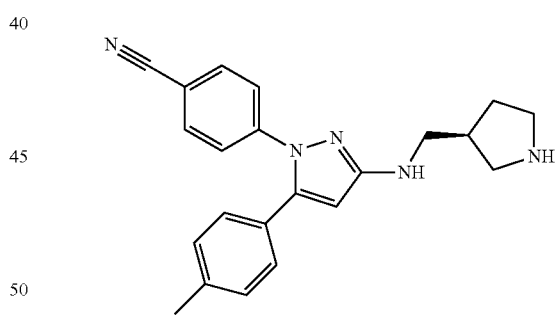

The title compound was prepared in 59% yield tert-butyl (3S)-3-[[[1-(4-cyanophenyl)-5-(4-methylphenyl)pyrazol-3-yl]-[(2-methylpropan-2-yl)oxycarbonyl]amino]methyl]pyrrolidine-1-carboxylate according to the procedure for the preparation of Example 43. $^1$H NMR (Methanol-$d^4$, 400 MHz): δ 7.80-7.74 (m, 2H), 7.51-7.45 (m, 2H), 7.26-7.17 (m, 4H), 3.52 (dd, J1=8.0 Hz, J2=12.0 Hz, 1H), 3.48-3.40 (m, 3H), 3.35-3.27 (m, 1H), 3.12 (dd, J1=8.0 Hz, J2=12.0 Hz, 1H), 2.84-2.76 (m, 1H), 2.36 (s, 3H), 2.33-2.23 (m, 1H), 1.87-1.84 (m, 1H). [M+H] Calc'd for $C_{22}H_{23}N_5$, 358; Found, 358.

Preparation 45A: tert-butyl (3R)-3-[[[1-(4-cyanophenyl)-5-(4-methylphenyl)pyrazol-3-yl]-[(2-methylpropan-2-yl)oxycarbonyl]amino]methyl]pyrrolidine-1-carboxylate

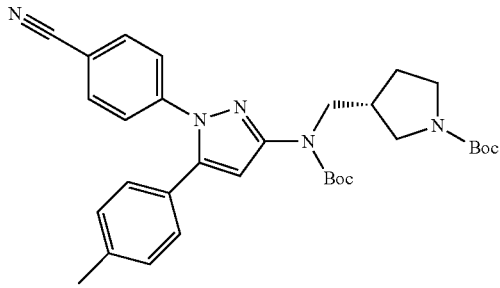 [SMILES: Cc1ccc(-c2cc(N(C[C@@H]3CCN(C(=O)OC(C)(C)C)C3)C(=O)OC(C)(C)C)nn2-c2ccc(C#N)cc2)cc1]

The title compound was prepared in 40% from tert-butyl N-[1-(4-cyanophenyl)-5-(4-methylphenyl)pyrazol-3-yl]carbamate and tert-butyl (3R)-3-[(4-methylphenyl)sulfonyloxymethyl]pyrrolidine-1-carboxylate according to the procedure for preparation 43D. $^1$H NMR (CDCl$_3$, 400 MHz): δ 7.57 (d, J=8.0 Hz, 2H), 7.37 (d, J=8.0 Hz, 2H), 7.21-7.09 (m, 4H), 6.82 (br. s, 1H), 4.08-3.90 (m, 2H), 3.58-3.41 (m, 2H), 3.34-3.30 (m, 1H), 3.17 (br. s, 1H), 2.75 (m, 1H), 2.39 (s, 3H), 2.04-1.93 (m, 1H), 1.73 (m, 1H), 1.53-1.61 (s, 9H), 1.45 (s, 9H). [M+H] Calc'd for C$_{32}$H$_{39}$N$_5$O$_4$, 558; Found, 558.

Example 45: 4-[5-(4-methylphenyl)-3-[[(3R)-pyrrolidin-3-yl]methylamino]pyrazol-1-yl]benzonitrile

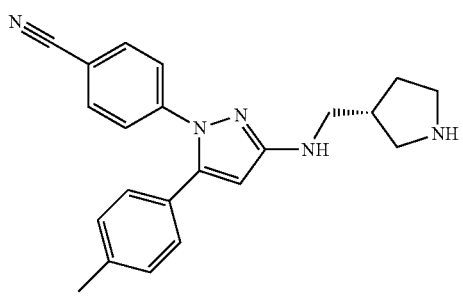 [SMILES: Cc1ccc(-c2cc(NC[C@@H]3CCNC3)nn2-c2ccc(C#N)cc2)cc1]

The title compound was prepared in 33% yield tert-butyl (3R)-3-[[[1-(4-cyanophenyl)-5-(4-methylphenyl)pyrazol-3-yl]-[(2-methylpropan-2-yl)oxycarbonyl]amino]methyl]pyrrolidine-1-carboxylate according to the procedure for the preparation of Example 43. $^1$H NMR (Methanol-d$_4$, 400 MHz): δ 7.79-7.70 (d, J=8.4 Hz, 2H), 7.46 (d, J=8.4 Hz, 2H), 7.26-7.15 (m, 4H), 3.51 (m, 1H), 3.47-3.39 (m, 3H), 3.34-3.30 (m, 1H), 3.12 (m, 1H), 2.86-2.75 (m, 1H), 2.36 (s, 3H), 2.32-2.22 (m, 1H), 1.87 (m, 1H). [M+H] Calc'd for C$_{22}$H$_{23}$N$_5$, 358; Found, 358.

Preparation 46A: tert-butyl 4-[[[1-(4-cyanophenyl)-5-(4-methylphenyl)pyrazol-3-yl]-[(2-methylpropan-2-yl)oxycarbonyl]amino]methyl]piperidine-1-carboxylate A mixture of tert-butyl N-[1-(4-cyanophenyl)-5-(4-methylphenyl)pyrazol-3-yl]carbamate (80 mg, 0.21 mmol), tert-butyl 4-[(4-methylphenyl)sulfonyloxymethyl]piperidine-1-carboxylate (72 mg, 0.26 mmol) and Cs$_2$CO$_3$ (210 mg, 0.64 mmol) in DMF (6 mL) was refluxed at 90° C. for 16 h. The mixture was extracted with EtOAc (20 mL×3). The combined organic layers were washed with brine (20 mL×2) and dried over Na$_2$SO$_4$. The solvent was removed in vacuo and the crude residue was purified by column chromatography (0-33%, EtOAc:PE) to give 82 mg (67%) of the title compound as yellow solid. $^1$H NMR (CDCl$_3$, 400 MHz): δ 7.57 (d, J=8.4 Hz, 2H), 7.37 (d, J=8.4 Hz, 2H), 7.20-7.12 (m, 4H), 6.80 (br. S., 1H), 4.17-4.04 (m, 2H), 3.87 (d, J=7.2 Hz, 2H), 2.70 (t, J=12.4 Hz, 2H), 2.41 (s, 3H), 2.09-1.98 (m, 1H), 1.70 (d, J=12.4 Hz, 2H), 1.56 (s, 9H), 1.47 (s, 9H), 1.32-1.19 (m, 2H). [M+H] Calc'd for C$_{33}$H$_{41}$N$_5$O$_4$, 572; Found, 572.

Example 46: 4-[5-(4-methylphenyl)-3-(piperidin-4-ylmethylamino)pyrazol-1-yl]benzonitrile

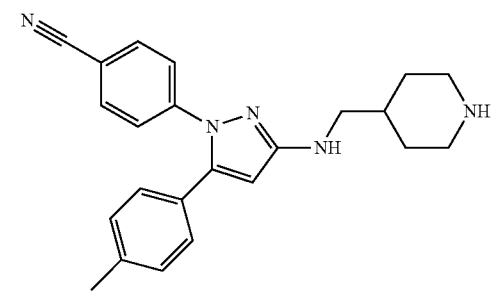 [SMILES: Cc1ccc(-c2cc(NCC3CCNCC3)nn2-c2ccc(C#N)cc2)cc1]

The HCl salt of the title compound was prepared in 57% yield from tert-butyl 4-[[[1-(4-cyanophenyl)-5-(4-methylphenyl)pyrazol-3-yl]-[(2-methylpropan-2-yl)oxycarbonyl]amino]methyl]piperidine-1-carboxylate according to the procedure for the preparation of Example 43. $^1$H NMR (Methanol-d$_4$, 400 MHz): δ 8.51 (brs, 2H), 7.65 (d, J=8.0 Hz, 2H), 7.36 (d, J=8.0 Hz, 2H), 7.22 (d, J=8.0 Hz, 2H), 7.15 (d, J=8.0 Hz, 2H), 5.95 (s, 1H), 3.44 (d, J=12.0 Hz, 2H), 3.22 (d, J=6.4 Hz, 2H), 3.05-2.98 (m, 2H), 2.38 (s, 3H), 2.16-1.98 (m, 3H), 1.56-1.41 (m, 2H). [M+H] Calc'd for C$_{23}$H$_{25}$N$_5$, 372; Found, 372.

Preparation 47A: tert-butyl (1S,5R)-6-[[[1-(4-cyanophenyl)-5-(4-methylphenyl)pyrazol-3-yl]-[(2-methylpropan-2-yl)oxycarbonyl]amino]methyl]-3-azabicyclo[3.1.0]hexane-3-carboxylate

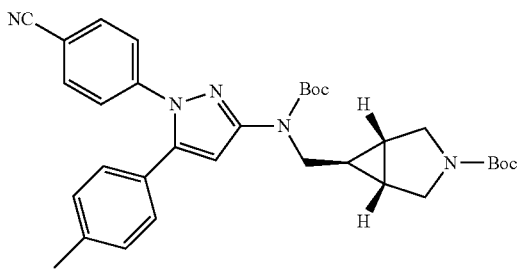 [SMILES: Cc1ccc(-c2cc(N(C[C@H]3[C@@H]4CN(C(=O)OC(C)(C)C)C[C@@H]43)C(=O)OC(C)(C)C)nn2-c2ccc(C#N)cc2)cc1]

A mixture of tert-butyl N-[1-(4-cyanophenyl)-5-(4-methylphenyl)pyrazol-3-yl]carbamate (50.0 mg, 0.133 mmol), tert-butyl (1S,5R)-6-(chloromethyl)-3-azabicyclo[3.1.0]hexane-3-carboxylate (41.0 mg, 0.14 mmol), Cs$_2$CO$_3$ (130.0 mg, 0.4 mmol) in DMF (6 mL) was refluxed at 90° C. for 16 h. The mixture was extracted with EA (20 mL×3). The combined organic layers were washed with brine (20 mL×2) and dried over Na$_2$SO$_4$. The solvent was evaporated under vacuum to give a crude product, which was purified by prep-HPLC to give the title compound (38.0 mg, 50.0%) as yellow oil. $^1$H NMR (CDCl$_3$, 400 MHz): δ 7.58 (d, J=8.0 Hz, 2H), 7.37 (d, J=8.0 Hz, 2H), 7.19-7.13 (m, 4H), 6.80 (br. s, 1H), 3.88 (d, J=6.8 Hz, 2H), 3.62-3.47 (m, 2H), 3.39-3.28 (m, 2H), 2.39 (s, 3H), 1.62 (s, 2H), 1.57 (s, 9H), 1.44-1.40 (s, 9H), 1.17 (m, 1H). [M+H] Calc'd for C$_{33}$H$_{39}$N$_5$O$_4$, 570; Found, 570.

Example 47: 4-[3-[[(1S,5R)-3-azabicyclo[3.1.0]hexan-6-yl]methylamino]-5-(4-methylphenyl)pyrazol-1-yl]benzonitrile

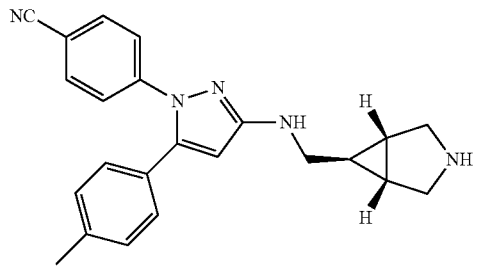 [SMILES: Cc1ccc(-c2cc(NC[C@H]3[C@@H]4CNC[C@@H]43)nn2-c2ccc(C#N)cc2)cc1]

To a solution of tert-butyl (1S,5R)-6-[[[1-(4-cyanophenyl)-5-(4-methylphenyl)pyrazol-3-yl]-[(2-methylpropan-2-yl)oxycarbonyl]amino]methyl]-3-azabicyclo[3.1.0]hexane-3-carboxylate (38.0 mg, 0.067 mmol) in DCM (5 mL) was added HCl/dioxane (4 M, 10 mL) dropwise at 0° C.~−10° C. The mixture was stirred at RT for 2 h. The mixture was concentrated under vacuum to give a crude product, which was purified by prep-HPLC to give the title compound (24.0 mg, 38.7%) as yellow oil. $^1$H NMR (Methanol-d$_4$, 400 MHz): δ 7.72 (d, J=8.0 Hz, 2H), 7.43 (d, J=7.6 Hz, 2H), 7.24-7.14 (m, 4H), 3.47-3.39 (m, 4H), 3.34-3.31 (m, 2H), 2.35 (s, 3H), 1.91 (br. s., 2H), 1.36 (m, 1H). [M+H] Calc'd for C$_{23}$H$_{23}$N$_5$, 370; Found, 370.

Preparation 48: tert-butyl 4-[6-(4-cyanophenyl)-5-(4-methylphenyl)pyrazolo[4,3-b]pyridin-1-yl]piperidine-1-carboxylate

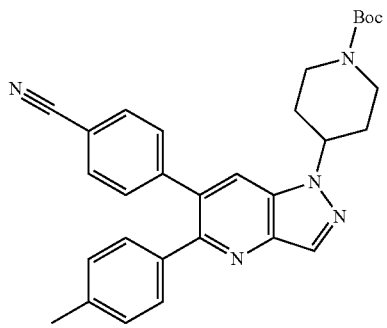 [SMILES: Cc1ccc(-c2nc3cnn(C4CCN(C(=O)OC(C)(C)C)CC4)c3cc2-c2ccc(C#N)cc2)cc1]

To a mixture of 4-[5-(4-methylphenyl)-1H-pyrazolo[4,3-b]pyridin-6-yl]benzonitrile (80 mg, 0.258 mmol) and tert-butyl 4-bromopiperidine-1-carboxylate (341 mg, 1.29 mmol) in DMF (10 mL) was added Cs$_2$CO$_3$ (252 mg, 0.77 mmol). The mixture was stirred at 60° C. overnight. The mixture was diluted with EtOAc (30 mL) and water (30 mL). The aqueous layer was extracted with EtOAc (50 mL×3). The combined organic layers were washed with water (30 mL×2), brine, dried over Na$_2$SO$_4$, filtered, concentrated and purified by prep-HPLC to give 48 mg (38%) the title compound as a white solid. $^1$H NMR (CDCl$_3$, 400 MHz) δ 8.32 (s, 1H), 7.78 (s, 1H), 7.59 (d, J=8.4 Hz, 2H), 7.35 (d, J=8.4 Hz, 2H), 7.19 (d, J=8.0 Hz, 2H), 7.07 (d, J=8.0 Hz, 2H), 4.64-4.58 (m, 1H), 4.36-4.32 (m, 2H), 3.00-2.95 (m, 2H), 2.34 (s, 3H), 2.30-2.23 (m, 2H) 2.07 (d, J=10.8 Hz, 2H), 1.50 (s, 9H). [M+H] Calc'd for C$_{30}$H$_{31}$N$_5$O$_2$, 494; Found, 494.

Example 48: 4-[5-(4-methylphenyl)-1-piperidin-4-ylpyrazolo[4,3-b]pyridin-6-yl]benzonitrile

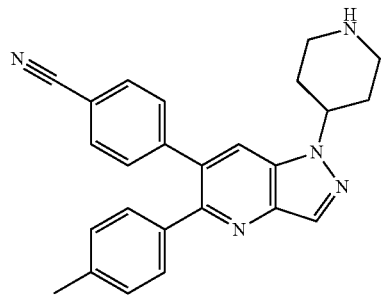 [SMILES: Cc1ccc(-c2nc3cnn(C4CCNCC4)c3cc2-c2ccc(C#N)cc2)cc1]

The title compound was prepared as the HCl salt in 75% yield from tert-butyl 4-[6-(4-cyanophenyl)-5-(4-methylphenyl)pyrazolo[4,3-b]pyridin-1-yl]piperidine-1-carboxylate according to the procedure for the preparation of Example 3. $^1$H NMR (DMSO-d$_6$, 400 MHz) δ 9.67-9.64 (brs, 1H), 9.50-9.48 (brs, 1H), 8.45 (s, 1H), 8.43 (s, 1H), 7.81 (d, J=8.4 Hz, 2H), 7.25 (d, J=8.4 Hz, 2H), 7.16 (d, J=8.4 Hz, 2H), 7.09 (d, J=8.0 Hz, 2H), 5.18-5.13 (m, 1H), 3.45-3.41 (m, 2H), 3.12-3.08 (m, 2H), 2.50-2.45 (m, 2H), 2.27 (s, 3H), 2.15-2.13 (m, 2H). [M+H] Calc'd for C$_{25}$H$_{23}$N, 394; Found, 394.

179

Preparation 49A. tert-butyl-N-[1-(6-chloropyrazin-2-yl)piperidin-4-yl]carbamate

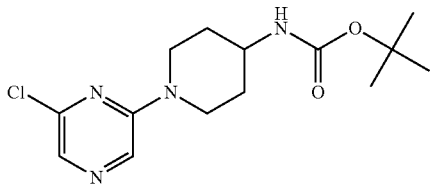 [SMILES: CC(C)(C)OC(=O)NC1CCN(c2cncc(Cl)n2)CC1]

A round-bottom flask containing 2,6-dichloropyrazine (5.0 g, 33.6 mmol), 4-(N-Boc-amino)piperidine (6.7 g, 33.6 mmol), and Et$_3$N (4.7 mL, 33.6 mmol) in NMP (50 mL) was heated to 120° C. for 2 h. The resulting mixture was poured into ice-water and extracted with ethyl acetate (3*100 mL). The organic layers were washed with brine, dried with Na$_2$SO$_4$, and concentrated in vacuo. The residue was triturated with PE/MTBE (5:1) to afford crude tert-butyl-N-[1-(6-chloropyrazin-2-yl)piperidin-4-yl]carbamate (7.9 g, 75%) as a off-white solid. $^1$H NMR (300 MHz, CDCl$_3$): δ 1.38-1.45 (2H, m), 1.45 (9H, s) 2.04-2.09 (2H, m), 3.01-3.10 (2H, m), 3.69-3.74 (1H, m), 4.20-4.27 (2H, m), 4.46-4.49 (1H, m), 7.78 (1H, s), 7.98 (1H, s). [M+H] Calc'd for C$_{14}$H$_{21}$ClN$_4$O$_2$, 313; Found, 313.

Preparation 49B. tert-butyl N-{1-[6-(4-cyano-3-fluorophenyl)pyrazin-2-yl]piperidin-4-yl}carbamate

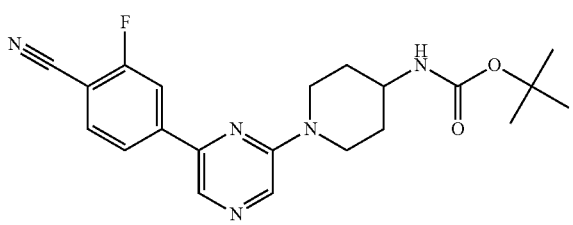 [SMILES: CC(C)(C)OC(=O)NC1CCN(c2cncc(-c3ccc(C#N)c(F)c3)n2)CC1]

To round-bottom flask charged with tert-butyl-N-[1-(6-chloropyrazin-2-yl)piperidin-4-yl]carbamate (1.0 g, 3.21 mmol) in ACN/H$_2$O (3:1, 24 mL) was added (4-cyano-3-fluorophenyl)boronic acid (0.64 g, 3.85 mmol), Pd(OAc)$_2$ (36 mg, 0.16 mmol), PPh$_3$ (85 mg, 0.32 mmol), and K$_3$PO$_4$ (1.0 g, 4.82 mmol). The reaction mixture was kept at reflux under nitrogen atmosphere for 16 hrs. Upon completion, the mixture was poured into ice-water and filtered. The filter cake was dissolved in ethyl acetate and successively washed with brine, dried with Na$_2$SO$_4$, and concentrated in vacuo. The residue was triturated with PE to furnish tert-butyl N-{1-[6-(4-cyano-3-fluorophenyl)pyrazin-2-yl]piperidin-4-yl}carbamate (1.2 g, 94%) as a off-white solid. [M+H] Calc'd for C$_{21}$H$_{24}$FN$_5$O$_2$, 398; Found, 398.

180

Preparation 49C. tert-butyl N-{1-[5-bromo-6-(4-cyano-3-fluorophenyl)pyrazin-2-yl]piperidin-4-yl}carbamate

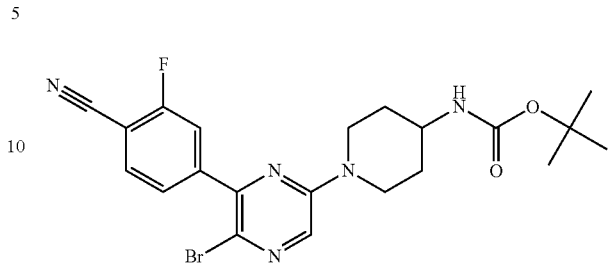

To a round-bottom flask charged tert-butyl N-{1-[6-(4-cyano-3-fluorophenyl)pyrazin-2-yl]piperidin-4-yl}carbamate (1.2 g, 3.1 mmol) in ACN (25 mL) was added NBS (0.61 g, 3.4 mmol) in ACN (5 mL), dropwise. The mixture was stirred for 2 h at ambient temperature. Upon completion, the reaction mixture quenched with water and extracted with ethyl acetate (3*50 mL). The organic layers were successively washed with water, brine, dried Na$_2$SO$_4$, and concentrated in vacuo. The residue was triturated with PE/MTBE (5:1) to afford crude tert-butyl N-{1-[5-bromo-6-(4-cyano-3-fluorophenyl)pyrazin-2-yl]piperidin-4-yl}carbamate (0.63 g, 43%) as a yellow solid. $^1$H NMR (400 MHz, CDCl$_3$): δ 1.37-1.45 (2H, m), 1.45 (9H, s) 2.07-2.10 (2H, m), 3.04-3.11 (2H, m), 3.70-3.75 (1H, m), 4.23-4.26 (2H, m), 4.47-4.49 (1H, m), 7.63 (1H, d, J=9.6 Hz), 7.68-7.72 (2H, m), 7.93 (1H, s). [M+H] Calc'd for C$_{21}$H$_{23}$BrFN$_5$O$_2$, 476; Found, 476.

Example 49. 4-[6-(4-aminopiperidin-1-yl)-3-(2-methyl-2H-indazol-5-yl)pyrazin-2-yl]-2-fluorobenzonitrile

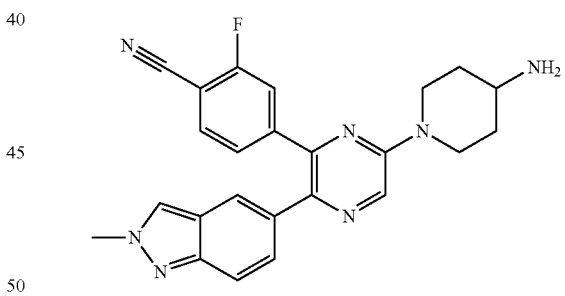

To a round-bottom flask charged with tert-butyl N-{1-[5-bromo-6-(4-cyano-3-fluorophenyl)pyrazin-2-yl]piperidin-4-yl}carbamate (0.6 g, 1.26 mmol) in ACN/H$_2$O (3:1, 48 mL) was added (2-methyl-2H-indazol-5-yl)boronic acid (0.45 g, 2.56 mmol), Pd(OAc)2 (14 mg, 0.063 mmol), S-PHOS (54 mg, 0.13 mmol) and K$_3$PO$_4$ (0.67 g, 3.15 mmol). The mixture was heated to reflux under nitrogen atmosphere for 16 hrs. Upon completion, the reaction mixture was poured into ice-water and filtered. The filter cake was dissolved in ethyl acetate and successively washed with brine, dried Na$_2$SO$_4$, and concentrated in vacuo. The residue was purified by column chromatography (gradient of 50-100% ethyl acetate in PE) and prep-HPLC to give a yellow solid. The solid was suspended in ethyl acetate followed by the addition of HCl (6 mL 10M in ethyl acetate) and stirred for 2 h at ambient temperature. Upon completion, the reaction mixture was concentrated in vacuo to afford the title compound (0.22 g, 37%) as a yellow solid. ¹H NMR (400 MHz, CD₃OD): δ 1.73-1.81 (2H, m), 2.20-2.22 (2H, m), 3.22-3.28 (2H, m), 3.51-3.57 (1H, m), 4.37 (3H, s), 4.70-4.73 (2H, m), 7.37 (1H, d, J=7.6 Hz), 7.51 (1H, d, J=9.6 Hz), 7.56 (1H, d, J=8.8 Hz), 7.66 (1H, dd, J=7.2 Hz, 7.6 Hz), 7.71 (1H, d, J=8.8 Hz), 8.01 (1H, s), 8.52 (1H, s), 8.73 (1H, s). [M+H] Calc'd for C₂₄H₂₂FN₇, 428; Found, 428.

Preparation 50A. tert-butyl-N-[1-(6-chloropyrazin-2-yl)piperidin-4-yl]N-methylcarbamate

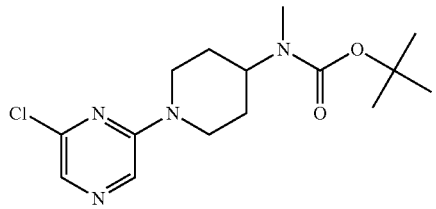 [SMILES: CN(C(=O)OC(C)(C)C)C1CCN(c2cncc(Cl)n2)CC1]

A round-bottom flask charged with 2,6-dichloropyrazine (1.0 g, 6.7 mmol), 4-(N-Boc-methylamino)piperidine (1.43 g, 6.7), and DIEA (1.7 g, 13 mmol) in DMF (20 mL) was kept at 100° C. for 2 h. The resulting mixture was poured into ice-water and extracted with ethyl acetate (3*100 mL). The organic layers were successively washed with brine, dried with Na₂SO₄, and concentrated in vacuo. The residue was triturated with PE to afford crude tert-butyl-N-[1-(6-chloropyrazin-2-yl)piperidin-4-yl]N-methylcarbamate (2.1 g, 96%) as a off-white solid. 1H NMR (300 MHz, CDCl₃): δ 1.48 (9H, s) 1.65-1.80 (4H, m), 2.72 (3H, s), 2.92-3.00 (2H, m), 4.12-4.37 (1H, m), 4.40-4.46 (2H, m), 7.78 (1H, s), 7.99 (1H, s). [M+H] Calc'd for C₁₅H₂₃ClN₄O₂, 327; Found, 327.

Preparation 50B. tert-butyl N-{1-[6-(4-cyano-3-fluorophenyl)pyrazin-2-yl]piperidin-4-yl}-N-methyl-carbamate

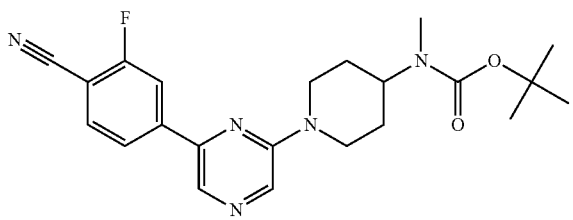 [SMILES: CN(C(=O)OC(C)(C)C)C1CCN(c2cncc(-c3ccc(C#N)c(F)c3)n2)CC1]

To a round-bottom flask charged with tert-butyl-N-[1-(6-chloropyrazin-2-yl)piperidin-4-yl]N-methylcarbamate (2.1 g, 6.4 mmol, 1.0 eq) in ACN/H₂O (3:1, 40 mL) was added (4-cyano-3-fluorophenyl)boronic acid (1.27 g, 7.7 mmol), Pd(OAc)2 (72 mg, 0.32 mmol), PPh₃ (170 mg, 0.64 mmol), and K₃PO₄ (2.0 g, 9.64 mmol). The reaction mixture was kept at refluxed under nitrogen atmosphere for 16 hrs. Upon completion, the mixture was poured into ice-water and filtered. The filter cake dissolved in ethyl acetate and successively washed with brine, dried with Na₂SO₄, and concentrated in vacuo. The residue was triturated with PE to furnish tert-butyl N-{1-[6-(4-cyano-3-fluorophenyl)pyrazin-2-yl]piperidin-4-yl}-N-methylcarbamate (2.3 g, 87%) as a yellow solid. ¹H NMR (300 MHz, CDCl₃): δ 1.48 (9H, s), 1.68-1.84 (4H, m), 2.72 (3H, s), 2.96-3.05 (2H, m), 4.25-4.32 (1H, m), 4.53-4.60 (2H, m), 7.69 (1H, dd, J=6.6 Hz, 8.1 Hz), 7.84-7.90 (2H, m), 8.19 (1H, s), 8.29 (1H, s). [M+H] Calc'd for C₂₂H₂₆FN₅O₂, 412; Found, 412.

Preparation 50C. tert-butyl N-{1-[5-bromo-6-(4-cyano-3-fluorophenyl)pyrazin-2-yl]piperidin-4-yl-N-methyl}carbamate

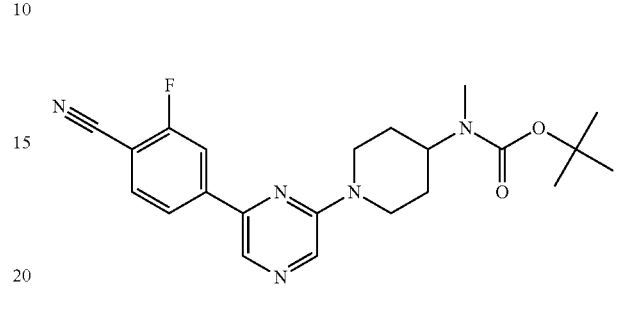

To a round-bottom flask charged tert-butyl-N-{1-[6-(4-cyano-3-fluorophenyl)pyrazin-2-yl]piperidin-4-yl}-N-methylcarbamate (2.3 g, 5.6 mmol) in ACN (25 mL) was added NBS (1.0 g, 5.6 mmol) in ACN (5 mL) dropwise. The mixture was stirred for 2 h at ambient temperature. Upon completion, the reaction mixture was extracted with ethyl acetate (3*100 mL) and the organic layers were successively washed with brine, dried Na₂SO₄, and concentrated in vacuo. The residue was triturated with PE/MTBE (5:1) to afford crude tert-butyl N-{1-[5-bromo-6-(4-cyano-3-fluorophenyl)pyrazin-2-yl]piperidin-4-yl-N-methyl}carbamate (2.0 g, Yield 73%) as a yellow solid. ¹H NMR (400 MHz, CDCl₃): δ 1.47 (9H, s), 1.63-1.81 (4H, m), 2.72 (3H, s), 2.94-3.01 (2H, m), 4.23-4.28 (1H, m), 4.41-4.45 (2H, m), 7.64 (1H, d, J=10.0 Hz), 7.69-7.71 (2H, m), 7.94 (1H, s). [M+H] Calc'd for C₂₂H₂₅BrFN₇O₂, 490; Found, 490.

Example 50. 2-fluoro-4-[3-(2-methyl-2H-indazol-5-yl)-6-[4-(methylamino)piperidin-1-yl]pyrazin-2-yl]benzonitrile

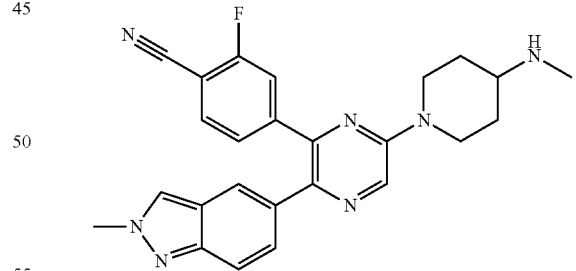

To a round-bottom flask charged with tert-butyl N-{1-[5-bromo-6-(4-cyano-3-fluorophenyl)pyrazin-2-yl]piperidin-4-yl}-N-methylcarbamate (1 g, 2.04 mmol) in ACN/H₂O (3:1, 80 mL) was added (2-methyl-2H-indazol-5-yl)boronic acid (0.54 g, 3.06 mmol), Pd(OAc)2 (23 mg, 0.10 mmol), S-PHOS (84 mg, 0.20 mmol) and H₃PO₄ (0.86 g, 4.0 mmol). The mixture was kept at reflux and under nitrogen atmosphere for 16 hrs. Upon completion, the reaction mixture was poured into ice-water and filtered. The filter cake was dissolved in ethyl acetate and successively washed with brine, dried Na₂SO₄, and concentrated in vacuo. The residue was purified by column chromatography (gradient of ethyl acetate 50-100% ethyl acetate in PE) and prep-HPLC to give a yellow solid. The solid was suspended in ethyl acetate followed by the addition of HCl (6 mL, 10M HCl-ethyl acetate) and stirred for 2 h at ambient temperature. Upon completion, the reaction was concentrated in vacuo to afford the title compound as the HCl salt (0.25 g, 27%). $^1$H NMR (300 MHz, CD$_3$OD): δ 1.77-1.81 (2H, m), 2.30-2.34 (2H, m), 2.78 (3H, s), 3.20-3.28 (2H, m), 3.31-3.33 (1H, m), 4.37 (3H, s), 4.72-4.77 (2H, m), 7.37 (1H, d, J=6.9 Hz), 7.49-7.54 (2H, m), 7.63-7.72 (2H, m), 8.01 (1H, s), 8.52 (1H, s), 8.70 (1H, s). [M+H] Calc'd for C$_{25}$H$_{24}$FN$_7$, 442; Found, 442.

Example 51. 4-[6-(4-aminopiperidin-1-yl)-3-(1-methyl-1H-indazol-5-yl)pyrazin-2-yl]-2-fluorobenzonitrile

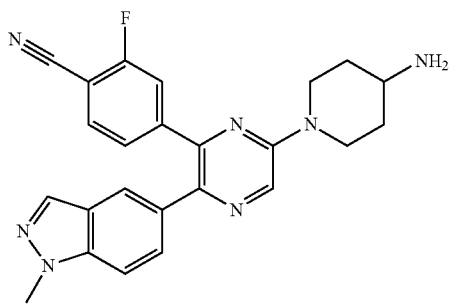 [SMILES: Cn1ncc2cc(-c3ncc(N4CCC(N)CC4)nc3-c3ccc(C#N)c(F)c3)ccc21]

The HCl salt of the title compound was prepared in 48% yield starting with tert-butyl N-{1-[5-bromo-6-(4-cyano-3-fluorophenyl)pyrazin-2-yl]piperidin-4-yl}carbamate and (1-methyl-1H-indazol-5-yl)boronic acid according to the procedure for the preparation of Example 49. $^1$H NMR (400 MHz, CD$_3$OD): δ 1.64-1.67 (2H, m), 2.09-2.11 (2H, m), 3.11-3.17 (2H, m), 3.41-3.44 (1H, m), 3.99 (3H, s), 4.58-4.62 (2H, m), 7.20-7.26 (2H, m), 7.39 (1H, d, J=6.8 Hz), 7.48-7.54 (2H, m), 7.77 (1H, s), 7.97 (1H, s), 8.38 (1H, s). [M+H] Calc'd for C$_{24}$H$_{22}$FN$_7$, 428; Found, 428.

Example 52. 4-[6-(4-aminopiperidin-1-yl)-3-(2-methyl-2H-indazol-6-yl)pyrazin-2-yl]-2-fluorobenzonitrile

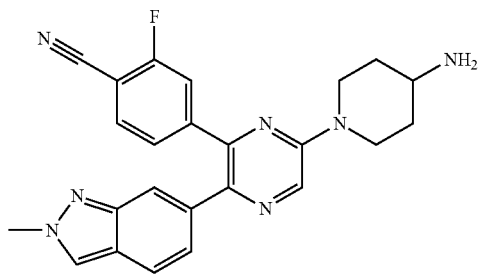 [SMILES: Cn1cc2ccc(-c3ncc(N4CCC(N)CC4)nc3-c3ccc(C#N)c(F)c3)cc2n1]

The HCl salt of the title compound was prepared in 33% yield using tert-butyl N-{1-[5-bromo-6-(4-cyano-3-fluorophenyl)pyrazin-2-yl]piperidin-4-yl}carbamate and (2-methyl-2H-indazol-6-yl)boronic acid according to the procedure for the preparation of Example 49. $^1$H NMR (400 MHz, CD$_3$OD): δ 1.69-1.79 (2H, m), 2.19-2.23 (2H, m), 3.18-3.26 (2H, m), 3.50-3.53 (1H, m), 4.34 (3H, s), 4.71-4.74 (2H, m), 7.25-7.30 (1H, m), 7.38-7.40 (1H, m), 7.50-7.53 (1H, m), 7.64-7.75 (2H, m), 7.84-7.90 (1H, m), 8.49 (1H, d, J=8.4 Hz), 8.66 (1H, s). [M+H] Calc'd for C$_{24}$H$_{22}$FN$_7$, 428; Found, 428.

Example 53. 4-[6-(4-aminopiperidin-1-yl)-3-(1-methyl-1H-1,2,3-benzotriazol-5-yl)pyrazin-2-yl]-2-fluorobenzonitrile

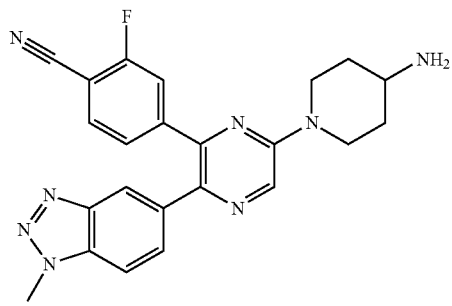 [SMILES: Cn1nnc2cc(-c3ncc(N4CCC(N)CC4)nc3-c3ccc(C#N)c(F)c3)ccc21]

The HCl salt of the title compound was prepared in 39% yield using tert-butyl N-{1-[5-bromo-6-(4-cyano-3-fluorophenyl)pyrazin-2-yl]piperidin-4-yl}carbamate and (1-methylbenzotriazole-5-yl) boronic acid according to the procedure for the preparation of Example 49. $^1$H NMR (300 MHz, CD$_3$OD): δ 1.63-1.76 (2H, m), 2.14-2.19 (2H, m), 3.12-3.20 (2H, m), 3.45-3.50 (1H, m), 4.34 (3H, s), 4.66-4.71 (2H, m), 7.30 (1H, dd, J=1.5 Hz, 8.1 Hz), 7.48 (1H, dd, J=1.5 Hz, 10.2 Hz), 7.53 (1H, dd, J=1.5 Hz, 8.7 Hz), 7.60 (1H, dd, J=6.6 Hz, 8.1 Hz), 7.73 (1H, d, J=8.7 Hz), 7.96 (1H, s), 8.44 (1H, s). [M+H] Calc'd for C$_{23}$H$_{21}$FN$_8$, 429; Found, 429.

Example 54. 4-[6-(4-aminopiperidin-1-yl)-3-{3-methyl-3H-[1,2,3]triazolo[4,5-b]pyridin-6-yl}pyrazin-2-yl]-2-fluorobenzonitrile

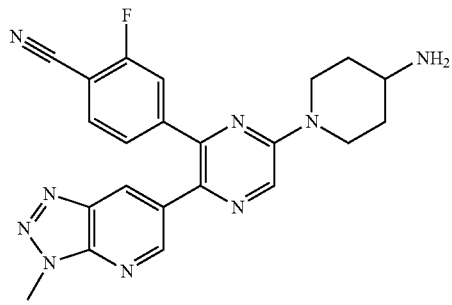 [SMILES: Cn1nnc2cc(-c3ncc(N4CCC(N)CC4)nc3-c3ccc(C#N)c(F)c3)cnc21]

The HCl salt of the title compound was prepared in 8% yield using tert-butyl N-{1-[5-bromo-6-(4-cyano-3-fluorophenyl)pyrazin-2-yl]piperidin-4-yl}carbamate and 4,4,5,5-tetramethyl-2-(3-methyl(1,2,3-triazolino[5,4-b]pyridin-6-yl))-1,3,2-dioxaborolane according to the procedure for the preparation of Example 49. $^1$H NMR (400 MHz, DMSO-d$_6$): δ 1.56-1.65 (2H, m), 2.05-2.08 (2H, m), 3.07-3.14 (2H, m), 3.37-3.39 (1H, m), 4.30 (3H, s), 4.54-4.57 (2H, m), 7.31-7.33 (1H, d, J=8.4 Hz), 7.67 (1H, d, J=10.0 Hz), 7.80-7.84 (1H, m), 8.30 (3H, br), 8.40 (1H, s), 8.61 (1H, s), 8.66 (1H, s). [M+H] Calc'd for C$_{22}$H$_{20}$FN$_9$, 430; Found, 430.

Example 55. 4-[6-(4-aminopiperidin-1-yl)-3-{1-methyl-1H-pyrrolo[2,3-b]pyridin-5-yl}pyrazin-2-yl]-2-fluorobenzonitrile

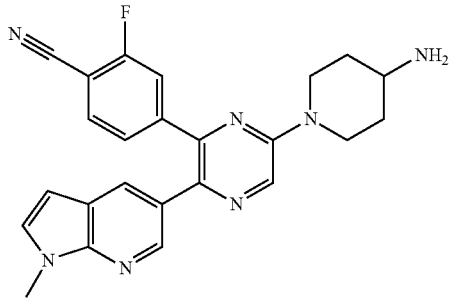 [SMILES: Cn1ccc2cc(-c3ncc(N4CCC(N)CC4)nc3-c3ccc(C#N)c(F)c3)cnc21]

The HCl salt of the title compound was prepared in 53% yield using tert-butyl N-{1-[5-bromo-6-(4-cyano-3-fluorophenyl)pyrazin-2-yl]piperidin-4-yl}carbamate and 4,4,5,5-tetramethyl-2-(1-methylpyrrolo[2,3-b]pyridin-5-yl)-1,3,2-dioxaborolane according to the procedure for the preparation of Example 49. $^1$H NMR (400 MHz, CD$_3$OD): δ 1.71-1.74 (2H, m), 2.19-2.22 (2H, m), 3.16-3.22 (2H, m), 3.50-3.54 (1H, m), 4.03 (3H, s), 4.71-4.74 (2H, m), 6.81 (1H, s), 7.39 (1H, d, J=8.0 Hz), 7.61 (1H, d, J=10.0 Hz), 7.67-7.71 (2H, m), 8.41 (1H, s), 8.50-8.52 (2H, m). [M+H] Calc'd for C$_{24}$H$_{22}$FN$_7$, 428; Found, 428.

Example 56. 2-fluoro-4-{6-[4-(methylamino)piperidyl]-3-(1-methylbenzotriazol-5-yl)pyrazin-2-yl}benzenecarbonitrile

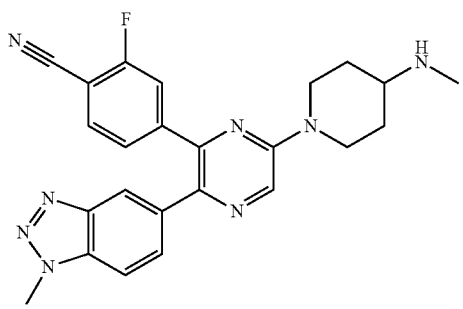

The HCl salt of the title compound was prepared in 80% yield using (tert-butoxy)-N-{1-[5-bromo-6-(4-cyano-3-fluorophenyl)pyrazin-2-yl](4-piperidyl)}-N-methylcarboxamide and (1-methylbenzotriazole-5-yl)boronic acid according to the procedure for the preparation of Example 50. $^1$H NMR (400 MHz, CD$_3$OD): δ 1.68-1.78 (2H, m), 2.25-2.30 (2H, m), 2.77 (3H, s), 3.16-3.23 (2H, m), 3.42-3.49 (1H, m), 4.37 (3H, s), 4.72-4.86 (2H, m), 7.31 (1H, d, J=8.0 Hz), 7.50 (1H, d, J=10.4 Hz), 7.53 (1H, d, J=8.8 Hz), 7.62 (1H, dd, J=6.8 Hz, 8.0 Hz), 7.79 (1H, d, J=8.8 Hz), 8.05 (1H, s), 8.50 (1H, s). [M+H] Calc'd for C$_{24}$H$_{23}$FN$_8$, 443; Found, 443.

Example 57. 4-{3-[6-(dimethylamino)(3-pyridyl)]-6-[4-(methylamino) piperidyl]pyrazin-2-yl}-2-fluorobenzenecarbonitrile

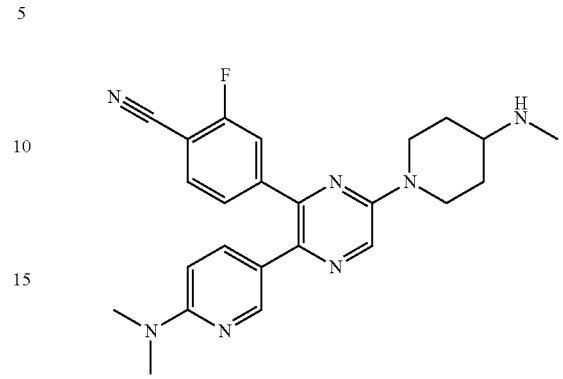

The HCl salt of the title compound was prepared in 77% yield using (tert-butoxy)-N-{1-[5-bromo-6-(4-cyano-3-fluorophenyl)pyrazin-2-yl](4-piperidyl)}-N-methylcarboxamide and (6-dimethylamino-pyridin-3-yl)boronic acid according to the procedure for the preparation of Example 50. $^1$H NMR (400 MHz, CD$_3$OD): δ 1.61-1.72 (2H, m), 2.22-2.27 (2H, m), 2.76 (3H, s), 3.08-3.15 (2H, m), 3.30 (6H, s), 3.36-3.45 (1H, m), 4.68-4.73 (2H, m), 7.17 (1H, dd, J=9.2 Hz, 1.6 Hz), 7.47 (1H, dd, J=1.2 Hz, 8.0 Hz), 7.61 (1H, dd, J=1.2 Hz, 10.4 Hz), 7.78 (1H, dd, J=6.8 Hz, 8.0 Hz), 7.84-7.87 (1H, m), 7.87 (1H, s), 8.45 (1H, s). [M+H] Calc'd for C$_{24}$H$_{26}$FN$_7$, 432; Found, 432.

Example 58. 4-{3-[2-(dimethylamino)pyrimidin-5-yl]-6-[4-(methylamino)piperidyl]pyrazin-2-yl}-2-fluorobenzenecarbonitrile

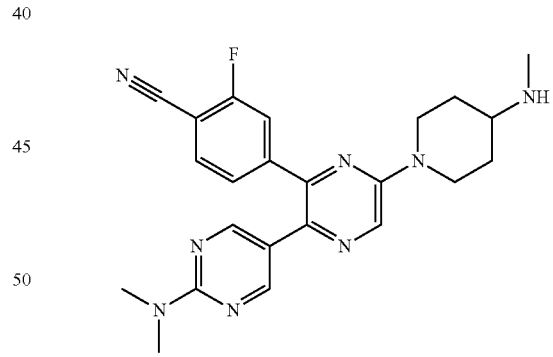

The HCl salt of the title compound was prepared in 59% yield using (tert-butoxy)-N-{1-[5-bromo-6-(4-cyano-3-fluorophenyl)pyrazin-2-yl](4-piperidyl)}-N-methylcarboxamide and Dimethyl-[5-(4,4,5,5-tetramethyl-[1,3,2]dioxaborolan-2-yl)-pyrimidin-2-yl]-amine according to the procedure for the preparation of Example 102. $^1$H NMR (400 MHz, CD$_3$OD): δ 1.61-1.71 (2H, m), 2.22-2.27 (2H, m), 2.76 (3H, s), 3.30 (6H, s), 3.08-3.14 (2H, m), 3.36-3.44 (1H, m), 4.67-4.73 (2H, m), 7.50 (1H, dd, J=1.2 Hz, 8.0 Hz), 7.64 (1H, dd, J=1.2 Hz, 10.4 Hz), 7.78 (1H, dd, J=6.8 Hz, 8.0 Hz), 8.42 (2H, s), 8.46 (1H, s). [M+H] Calc'd for C$_{23}$H$_{25}$FN$_8$, 433; Found, 433.

Example 59. 2-fluoro-4-{6-[4-(methylamino)piperidyl]-3-(1-methylpyrazolo[5,4-b]pyridin-5-yl)pyrazin-2-yl}benzenecarbonitrile

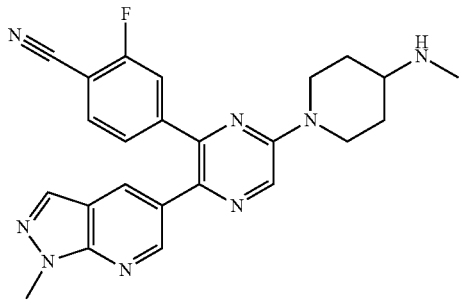 [SMILES: CNC1CCN(c2cnc(-c3cnc4c(cnn4C)c3)c(-c3ccc(C#N)c(F)c3)n2)CC1]

The HCl salt of the title compound was prepared in 91% yield using (tert-butoxy)-N-{1-[5-bromo-6-(4-cyano-3-fluorophenyl)pyrazin-2-yl](4-piperidyl)}-N-methylcarboxamide and 4,4,5,5-tetramethyl-2-(1-methylpyrazolo[5,4-b]pyridin-5-yl)-1,3,2-dioxaborolane according to the procedure for the preparation of Example 50. $^1$H NMR (400 MHz, CD$_3$OD): δ 1.67-1.71 (2H, m), 2.25-2.28 (2H, m), 2.79 (3H, s), 3.10-3.14 (2H, m), 3.42-3.44 (1H, m), 4.12 (3H, s), 4.71-4.75 (2H, m), 7.30 (1H, dd, J=1.6 Hz, 8.0 Hz), 7.54 (1H, dd, J=1.2 Hz, 10.4 Hz), 7.63 (1H, dd, J=0.8 Hz, 6.8 Hz), 8.08 (1H, s), 8.21 (1H, s), 8.47 (1H, s), 8.48 (s, 1H). [M+H] Calc'd for C$_{24}$H$_{23}$FN$_8$, 443; Found, 443.

Example 60. 4-{6-[4-(dimethylamino)piperidyl]-3-(2-methyl(2H-indazol-5-yl))pyrazin-2-yl}-2-fluorobenzenecarbonitrile

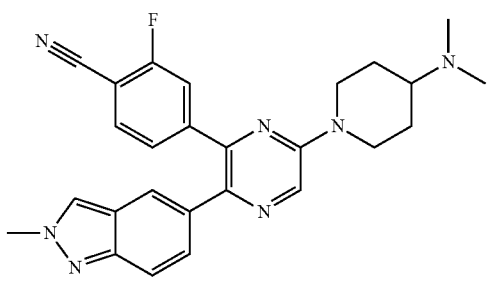

The HCl salt of the title compound was prepared in 13% yield using 4-{6-[4-(dimethylamino)piperidyl]-3-bromopyrazin-2-yl}-2-fluorobenzenecarbonitrile and (2-methyl-2H-indazol-5-yl)boronic acid according to the procedure for the preparation of Example 49. $^1$H NMR (400 MHz, CD$_3$OD): δ 1.79-1.83 (2H, m), 2.22-2.25 (2H, m), 2.94 (6H, s), 3.08-3.14 (2H, m), 3.57-3.58 (1H, m), 4.23 (3H, s), 4.77-4.81 (2H, m), 7.28 (1H, dd, J=1.6 Hz, 9.2 Hz), 7.34 (1H, dd, J=1.2 Hz, 8.0 Hz), 7.52 (1H, dd, J=1.2 Hz, 10.4 Hz), 7.57-7.63 (2H, m) 7.69 (1H, s), 8.21 (1H, s), 8.42 (1H, s). [M+H] Calc'd for C$_{26}$H$_{26}$FN$_7$, 456; Found, 456.

Example 61. 2-fluoro-4-[3-(6-fluoro-1-methylbenzimidazol-5-yl)-6-[4-(methylamino)piperidin-1-yl]pyrazin-2-yl]benzonitrile

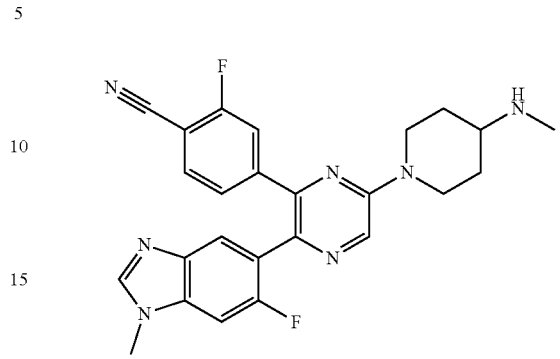

The HCl salt of the title compound was prepared in 53% yield using (tert-butoxy)-N-{1-[5-bromo-6-(4-cyano-3-fluorophenyl)pyrazin-2-yl](4-piperidyl)}-N-methylcarboxamide and 6-fluoro-1-methyl-5-(4,4,5,5-tetramethyl-1,3,2-dioxaborolan-2-yl)-1H-1,3-benzodiazole according to the procedure for the preparation of Example 50. $^1$H NMR (400 MHz, DMSO-d$_6$) δ ppm 1.51-1.66 (m, 2H), 2.07-2.24 (m, 2H), 2.59 (s, 3H), 2.99-3.15 (m, 2H), 3.95 (s, 3H), 4.57-4.69 (m, 2H), 7.26-7.36 (m, 1H), 7.53-7.61 (m, 1H), 7.63-7.76 (m, 1H), 7.77-7.87 (m, 1H), 7.92-8.02 (m, 1H), 8.49-8.64 (m, 1H), 8.80-8.95 (m, 2H), 9.02-9.17 (m, 1H). [M+H] Calc'd for C$_{25}$H$_{23}$F$_2$N$_7$, 460; Found, 460.

Example 62. 4-[3-(6,7-difluoro-1-methylbenzimidazol-5-yl)-6-[4-(methylamino) piperidin-1-yl]pyrazin-2-yl]-2-fluorobenzonitrile

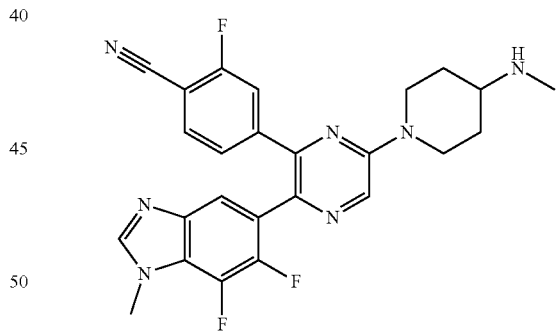

The HCl salt of the title compound was prepared in 37% yield using (tert-butoxy)-N-{1-[5-bromo-6-(4-cyano-3-fluorophenyl)pyrazin-2-yl](4-piperidyl)}-N-methylcarboxamide and 6,7-difluoro-1-methyl-5-(4,4,5,5-tetramethyl-1,3,2-dioxaborolan-2-yl)-1H-1,3-benzodiazole according to the procedure for the preparation of Example 50. $^1$H NMR (400 MHz, DMSO-d$_6$) δ ppm 1.46-1.70 (m, 2H), 1.99-2.25 (m, 2H), 2.59 (s, 3H), 2.95-3.16 (m, 2H), 3.26-3.54 (m, 2H), 4.00 (s, 3H), 4.51-4.69 (m, 2H), 7.21-7.38 (m, 1H), 7.42-7.66 (m, 2H), 7.77-7.86 (m, 1H), 8.22-8.44 (s, 1H), 8.54-8.64 (s, 1H), 8.72-8.88 (m, 2H). [M+H] Calc'd for C$_{25}$H$_{22}$F$_3$N$_7$, 478; Found, 478.

Example 63. 2-fluoro-4-[6-[4-(methylamino)piperidin-1-yl]-3-(1-propan-2-ylbenzimidazol-5-yl)pyrazin-2-yl]benzonitrile

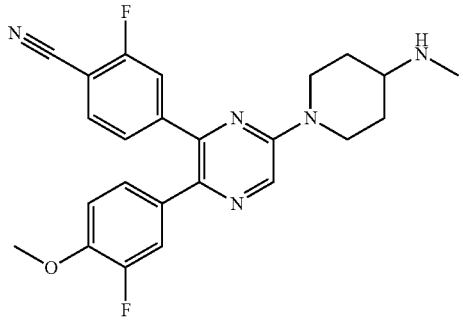 [SMILES: CNC1CCN(c2cnc(-c3ccc(OC)c(F)c3)c(-c3ccc(C#N)c(F)c3)n2)CC1]

The HCl salt of the title compound was prepared in 94% yield using (tert-butoxy)-N-{1-[5-bromo-6-(4-cyano-3-fluorophenyl)pyrazin-2-yl](4-piperidyl)}-N-methylcarboxamide and (3-fluoro-4-methoxyphenyl)boronic acid according to the procedure for the preparation of Example 50. $^1$H NMR (400 MHz, DMSO-$d_6$) δ ppm 1.46-1.70 (m, 2H), 1.99-2.25 (m, 2H), 2.55-2.64 (m, 3H), 2.95-3.16 (m, 2H), 3.26-3.54 (m, 2H), 4.00 (s, 3H), 4.51-4.69 (m, 2H), 7.21-7.38 (m, 1H), 7.42-7.66 (m, 2H), 7.77-7.86 (m, 1H), 8.22-8.44 (m, 1H), 8.54-8.64 (m, 1H), 8.72-8.88 (m, 2H). [M+H] Calc'd for $C_{24}H_{23}F_2N_5O$, 436; Found, 436.

Example 64. 2-fluoro-4-[3-[2-(1-hydroxycyclopentyl)ethynyl]-6-[4-(methylamino) piperidin-1-yl]pyrazin-2-yl]benzonitrile

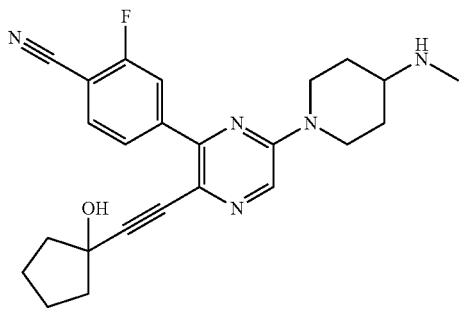 [SMILES: CNC1CCN(c2cnc(C#CC3(O)CCCC3)c(-c3ccc(C#N)c(F)c3)n2)CC1]

The title compound was prepared in 25% yield using 4-{3-bromo-6-[4-(methylamino)piperidin-1-yl]pyrazin-2-yl}-2-fluorobenzonitrile and 1-ethynylcyclopentan-1-ol according to the procedure for the preparation of Example 27. $^1$H NMR (400 MHz, CDCl$_3$) δ ppm 1.36-1.56 (m, 2H), 1.69-1.82 (m, 2H), 1.82-1.92 (m, 2H), 2.03-2.12 (m, 2H), 2.43-2.57 (m, 6H), 2.66-2.80 (m, 1H), 2.85-3.00 (m, 1H), 3.05-3.24 (m, 2H), 4.29-4.45 (m, 2H), 7.18-7.34 (m, 1H), 7.57-7.78 (m, 1H), 7.90-8.05 (m, 2H), 8.09-8.20 (m, 1H). [M+H] Calc'd for $C_{24}H_{26}FN_5O$, 420; Found, 420.

Example 65. 2-fluoro-4-[6-[4-(methylamino)piperidin-1-yl]-3-(1-methylbenzimidazol-5-yl)pyrazin-2-yl]benzonitrile

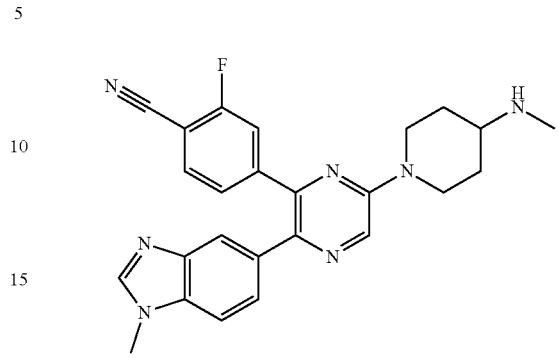

The HCl salt of the title compound was prepared in 48% yield using (tert-butoxy)-N-{1-[5-bromo-6-(4-cyano-3-fluorophenyl)pyrazin-2-yl](4-piperidyl)}-N-methylcarboxamide and 6,7-difluoro-1-methyl-5-(4,4,5,5-tetramethyl-1,3,2-dioxaborolan-2-yl)-1H-1,3-benzodiazole according to the procedure for the preparation of Example 50. $^1$H NMR (400 MHz, DMSO-$d_6$) δ ppm 1.50-1.77 (m, 2H), 2.11-2.21 (m, 2H), 2.56 (br. s., 3H), 2.95-3.12 (m, 2H), 3.24-3.39 (m, 1H), 3.43-3.82 (m, 1H), 4.05 (s, 3H), 4.56-4.65 (m, 2H), 7.17-7.38 (m, 1H), 7.41-7.54 (m, 1H), 7.56-7.71 (m, 1H), 7.78-7.90 (m, 3H), 8.52-8.64 (m, 1H), 9.06-9.25 (br, 2H), 9.49-9.59 (s, 1H). [M+H] Calc'd for $C_{25}H_{24}FN_7$, 442; Found, 442.

Example 66. 2-fluoro-4-[3-(3-hydroxy-3-methylbut-1-ynyl)-6-[4-(methylamino) piperidin-1-yl]pyrazin-2-yl]benzonitrile

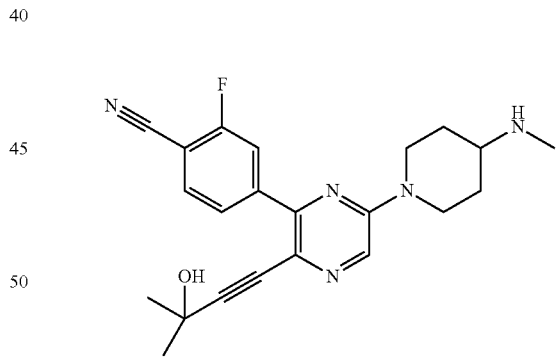

The title compound was prepared in 34% yield using 4-{3-bromo-6-[4-(methylamino)piperidin-1-yl]pyrazin-2-yl}-2-fluorobenzonitrile and 2-methylbut-3-yn-2-ol according to the procedure for the preparation of Example 27. $^1$H NMR (400 MHz, CDCl$_3$) δ ppm 1.39-1.50 (m, 2H), 1.98-2.13 (m, 2H), 2.17-2.39 (m, 3H), 2.50 (s, 3H), 2.71-2.80 (m, 1H), 2.88 (s, 3H), 2.96 (s, 3H), 3.07-3.19 (m, 2H), 4.26-4.46 (m, 2H), 7.16-7.38 (m, 1H), 7.57-7.76 (m, 1H), 7.89-8.08 (m, 3H), 8.10-8.22 (m, 1H). [M+H] Calc'd for $C_{22}H_{24}FN_5O$, 394; Found, 394.

Example 67. 2-fluoro-4-[3-(6-fluoro-1-propan-2-ylbenzimidazol-5-yl)-6-[4-(methylamino)piperidin-1-yl]pyrazin-2-yl]benzonitrile

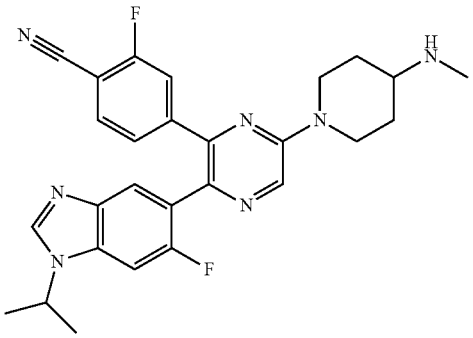 [SMILES: CNC1CCN(c2cnc(-c3cc4ncn(C(C)C)c4cc3F)c(-c3ccc(C#N)c(F)c3)n2)CC1]

The HCl salt of the title compound was prepared in 46% yield using (tert-butoxy)-N-{1-[5-bromo-6-(4-cyano-3-fluorophenyl)pyrazin-2-yl](4-piperidyl)}-N-methylcarboxamide and 6-fluoro-1-(propan-2-yl)-5-(4,4,5,5-tetramethyl-1,3,2-dioxaborolan-2-yl)-1H-1,3-benzodiazole according to the procedure for the preparation of Example 50. $^1$H NMR (400 MHz, DMSO-$d_6$) δ ppm 1.58 (d, J=6.57 Hz, 8H), 2.09-2.24 (m, 2H), 2.56 (br. s., 3H), 2.98-3.14 (m, 2H), 3.25-3.37 (m, 1H), 3.41-3.80 (m, 1H), 4.51-4.71 (m, 3H), 4.79-5.06 (m, 2H), 7.28-7.44 (m, 1H), 7.53-7.64 (m, 1H), 7.77-7.95 (m, 2H), 7.95-8.07 (m, 1H), 8.54-8.67 (m, 1H), 8.99-9.27 (m, 2H), 9.46-9.65 (m, 1H). [M+H] Calc'd for $C_{27}H_{27}F_2N_7$, 488; Found, 488.

Example 68. 2-fluoro-4-[6-[4-(methylamino)piperidin-1-yl]-3-(1-propan-2-ylbenzimidazol-5-yl)pyrazin-2-yl]benzonitrile

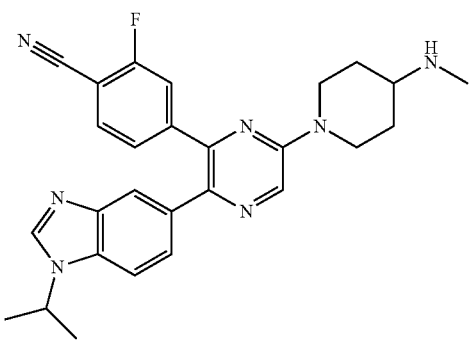 [SMILES: CNC1CCN(c2cnc(-c3ccc4c(c3)ncn4C(C)C)c(-c3ccc(C#N)c(F)c3)n2)CC1]

The HCl salt of the title compound was prepared in 49% yield using (tert-butoxy)-N-{1-[5-bromo-6-(4-cyano-3-fluorophenyl)pyrazin-2-yl](4-piperidyl)}-N-methylcarboxamide and 1-(propan-2-yl)-5-(4,4,5,5-tetramethyl-1,3,2-dioxaborolan-2-yl)-1H-1,3-benzodiazole according to procedure for the preparation of Example 50. $^1$H NMR (400 MHz, Methanol-$d_4$) δ ppm 2.07-2.26 (m, 2H), 2.56-2.63 (m, 3H), 2.98-3.10 (m, 2H), 3.64-3.78 (m, 9H), 4.53-4.69 (m, 2H), 4.92-5.11 (m, 1H), 7.29-7.36 (m, 1H), 7.42-7.49 (m, 1H), 7.60-7.69 (m, 1H), 7.83-7.97 (m, 2H), 8.52-8.66 (m, 1H), 9.36-9.56 (m, 1H). [M+H] Calc'd for $C_{27}H_{28}FN_7$, 470; Found, 470.

Example 69. 4-[3-(1-ethyl-6-fluorobenzimidazol-5-yl)-6-[4-(methylamino)piperidin-1-yl]pyrazin-2-yl]-2-fluorobenzonitrile

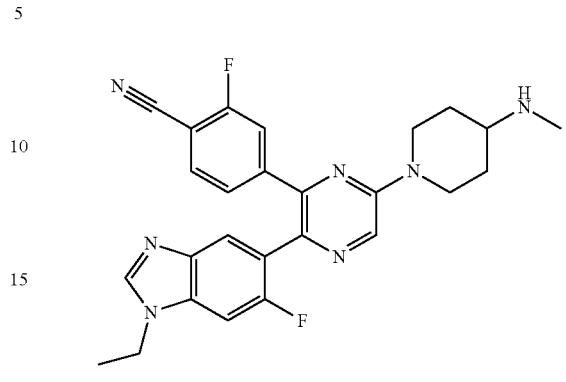

The HCl salt of the title compound was prepared in 45% yield using (tert-butoxy)-N-{1-[5-bromo-6-(4-cyano-3-fluorophenyl)pyrazin-2-yl](4-piperidyl)}-N-methylcarboxamide and 1-ethyl-6-fluoro-5-(4,4,5,5-tetramethyl-1,3,2-dioxaborolan-2-yl)-1H-1,3-benzodiazole according to the procedure for the preparation of Example 50. $^1$H NMR (400 MHz, DMSO-$d_6$) δ ppm 1.49 (m, 3H), 1.55-1.71 (m, 2H), 2.10-2.23 (m, 2H), 2.58 (s, 3H), 2.95-3.13 (m, 2H), 3.27-3.40 (m, 1H), 3.44-3.54 (m, 2H), 3.65-3.76 (m, 2H), 4.36-4.47 (m, 2H), 4.55-4.68 (m, 2H), 7.22-7.40 (m, 1H), 7.56-7.69 (m, 1H), 7.84-7.95 (m, 2H), 8.03 (br. s., 1H), 8.61 (s., 1H), 9.11 (br. s., 2H), 9.46 (br. s., 1H). [M+H] Calc'd for $C_{26}H_{25}F_2N_7$, 474; Found, 474.

Example 70. 4-[6-(4-aminopiperidin-1-yl)-3-(6-fluoro-1-propan-2-ylbenzimidazol-5-yl)pyrazin-2-yl]-2-fluorobenzonitrile

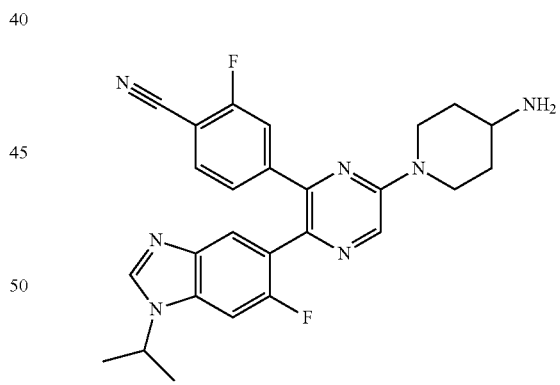

The HCl salt of the title compound was prepared in 45% yield using tert-butyl N-{1-[5-bromo-6-(4-cyano-3-fluorophenyl)pyrazin-2-yl]piperidin-4-yl}carbamate and 6-fluoro-1-(propan-2-yl)-5-(4,4,5,5-tetramethyl-1,3,2-dioxaborolan-2-yl)-1H-1,3-benzodiazole according to the procedure for the preparation of Example 49. $^1$H NMR (400 MHz, DMSO-$d_6$) δ ppm 1.60 1.46-1.74 (m, 10H), 1.97-2.16 (m, 2H), 3.00-3.17 (m, 2H), 3.57 (s, 3H), 3.60-3.75 (m, 2H), 4.48-4.67 (m, 2H), 4.85-5.03 (m, 1H), 7.25-7.42 (m, 1H), 7.54-7.67 (m, 1H), 7.76-7.97 (m, 2H), 7.97-8.06 (m, 1H), 8.56-8.64 (s, 1H), 9.46-9.61 (m, 1H). [M+H] Calc'd for $C_{26}H_{25}F_2N_7$, 474; Found, 474.

Example 71. 4-[6-(4-aminopiperidin-1-yl)-3-(1-ethyl-6-fluorobenzimidazol-5-yl)pyrazin-2-yl]-2-fluorobenzonitrile

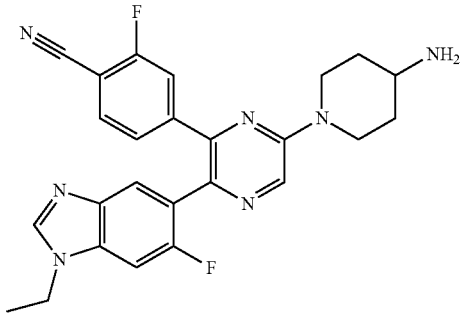 [SMILES: CCn1cnc2cc(-c3ncc(N4CCC(N)CC4)nc3-c3ccc(C#N)c(F)c3)c(F)cc21]

The HCl salt of the title compound was prepared in 60% yield using tert-butyl N-{1-[5-bromo-6-(4-cyano-3-fluorophenyl)pyrazin-2-yl]piperidin-4-yl}carbamate and 1-ethyl-6-fluoro-5-(4,4,5,5-tetramethyl-1,3,2-dioxaborolan-2-yl)-1H-1,3-benzodiazole according to the procedure for the preparation of Example 49. $^1$H NMR (400 MHz, DMSO-d$_6$) δ ppm 1.40-1.55 (m, 3H), 1.55-1.70 (m, 2H), 1.97-2.15 (m, 2H), 3.01-3.23 (m, 3H), 3.66-3.76 (m, 2H), 4.35-4.50 (m, 2H), 4.51-4.65 (m, 2H), 7.30-7.41 (m, 1H), 7.52-7.67 (m, 1H), 7.78-7.94 (m, 2H), 8.00-8.09 (m, 1H), 8.16-8.33 (m, 1H), 8.59 (br. s., 1H), 9.52 (br. s., 1H). [M+H] Calc'd for C$_{25}$H$_{23}$F$_2$N$_7$, 460; Found, 460.

Example 72. 4-[6-(4-aminopiperidin-1-yl)-3-(1-propan-2-ylbenzimidazol-5-yl)pyrazin-2-yl]-2-fluorobenzonitrile

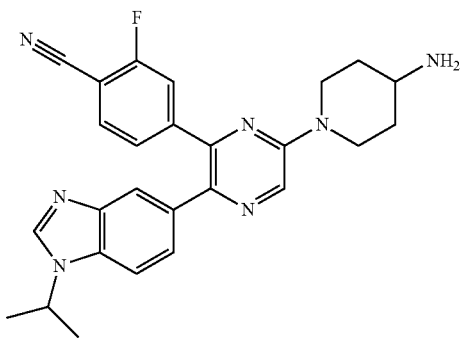 [SMILES: CC(C)n1cnc2cc(-c3ncc(N4CCC(N)CC4)nc3-c3ccc(C#N)c(F)c3)ccc21]

The HCl salt of the title compound was prepared in 42% yield using tert-butyl N-{1-[5-bromo-6-(4-cyano-3-fluorophenyl)pyrazin-2-yl]piperidin-4-yl}carbamate and 1-(propan-2-yl)-5-(4,4,5,5-tetramethyl-1,3,2-dioxaborolan-2-yl)-1H-1,3-benzodiazole according to the procedure for the preparation of Example 49. $^1$H NMR (400 MHz, DMSO-d$_6$) δ ppm 1.45-1.68 (m, 2H), 1.60 (d, J=6.82 Hz, 6H), 1.97-2.09 (m, 2H), 3.02-3.17 (m, 2H), 3.44-3.52 (m, 2H), 3.65-3.81 (m, 1H), 4.47-4.71 (m, 2H), 4.87-5.07 (m, 1H), 7.22-7.35 (m, 1H), 7.42-7.53 (m, 1H), 7.56-7.68 (m, 1H), 7.69-7.80 (m, 1H), 7.80-7.89 (m, 1H), 7.89-7.97 (m, 1H), 8.50-8.64 (m, 1H), 9.40-9.54 (m, 1H). [M+H] Calc'd for C$_{26}$H$_{26}$FN$_7$, 456; Found, 456.

Example 73. 4-[6-(4-aminopiperidin-1-yl)-3-(6,7-difluoro-1-propan-2-ylbenzimidazol-5-yl)pyrazin-2-yl]-2-fluorobenzonitrile

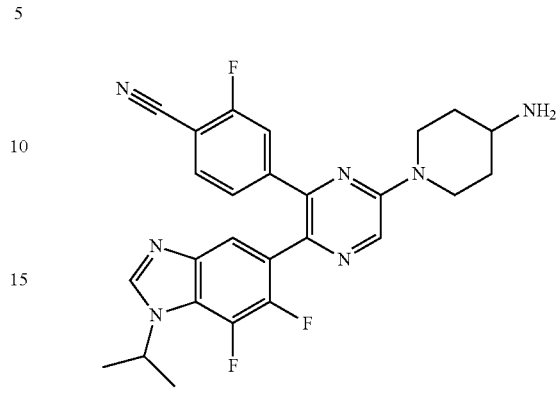

The HCl salt of the title compound was prepared in 40% yield using tert-butyl N-{1-[5-bromo-6-(4-cyano-3-fluorophenyl)pyrazin-2-yl]piperidin-4-yl}carbamate and 6,7-difluoro-1-methyl-5-(4,4,5,5-tetramethyl-1,3,2-dioxaborolan-2-yl)-1H-1,3-benzodiazole according to the procedure for the preparation of Example 49. $^1$H NMR (400 MHz, DMSO-d$_6$) δ ppm 1.47-1.62 (m, 2H), 1.56 (d, J=6.57 Hz, 6H), 1.97-2.10 (m, 2H), 2.99-3.17 (m, 2H), 3.45-3.53 (m, 2H), 3.61-3.76 (m, 2H), 4.47-4.66 (m, 2H), 4.75-5.01 (m, 1H), 7.18-7.38 (m, 1H), 7.52-7.68 (m, 2H), 7.77-7.89 (m, 1H), 7.89-8.03 (m, 1H), 8.42-8.69 (m, 2H). [M+H] Calc'd for C$_{26}$H$_{24}$F$_3$N$_7$, 492; Found, 492.

Example 74. 4-[6-(4-aminopiperidin-1-yl)-3-(1-ethyl-6,7-difluorobenzimidazol-5-yl)pyrazin-2-yl]-2-fluorobenzonitrile

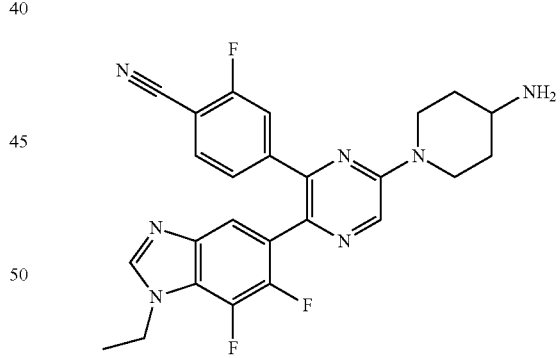

The HCl salt of the title compound was prepared in 64% yield using tert-butyl N-{1-[5-bromo-6-(4-cyano-3-fluorophenyl)pyrazin-2-yl]piperidin-4-yl}carbamate and 1-ethyl-6,7-difluoro-5-(4,4,5,5-tetramethyl-1,3,2-dioxaborolan-2-yl)-1H-1,3-benzodiazole according to the procedure for the preparation of Example 49. $^1$H NMR (400 MHz, DMSO-d$_6$) δ ppm 1.49-1.58 (m, 3H), 1.58-1.73 (m, 2H), 1.98-2.18 (m, 2H), 2.97-3.19 (m, 2H), 3.54-3.66 (m, 1H), 3.66-3.76 (m, 2H), 4.43-4.68 (m, 4H), 7.22-7.38 (m, 1H), 7.58-7.71 (m, 1H), 7.74-7.91 (m, 2H), 8.57-8.65 (m, 1H), 9.57 (br. s., 1H). [M+H] Calc'd for C$_{25}$H$_{22}$F$_3$N$_7$, 478; Found, 478.

Example 75. 4-[6-(4-aminopiperidin-1-yl)-3-(6,7-difluoro-1-methylbenzimidazol-5-yl)pyrazin-2-yl]-2-fluorobenzonitrile

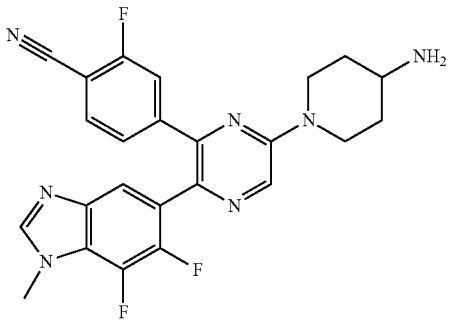 [SMILES: Cn1cnc2cc(-c3ncc(N4CCC(N)CC4)nc3-c3ccc(C#N)c(F)c3)c(F)c(F)c21]

The HCl salt of the title compound was prepared in 51% yield using tert-butyl N-{1-[5-bromo-6-(4-cyano-3-fluorophenyl)pyrazin-2-yl]piperidin-4-yl}carbamate and 6,7-difluoro-1-methyl-5-(4,4,5,5-tetramethyl-1,3,2-dioxaborolan-2-yl)-1H-1,3-benzodiazole according to the procedure for the preparation of Example 49. $^1$H NMR (400 MHz, DMSO-$d_6$) δ ppm 1.51-1.68 (m, 2H), 1.93-2.10 (m, 2H), 2.96-3.18 (m, 2H), 3.62-3.75 (m, 4H), 4.00 (s (, 3H), 4.47-4.62 (m, 2H), 7.22-7.35 (m, 1H), 7.43-7.65 (m, 2H), 7.75-7.78 (m, 1H), 8.01-8.21 (m, 2H), 8.40 (s, 1H), 8.61 (s, 1H). [M+H] Calc'd for $C_{24}H_{20}F_3N_7$, 464; Found, 464.

II. Biological Evaluation

Example 1a: In Vitro Enzyme Inhibition Assay—LSD-1

This assay determines the ability of a test compound to inhibit LSD1 demethylase activity. *E. coli* expressed full-length human LSD1 (Accession number O60341) was purchased from Active Motif (Cat #31334).

The enzymatic assay of LSD1 activity is based on Time Resolved-Fluorescence Resonance Energy Transfer (TR-FRET) detection. The inhibitory properties of compounds to LSD1 were determined in 384-well plate format under the following reaction conditions: 0.1 nM LSD1, 50 nM H3K4me1-biotin labeled peptide (Anaspec cat #64355), 2 μM FAD in assay buffer of 50 mM HEPES, pH7.3, 10 mM NaCl, 0.005% Brij35, 0.5 mM TCEP, 0.2 mg/ml BSA. Reaction product was determined quantitatively by TR-FRET after the addition of detection reagent Phycolink Streptavidin-allophycocyanin (Prozyme) and Europium-anti-unmodified histone H3 lysine 4 (H3K4) antibody (PerkinElmer) in the presence of LSD1 inhibitor such as 1.8 mM of Tranylcypromine hydrochloride (2-PCPA) in LANCE detection buffer (PerkinElmer) to final concentration of 12.5 nM and 0.25 nM respectively.

The assay reaction was performed according to the following procedure: 2 μL of the mixture of 150 nM H3K4me1-biotin labeled peptide with 2 μL of 11-point serial diluted test compound in 3% DMSO was added to each well of plate, followed by the addition of 2 μL of 0.3 nM LSD1 and 6 μM of FAD to initiate the reaction. The reaction mixture was then incubated at room temperature for one hour, and terminated by the addition of 6 μL of 1.8 mM 2-PCPA in LANCE detection buffer containing 25 nM Phycolink Streptavidin-allophycocyanin and 0.5 nM Europium-anti-unmodified H3K4 antibody. Plates were read by EnVision Multilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

The ability of the compounds disclosed herein to inhibit LSD1 activity was quantified and the respective $IC_{50}$ value was determined. Table 3 provides the $IC_{50}$ values of various substituted heterocyclic compounds disclosed herein.

TABLE 3

| Chemical Synthesis Example | Name | LSD1 $IC_{50}$ |
|---|---|---|
| 1 | 4-[5-(4-methylphenyl)-1-[[(3R)-pyrrolidin-3-yl]methyl]pyrrolo[3,2-b]pyridin-6-yl]benzonitrile | A |
| 2 | 4-[5-chloro-1-[[(3R)-pyrrolidin-3-yl]methyl]pyrrolo[3,2-b]pyridin-6-yl]benzonitrile | B |
| 3 | 4-[5-(4-methylphenyl)-1-[[(3S)-pyrrolidin-3-yl]methyl]pyrrolo[3,2-b]pyridin-6-yl]benzonitrile | A |
| 4 | 4-[5-chloro-1-[[(3S)-pyrrolidin-3-yl]methyl]pyrrolo[3,2-b]pyridin-6-yl]benzonitrile | B |
| 5 | 4-[5-(4-fluorophenyl)-1-[[(3S)-pyrrolidin-3-yl]methyl]pyrrolo[3,2-b]pyridin-6-yl]benzonitrile | A |
| 6 | 4-[5-morpholin-4-yl-1-[[(3R)-pyrrolidin-3-yl]methyl]pyrrolo[3,2-b]pyridin-6-yl]benzonitrile | B |
| 7 | 4-[5-morpholin-4-yl-1-[[(3S)-pyrrolidin-3-yl]methyl]pyrrolo[3,2-b]pyridin-6-yl]benzonitrile | A |
| 8 | 4-[1-[(3-fluoropyrrolidin-3-yl)methyl]-5-morpholin-4-ylpyrrolo[3,2-b]pyridin-6-yl]benzonitrile | B |
| 9 | 4-[1-[(3-fluoropyrrolidin-3-yl)methyl]-5-(4-methylphenyl)pyrrolo[3,2-b]pyridin-6-yl]benzonitrile | A |
| 10 | 4-[5-(4-methylphenyl)-1-[[(2R)-morpholin-2-yl]methyl]pyrrolo[3,2-b]pyridin-6-yl]benzonitrile | A |
| 11 | 4-[5-(4-fluorophenyl)-1-[[(2R)-morpholin-2-yl]methyl]pyrrolo[3,2-b]pyridin-6-yl]benzonitrile | A |
| 12 | 4-[1-(3-aminopropyl)-5-(4-methylphenyl)pyrrolo[3,2-b]pyridine-6-yl]benzonitrile | A |
| 13 | 4-[5-(4-methylphenyl)-1-(pyrrolidin-3-ylmethyl)pyrazolo[4,3-b]pyridin-6-yl]benzonitrile | A |
| 14 | 4-[5-(4-methylphenyl)-1-(piperidin-4-ylmethyl)pyrazolo[4,3-b]pyridin-6-yl]benzonitrile | A |
| 15 | 4-[1-[[(1S,5R)-3-azabicyclo[3.1.0]hexan-6-yl]methyl]-5-(4-methylphenyl)pyrazolo[4,3-b]pyridin-6-yl]benzonitrile | A |
| 16 | 4-[5-(4-methylphenyl)-2-{[(3S)-pyrrolidin-3-ylmethyl]amino}pyrimidin-4-yl]benzonitrile | A |
| 17 | 4-(5-chloro-2-{[(3S)-pyrrolidin-3-ylmethyl]amino}pyrimidin-4-yl)benzonitrile | B |
| 18 | 4-[5-(4-fluorophenyl)-2-{[(3S)-pyrrolidin-3-ylmethyl]amino}pyrimidin-4-yl]benzonitrile | A |
| 19 | 4-[5-(4-chlorophenyl)-2-{[(3S)-pyrrolidin-3-ylmethyl]amino}pyrimidin-4-yl]benzonitrile | A |
| 20 | 4-[5-(4-methylphenyl)-2-[(3R)-pyrrolidin-3-ylmethoxy]pyrimidin-4-yl]benzonitrile | A |
| 21 | 4-{2-[(3aR,6aS)-octahydropyrrolo[3,4-c]pyrrol-2-yl]-5-(4-methylphenyl)pyrimidin-4-yl}benzonitrile | A |
| 22 | 4-[5-(4-methylphenyl)-2-{octahydro-1H-pyrrolo[3,4-c]pyridin-5-yl}pyrimidin-4-yl]benzonitrile | A |
| 23 | 4-{2-[(3aR,8aS)-decahydropyrrolo[3,4-d]azepin-6-yl]-5-(4-methylphenyl)pyrimidin-4-yl}benzonitrile | A |
| 24 | 4-{2-[(3aR,8aS)-decahydropyrrolo[3,4-d]azepin-6-yl]-5-(4-fluorophenyl)pyrimidin-4-yl}benzonitrile | A |
| 25 | 4-(2-{[(3S)-pyrrolidin-3-ylmethyl]amino}-5-[4-(trifluoromethyl)phenyl]pyrimidin-4-yl)benzonitrile | A |
| 26 | 4-[5-(2-cyclopropylethynyl)-2-{[(3S)-pyrrolidin-3-ylmethyl]amino}pyrimidin-4-yl]benzonitrile | A |
| 27 | 4-(2-{[(3aR,5S,6aS)-octahydrocyclopenta[c]pyrrol-5-yl]amino}-5-(4-methylphenyl)pyrimidin-4-yl)benzonitrile | B |
| 28 | (±)-4-(2-{[(3-fluoropyrrolidin-3-yl)methyl]amino}-5-(4-methylphenyl)pyrimidin-4-yl)benzonitrile | A |
| 29 | (±)-4-[5-(4-methylphenyl)-2-[(piperidin-3-yl)amino]pyrimidin-4-yl]benzonitrile | A |

TABLE 3-continued

| Chemical Synthesis Example | Name | LSD1 IC$_{50}$ |
|---|---|---|
| 30 | (±)-4-[5-(4-methylphenyl)-2-[(piperidin-3-yl)amino]pyrimidin-4-yl]benzonitrile | A |
| 31 | (±)-4-[5-(4-methylphenyl)-2-[(piperidin-3-ylmethyl)amino]pyrimidin-4-yl]benzonitrile | A |
| 32 | 4-[5-(4-methylphenyl)-2-[(piperidin-4-ylmethyl)amino]pyrimidin-4-yl]benzonitrile | A |
| 33 | (±)-4-[5-(4-methylphenyl)-2-[(morpholin-2-ylmethyl)amino]pyrimidin-4-yl]benzonitrile | A |
| 34 | (±)-4-[5-(4-fluorophenyl)-2-[(morpholin-2-ylmethyl)amino]pyrimidin-4-yl]benzonitrile | B |
| 35 | 4-(2-{2,7-diazaspiro[4.4]nonan-2-yl}-5-(4-methylphenyl)pyrimidin-4-yl)benzonitrile | A |
| 36 | 4-(2-{2,8-diazaspiro[4.5]decan-2-yl}-5-(4-methylphenyl)pyrimidin-4-yl)benzonitrile | A |
| 37 | 4-[5-(4-methylphenyl)-2-{octahydro-1H-pyrrolo[3,4-c]pyridin-2-yl}pyrimidin-4-yl]benzonitrile | A |
| 38 | 4-[5-(4-methylphenyl)-2-{octahydro-1H-pyrrolo[3,2-c]pyridin-5-yl}pyrimidin-4-yl]benzonitrile | A |
| 39 | 4-(2-{2,8-diazaspiro[4.5]decan-8-yl}-5-(4-methylphenyl)pyrimidin-4-yl)benzonitrile | A |
| 40 | 4-(2-{1,8-diazaspiro[4.5]decan-8-yl}-5-(4-methylphenyl)pyrimidin-4-yl)benzonitrile | A |
| 41 | 4-[5-(4-methylphenyl)-2-{9-oxa-3,7-diazabicyclo[3.3.1]nonan-3-yl}pyrimidin-4-yl]benzonitrile | B |
| 42 | 4-[5-(4-fluorophenyl)-2-{9-oxa-3,7-diazabicyclo[3.3.1]nonan-3-yl}pyrimidin-4-yl]benzonitrile | B |
| 43 | 4-[5-(4-methylphenyl)-3-(pyrrolidin-3-ylmethylamino)pyrazol-1-yl]benzonitrile | A |
| 44 | 4-[5-(4-methylphenyl)-3-[[(3S)-pyrrolidin-3-yl]methylamino]pyrazol-1-yl]benzonitrile | A |
| 45 | 4-[5-(4-methylphenyl)-3-[[(3R)-pyrrolidin-3-yl]methylamino]pyrazol-1-yl]benzonitrile | A |
| 46 | 4-[5-(4-methylphenyl)-3-(piperidin-4-ylmethylamino)pyrazol-1-yl]benzonitrile | A |
| 47 | 4-[3-[[(1S,5R)-3-azabicyclo[3.1.0]hexan-6-yl]methylamino]-5-(4-methylphenyl)pyrazol-1-yl]benzonitrile | A |
| 48 | 4-[5-(4-methylphenyl)-1-[[(2R)-morpholin-2-yl]methyl]pyrrolo[3,2-b]pyridin-6-yl]benzonitrile | B |
| 49 | 4-[6-(4-aminopiperidin-1-yl)-3-(2-methyl-2H-indazol-5-yl)pyrazin-2-yl]-2-fluorobenzonitrile | A |
| 50 | 2-fluoro-4-[3-(2-methyl-2H-indazol-5-yl)-6-[4-(methylamino)piperidin-1-yl]pyrazin-2-yl]benzonitrile | A |
| 51 | 4-[6-(4-aminopiperidin-1-yl)-3-(1-methyl-1H-indazol-5-yl)pyrazin-2-yl]-2-fluorobenzonitrile | A |
| 52 | 4-[6-(4-aminopiperidin-1-yl)-3-(2-methyl-2H-indazol-6-yl)pyrazin-2-yl]-2-fluorobenzonitrile | A |
| 53 | 4-[6-(4-aminopiperidin-1-yl)-3-(1-methyl-1H-1,2,3-benzotriazol-5-yl)pyrazin-2-yl]-2-fluorobenzonitrile | A |
| 54 | 4-[6-(4-aminopiperidin-1-yl)-3-{3-methyl-3H-[1,2,3]triazolo[4,5-b]pyridin-6-yl}pyrazin-2-yl]-2-fluorobenzonitrile | A |
| 55 | 4-[6-(4-aminopiperidin-1-yl)-3-{1-methyl-1H-pyrrolo[2,3-b]pyridin-5-yl}pyrazin-2-yl]-2-fluorobenzonitrile | A |
| 56 | 2-fluoro-4-{6-[4-(methylamino)piperidyl]-3-(1-methylbenzotriazol-5-yl)pyrazin-2-yl}benzenecarbonitrile | A |
| 57 | 4-{3-[6-(dimethylamino)(3-pyridyl)]-6-[4-(methylamino)piperidyl]pyrazin-2-yl}-2-fluorobenzenecarbonitrile | A |
| 58 | 4-{3-[2-(dimethylamino)pyrimidin-5-yl]-6-[4-(methylamino)piperidyl]pyrazin-2-yl}-2-fluorobenzenecarbonitrile | A |
| 59 | 2-fluoro-4-{6-[4-(methylamino)piperidyl]-3-(1-methylpyrazolo[5,4-b]pyridin-5-yl)pyrazin-2-yl}benzenecarbonitrile | A |
| 60 | 4-{6-[4-(dimethylamino)piperidyl]-3-(2-methyl(2H-indazol-5-yl))pyrazin-2-yl}-2-fluorobenzenecarbonitrile | A |
| 61 | 2-fluoro-4-[3-(6-fluoro-1-methylbenzimidazol-5-yl)-6-[4-(methylamino)piperidin-1-yl]pyrazin-2-yl]benzonitrile | A |
| 62 | 4-[3-(6,7-difluoro-1-methylbenzimidazol-5-yl)-6-[4-(methylamino)piperidin-1-yl]pyrazin-2-yl]-2-fluorobenzonitrile | A |
| 63 | 2-fluoro-4-[6-[4-(methylamino)piperidin-1-yl]-3-(1-propan-2-ylbenzimidazol-5-yl)pyrazin-2-yl]benzonitrile | A |
| 64 | 2-fluoro-4-[3-[2-(1-hydroxycyclopentyl)ethynyl]-6-[4-(methylamino)piperidin-1-yl]pyrazin-2-yl]benzonitrile | A |
| 65 | 2-fluoro-4-[6-[4-(methylamino)piperidin-1-yl]-3-(1-methylbenzimidazol-5-yl)pyrazin-2-yl]benzonitrile | A |
| 66 | 2-fluoro-4-[3-(3-hydroxy-3-methylbut-1-ynyl)-6-[4-(methylamino)piperidin-1-yl]pyrazin-2-yl]benzonitrile | A |
| 67 | 2-fluoro-4-[3-(6-fluoro-1-propan-2-ylbenzimidazol-5-yl)-6-[4-(methylamino)piperidin-1-yl]pyrazin-2-yl]benzonitrile | A |
| 68 | 2-fluoro-4-[6-[4-(methylamino)piperidin-1-yl]-3-(1-propan-2-ylbenzimidazol-5-yl)pyrazin-2-yl]benzonitrile | A |
| 69 | 4-[3-(1-ethyl-6-fluorobenzimidazol-5-yl)-6-[4-(methylamino)piperidin-1-yl]pyrazin-2-yl]-2-fluorobenzonitrile | A |
| 70 | 4-[6-(4-aminopiperidin-1-yl)-3-(6-fluoro-1-propan-2-ylbenzimidazol-5-yl)pyrazin-2-yl]-2-fluorobenzonitrile | A |
| 71 | 4-[6-(4-aminopiperidin-1-yl)-3-(1-ethyl-6-fluorobenzimidazol-5-yl)pyrazin-2-yl]-2-fluorobenzonitrile | A |
| 72 | 4-[6-(4-aminopiperidin-1-yl)-3-(1-propan-2-ylbenzimidazol-5-yl)pyrazin-2-yl]-2-fluorobenzonitrile | A |
| 73 | 4-[6-(4-aminopiperidin-1-yl)-3-(6,7-difluoro-1-propan-2-ylbenzimidazol-5-yl)pyrazin-2-yl]-2-fluorobenzonitrile | A |
| 74 | 4-[6-(4-aminopiperidin-1-yl)-3-(1-ethyl-6,7-difluorobenzimidazol-5-yl)pyrazin-2-yl]-2-fluorobenzonitrile | A |
| 75 | 4-[6-(4-aminopiperidin-1-yl)-3-(6,7-difluoro-1-methylbenzimidazol-5-yl)pyrazin-2-yl]-2-fluorobenzonitrile | A |

Note:
Biochemical assay IC$_{50}$ data are designated within the following ranges:
A: ≤100 Nm;
B: >100 nM to ≤1,000 Nm;
C: >1,000 nM to ≤10,000 Nm;
D: >10,000 Nm

Example 2: In Vitro Enzyme Inhibition Assay—MAO Selectivity

Human recombinant monoamine oxidase proteins MAO-A and MAO-B are obtained. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay is performed. 3-(2-Aminophenyl)-3-oxopropanamine (kynuramine dihydrobromide, Sigma Aldrich), a non-fluorescent compound is chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity is estimated by measuring the conversion of kynuramine into 4-hydroxyquinoline. Assays are conducted in 96-well black plates with clear bottom (Corning) in a final volume of 100 μl. The assay buffer is 100 mM HEPES, pH 7.5. Each experiment is performed in triplicate within the same experiment.

Briefly, a fixed amount of MAO (0.25 μg for MAO-A and 0.5 μg for AO-B) is incubated on ice for 15 minutes in the reaction buffer, in the absence and/or in the presence of various concentrations of compounds as disclosed herein (e.g., from 0 to 50 µM, depending on the inhibitor strength). Tranylcypromine (Biomol International) is used as a control for inhibition.

After leaving the enzyme(s) interacting with the test compound, 60 to 90 µM of kynuramine is added to each reaction for MAO-B and MAO-A assay respectively, and the reaction is left for 1 hour at 37° C. in the dark. The oxidative deamination of the substrate is stopped by adding 50 µl of 2N NaOH. The conversion of kynuramine to 4-hydroxyquinoline, is monitored by fluorescence (excitation at 320 nm, emission at 360 nm) using a microplate reader (Infinite 200, Tecan). Arbitrary units are used to measure levels of fluorescence produced in the absence and/or in the presence of test compound.

The maximum of oxidative deamination activity is obtained by measuring the amount of 4-hydroxyquinoline formed from kynuramine deamination in the absence of test compound and corrected for background fluorescence. The Ki ($IC_{50}$) of each inhibitor is determined at Vmax/2.

Example 3: LSD1 CD11b Cellular Assay

To analyze LSD1 inhibitor efficacy in cells, a CD11b flow cytometry assay was performed. LSD1 inhibition induces CD11b expression in THP-1 (AML) cells which can be measured by flow cytometry. THP-1 cells were seeded at 100,000 cells/well in 10% Fetal Bovine Serum containing RPMI 1640 media in a 24 well plate with a final volume of 500 µL per well. LSD1 test compounds were serially diluted in DMSO. The dilutions were added to each well accordingly to a final concentration of 0.2% DMSO. The cells were incubated at 37 degrees Celsius in 5% CO2 for 4 days. 250 µL of each well was transferred to a well in a 96 well round bottom plate. The plate was centrifuged at 1200 rpm at 4 degrees Celsius in a Beckman Coulter Alegra 6KR centrifuge for 5 minutes. The media was removed leaving the cells at the bottom of the wells. The cells were washed in 100 µL cold HBSS (Hank's Balanced Salt Solution) plus 2% BSA (Bovine Serum Albumin) solution and centrifuged at 1200 rpm at 4 degrees Celsius for 5 minutes. The wash was removed. The cells were resuspended in 100 µL HBSS plus 2% BSA containing 1:15 dilution of APC conjugated mouse anti-CD11b antibody (BD Pharmingen Cat #555751) and incubated on ice for 25 minutes. The cells were centrifuged and washed two times in 100 µl HBSS plus 2% BSA. After the final spin the cells were resuspended in 100 µL HBSS plus 2% BSA containing 1 ug/mL DAPI (4',6-diamidino-2-phenylindole). The cells were then analyzed by flow cytometry in a BD FACSAria machine. Cells were analyzed for CD11b expression. The percent of CD11b expressing cells for each inhibitor concentration was used to determine an $IC_{50}$ curve for each compound analyzed.

Table 4 provides the cellular IC50 values of various substituted heterocyclic compounds disclosed herein.

TABLE 4

| Chemical Synthesis Example | Name | Cellular $IC_{50}$ |
|---|---|---|
| 1 | 4-[5-(4-methylphenyl)-1-[[(3R)-pyrrolidin-3-yl]methyl]pyrrolo[3,2-b]pyridin-6-yl]benzonitrile | A |
| 2 | 4-[5-chloro-1-[[(3R)-pyrrolidin-3-yl]methyl]pyrrolo[3,2-b]pyridin-6-yl]benzonitrile | C |
| 3 | 4-[5-(4-methylphenyl)-1-[[(3S)-pyrrolidin-3-yl]methyl]pyrrolo[3,2-b]pyridin-6-yl]benzonitrile | A |
| 4 | 4-[5-chloro-1-[[(3S)-pyrrolidin-3-yl]methyl]pyrrolo[3,2-b]pyridin-6-yl]benzonitrile | C |
| 5 | 4-[5-(4-fluorophenyl)-1-[[(3S)-pyrrolidin-3-yl]methyl]pyrrolo[3,2-b]pyridin-6-yl]benzonitrile | C |
| 6 | 4-[5-morpholin-4-yl-1-[[(3R)-pyrrolidin-3-yl]methyl]pyrrolo[3,2-b]pyridin-6-yl]benzonitrile | C |
| 7 | 4-[5-morpholin-4-yl-1-[[(3S)-pyrrolidin-3-yl]methyl]pyrrolo[3,2-b]pyridin-6-yl]benzonitrile | B |
| 9 | 4-[1-[(3-fluoropyrroridin-3-yl)methyl]-5-(4-methylphenyl)pyrrolo[3,2-b]pyridin-6-yl]benzonitrile | B |
| 10 | 4-[5-(4-methylphenyl)-1-[[(2R)-morpholin-2-yl]methyl]pyrrolo[3,2-b]pyridin-6-yl]benzonitrile | C |
| 11 | 4-[5-(4-fluorophenyl)-1-[[(2R)-morpholin-2-yl]methyl]pyrrolo[3,2-b]pyridin-6-yl]benzonitrile | C |
| 12 | 4-[1-(3-aminopropyl)-5-(4-methylphenyl)pyrrolo[3,2-b]pyridine-6-yl]benzonitrile | B |
| 13 | 4-[5-(4-methylphenyl)-1-(pyrrolidin-3-ylmethyl)pyrazolo[4,3-b]pyridin-6-yl]benzonitrile | A |
| 14 | 4-[5-(4-methylphenyl)-1-(piperidin-4-ylmethyl)pyrazolo[4,3-b]pyridin-6-yl]benzonitrile | A |
| 15 | 4-[1-[[(1S,5R)-3-azabicyclo[3.1.0]hexan-6-yl]methyl]-5-(4-methylphenyl)pyrazolo[4,3-b]pyridin-6-yl]benzonitrile | A |
| 16 | 4-[5-(4-methylphenyl)-2-{[(3S)-pyrrolidin-3-ylmethyl]amino}pyrimidin-4-yl]benzonitrile | A |
| 18 | 4-[5-(4-fluorophenyl)-2-{[(3S)-pyrrolidin-3-ylmethyl]amino}pyrimidin-4-yl]benzonitrile | B |
| 19 | 4-[5-(4-chlorophenyl)-2-{[(3S)-pyrrolidin-3-ylmethyl]amino}pyrimidin-4-yl]benzonitrile | B |
| 20 | 4-[5-(4-methylphenyl)-2-[(3R)-pyrrolidin-3-ylmethoxy]pyrimidin-4-yl]benzonitrile | B |
| 21 | 4-{2-[(3aR,6aS)-octahydropyrrolo[3,4-c]pyrrol-2-yl]-5-(4-methylphenyl)pyrimidin-4-yl}benzonitrile | A |
| 22 | 4-[5-(4-methylphenyl)-2-{octahydro-1H-pyrrolo[3,4-c]pyridin-5-yl}pyrimidin-4-yl]benzonitrile | A |
| 23 | 4-{2-[(3aR,8aS)-decahydropyrrolo[3,4-d]azepin-6-yl]-5-(4-methylphenyl)pyrimidin-4-yl}benzonitrile | A |
| 25 | 4-(2-{[(3S)-pyrrolidin-3-ylmethyl]amino}-5-[4-(trifluoromethyl)phenyl]pyrimidin-4-yl)benzonitrile | B |
| 26 | 4-[5-(2-cyclopropylethynyl)-2-{[(3S)-pyrrolidin-3-ylmethyl]amino}pyrimidin-4-yl]benzonitrile | B |
| 27 | 4-(2-{[(3aR,5S,6aS)-octahydrocyclopenta[c]pyrrol-5-yl]amino}-5-(4-methylphenyl)pyrimidin-4-yl)benzonitrile | B |
| 28 | (±)-4-(2-{[(3-fluoropyrrolidin-3-yl)methyl]amino}-5-(4-methylphenyl)pyrimidin-4-yl)benzonitrile | B |
| 29 | (±)-4-[5-(4-methylphenyl)-2-[(piperidin-3-yl)amino]pyrimidin-4-yl]benzonitrile | B |
| 37 | 4-[5-(4-methylphenyl)-2-{octahydro-1H-pyrrolo[3,4-c]pyridin-2-yl}pyrimidin-4-yl]benzonitrile | B |
| 43 | 4-[5-(4-methylphenyl)-3-(pyrrolidin-3-ylmethylamino)pyrazol-1-yl]benzonitrile | A |
| 44 | 4-[5-(4-methylphenyl)-3-[[(3S)-pyrrolidin-3-yl]methylamino]pyrazol-1-yl]benzonitrile | B |
| 45 | 4-[5-(4-methylphenyl)-3-[[(3R)-pyrrolidin-3-yl]methylamino]pyrazol-1-yl]benzonitrile | B |
| 46 | 4-[5-(4-methylphenyl)-3-(piperidin-4-ylmethylamino)pyrazol-1-yl]benzonitrile | B |
| 47 | 4-[3-[[(1S,5R)-3-azabicyclo[3.1.0]hexan-6-yl]methylamino]-5-(4-methylphenyl)pyrazol-1-yl]benzonitrile | B |
| 48 | 4-[5-(4-methylphenyl)-1-[[(2R)-morpholin-2-yl]methyl]pyrrolo[3,2-b]pyridin-6-yl]benzonitrile | D |
| 49 | 4-[6-(4-aminopiperidin-1-yl)-3-(2-methyl-2H-indazol-5-yl)pyrazin-2-yl]-2-fluorobenzonitrile | A |
| 50 | 2-fluoro-4-[3-(2-methyl-2H-indazol-5-yl)-6-[4-(methylamino)piperidin-1-yl]pyrazin-2-yl]benzonitrile | A |

TABLE 4-continued

| Chemical Synthesis Example | Name | Cellular IC$_{50}$ |
|---|---|---|
| 51 | 4-[6-(4-aminopiperidin-1-yl)-3-(1-methyl-1H-indazol-5-yl)pyrazin-2-yl]-2-fluorobenzonitrile | A |
| 52 | 4-[6-(4-aminopiperidin-1-yl)-3-(2-methyl-2H-indazol-6-yl)pyrazin-2-yl]-2-fluorobenzonitrile | A |
| 53 | 4-[6-(4-aminopiperidin-1-yl)-3-(1-methyl-1H-1,2,3-benzotriazol-5-yl)pyrazin-2-yl]-2-fluorobenzonitrile | A |
| 54 | 4-[6-(4-aminopiperidin-1-yl)-3-{3-methyl-3H-[1,2,3]triazolo[4,5-b]pyridin-6-yl}pyrazin-2-yl]-2-fluorobenzonitrile | A |
| 55 | 4-[6-(4-aminopiperidin-1-yl)-3-{1-methyl-1H-pyrrolo[2,3-b]pyridin-5-yl}pyrazin-2-yl]-2-fluorobenzonitrile | A |
| 56 | 2-fluoro-4-{6-[4-(methylamino)piperidyl]-3-(1-methylbenzotriazol-5-yl)pyrazin-2-yl}benzenecarbonitrile | A |
| 57 | 4-{3-[6-(dimethylamino)(3-pyridyl)]-6-[4-(methylamino)piperidyl]pyrazin-2-yl}-2-fluorobenzenecarbonitrile | A |
| 58 | 4-{3-[2-(dimethylamino)pyrimidin-5-yl]-6-[4-(methylamino)piperidyl]pyrazin-2-yl}-2-fluorobenzenecarbonitrile | A |
| 59 | 2-fluoro-4-{6-[4-(methylamino)piperidyl]-3-(1-methylpyrazolo[5,4-b]pyridin-5-yl)pyrazin-2-yl}benzenecarbonitrile | A |
| 60 | 4-{6-[4-(dimethylamino)piperidyl]-3-(2-methyl(2H-indazol-5-yl))pyrazin-2-yl}-2-fluorobenzenecarbonitrile | A |
| 61 | 2-fluoro-4-[3-(6-fluoro-1-methylbenzimidazol-5-yl)-6-[4-(methylamino)piperidin-1-yl]pyrazin-2-yl]benzonitrile | A |
| 62 | 4-[3-(6,7-difluoro-1-methylbenzimidazol-5-yl)-6-[4-(methylamino)piperidin-1-yl]pyrazin-2-yl]-2-fluorobenzonitrile | A |
| 63 | 2-fluoro-4-[6-[4-(methylamino)piperidin-1-yl]-3-(1-propan-2-ylbenzimidazol-5-yl)pyrazin-2-yl]benzonitrile | A |
| 64 | 2-fluoro-4-[3-[2-(1-hydroxycyclopentyl)ethynyl]-6-[4-(methylamino)piperidin-1-yl]pyrazin-2-yl]benzonitrile | A |
| 65 | 2-fluoro-4-[6-[4-(methylamino)piperidin-1-yl]-3-(1-methylbenzimidazol-5-yl)pyrazin-2-yl]benzonitrile | A |
| 66 | 2-fluoro-4-[3-(3-hydroxy-3-methylbut-1-ynyl)-6-[4-(methylamino)piperidin-1-yl]pyrazin-2-yl]benzonitrile | A |
| 67 | 2-fluoro-4-[3-(6-fluoro-1-propan-2-ylbenzimidazol-5-yl)-6-[4-(methylamino)piperidin-1-yl]pyrazin-2-yl]benzonitrile | A |
| 68 | 2-fluoro-4-[6-[4-(methylamino)piperidin-1-yl]-3-(1-propan-2-ylbenzimidazol-5-yl)pyrazin-2-yl]benzonitrile | A |
| 69 | 4-[3-(1-ethyl-6-fluorobenzimidazol-5-yl)-6-[4-(methylamino)piperidin-1-yl]pyrazin-2-yl]-2-fluorobenzonitrile | A |
| 70 | 4-[6-(4-aminopiperidin-1-yl)-3-(6-fluoro-1-propan-2-ylbenzimidazol-5-yl)pyrazin-2-yl]-2-fluorobenzonitrile | A |
| 71 | 4-[6-(4-aminopiperidin-1-yl)-3-(1-ethyl-6-fluorobenzimidazol-5-yl)pyrazin-2-yl]-2-fluorobenzonitrile | A |
| 72 | 4-[6-(4-aminopiperidin-1-yl)-3-(1-propan-2-ylbenzimidazol-5-yl)pyrazin-2-yl]-2-fluorobenzonitrile | A |
| 73 | 4-[6-(4-aminopiperidin-1-yl)-3-(6,7-difluoro-1-propan-2-ylbenzimidazol-5-yl)pyrazin-2-yl]-2-fluorobenzonitrile | A |
| 74 | 4-[6-(4-aminopiperidin-1-yl)-3-(1-ethyl-6,7-difluorobenzimidazol-5-yl)pyrazin-2-yl]-2-fluorobenzonitrile | A |
| 75 | 4-[6-(4-aminopiperidin-1-yl)-3-(6,7-difluoro-1-methylbenzimidazol-5-yl)pyrazin-2-yl]-2-fluorobenzonitrile | A |

Cellular assay IC$_{50}$ data are designated within the following ranges:
A: ≤0.10 μM;
B: >0.10 μM to ≤1.0 μM;
C: >1.0 μM to ≤10 μM;
D: >10 μM

Example 4: In Vivo Xenograph Study—MCF-7 Xenograph

Time release pellets containing 0.72 mg 17-β Estradiol are subcutaneously implanted into nu/nu mice. MCF-7 cells are grown in RPMI containing 10% FBS at 5% CO2, 37° C. Cells are spun down and re-suspended in 50% RPMI (serum free) and 50% Matrigel at 1×10$^7$ cells/mL. MCF-7 cells are subcutaneously injected (100 μL/animal) on the right flank 2-3 days post pellet implantation and tumor volume (length× width2/2) is monitored bi-weekly. When tumors reach an average volume of ~200 mm3 animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 5: In Vivo Xenograph Study—LNCaP Xenograph

LNCaP cells with a stable knockdown of LSD1 (shLSD1 cells) or control cells (such as shNTC cells) are inoculated in the dorsal flank of nude mice by subcutaneous injection (such as 3×10$^6$ cells in 100 μl of 50% RPMI 1640/BD Matrigel). Mouse weight and tumor size are measured once per week and tumor volume is estimated using the formula (7i/6)(L×W), where L=length of tumor and W=width of tumor. A two sample t-test is performed to determine statistical differences in mean tumor volume between the two groups.

Unmodified LNCaP cells are inoculated by subcutaneous injection into the dorsal flank of nude mice (such as 3×10$^6$ cells in 100 μl of 50% RPMI 1640/BD Matrigel). After three weeks, mice are injected intraperitoneal once per day with water (control), pargyline (0.53 mg or 1.59 mg; 1 or 3 mM final concentration, assuming 70% bioavailability), or XB154 (4 or 20 μg; 1 or 5 μM final concentration, assuming 70% bioavailability) or treated with a test compound (5 mg/kg each week or 10 mg/kg each week). Treatment continues for three weeks, during which time mouse weight and tumor volume are measured as above.

shLSD1 LNCaP cells or control cells are injected in nude mice as above. After three weeks, mice are treated with 2.6 μg mitomycin C (predicted final concentration of 1 μM assuming 40% bioavailability), olaparib (for example, about 0.5 mg/kg to 25 mg/kg), or vehicle intraperitoneal once per day for three weeks. In other examples, unmodified LNCaP cells are injected in nude mice as above.

After three weeks, mice are treated with test compounds, or vehicle as above, plus MMC or olaparib. Treatment continues for three weeks, during which time mouse weight and tumor volume are measured as above.

A decrease in tumor volume compared to control in mice injected with shLSD1 cells indicates that LSD1 inhibition decreases tumor growth in vivo.

Similarly, a decrease in tumor volume compared to control in mice injected with LNCaP cells and treated with a compound disclosed herein indicates that LSD1 inhibition decreases tumor growth in vivo. Finally, a decrease in tumor volume in mice injected with LNCaP cells and treated with a compound disclosed herein plus olaparib as compared to mice treated with a compound disclosed herein alone indicates that inhibition of LSD1 plus inhibition of PARP decreases tumor growth in vivo.

The harvested xenograft tissue is examined for evidence of LSD1 inhibition. This is assessed with Western blots to examine global levels of the 2MK4 and 2MK9 histone marks, expression of FA/BRCA genes, FANCD2 ubiquitination, and LSD1 protein levels in the cases of the shRNA cells. A decrease in one or more of these parameters indicates the effective inhibition of LSD 1. Additionally, effects on DNA damage repair are assessed with staining for H2AX foci.

III. Preparation of Pharmaceutical Dosage Forms

Example 1: Oral Tablet

A tablet is prepared by mixing 48% by weight of a compound of Formula (I), (II) or (III), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A method for treating acute myeloid leukemia, breast or prostate cancer in a patient in need thereof comprising administering a therapeutically effective dose of a compound of Formula (IV)

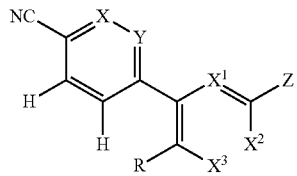

(IV)

wherein the compound of Formula (IV) includes pharmaceutically acceptable sails thereof, wherein,
X and Y are each independently chosen from C—H, C—F, C—$CH_3$, or N;
Z is —G, —$CH_2$-G, —$CH_2$—$CH_2$-G, —N($R^1$)-G, —N($R^1$)—$CH_2$-G, —O-G, —O—$CH_2$-G, or —C(O)N($R^2$)($R^3$);
$X^1$, $X^2$, and $X^3$ are each independently selected from N or C—$R^4$, provided that at least one of $X^1$, $X^2$, or $X^3$ is N;
G is carbocyclyl, aryl, or heterocyclyl;
$R^1$ is hydrogen or alkyl;
$R^2$ and $R^3$ are independently selected from hydrogen, alkyl, heterocyclyl, heterocyclylalkyl, or optionally, $R^2$ and $R^3$ join to form an N-linked heterocyclyl ring system;

$R^4$ is hydrogen, halogen, $C_1$-$C_3$ alkyl or $C_1$-$C_3$ alkoxy; and
R is heteroaryl, alkynyl, or cycloalkylalkynylene.
2. The method of claim 1, wherein R is heteroaryl.
3. The method of claim 1, wherein Formula (IV) is Formula (IVc):

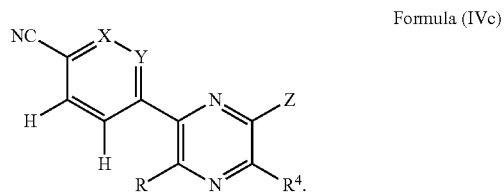

Formula (IVc)

4. The method of claim 1, wherein X is C—F.
5. The method of claim 1, wherein Y is C N—H.
6. The method of claim 1, wherein Z is —N($R^1$)N-G.
7. The method of claim 1, wherein $R^1$ is alkyl.
8. The method of claim 1, wherein $R^4$ is hydrogen.
9. The method of claim 1, wherein G is a heterocyclyl.
10. The method of claim 1, wherein G is a nitrogen-containing heterocyclyl.
11. The method of claim 10, wherein the nitrogen-containing heterocyclyl is a 5- or 6-membered heterocyclyl.
12. The method of claim 11, wherein the heterocyclyl is chosen from:

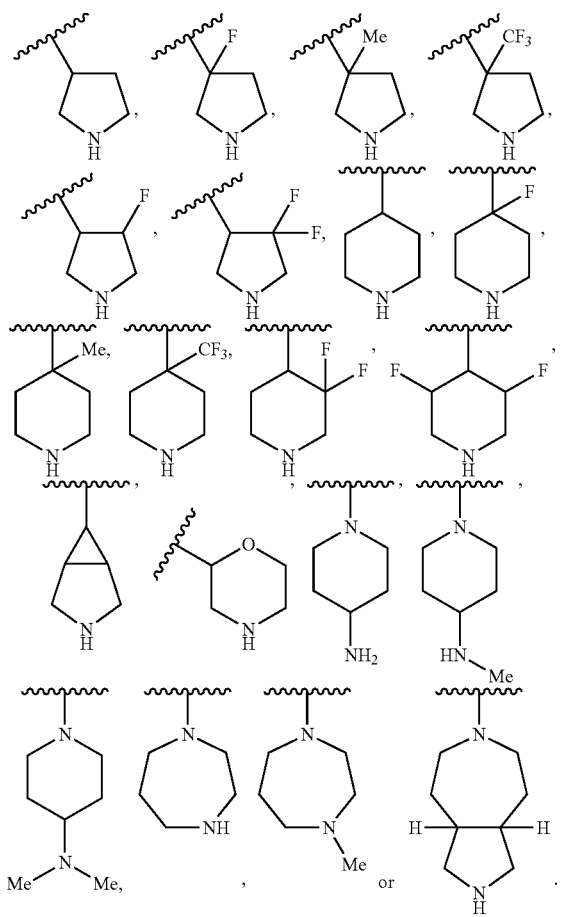

13. The method of claim 2, wherein R is a bicyclic nitrogen-containing heteroaryl.

14. The method of claim 13, wherein R is chosen from:

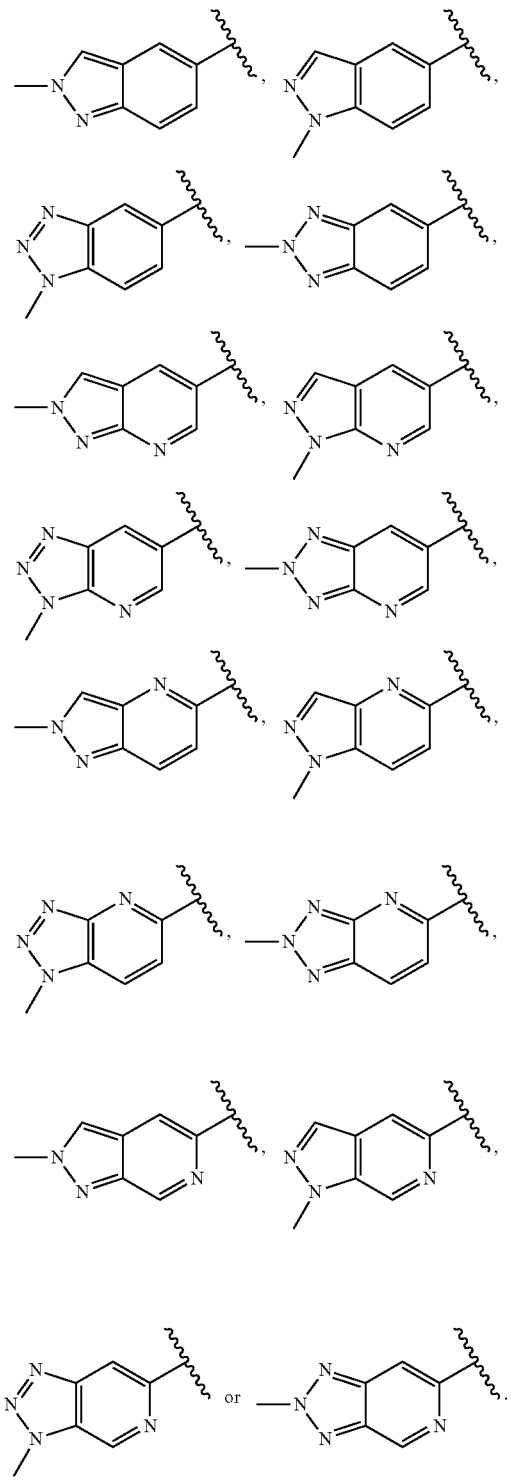

15. A method for treating acute myeloid leukemia, breast or prostate cancer in a patient in need thereof comprising administering a therapeutically effective dose of a compound of Formula (IVc)

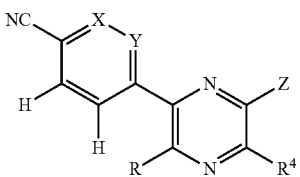

Formula (IVc)

wherein the compound of Formula (IVc) includes pharmaceutically acceptable salts thereof, wherein, X is C—F;

Y is C—H;

Z is -G, —CH$_2$-G, —CH$_2$—CH$_2$-G, —N(R$^1$)-G, —N(R$^1$)—CH$_2$-G, —O-G, —O—CH$_2$-G, or —C(O)N(R$^2$)(R$^3$), wherein G is carbocyclyl, aryl, heterocyclyl or heteroaryl;

R$^1$ is hydrogen or alkyl, and R$^2$ and R$^3$ are independently selected from hydrogen, alkyl, heterocyclyl, or heterocyclylalkyl, or optionally, R$^2$ and R$^3$ join to form an N-linked heterocyclyl ring system;

R is aryl, heteroaryl, alkynyl, or cycloalkylalkynylene; and

R$^4$ is hydrogen.

16. The method of claim 15, wherein R is a bicyclic nitrogen-containing heteroaryl.

17. The method of claim 16, wherein R is:

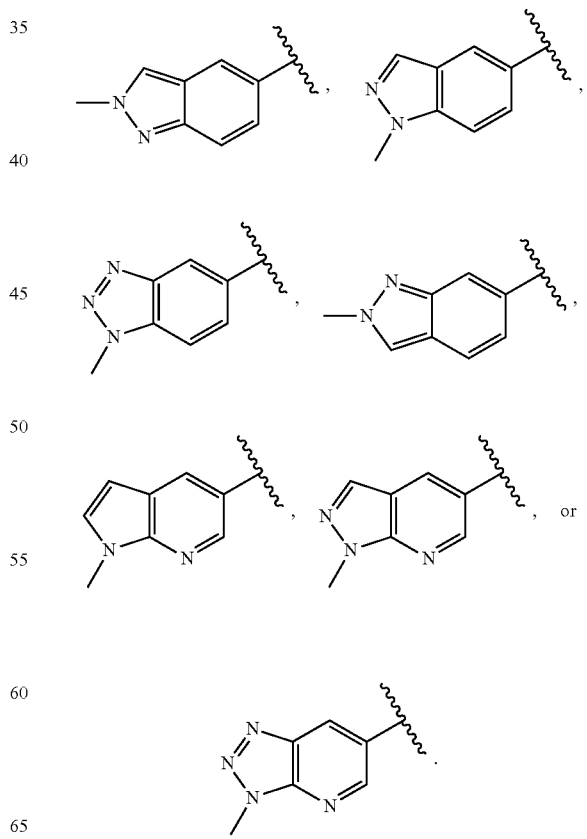

18. The method of claim 15, wherein G is

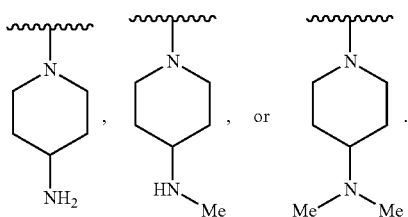

19. A method of regulating gene transcription in a cell comprising inhibiting lysine-specific demethylase 1 activity by exposing the lysine-specific demethylase 1 enzyme to a compound of Formula (IV):

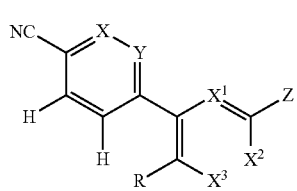

wherein the compound of Formula (IV) includes pharmaceutically acceptable salts thereof, wherein,
X and Y are each independently chosen from C—H, C—F, C—CH$_3$, or N;
Z is -G, —CH$_2$-G, —CH$_2$—CH$_2$-G, —N(R$^1$)-G, —N(R$^1$)—CH$_2$-G, —O-G, —O—CH$_2$-G, or —C(O)N(R$^2$)(R$^3$);
X$^1$, X$^2$, and X$^3$ are each independently selected from N or C—R$^4$, provided that at least one of X$^1$, X$^2$, or X$^3$ is N;
G is carbocyclyl, aryl, or heterocyclyl;
R$^1$ is hydrogen or alkyl;
R$^2$ and R$^3$ are independently selected from hydrogen, alkyl, heterocyclyl, heterocyclylalkyl, or optionally, R$^2$ and R$^3$ join to form an N-linked heterocyclyl ring system;
R$^4$ is hydrogen, halogen, C$_1$-C$_3$ alkyl or C$_1$-C$_3$ alkoxy; and
R is heteroaryl, alkynyl, or cycloalkylalkynylene.

20. The method of claim 19, wherein R is heteroaryl.
21. The method of claim 19, wherein Formula (IV) is Formula (IVc):

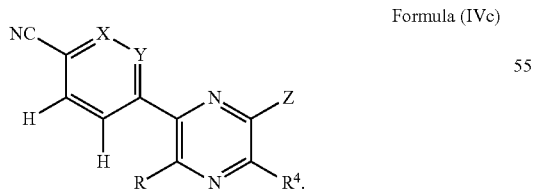

22. The method of claim 19, wherein X is C—F.
23. The method of claim 19, wherein Y is C—H.
24. The method of claim 19, wherein Z is —N(R$^1$)-G.
25. The method of claim 19, wherein R$^1$ is alkyl.
26. The method of claim 19, wherein R$^4$ is hydrogen.
27. The method of claim 19, wherein G is a heterocyclyl.

28. The method of claim 19, wherein G is a nitrogen-containing heterocyclyl.
29. The method of claim 28, wherein the nitrogen-containing heterocyclyl is a 5- or 6-membered heterocyclyl.
30. The method of claim 29, wherein the heterocyclyl is chosen from:

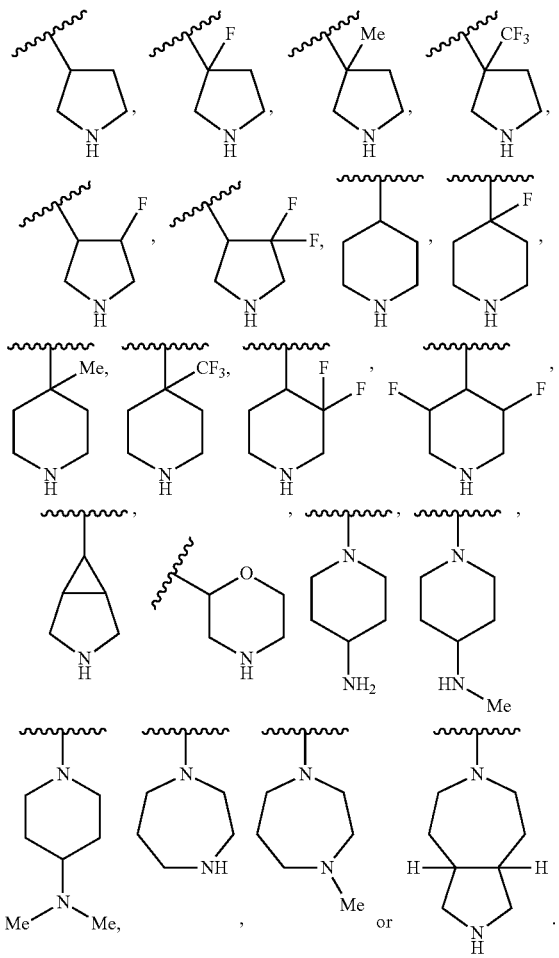

31. The method of claim 20, wherein R is a bicyclic nitrogen-containing heteroaryl.
32. The method of claim 31, wherein R is chosen from:

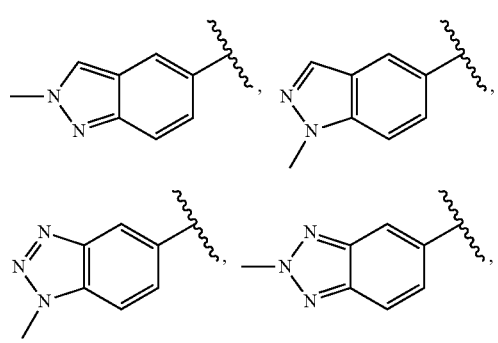

-continued

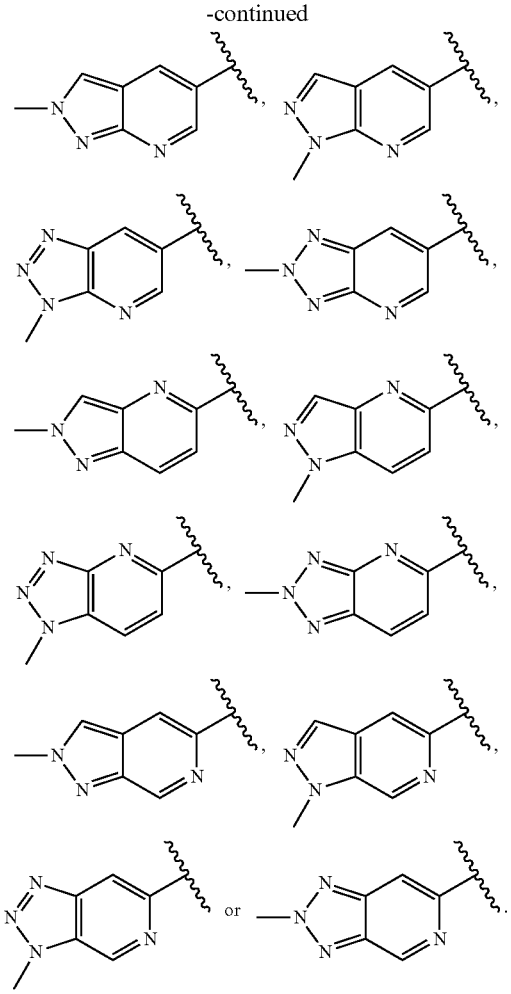

33. A method of regulating gene transcription in a cell comprising inhibiting lysine-specific demethylase 1 activity by exposing the lysine-specific demethylase 1 enzyme to a compound of Formula (IVc)

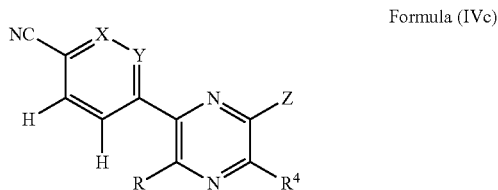

Formula (IVc)

wherein the compound of Formula (IVc) includes pharmaceutically acceptable salts thereof, wherein, X is C—F,
Y is C—H;
Z is -G, —CH2-G, —CH2-CH2-G, —N(R1)-G, —N(R1)-CH2-G, —O-G, —O—CH2-G, or —C(O)N(R2)(R3), wherein
G is carbocyclyl, aryl, heterocyclyl or heteroaryl;
$R^1$ is hydrogen or alkyl, and $R^2$ and $R^3$ are independently selected from hydrogen, alkyl, heterocyclyl, or heterocyclylalkyl, or optionally, $R^2$ and $R^3$ join to form an N-linked heterocyclyl ring system;
R is aryl, heteroaryl, alkynyl, or cycloalkylalkynylene; and
R4 is hydrogen.

34. The method of claim 33, wherein R is a bicyclic nitrogen-containing heteroaryl.

35. The method of claim 34, wherein R is:

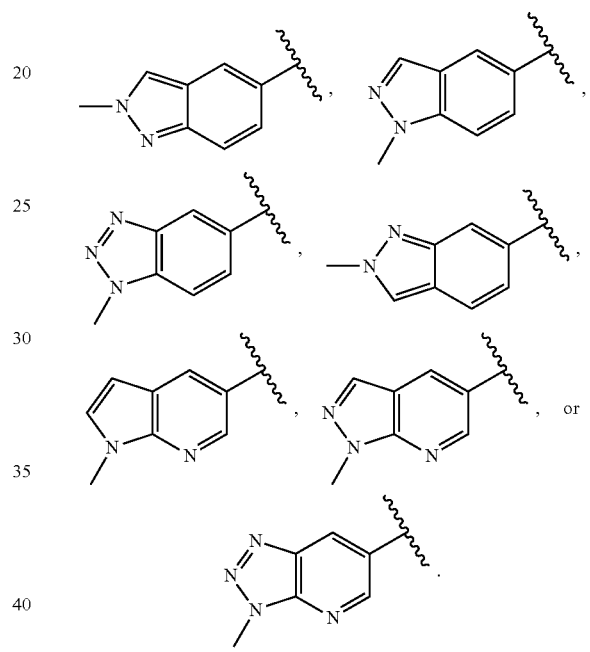

36. The method of claim 33, wherein G is

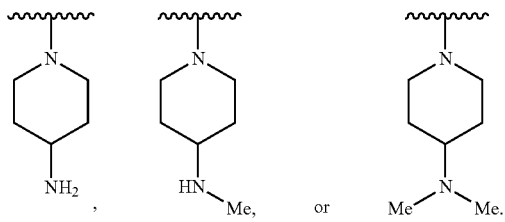 [SMILES: *N1CCC(N)CC1 ; "," ; *N1CCC(NC)CC1 ; "or" ; *N1CCC(N(C)C)CC1]

* * * * *